United States Patent
Shi et al.

(10) Patent No.: US 11,869,176 B2
(45) Date of Patent: Jan. 9, 2024

(54) HYPERSPECTRAL IMAGING SYSTEM

(71) Applicant: UNIVERSITY OF SOUTHERN CALIFORNIA, Los Angeles, CA (US)

(72) Inventors: Wen Shi, Los Angeles, CA (US); Eun Sang Koo, Los Angeles, CA (US); Scott E. Fraser, Los Angeles, CA (US); Francesco Cutrale, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 262 days.

(21) Appl. No.: 17/427,890

(22) PCT Filed: Jan. 31, 2020

(86) PCT No.: PCT/US2020/016233
§ 371 (c)(1),
(2) Date: Aug. 2, 2021

(87) PCT Pub. No.: WO2020/160485
PCT Pub. Date: Aug. 6, 2020

(65) Prior Publication Data
US 2022/0108430 A1    Apr. 7, 2022

Related U.S. Application Data

(60) Provisional application No. 62/799,647, filed on Jan. 31, 2019.

(51) Int. Cl.
*G06T 5/10* (2006.01)
*G01J 3/28* (2006.01)
(Continued)

(52) U.S. Cl.
CPC .............. *G06T 5/10* (2013.01); *G01J 3/2823* (2013.01); *G06T 5/002* (2013.01); *A61B 5/0075* (2013.01);
(Continued)

(58) Field of Classification Search
CPC . G06T 5/10; G06T 5/002; G06T 2207/10024; G06T 2207/20056;
(Continued)

(56) References Cited

U.S. PATENT DOCUMENTS

2012/0082362 A1\* 4/2012 Diem .................... A61B 5/418
382/133
2012/0276578 A1\* 11/2012 Stringari ............ G01N 21/6486
435/288.7
(Continued)

FOREIGN PATENT DOCUMENTS

WO WO-2004021050 A2 \* 3/2004 ............... A61B 3/12
WO WO-2017223206 A1 \* 12/2017 ............ G01J 3/2823
WO 2018/089383 A1 5/2018

OTHER PUBLICATIONS

Ranjit, S., Malacrida, L., Jameson, D. M. & Gratton, E. "Fit-free analysis of fluorescence lifetime imaging data using the phasor approach" Nat. Protoc. 13, 1979-2004 (2018).
(Continued)

*Primary Examiner* — Fernando Alcon
(74) *Attorney, Agent, or Firm* — McDermott Will & Emery LLP

(57) ABSTRACT

This invention relates to a hyperspectral imaging system for denoising and/or color unmixing multiple overlapping spectra in a low signal-to-noise regime with a fast analysis time. This system may carry out Hyper-Spectral Phasors (HySP) calculations to effectively analyze hyper-spectral time-lapse data. For example, this system may carry out Hyper-Spectral
(Continued)

Phasors (HySP) calculations to effectively analyze five-dimensional (5D) hyper-spectral time-lapse data. Advantages of this imaging system may include: (a) fast computational speed, (b) the ease of phasor analysis, and (c) a denoising algorithm to obtain the minimally-acceptable signal-to-noise ratio (SNR). An unmixed color image of a target may be generated. These images may be used in diagnosis of a health condition, which may enhance a patient's clinical outcome and evolution of the patient's health.

20 Claims, 122 Drawing Sheets
(76 of 122 Drawing Sheet(s) Filed in Color)

(51) Int. Cl.
G06T 5/00 (2006.01)
A61B 5/00 (2006.01)

(52) U.S. Cl.
CPC ..... A61B 5/441 (2013.01); G06T 2207/10024 (2013.01); G06T 2207/20056 (2013.01)

(58) Field of Classification Search
CPC ....... G06T 5/003; G01J 3/2823; G01J 3/0264; G01J 3/10; A61B 5/0075; A61B 5/441; A61B 5/14552; A61B 5/443; A61B 5/444; A61B 5/445
See application file for complete search history.

(56) References Cited

U.S. PATENT DOCUMENTS

| | | | | |
|---|---|---|---|---|
| 2012/0328178 | A1* | 12/2012 | Remiszewski | G06V 20/69 382/133 |
| 2018/0088051 | A1* | 3/2018 | Georgakoudi | G06T 7/20 |
| 2019/0287222 | A1* | 9/2019 | Cutrale | H04N 23/11 |

OTHER PUBLICATIONS

Zipfel, W. R. et al. "Live tissue intrinsic emission microscopy using multiphoton-excited native fluorescence and second harmonic generation" Proc. Natl. Acad. Sci. 100, pp. 7075-7080 (2003).
Rock, J. R., Randell, S. H. & Hogan, B. L. M. "Airway basal stem cells: a perspective on their roles in epithelial homeostasis and remodeling" Dis. Model. Mech. 3, pp. 545-556 (2010).
Rock, J. R. et al. "Basal cells as stem cells of the mouse trachea and human airway epithelium" Proc. Natl. Acad. Sci. (2009). doi:10.1073/pnas.0906850106.
Bird, D. K. et al. "Metabolic mapping of MCF10A human breast cells via multiphoton fluorescence lifetime imaging of the coenzyme NADH" Cancer Res. 65, pp. 8766-8773 (2005).
Lakowicz, J. R., Szmacinski, H., Nowaczyk, K. & Johnson, M. L. "Fluorescence lifetime imaging of free and protein-bound NADH" Proc. Natl. Acad. Sci. (1992). doi:10.1073/pnas.89.4.1271.
Skala, M. C. et al. "In vivo multiphoton microscopy of NADH and FAD redox states, fluorescence lifetimes, and cellular morphology in precancerous epithelia" Proc. Natl. Acad. Sci. (2007). doi:10.1073/pnas.0708425104.
Sharick, J. T. et al. "Protein-bound NAD(P)H Lifetime is Sensitive to Multiple Fates of Glucose Carbon" Sci. Rep. (2018). doi:10.1038/s41598-018-23691-x.
Stringari, C. et al. "Phasor approach to fluorescence lifetime microscopy distinguishes different metabolic states of germ cells in a live tissue" Proc. Natl. Acad. Sci. 108, 13582-13587 (2011).
Stringari, C. et al. "Multicolor two-photon imaging of endogenous fluorophores in living tissues by wavelength mixing" Sci. Rep. (2017). doi:10.1038/s41598-017-03359-8.

Sun, Y. et al. "Endoscopic fluorescence lifetime imaging for in vivo intraoperative diagnosis of oral carcinoma" in Microscopy and Microanalysis (2013). doi:10.1017/S1431927613001530.
Ghukasyan, V. V. & Kao, F. J. "Monitoring cellular metabolism with fluorescence lifetime of reduced nicotinamide adenine dinucleotide" J. Phys. Chem. C (2009). doi:10.1021/jp810931u.
Walsh, A. J. et al. "Quantitative optical imaging of primary tumor organoid metabolism predicts drug response in breast cancer" Cancer Res. (2014). doi:10.1158/0008-5472.CAN-14-0663.
Conklin, M. W., Provenzano, P. P., Eliceiri, K. W., Sullivan, R. & Keely, P. J. "Fluorescence lifetime imaging of endogenous fluorophores in histopathology sections reveals differences between normal and tumor epithelium in carcinoma in situ of the breast" Cell Biochem. Biophys. (2009). doi:10.1007/s12013-009-9046-7.
Browne, A. W. et al. "Structural and functional characterization of human stemcell-derived retinal organoids by live imaging" Investig. Ophthalmol. Vis. Sci. (2017). doi:10.1167/iovs.16-20796.
Weissman, T. A. & Pan, Y. A. "Brainbow: New resources and emerging biological applications for multicolor genetic labeling and analysis" Genetics 199, pp. 293-306 (2015).
Pan, Y. A., Livet, J., Sanes, J. R., Lichtman, J. W. & Schier, A. F. "Multicolor brainbow imaging in Zebrafish" Cold Spring Harb. Protoc. 6, (2011).
Raj, B. et al. "Simultaneous single-cell profiling of lineages and cell types in the vertebrate brain" Nat. Biotechnol. 36, pp. 442-450 (2018).
Mahou, P. et al. "Multicolor two-photon tissue imaging by wavelength mixing" Nat. Methods 9, pp. 815-818 (2012).
Loulier, K. et al. "Multiplex Cell and Lineage Tracking with Combinatorial Labels" Neuron 81, pp. 505-520 (2014).
North, T. E. & Goessling, W. "Haematopoietic stem cells show their true colours" Nature Cell Biology 19, pp. 10-12 (2017).
Chen, C. H. et al. "Multicolor Cell Barcoding Technology for Long-Term Surveillance of Epithelial Regeneration in Zebrafish" Dev. Cell 36, pp. 668-680 (2016).
Vert, J., Tsuda, K. & Scholkopf, B. "A primer on kernel methods" Kernel Methods Comput. Biol. 35-70 (2004). doi:10.1017/CBO9781107415324.004.
Bruton, D. "{RGB} Values for visible wavelengths" (1996). Available at: http://www.physics.sfasu.edu/astro/color/spectra.html.
Huss, D. et al. "A transgenic quail model that enables dynamic imaging of amniote embryogenesis" Development 142, pp. 2850-2859 (2015).
Holst, J., Vignali, K. M., Burton, A. R. & Vignali, D. A. A. "Rapid analysis of Tcell selection in vivo using T cell-receptor retrogenic mice" Nat. Methods 3, pp. 191-197 (2006).
Kwan, K. M. et al. "The Tol2kit: A multisite gateway-based construction Kit for Tol2 transposon transgenesis constructs" Dev. Dyn. 236, pp. 3088-3099 (2007).
Kawakami, K. et al. "A transposon-mediated gene trap approach identifies developmentally regulated genes in zebrafish" Dev. Cell 7, pp. 133-144 (2004).
Urasaki, A., Morvan, G. & Kawakami, K. "Functional dissection of the Tol2 transposable element identified the minimal cis-sequence and a highly repetitive sequence in the subterminal region essential for transposition" Genetics 174, pp. 639-649 (2006).
White, R. M. et al. "Transparent Adult Zebrafish as a Tool for In Vivo Transplantation Analysis" Cell Stem Cell 2, pp. 183-189 (2008).
Arnesano, C., Santoro, Y. & Gratton, E. "Digital parallel frequency-domain spectroscopy for tissue imaging" J. Biomed. Opt. 17, 0960141 (2012).
International Search Report and Written Opinion issued in corresponding International Application No. PCT/US2020/016233, dated Jun. 3, 2020.
Malacrida et al. "LAURDAN Fluorescence and Phasor Plots Reveal the Effects of a H2O2bolus in NIH-3T3 Fibroblast Membranes Dynamics and Hydration" Free Radical Biology and Medicine, vol. 128, Nov. 20, 2018, pp. 144-156.
Fereidouni et al. "Multispectral Analysis Tools Can Increase Utility of RGB Color Images in Histology" Journal of Optics, Institute of Physics Publishing, vol. 20, No. 4, Mar. 15, 2018.

(56) References Cited

OTHER PUBLICATIONS

Garini, Y., Young, I. T. and McNamara, G. "Spectral imaging: principles and applications" Cytometry A 69, pp. 735-747 (2006).

Dickinson, M. E., Simbuerger, E., Zimmermann, B., Waters, C. W. and Fraser, "Multiphoton excitation spectra in biological samples" Journal of Biomedical Optics 8, pp. 329-338 (2003).

Dickinson, M. E., Bearman, G., Tille, S., Lansford, R. & Fraser, S. E. "Multispectral imaging and linear unmixing add a whole new dimension to laser scanning fluorescence microscopy" Biotechniques 31, pp. 1272-1278 (2001).

Levenson, R. M. and Mansfield, J. R. "Multispectral imaging in biology and medicine: Slices of life" Cytometry A 69, pp. 748-758 (2006).

Jahr, W., Schmid, B., Schmied, C., Fahrbach, F. O. & Huisken, J. "Hyperspectral light sheet microscopy" Nat. Commun. 6, (2015).

Lansford, R., Bearman, G. and Fraser, S. E. "Resolution of multiple green fluorescent protein color variants and dyes using two-photon microscopy and imaging spectroscopy" Journal of Biomedical Optics 6, pp. 311-318 (2001).

Zimmermann, T. "Spectral Imaging and Linear Unmixing in Light Microscopy" Adv Biochem Engin/Biotechnol, 95 pp. 245-265 (2005).

Jolliffe, Ian. "Principal component analysis" John Wiley & Sons, Ltd, (2002).

Gong, P. and Zhang, A. "Noise Effect on Linear Spectral Unmixing" Geographic Information Sciences 5(1), (1999).

Mukamel, E. A., Nimmerjahn, A., and Schnitzer M.J. "Automated Analysis of Cellular Signals from Large-Scale Calcium Imaging Data" Neuron, 63(6), pp. 747-760.

Clayton, A. H., Hanley, Q. S. & Verveer, P. J. "Graphical representation and multicomponent analysis of single-frequency fluorescence lifetime imaging microscopy data" J. Microsc. 213, pp. 1-5 (2004).

Redford, G. I. & Clegg, R. M. "Polar plot representation for frequency-domain analysis of fluorescence lifetimes" J. Fluoresc. 15, pp. 805-815 (2005).

Digman M A, Caiolfa V R, Zamai M and Gratton E. "The phasor approach to fluorescence lifetime imaging analysis" Biophys. J. 94 pp. 14-16 (2008).

Fereidouni F., Bader A.N. and Gerritsen H.C. "Spectral phasor analysis allows rapid and reliable unmixing of fluorescence microscopy spectral images" Opt. Express 20, pp. 12729-12741 (2012).

Andrews L.M., Jones M.R., Digman M.A., Gratton E. "Spectral phasor analysis of Pyronin Y labeled RNA microenvironments in living cells" Biomed. Op. Express 4 (1), pp. 171-177 (2013).

Cutrale F., Salih A. and Gratton E. "Spectral phasor approach for fingerprinting of photo-activatable fluorescent proteins Dronpa, Kaede and KikGR" Methods Appl. Fluoresc. 1 (3) (2013) 035001.

Cranfill P.J., Sell B.R., Baird M.A., Allen J.R., Lavagnino Z., de Gruiter H.M., Kremers G., Davidson M.W., Ustione A., Piston D.W., "Quantitative assessment of fluorescent proteins" Nature Methods 13, pp. 557-562 (2016).

Chen, H., Gratton, E., & Digman, M. A. "Spectral Properties and Dynamics of Gold Nanorods Revealed by EMCCD-Based Spectral Phasor Method" Microscopy Research and Technique, 78(4), pp. 283-293 (2015).

Vermot, J., Fraser, S. E., Liebling, M. "Fast fluorescence microscopy for imaging the dynamics of embryonic development" HFSP Journal, vol. 2, pp. 143-155, (2008).

Dalal, R.B., Digman, M.A., Horwitz, A.F. , Vetri, V., Gratton, E., "Determination of particle No. and brightness using a laser scanning confocal microscope operating in the analog mode" Microsc. Res. Tech., 71(1) pp. 69-81 (2008).

Fereidouni, F., Reitsma, K., Gerritsen, H.C. "High speed multispectral fluorescence lifetime imaging" Optics Express, 21(10), pp. 11769-11782 (2013).

Trinh, L.A. et al., "A versatile gene trap to visualize and interrogate the function of the vertebrate proteome" Genes & development, 25(21), pp. 2306-2320 (2011).

Jin S. W., Beis D., Mitchell T., Chen J. N., Stainier D. Y. "Cellular and molecular analyses of vascular tube and lumen formation in zebrafish" Development 132, pp. 5199-5209 (2005).

Livet, J., Weissman, T. A., Kang, H., Draft, R. W., Lu, J., Bennis, R. A., Sanes, J.R., Lichtman J.W. "Transgenic strategies for combinatorial expression of fluorescent proteins in the nervous system" Nature, 450(7166), pp. 56-62 (2007).

Lichtman, J. W., Livet, J., & Sanes, J. R. "A technicolour approach to the connectome" Nature Reviews Neuroscience, 9(6), pp. 417-422 (2008).

Pan, Y. A., Freundlich, T., Weissman, T. A., Schoppik, D., Wang, X. C., Zimmerman, S., Ciruna, B., Sanes, J.R., Lichtman, J.W., Schier A.F. "Zebrabow: multispectral cell labeling for cell tracing and lineage analysis in zebrafish" Development, 140(13), pp. 2835-2846. (2013).

Megason, S.G. "In toto imaging of embryogenesis with confocal time-lapse microscopy" Methods in molecular biology, 546 pp. 317-332 (2009).

Sinclair, M. B., Haaland, D. M., Timlin, J. A. & Jones, H. D. T. "Hyperspectral confocal microscope" Appl. Opt. 45, 6283 (2006).

Valm, A. M. et al. "Applying systems-level spectral imaging and analysis to reveal the organelle interactome" Nature 546, pp. 162-167 (2017).

Hiraoka, Y., Shimi, T. & Haraguchi, T. "Multispectral Imaging Fluorescence Microscopy for Living Cells" Cell Struct. Funct. 27, pp. 367-374 (2002).

Jacobson, N. P. & Gupta, M. R. "Design goals and solutions for display of hyperspectral images" in Proceedings—International Conference on Image Processing ICIP 2, pp. 622-625 (2005).

Hotelling, H. "Analysis of a complex of statistical variables into principal components" J. Educ. Psychol. 24, pp. 417-441 (1933).

Abdi, H. & Williams, L. J. "Principal component analysis" Wiley Interdisciplinary Reviews: Computational Statistics 2, pp. 433-459 (2010).

Tyo, J. S., Konsolakis, A., Diersen, D. I. & Olsen, R. C. "Principal-components-based display strategy for spectral imagery" IEEE Trans. Geosci. Remote Sens. 41, pp. 708-718 (2003).

Wilson, T. A. "Perceptual-based image fusion for hyperspectral data" IEEE Trans. Geosci. Remote Sens. 35, pp. 1007-1017 (1997).

Long, Y., Li, H. C., Celik, T., Longbotham, N. & Emery, W. J. "Pairwise-distance-analysis-driven dimensionality reduction model with double mappings for hyperspectral image visualization" Remote Sens. 7, pp. 7785-7808 (2015).

Kotwal, K. & Chaudhuri, S. "A Bayesian approach to visualization-oriented hyperspectral image fusion" Inf. Fusion 14, pp. 349-360 (2013).

Kotwal, K. & Chaudhuri, S. "Visualization of Hyperspectral Images Using Bilateral Filtering" IEEE Trans. Geosci. Remote Sens. 48, pp. 2308-2316 (2010).

Zhao, W. & Du, S. "Spectral-Spatial Feature Extraction for Hyperspectral Image Classification: A Dimension Reduction and Deep Learning Approach" IEEE Trans. Geosci. Remote Sens. 54, pp. 4544-4554 (2016).

Zhang, Y., De Backer, S. & Scheunders, P. "Noise-resistant wavelet-based Bayesian fusion of multispectral and hyperspectral images" IEEE Trans. Geosci. Remote Sens. 47, pp. 3834-3843 (2009).

A, R. "SVD Based Image Processing Applications: State of the Art, Contributions and Research Challenges" Int. J. Adv. Comput. Sci. Appl. 3, pp. 26-34 (2012).

Vergeldt, F. J. et al. "Multi-component quantitative magnetic resonance imaging by phasor representation" Sci. Rep. 7, (2017).

Lanzanò, L. et al. "Encoding and decoding spatio-temporal information for super-resolution microscopy" Nat. Commun. 6, (2015).

Cutrale, F. et al. "Hyperspectral phasor analysis enables multiplexed 5D in vivo imaging" Nat. Methods 14, pp. 149-152 (2017).

Radaelli, F. et al. "μmAPPS: A novel phasor approach to second harmonic analysis for in vitro-in vivo investigation of collagen microstructure" Sci. Rep. 7, (2017).

Scipioni, L., Gratton, E., Diaspro, A. & Lanzanò, L. "Phasor Analysis of Local ICS Detects Heterogeneity in Size and Number of Intracellular Vesicles" Biophys. J. (2016). doi:10.1016/j.bpj.2016.06.029.

(56) References Cited

OTHER PUBLICATIONS

Sarmento, M. J. et al. "Exploiting the tunability of stimulated emission depletion microscopy for super-resolution imaging of nuclear structures" Nat. Commun. (2018). doi: 10.1038/s41467-018-05963-2.
Scipioni, L., Di Bona, M., Vicidomini, G., Diaspro, A. & Lanzanò, L. "Local raster image correlation spectroscopy generates high-resolution intracellular diffusion maps" Commun. Biol. (2018). doi:10.1038/s42003-017-0010-6.

\* cited by examiner

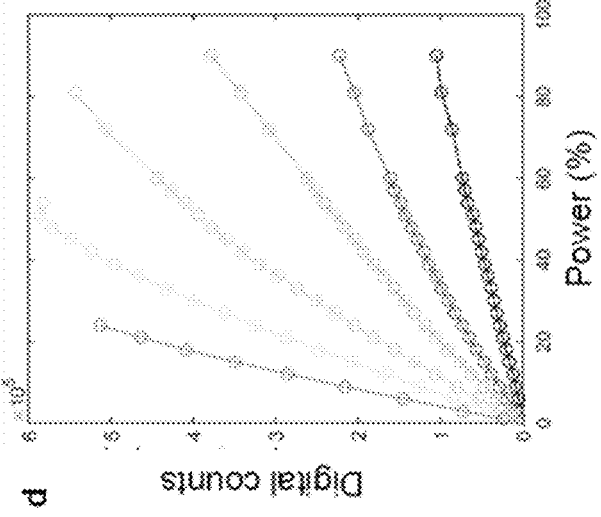
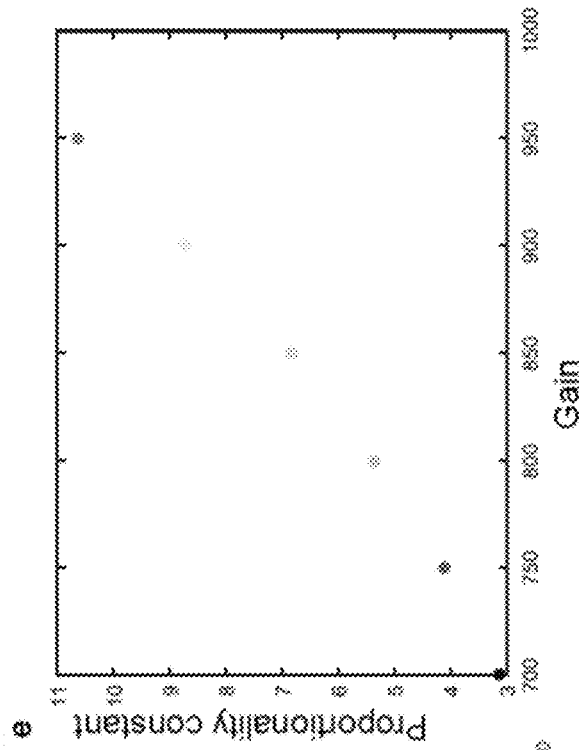
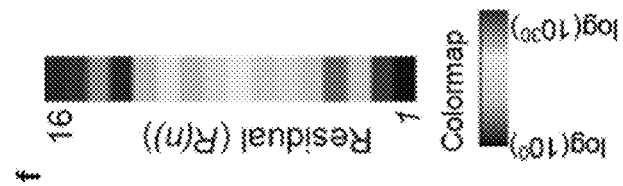

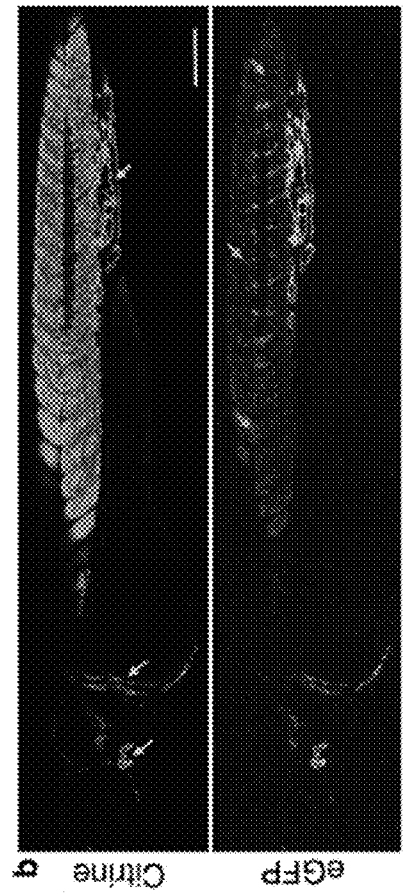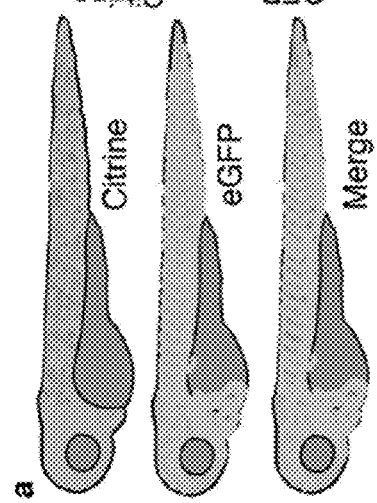

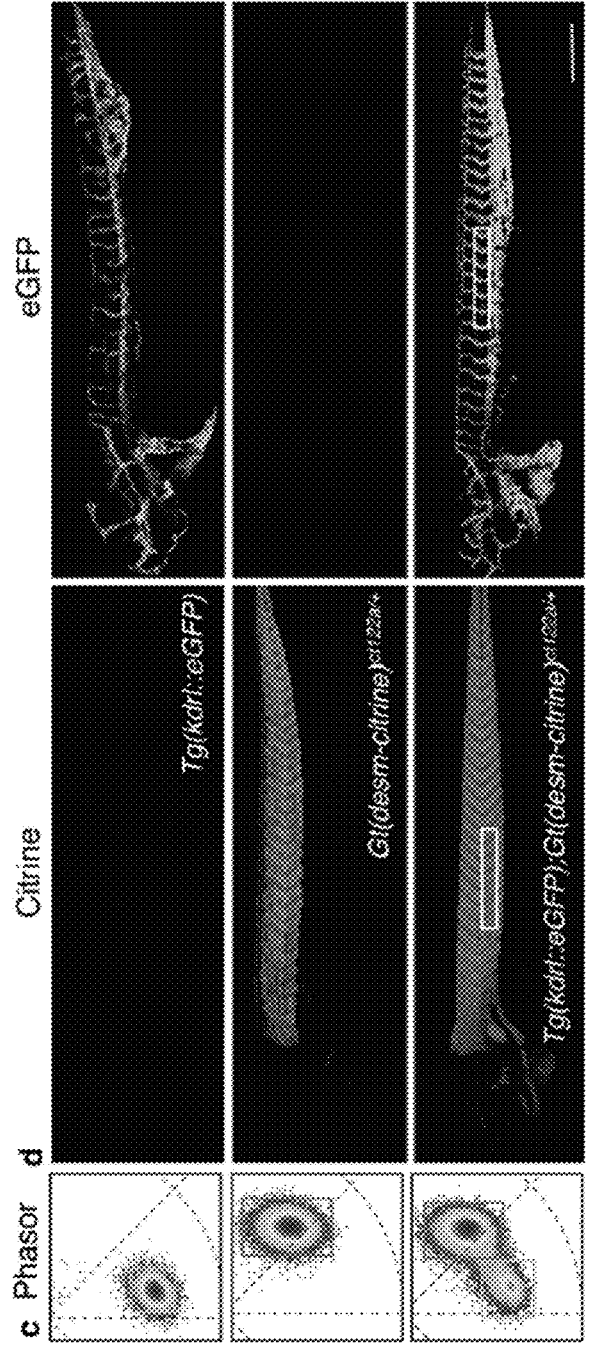

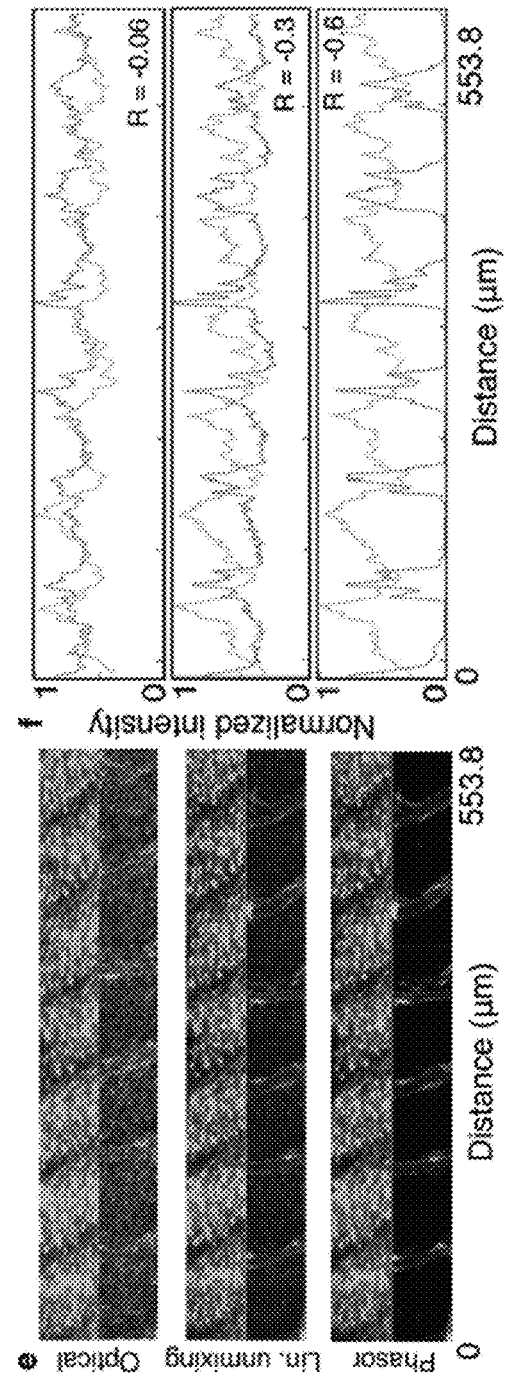

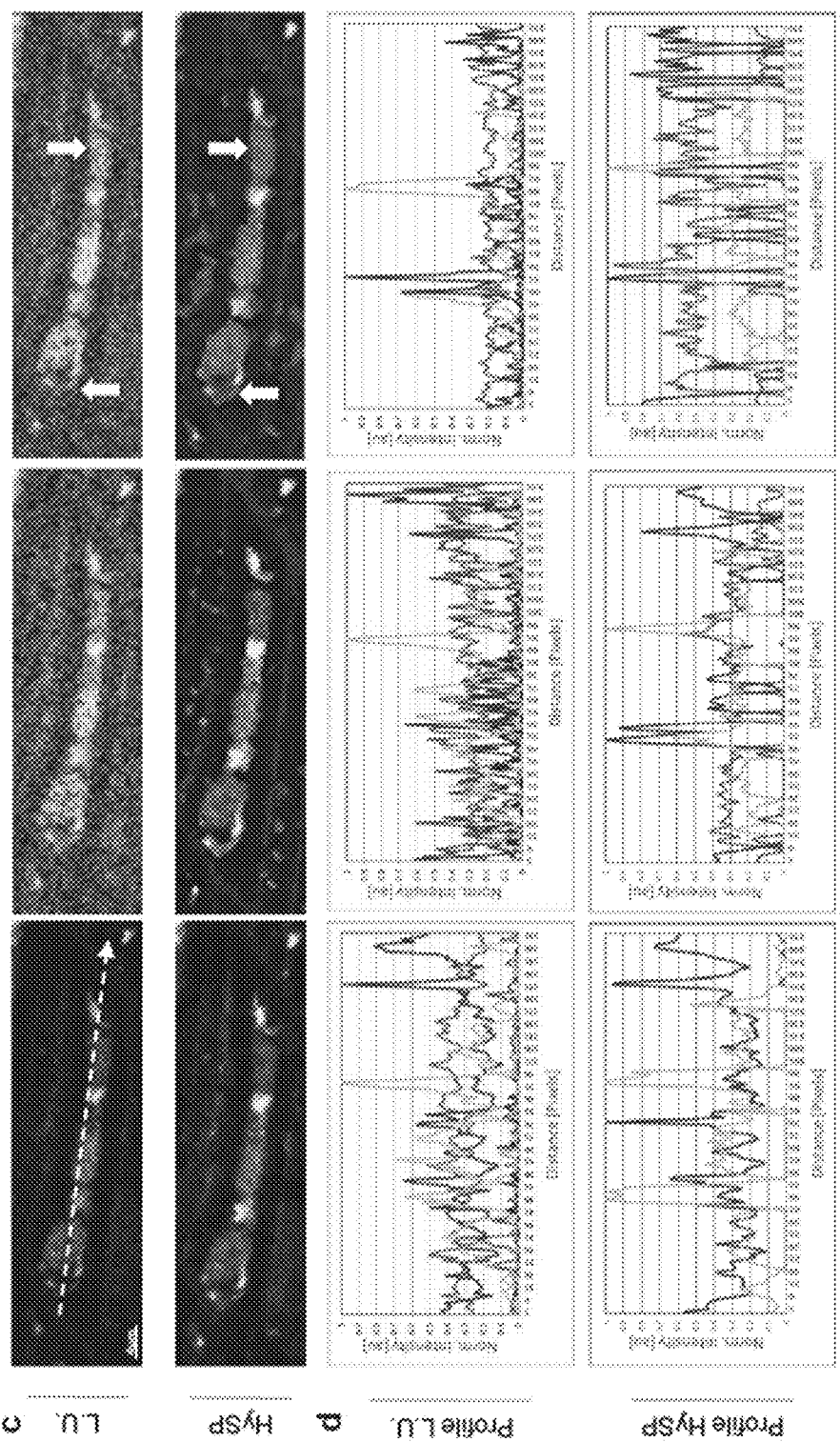

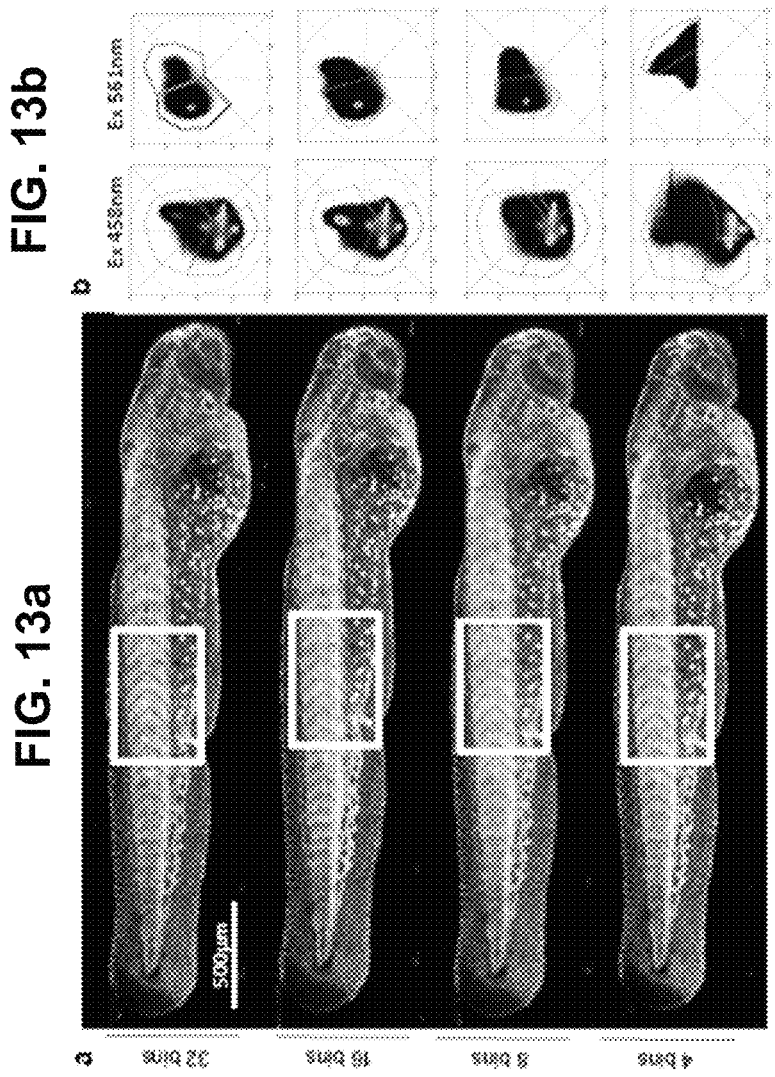

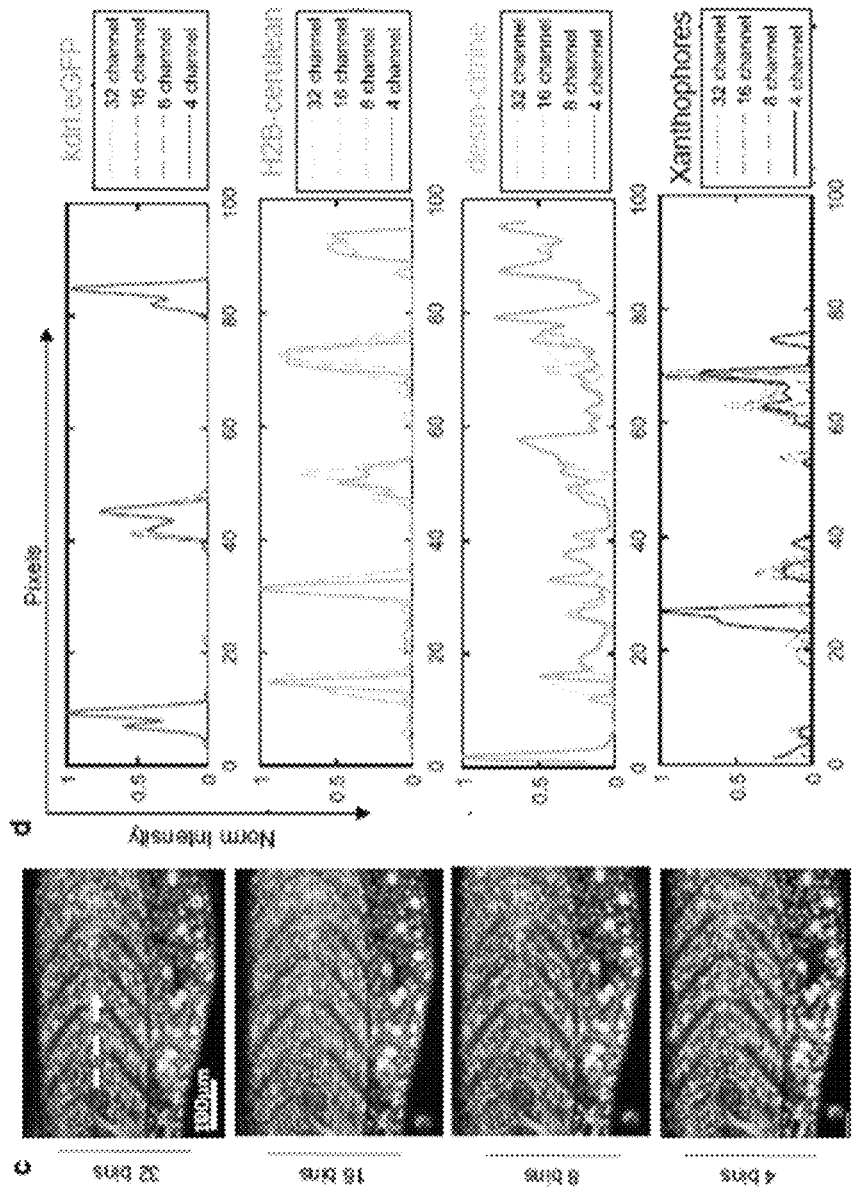

FIG. 24a
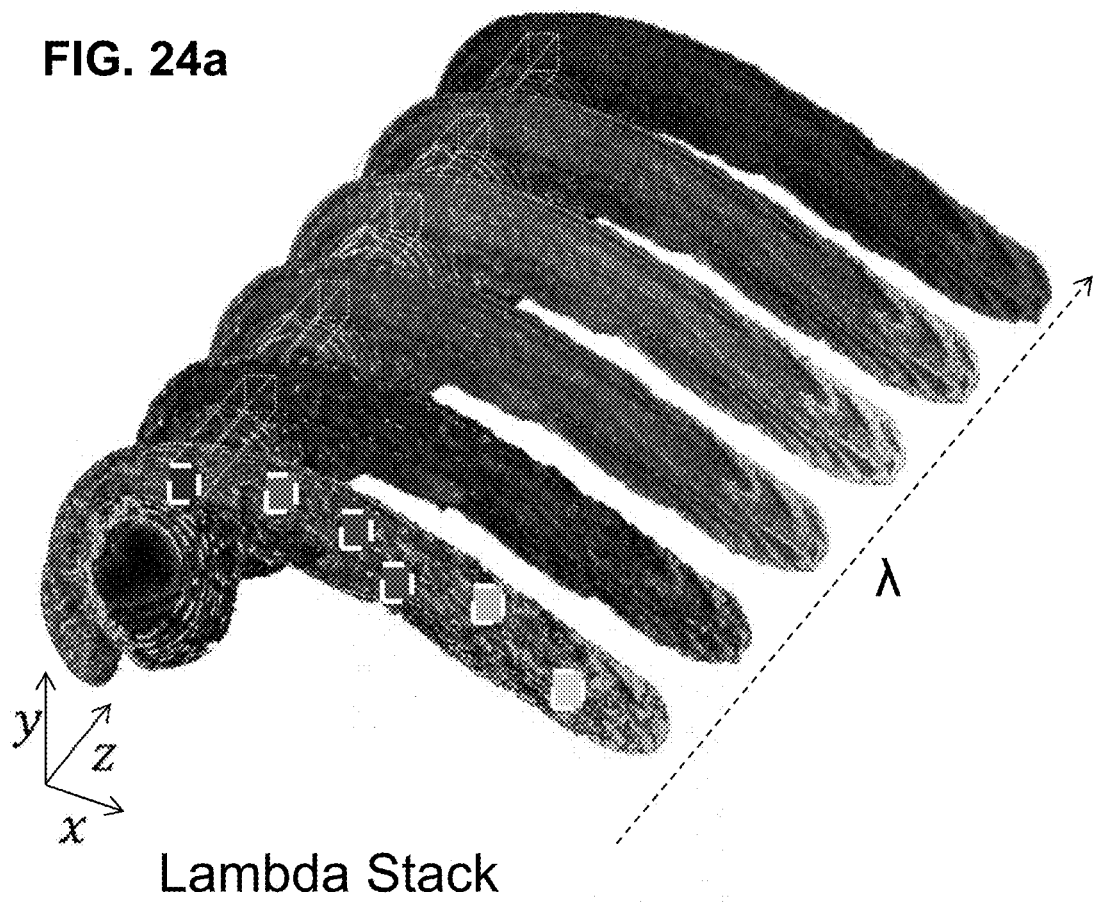
Lambda Stack
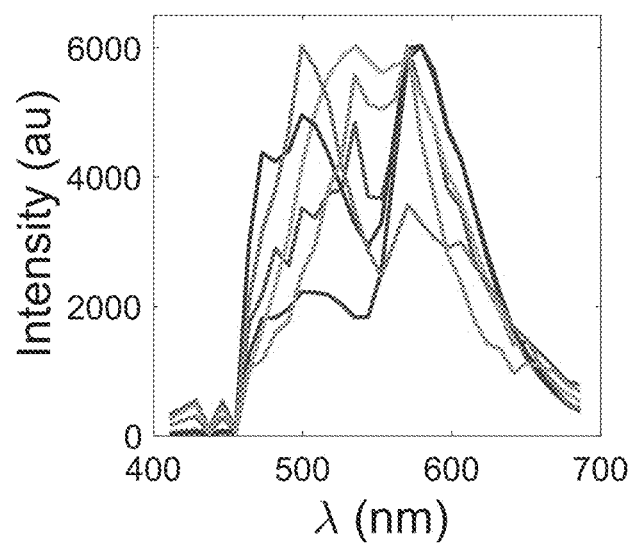
FIG. 24b

Standard Representation
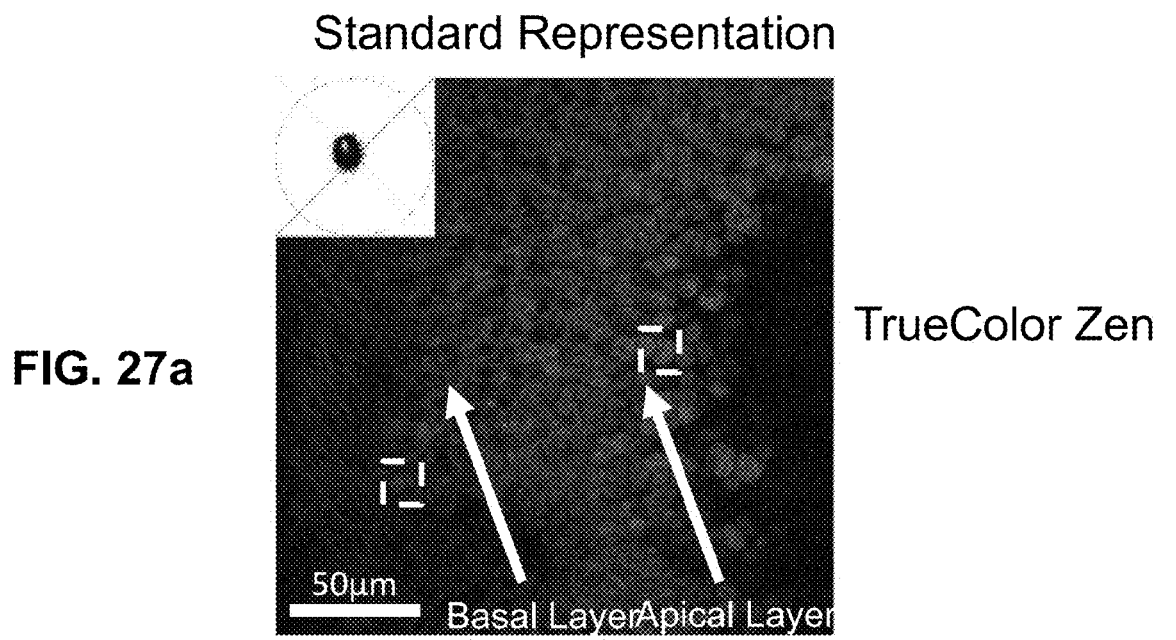
FIG. 27a
TrueColor Zen
Spectrally Encoded Enhanced Representations
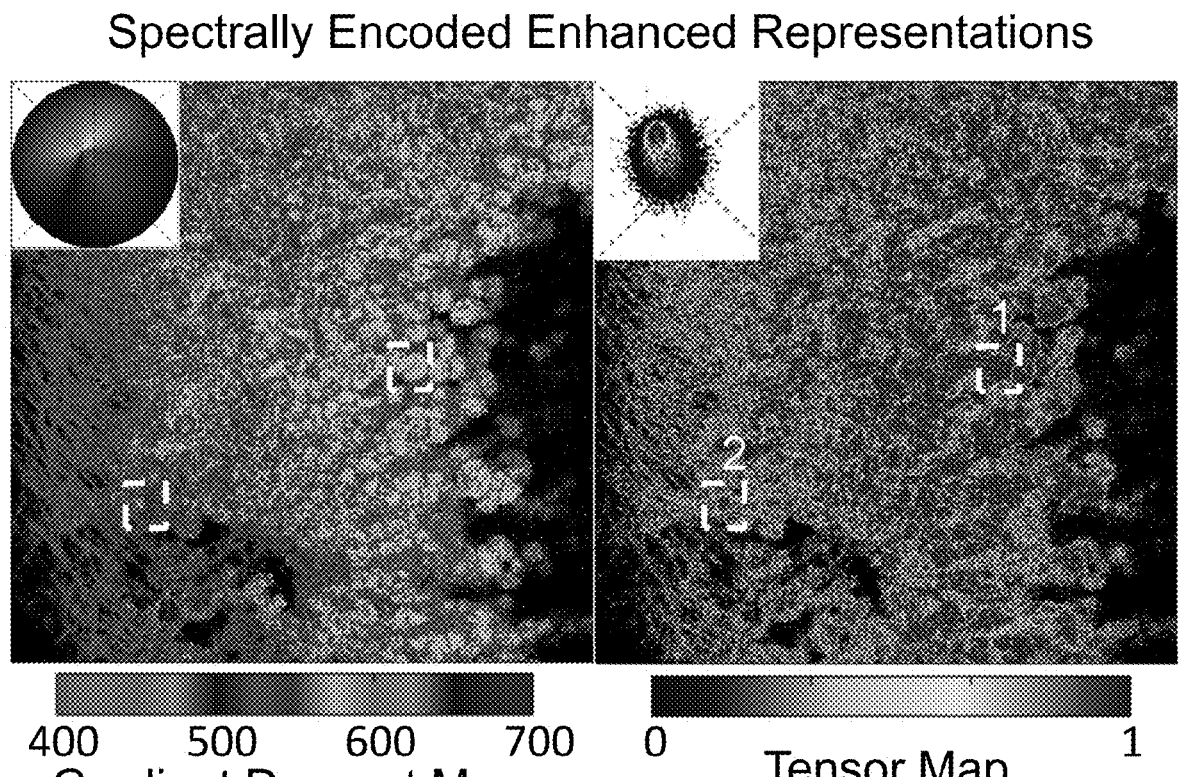
FIG. 27b
Gradient Descent Map
Mode: Max Morph
FIG. 27c
Tensor Map True Color 32Ch Angular Map Mode: scaled

Region 3

Region 2

Region 1

True Color 32Ch

Angular Map
Mode: scaled

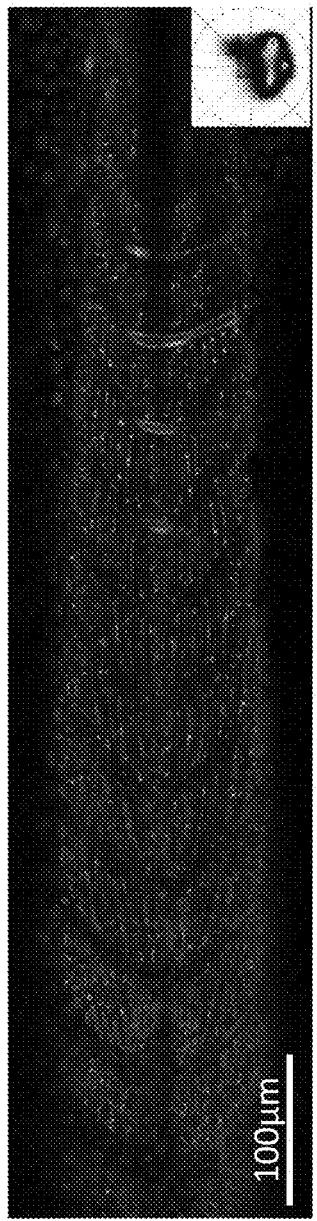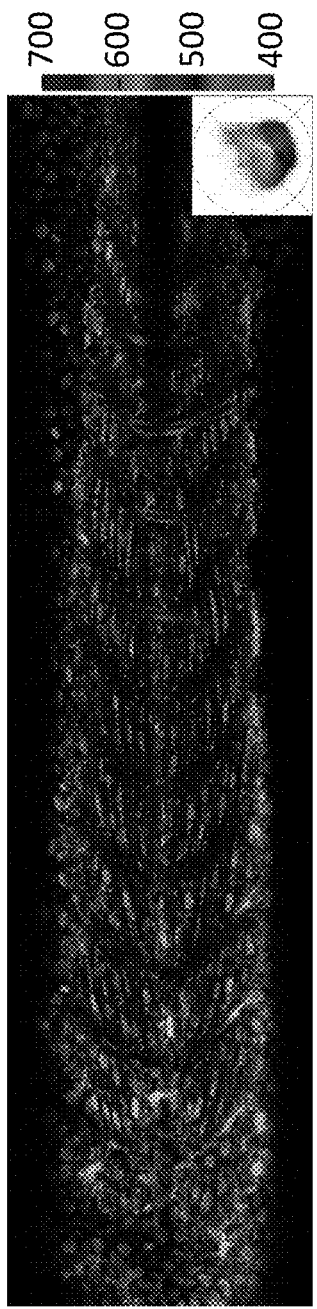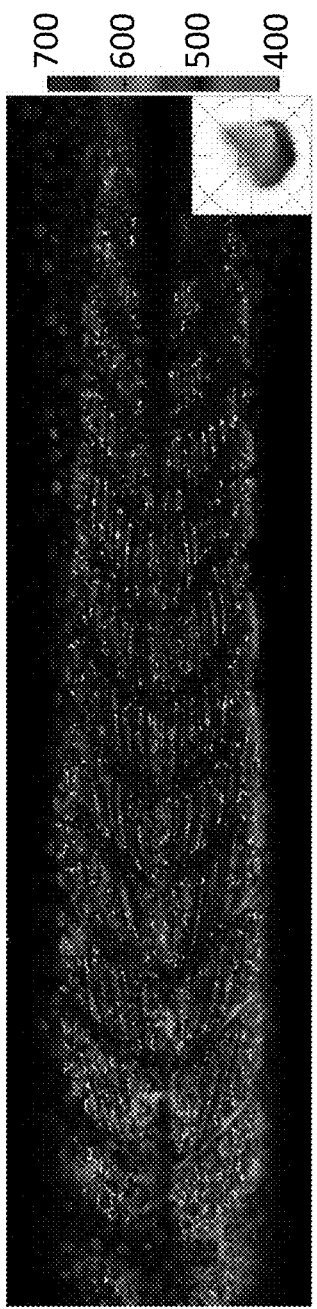
FIG. 29a True Color Zen
FIG. 29b Angular Map Mode: mass morph
FIG. 29c Gradient Descent Map Mode: max morph

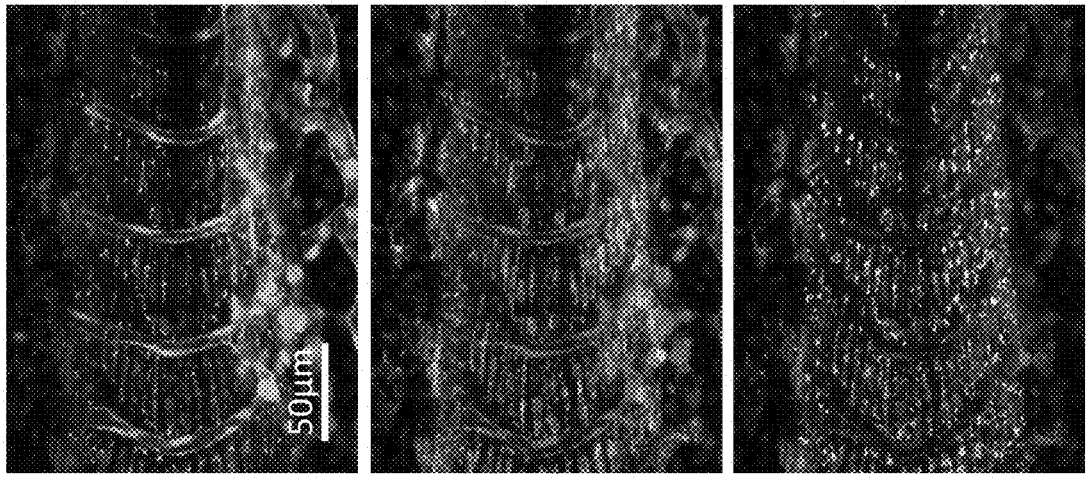
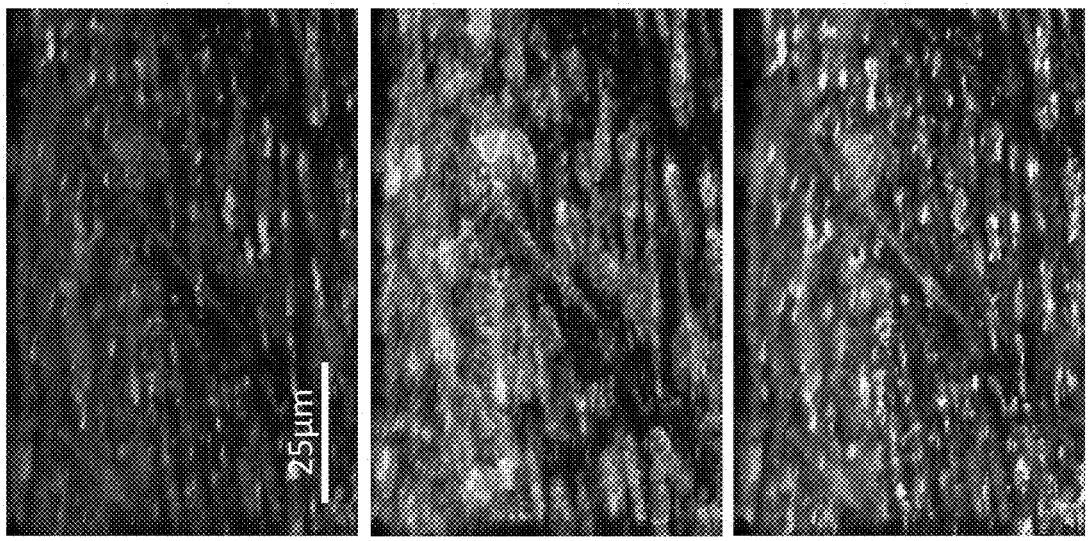
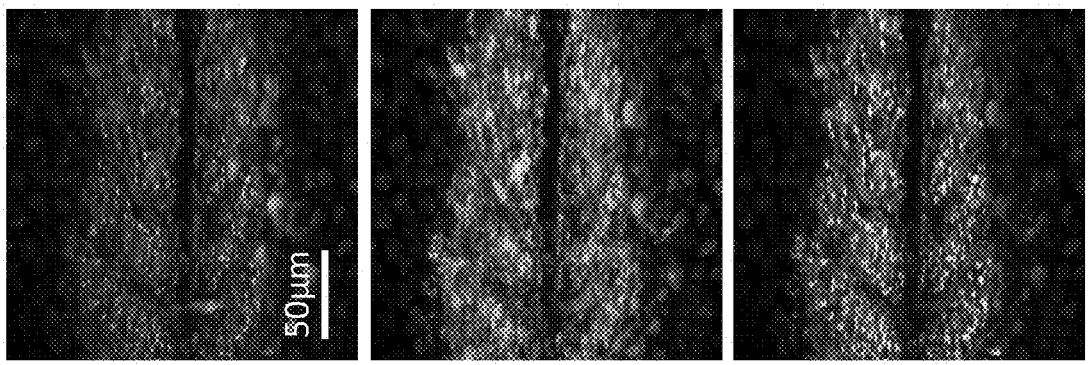
FIG. 29f
FIG. 29e
FIG. 29d
True Color 32Ch | Angular Map Mode: mass morph | Gradient Descent Map Mode: max morph

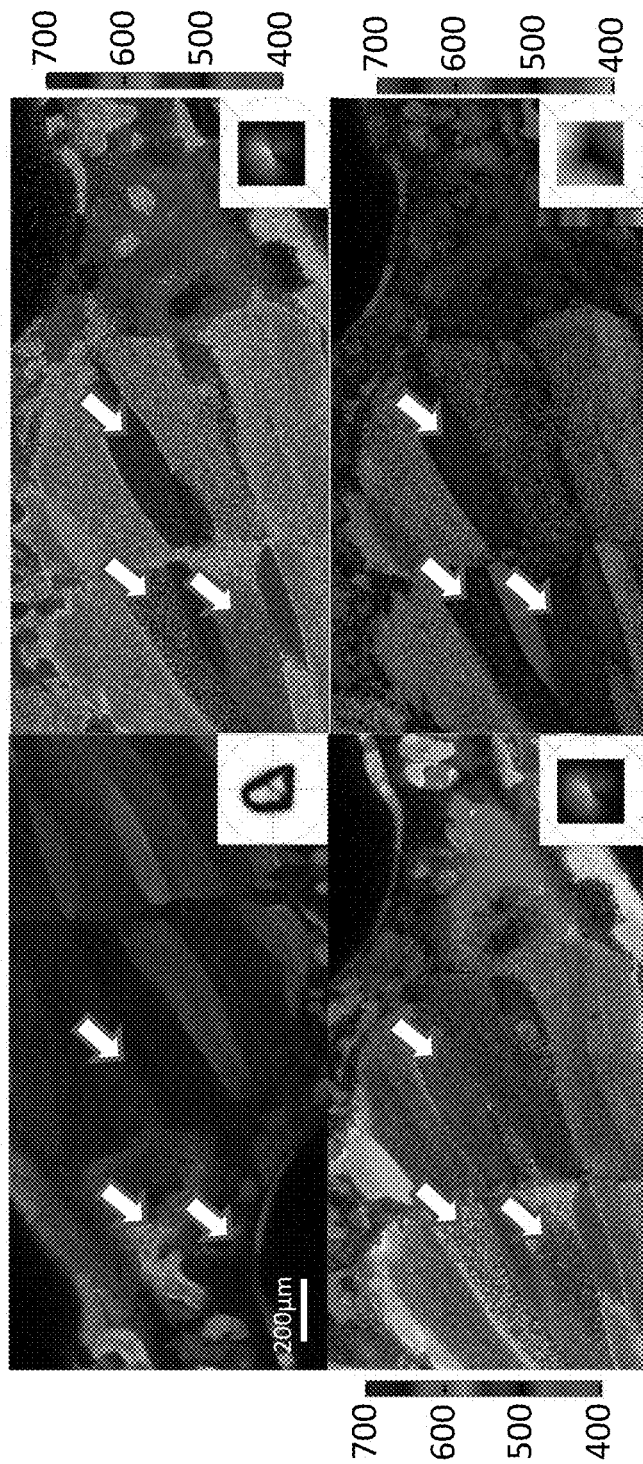

SEER and ICA Total Run Time

ICA Run Time Components

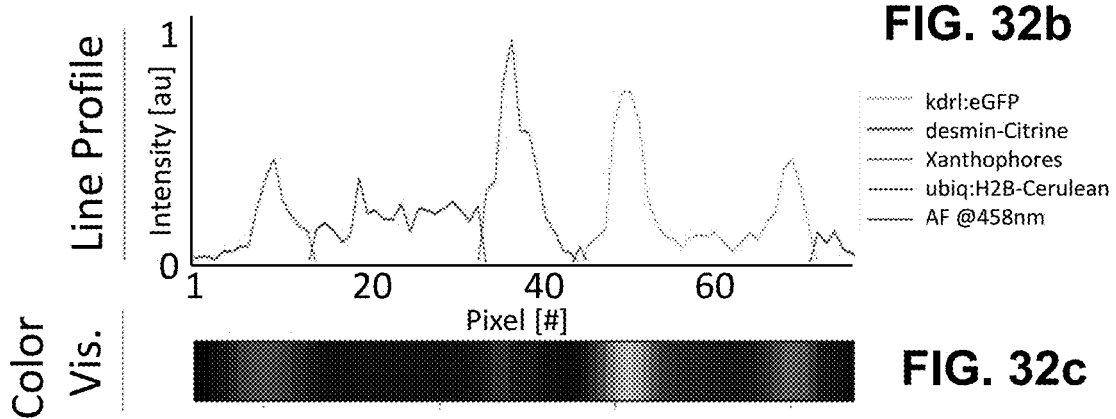
FIG. 32b
FIG. 32c
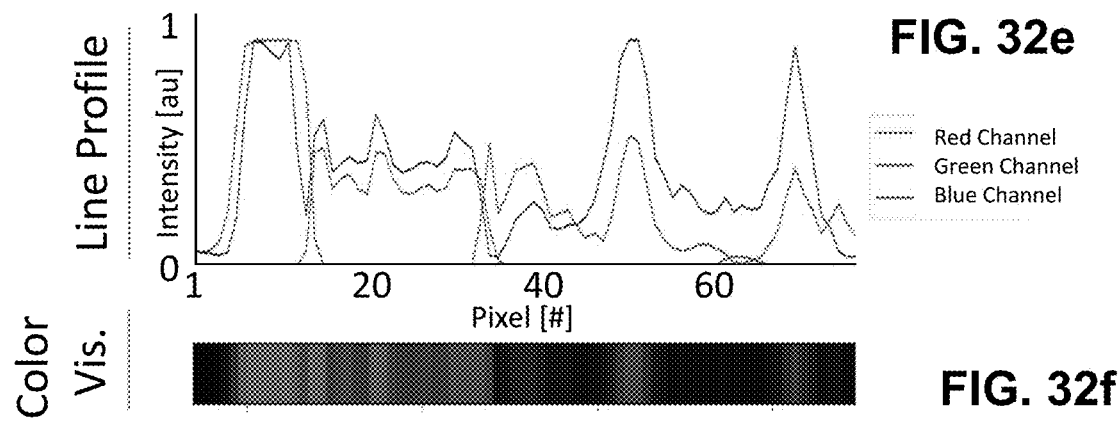
FIG. 32e
FIG. 32f
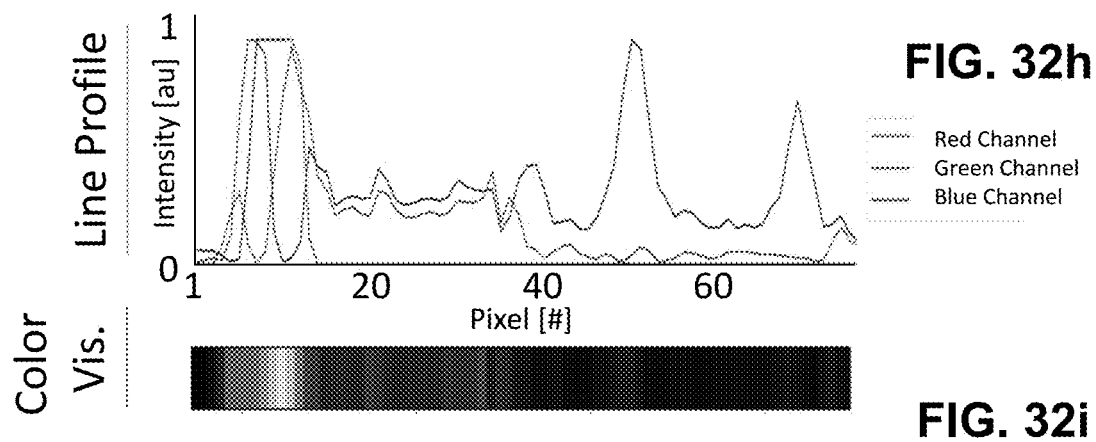
FIG. 32h
FIG. 32i

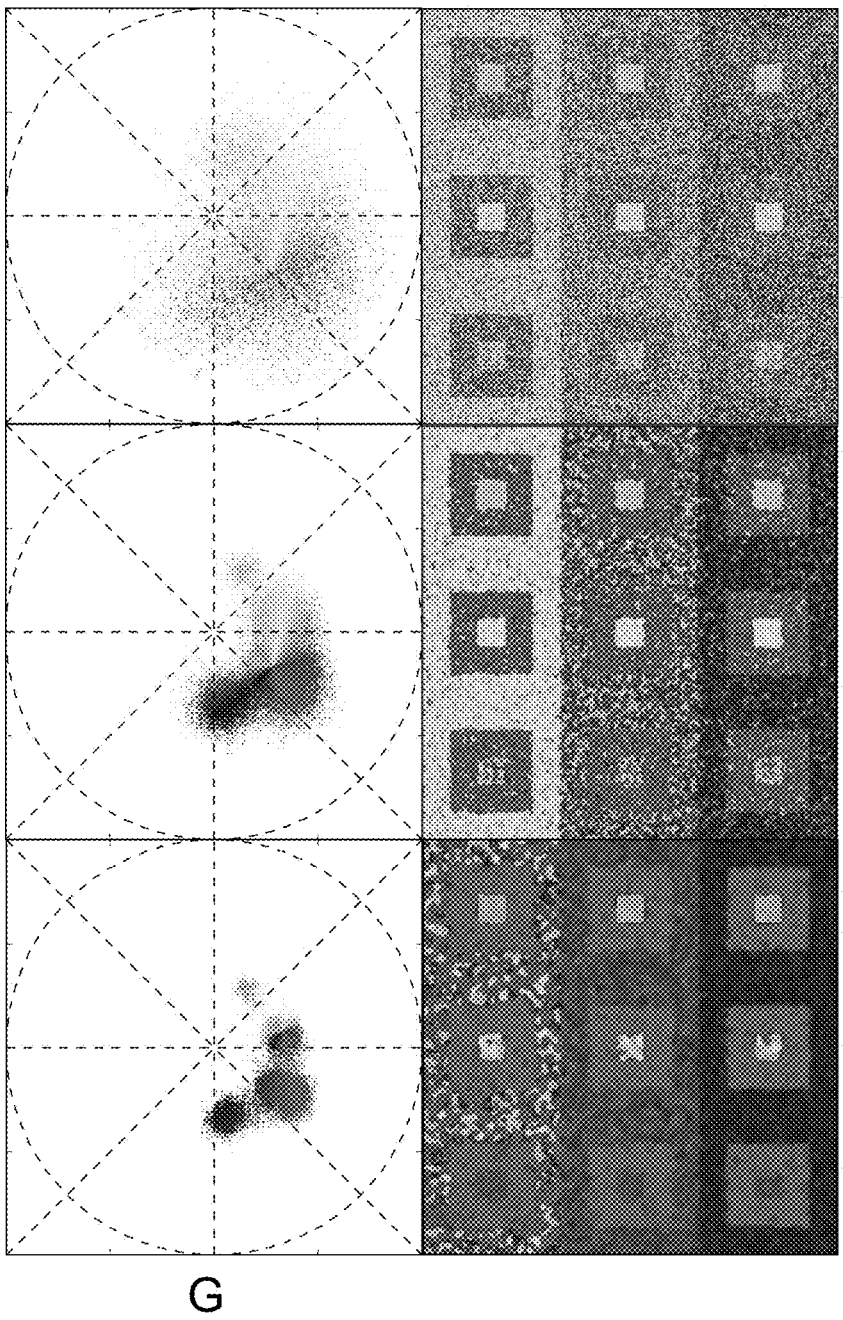

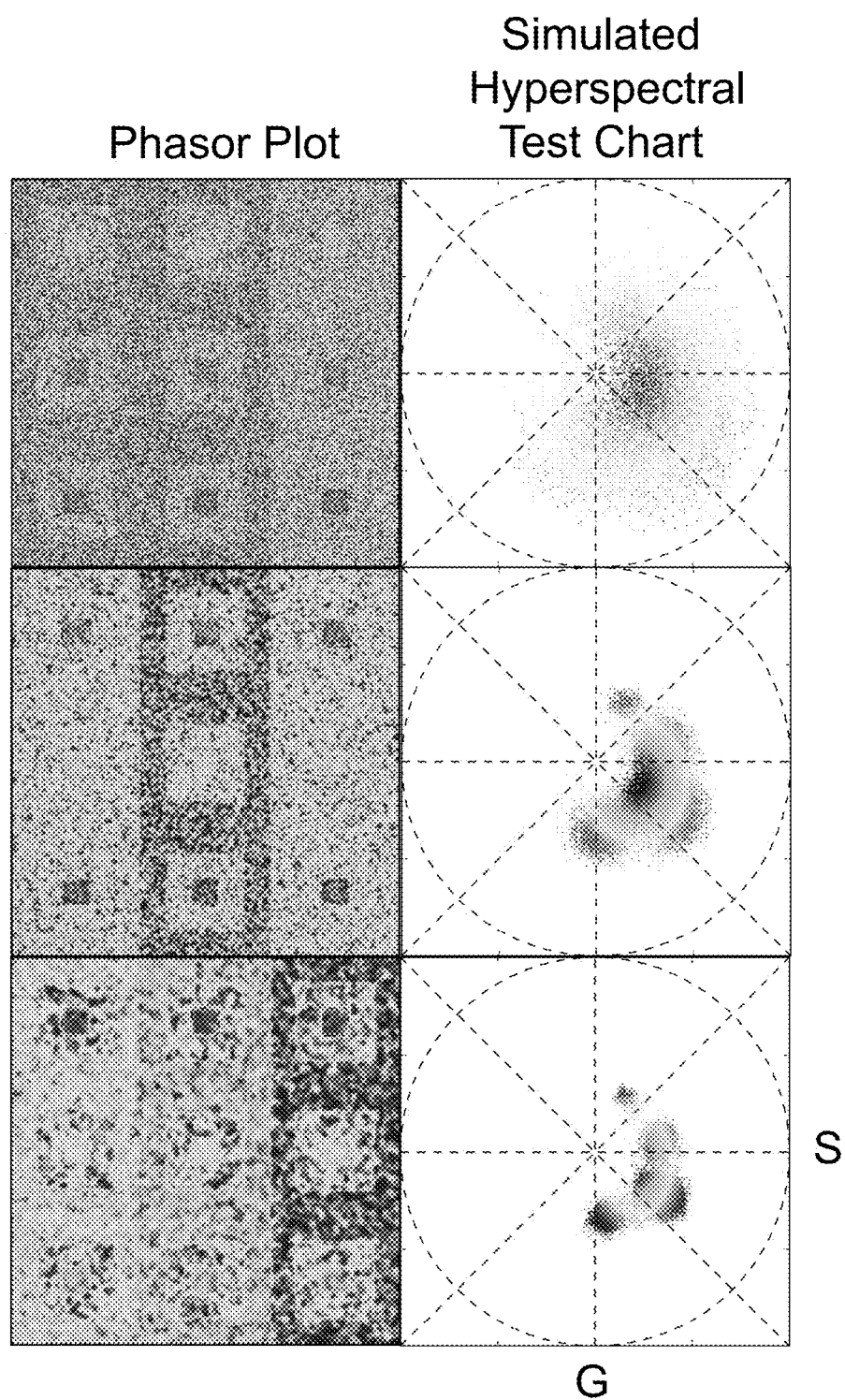

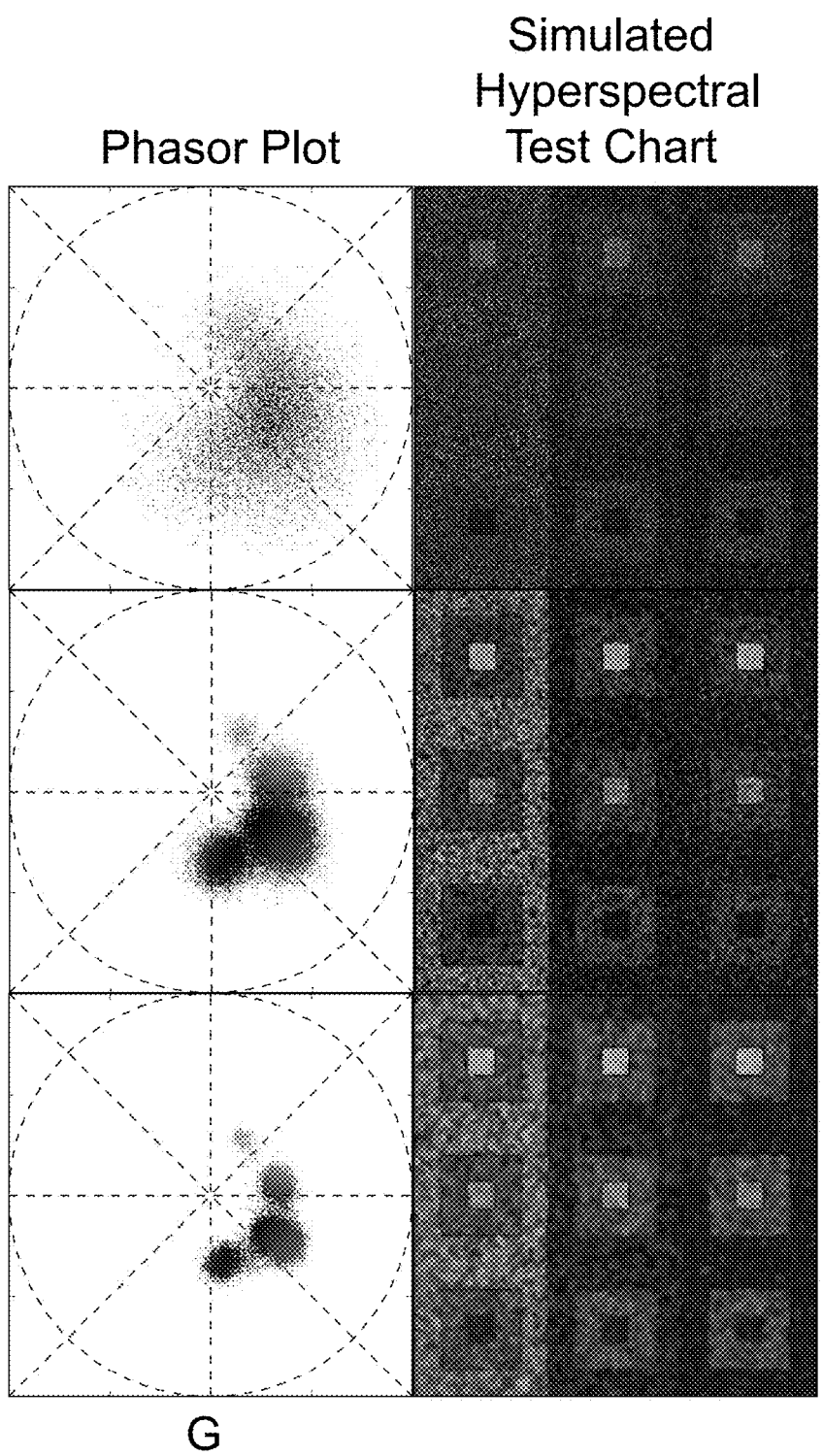
FIG. 42a No Filter
FIG. 42c 1x Filter
FIG. 42e 5x Filter
Gradient Ascent Map Scaled Mode
Phasor Plot
Simulated Hyperspectral Test Chart

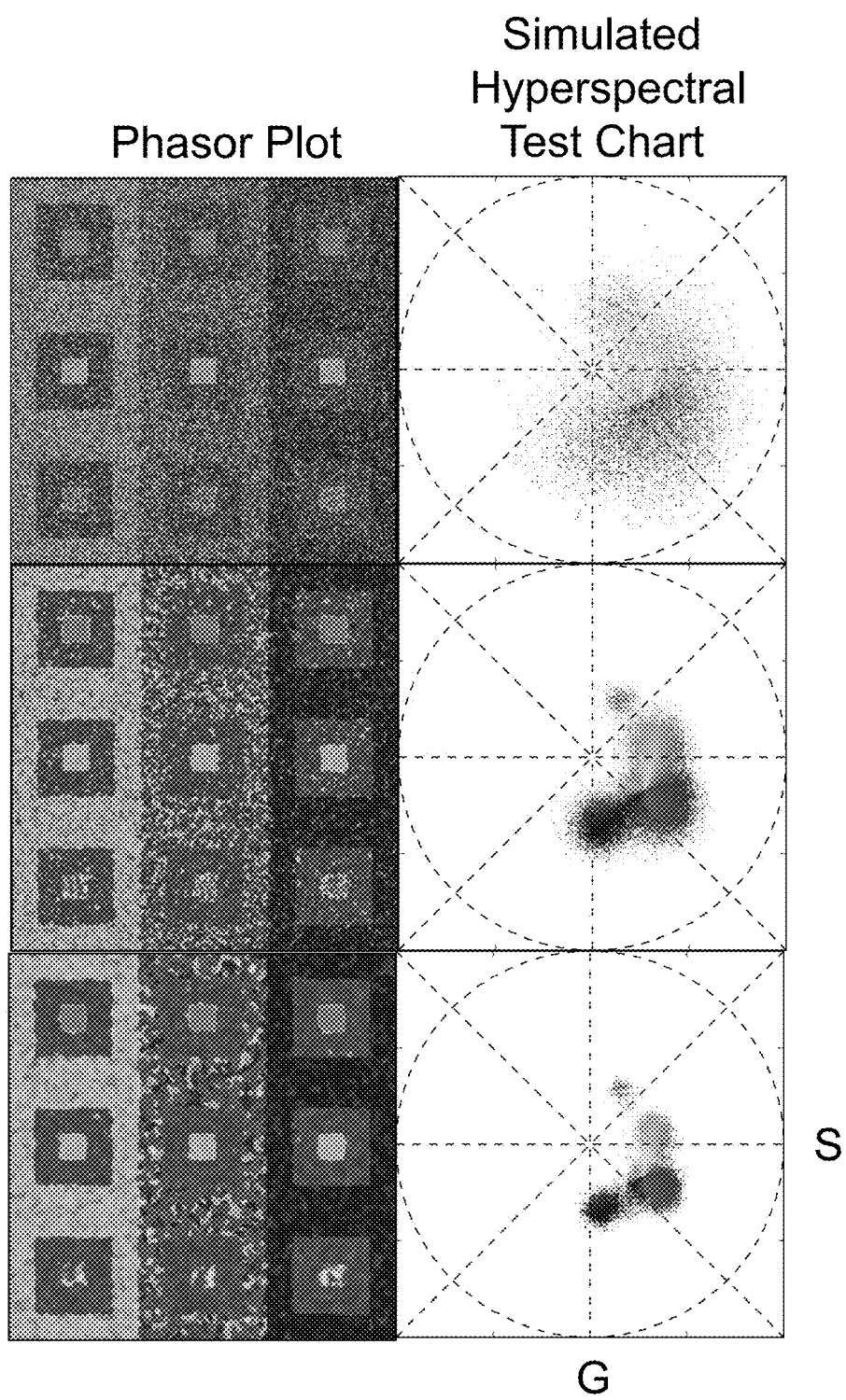

SEER RGB Mask

Avg. Spectrum

True Color 32 Ch.

Peak Wavelength Mask

Gauss Default Mask

Gauss r=.1 Mask

Gauss r=.2 Mask
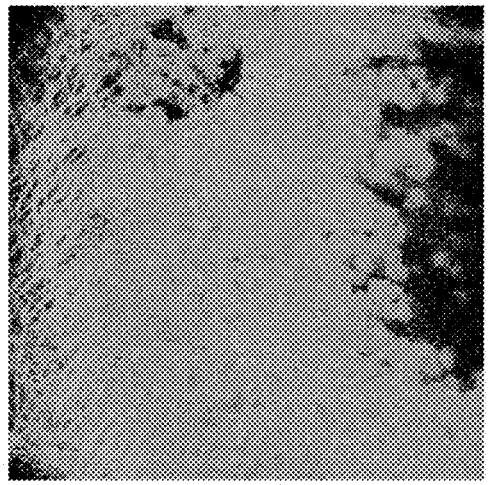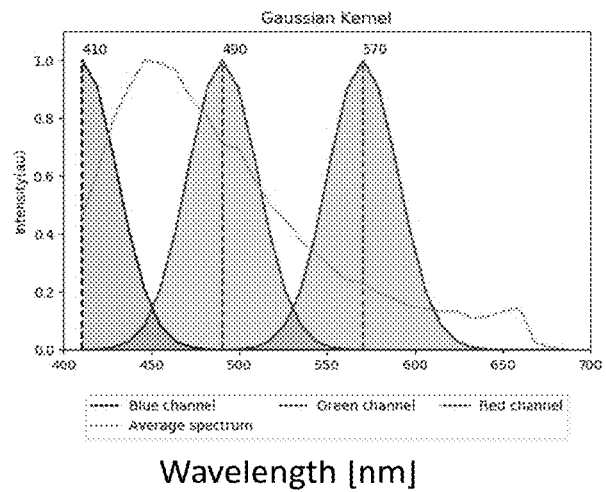
FIG. 43g
Gauss r=.3 Mask
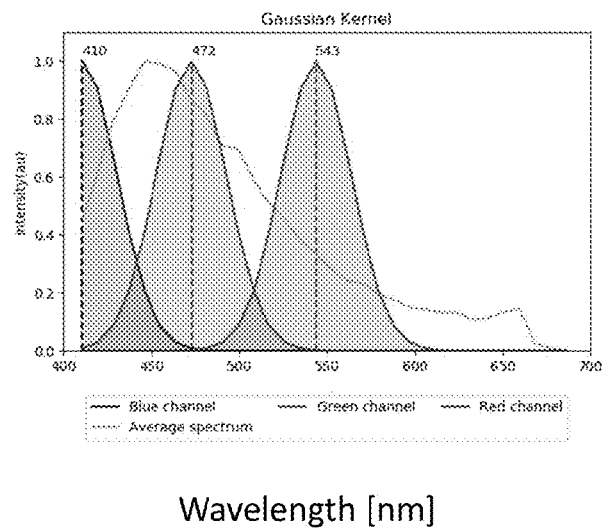
FIG. 43h

A:
(G,S) = (0.476, 0.379)
$(\tau_{phase}, \tau_{modulation}) = (1.582, 2.593)$

B:
(G,S) = (0.365, 0.410)
$(\tau_{phase}, \tau_{modulation}) = (2.235, 3.032)$

C:
$(\tau_{phase}, \tau_{modulation}) = (3.227, 3.210)$

D:
$(\tau_{phase}, \tau_{modulation}) = (0.402, 0.451)$

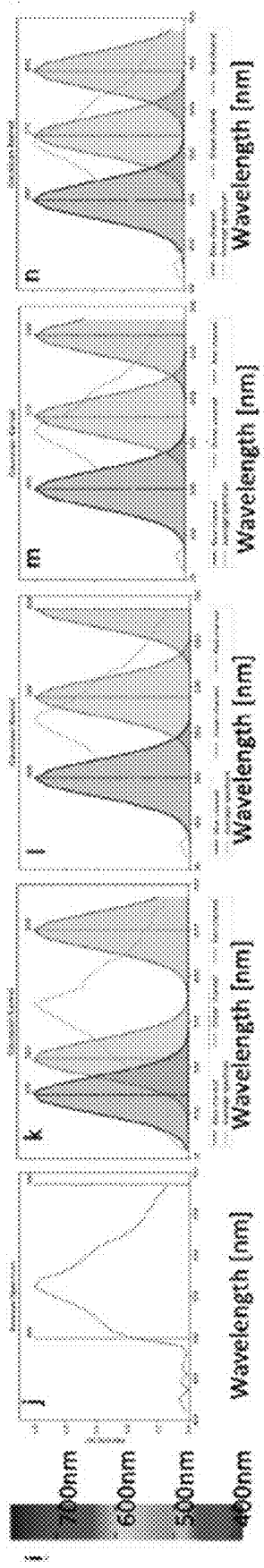

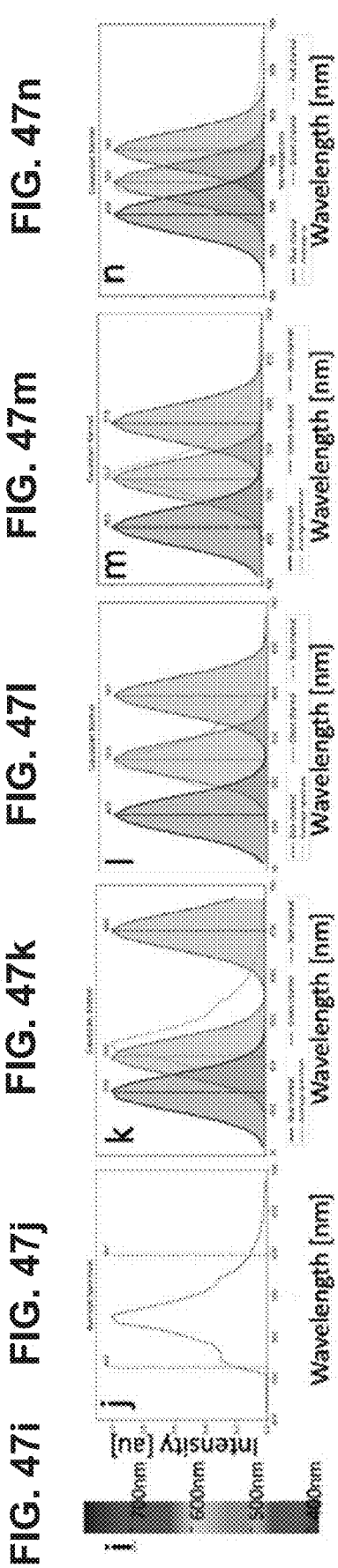

SEER RGB Mask
FIG. 49a
Avg. Spectrum
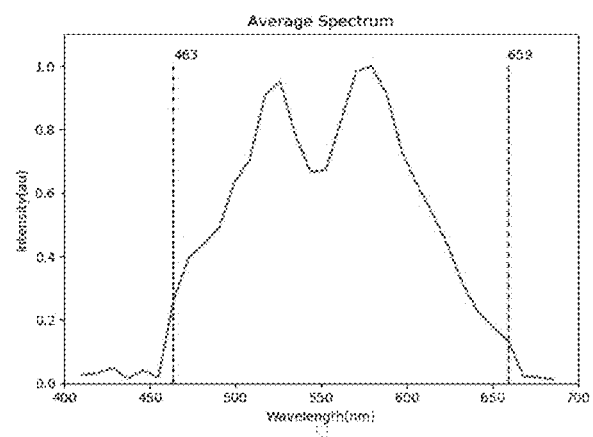
FIG. 49b
True Color 32 Ch.
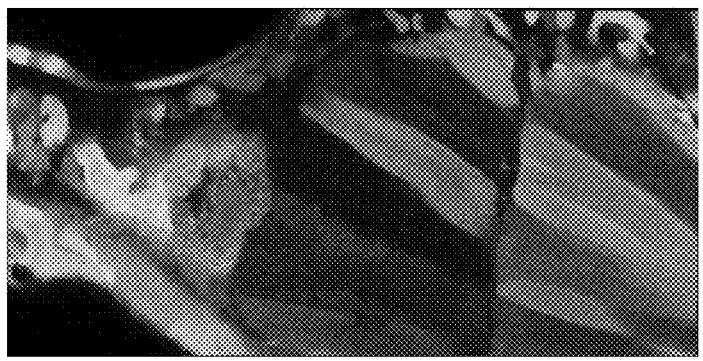
FIG. 49c
FIG. 49i
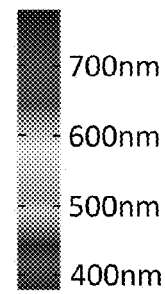
700nm
600nm
500nm
400nm
Peak Wavelength Mask
FIG. 49d

Gauss Default Mask

Gauss r=.1 Mask

Gauss r=.2 Mask

Gauss r=.3 Mask

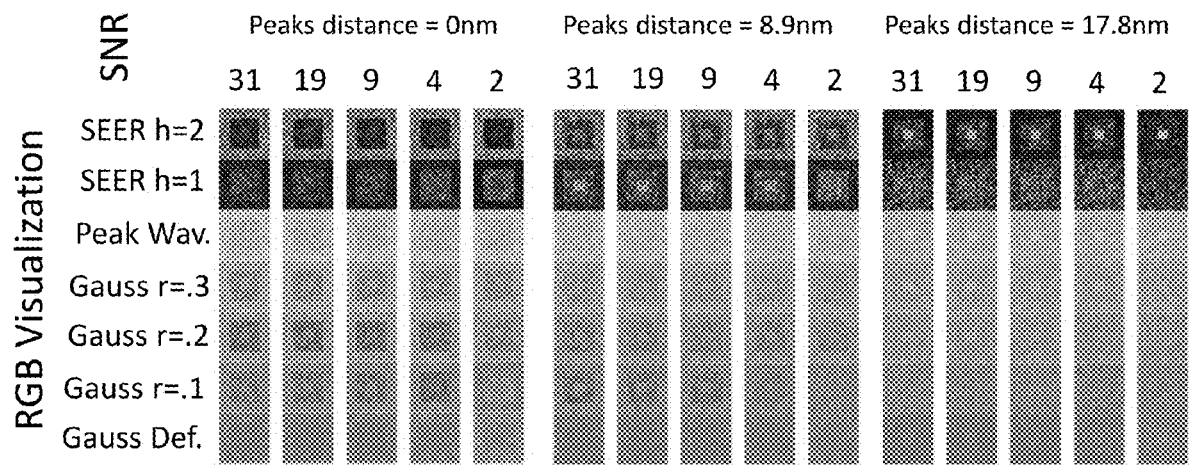
FIG. 50a   FIG. 50b   FIG. 50c
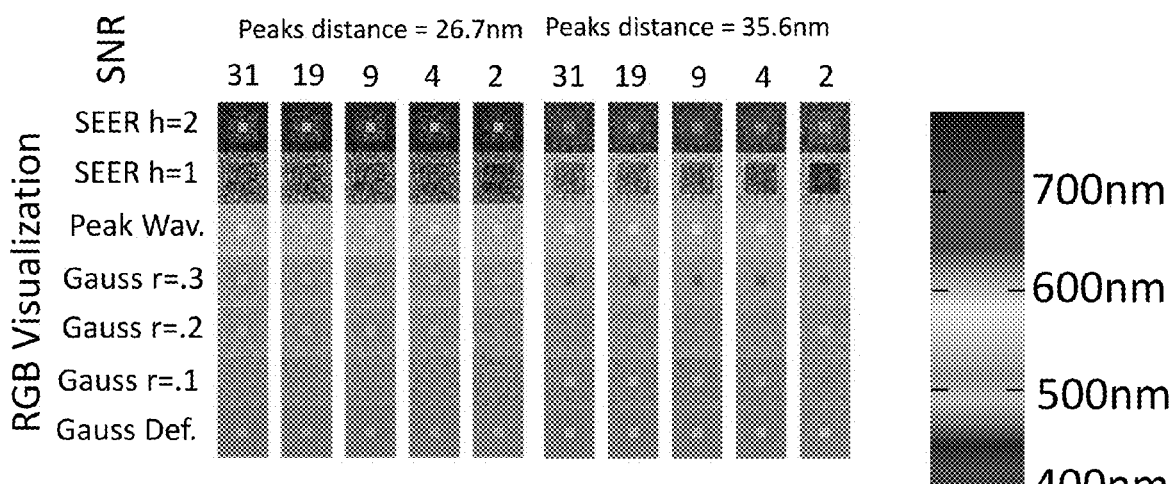
FIG. 50d   FIG. 50e
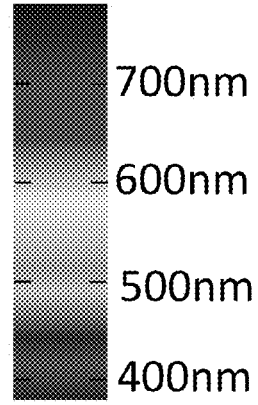
FIG. 50f

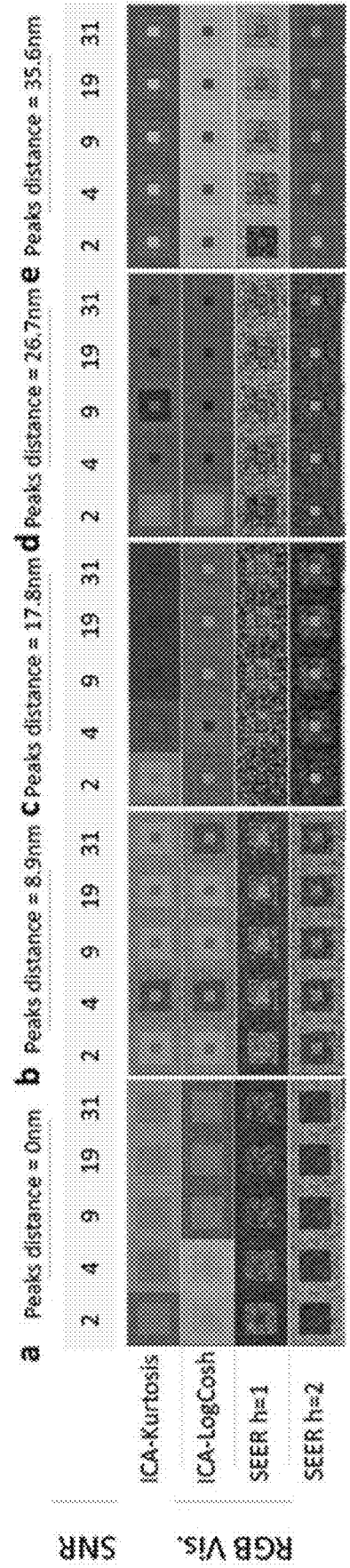

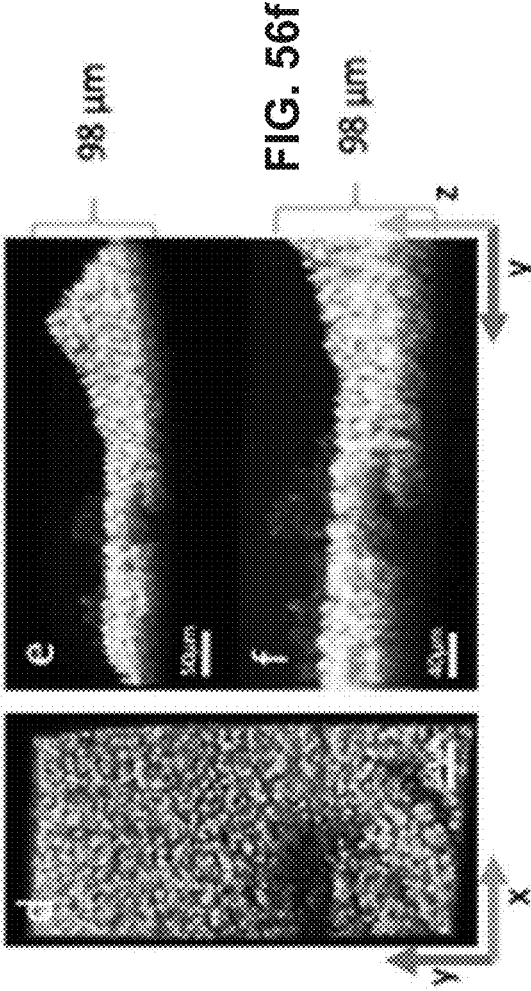
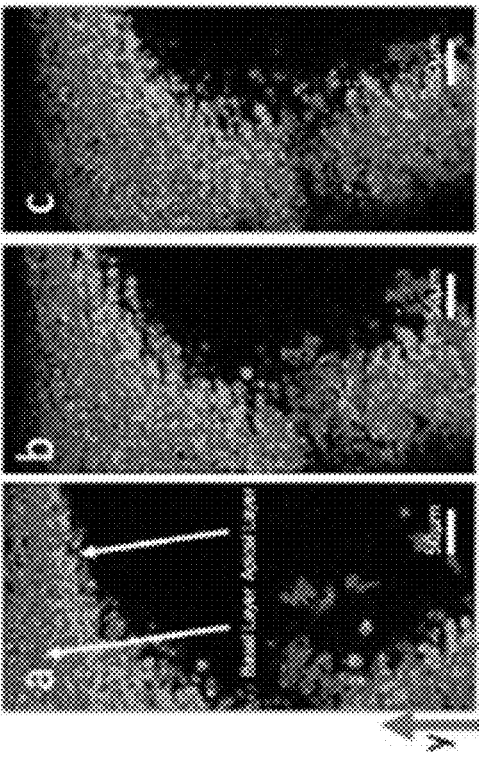
FIG. 56

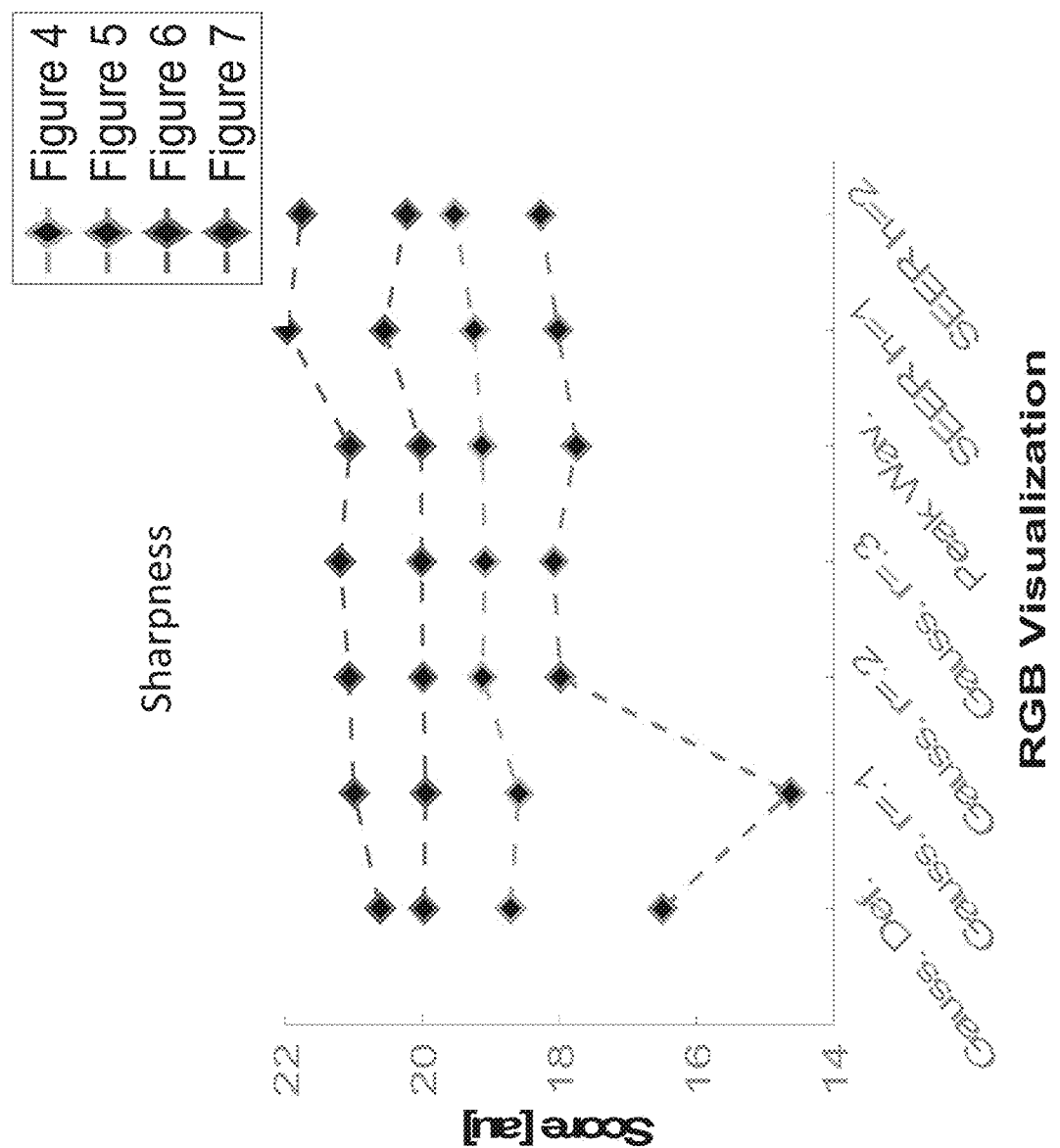

HYPERSPECTRAL IMAGING SYSTEM

CROSS-REFERENCE TO RELATED APPLICATION

This application is a U.S. National Phase Application of International Application No. PCT/US2020/016233, entitled: "A HYPERSPECTRAL IMAGING SYSTEM," filed on Jan. 31, 2020, which claims the benefit of U.S. provisional patent application 62/799,647, entitled "A Hyperspectral Imaging System," filed Jan. 31, 2019. The entire content of the complete contents of both which are incorporated herein by reference.

STATEMENT REGARDING FEDERALLY SPONSORED RESEARCH

This invention was made with government support from Department of Defense under Grant No. PR150666. The government has certain rights in the invention.

BACKGROUND

Technical Field

This disclosure relates to imaging systems. This disclosure also relates to hyperspectral imaging systems. This disclosure further relates to hyperspectral imaging systems that generate an unmixed color image of a target. This disclosure further relates to hyperspectral imaging systems that are used in diagnosing a health condition.

Description of Related Art

Multi-spectral imaging has emerged as a powerful tool in recent years to simultaneously study multiple labels in biological samples at sub-cellular, cellular and tissue levels [1,2] [all bracketed references are identified below]. Multi-spectral approaches can eliminate the contributions from sample autofluorescence, and permit high levels of signal multiplexing [3-5] since they can unambiguously identify dyes with indistinct spectra [6]. Despite these many advantages and the availability of commercial hardware with multispectral capabilities, these approaches have not been employed, as it has been challenging to simultaneously represent multi-dimensional data (x,y,z,λ,t), either for visual inspection or for quantitative analysis.

Typical approaches using linear unmixing [7] or principal component analysis [8] are computationally challenging and their performance degrades as light levels decrease [7,9]. In the case of time-lapse biological imaging, where the exciting light is usually kept low to minimize photo-toxicity, the noise results in inescapable errors in the processed images [7,9]. Complex datasets often require image segmentation or prior knowledge of the anatomy for such approaches to distinguish unique fluorescent signals in a region of interest [10].

A conventional Spectral Phasor (SP) [14-16] approach offers an efficient processing and rendering tool for multi-spectral data. SP uses Fourier transform to depict the spectrum of every pixel in an image as a point on the phasor plane (FIG. 1a), providing a density plot of the ensemble of pixels. Because SP offers single point representations on a 2D plot of even complex spectra, it simplifies both the interpretation of and interaction with multi-dimensional spectral data. Admixtures of multiple spectra can be graphically analyzed with computational ease. Thus, SP can be adapted to multispectral imaging, and has been shown to be useful for separating up to 3 colors for single time points in biological specimens [14, 15] excluding autofluorescence.

However, existing implementations of the SP approach have not been suitable for the analysis of in vivo multispectral time-lapse fluorescence imaging, especially for a high number of labels. This is primarily due to signal-to-noise (SNR) limitations related to photo-bleaching and photo-toxicity when imaging multiple fluorescent proteins with different biophysical properties [17]. Suitable excitation of multiple fluorophores requires a series of excitation wavelengths to provide good SNR images. However, increasing the number of excitation lines impacts the rate of photo-bleaching and can hamper the biological development dynamics. Furthermore, in the embryo, autofluorescence often increases with the number of excitation wavelengths. The alternative approach of using a single wavelength to excite multiple labels, while reducing the negative photo-effects and amount of autofluorescence, comes at the expense of reduced SNR.

The expanding palette of fluorescent proteins has enabled studies of spatio-temporal interaction of proteins, cells and tissues in vivo within living cells or developing embryos. However, time-lapse imaging of multiple labels remains challenging as noise, photo-bleaching and toxicity greatly compromise signal quality, and throughput can be limited by the time required to unmix spectral signals from multiple labels.

Hyperspectral fluorescence imaging is gaining popularity for it enables multiplexing of spatio-temporal dynamics across scales for molecules, cells and tissues with multiple fluorescent labels. This is made possible by adding the dimension of wavelength to the dataset. The resulting datasets are high in information density and often require lengthy analyses to separate the overlapping fluorescent spectra. Understanding and visualizing these large multi-dimensional datasets during acquisition and pre-processing can be challenging.

The hyperspectral imaging techniques may be used for medical purposes. For example, see Lu et al. "Medical Hyperspectral Imaging: a Review" *Journal of Biomedical Optics* 19(1), pages 010901-1 to 010901-23 (January 2014); Vasefi et al. "Polarization-Sensitive Hyperspectral Imaging in vivo: A Multimode Dermoscope for Skin Analysis" *Scientific Reports* 4, Article number: 4924 (2014); and Burlina et al. "Hyperspectral Imaging for Detection of Skin Related Conditions" U.S. Pat. No. 8,761,476 B2. The entire content of each of these publications is incorporated herein by reference.

Fluorescence Hyperspectral Imaging (fHSI) has become increasingly popular in recent years for the simultaneous imaging of multiple endogenous and exogenous labels in biological samples. Among the advantages of using multiple fluorophores is the capability to simultaneously follow differently labeled molecules, cells or tissues space- and time-wise. This is especially important in the field of biology where tissues, proteins and their functions within organisms are deeply intertwined, and there remain numerous unanswered questions regarding the relationship between individual components. fHSI empowers scientists with a more complete insight into biological systems with multiplexed information deriving from observation of the full spectrum for each point in the image.

Standard optical multi-channel fluorescence imaging differentiates fluorescent protein reporters through bandpass emission filters, selectively collecting signals based on wavelength. Spectral overlap between labels limits the number of fluorescent reporters that can be acquired and "background" signals are difficult to separate. fHSI overcomes these limitations, enabling separation of fluorescent proteins with overlapping spectra from the endogenous fluorescent contribution, expanding to a fluorescent palette that counts dozens of different labels with corresponding separate spectra.

The drawback of acquiring this vast multidimensional spectral information is an increase in complexity and computational time for the analysis, showing meaningful results only after lengthy calculations. To optimize experimental time, it is advantageous to perform an informed visualization of the spectral data during acquisition, especially for lengthy time-lapse recordings, and prior to performing analysis. Such preprocessing visualization allows scientists to evaluate image collection parameters within the experimental pipeline as well as to choose the most appropriate processing method. However, the challenge is to rapidly visualize subtle spectral differences with a set of three colors, compatible with displays and human eyes, while minimizing loss of information. As the most common color model for displays is RGB, where red, green and blue are combined to reproduce a broad array of colors, hyper- or multi-spectral datasets are typically reduced to three channels to be visualized. Thus, spectral information compression becomes the critical step for proper display of image information.

Dimensional reduction strategies are commonly used to represent multi-dimensional fHSI data. One strategy is to construct fixed spectral envelopes from the first three components produced by principal component analysis (PCA) or independent component analysis (ICA), converting a hyperspectral image to a three-band visualization. The main advantage of spectrally weighted envelopes is that it can preserve the human-eye perception of the hyperspectral images. Each spectrum is displayed with the most similar hue and saturation for tri-stimulus displays in order for the human eye to easily recognize details in the image. Another popular visualization technique is pixel-based image fusion, which preserves the spectral pairwise distances for the fused image in comparison to the input data. It selects the weights by evaluating the saliency of the measured pixel with respect to its relative spatial neighborhood distance. These weights can be further optimized by implementing widely applied mathematical techniques, such as Bayesian inference, by using a filters-bank for feature extraction or by noise smoothing.

A drawback to approaches such as Singular Value Decomposition to compute PCA bases and coefficients or generating the best fusion weights is that it can take numerous iterations for convergence. Considering that fHSI datasets easily exceed GigaBytes range and many cross the TeraBytes threshold, such calculations will be both computationally and time demanding. Furthermore, most visualization approaches have focused more on interpreting spectra as RGB colors and not on exploiting the full characterization that can be extracted from the spectral data.

RELATED ART REFERENCES

The following publications are related art for the background of this disclosure. One digit or two digit numbers in the box brackets before each reference, correspond to the numbers in the box brackets used in the other parts of this disclosure.

[1] Garini, Y., Young, I. T. and McNamara, G. Spectral imaging: principles and applications. Cytometry A 69: 735-747 (2006).
[2] Dickinson, M. E., Simbuerger, E., Zimmermann, B., Waters, C. W. and Fraser, S. E. Multiphoton excitation spectra in biological samples. Journal of Biomedical Optics 8: 329-338 (2003).
[3] Dickinson, M. E., Bearman, G., Tille, S., Lansford, R. & Fraser, S. E. Multi-spectral imaging and linear unmixing add a whole new dimension to laser scanning fluorescence microscopy. Biotechniques 31, 1272-1278 (2001).
[4] Levenson, R. M. and Mansfield, J. R. Multispectral imaging in biology and medicine: Slices of life. Cytometry A 69: 748-758 (2006).
[5] Jahr, W., Schmid, B., Schmied, C., Fahrbach, F. and Huisken, J. Hyperspectral light sheet microscopy. Nat Commun, 6, (2015)
[6] Lansford, R., Bearman, G. and Fraser, S. E. Resolution of multiple green fluorescent protein color variants and dyes using two-photon microscopy and imaging spectroscopy. Journal of Biomedical Optics 6: 311-318 (2001).
[7] Zimmermann, T. Spectral Imaging and Linear Unmixing in Light Microscopy. Adv Biochem Engin/Biotechnol (2005) 95: 245-265
[8] Jolliffe, Ian. Principal component analysis. John Wiley & Sons, Ltd, (2002).
[9] Gong, P. and Zhang, A. Noise Effect on Linear Spectral Unmixing. Geographic Information Sciences 5(1), (1999)
[10] Mukamel, E. A., Nimmerjahn, A., and Schnitzer M. J.; Automated Analysis of Cellular Signals from Large-Scale Calcium Imaging Data; Neuron, 63(6), 747-760
[11] Clayton, A. H., Hanley, Q. S. & Verveer, P. J. Graphical representation and multicomponent analysis of single-frequency fluorescence lifetime imaging microscopy data. J. Microsc. 213, 1-5 (2004)
[12] Redford, G. I. & Clegg, R. M. Polar plot representation for frequency-domain analysis of fluorescence lifetimes. J. Fluoresc. 15, 805-815 (2005).
[13] Digman M A, Caiolfa V R, Zamai M and Gratton E. The phasor approach to fluorescence lifetime imaging analysis. Biophys. J. 94 pp. 14-16 (2008)
[14] Fereidouni F., Bader A. N. and Gerritsen H. C. Spectral phasor analysis allows rapid and reliable unmixing of fluorescence microscopy spectral images. Opt. Express 20 12729-41 (2012)
[15] Andrews L. M., Jones M. R., Digman M. A., Gratton E. Spectral phasor analysis of Pyronin Y labeled RNA microenvironments in living cells. Biomed. Op. Express 4 (1) 171-177 (2013)
[16] Cutrale F., Salih A. and Gratton E. Spectral phasor approach for fingerprinting of photo-activatable fluorescent proteins Dronpa, Kaede and KikGR. Methods Appl. Fluoresc. 1 (3) (2013) 035001
[17] Cranfill P. J., Sell B. R., Baird M. A., Allen J. R., Lavagnino Z., de Gruiter H. M., Kremers G., Davidson M. W., Ustione A., Piston D. W., Quantitative assessment of fluorescent proteins, Nature Methods 13, 557-562 (2016).
[18] Chen, H., Gratton, E., & Digman, M. A. Spectral Properties and Dynamics of Gold Nanorods Revealed by EMCCD-Based Spectral Phasor Method. Microscopy Research and Technique, 78(4), 283-293 (2015)
[19] Vermot, J., Fraser, S. E., Liebling, M. "Fast fluorescence microscopy for imaging the dynamics of embryonic development," HFSP Journal, vol 2, pp. 143-155, (2008)
[20] Dalal, R. B., Digman, M. A., Horwitz, A. F., Vetri, V., Gratton, E., Determination of particle number and bright-

[20] ness using a laser scanning confocal microscope operating in the analog mode, *Microsc. Res. Tech.,* 71(1) pp. 69-81 (2008)

[21] Fereidouni, F., Reitsma, K., Gerritsen, H. C. High speed multispectral fluorescence lifetime imaging, *Optics Express,* 21(10), pp. 11769-11782 (2013)

[22] Hamamatsu Photonics K. K. Photomultiplier Technical Handbook. (1994) Hamamatsu Photonics K. K

[23] Trinh, L. A. et al., "A versatile gene trap to visualize and interrogate the function of the vertebrate proteome," *Genes & development,* 25(21), 2306-20(2011).

[24] Jin S. W., Beis D., Mitchell T., Chen J. N., Stainier D. Y. Cellular and molecular analyses of vascular tube and lumen formation in zebrafish. *Development* 132, 5199-5209 (2005)

[25] Livet, J., Weissman, T. A., Kang, H., Draft, R. W., Lu, J., Bennis, R. A., Sanes, J. R., Lichtman J. W. Transgenic strategies for combinatorial expression of fluorescent proteins in the nervous system. *Nature,* 450(7166), 56-62 (2007)

[26] Lichtman, J. W., Livet, J., & Sanes, J. R. A technicolour approach to the connectome. *Nature Reviews Neuroscience,* 9(6), 417-422 (2008).

[27] Pan, Y. A., Freundlich, T., Weissman, T. A., Schoppik, D., Wang, X. C., Zimmerman, S., Ciruna, B., Sanes, J. R., Lichtman, J. W., Schier A. F. Zebrabow: multispectral cell labeling for cell tracing and lineage analysis in zebrafish. *Development,* 140(13), 2835-2846. (2013)

[28] Westerfield M. The Zebrafish Book. (1994) Eugene, OR: University Oregon Press.

[29] Megason, S. G. In toto imaging of embryogenesis with confocal time-lapse microscopy. *Methods in molecular biology,* 546 pp. 317-32 (2009).

[30] Sinclair, M. B., Haaland, D. M., Timlin, J. A. & Jones, H. D. T. Hyperspectral confocal microscope. *Appl. Opt.* 45, 6283 (2006).

[31] Valm, A. M. et al. Applying systems-level spectral imaging and analysis to reveal the organelle interactome. *Nature* 546, 162-167 (2017).

[32] Hiraoka, Y., Shimi, T. & Haraguchi, T. Multispectral Imaging Fluorescence Microscopy for Living Cells. *Cell Struct. Funct.* 27, 367-374 (2002).

[33] Jacobson, N. P. & Gupta, M. R. Design goals and solutions for display of hyperspectral images. in Proceedings—International Conference on Image Processing, ICIP 2, 622-625 (2005).

[34] Hotelling, H. Analysis of a complex of statistical variables into principal components. *J. Educ. Psychol.* 24, 417-441 (1933).

[35] Abdi, H. & Williams, L. J. Principal component analysis. *Wiley Interdisciplinary Reviews: Computational Statistics* 2, 433-459 (2010).

[36] Tyo, J. S., Konsolakis, A., Diersen, D. I. & Olsen, R. C. Principal-components-based display strategy for spectral imagery. *IEEE Trans. Geosci. Remote Sens.* 41, 708-718 (2003).

[37] Wilson, T. A. Perceptual-based image fusion for hyperspectral data. *IEEE Trans. Geosci. Remote Sens.* 35, 1007-1017 (1997).

[38] Long, Y., Li, H. C., Celik, T., Longbotham, N. & Emery, W. J. Pairwise-distance-analysis-driven dimensionality reduction model with double mappings for hyperspectral image visualization. *Remote Sens.* 7, 7785-7808 (2015).

[39] Kotwal, K. & Chaudhuri, S. A Bayesian approach to visualization-oriented hyperspectral image fusion. *Inf. Fusion* 14, 349-360 (2013).

[40] Kotwal, K. & Chaudhuri, S. Visualization of Hyperspectral Images Using Bilateral Filtering. *IEEE Trans. Geosci. Remote Sens.* 48, 2308-2316 (2010).

[41] Zhao, W. & Du, S. Spectral-Spatial Feature Extraction for Hyperspectral Image Classification: A Dimension Reduction and Deep Learning Approach. *IEEE Trans. Geosci. Remote Sens.* 54, 4544-4554 (2016).

[42] Zhang, Y., De Backer, S. & Scheunders, P. Noise-resistant wavelet-based Bayesian fusion of multispectral and hyperspectral images. *IEEE Trans. Geosci. Remote Sens.* 47, 3834-3843 (2009).

[43] A, R. SVD Based Image Processing Applications: State of The Art, Contributions and Research Challenges. *Int. J. Adv. Comput. Sci. Appl.* 3, 26-34 (2012).

[44] Vergeldt, F. J. et al. Multi-component quantitative magnetic resonance imaging by phasor representation. *Sci. Rep.* 7, (2017).

[45] Lanzanò, L. et al. Encoding and decoding spatiotemporal information for super-resolution microscopy. *Nat. Commun.* 6, (2015).

[46] Cutrale, F. et al. Hyperspectral phasor analysis enables multiplexed 5D in vivo imaging. *Nat. Methods* 14, 149-152 (2017).

[47] Radaelli, F. et al. µmAPPS: A novel phasor approach to second harmonic analysis for in vitro-in vivo investigation of collagen microstructure. *Sci. Rep.* 7, (2017).

[48] Scipioni, L., Gratton, E., Diaspro, A. & Lanzanò, L. Phasor Analysis of Local ICS Detects Heterogeneity in Size and Number of Intracellular Vesicles. *Biophys. J.* (2016). doi:10.1016/j.bpj.2016.06.029

[49] Sarmento, M. J. et al. Exploiting the tunability of stimulated emission depletion microscopy for super-resolution imaging of nuclear structures. *Nat. Commun.* (2018). doi:10.1038/s41467-018-05963-2

[50] Scipioni, L., Di Bona, M., Vicidomini, G., Diaspro, A. & Lanzanò, L. Local raster image correlation spectroscopy generates high-resolution intracellular diffusion maps. *Commun. Biol.* (2018). doi:10.1038/s42003-017-0010-6

[51] Ranjit, S., Malacrida, L., Jameson, D. M. & Gratton, E. Fit-free analysis of fluorescence lifetime imaging data using the phasor approach. *Nat. Protoc.* 13, 1979-2004 (2018).

[52] Zipfel, W. R. et al. Live tissue intrinsic emission microscopy using multiphoton-excited native fluorescence and second harmonic generation. *Proc. Natl. Acad. Sci.* 100, 7075-7080 (2003).

[53] Rock, J. R., Randell, S. H. & Hogan, B. L. M. Airway basal stem cells: a perspective on their roles in epithelial homeostasis and remodeling. *Dis. Model. Mech.* 3, 545-556 (2010).

[54] Rock, J. R. et al. Basal cells as stem cells of the mouse trachea and human airway epithelium. *Proc. Natl. Acad. Sci.* (2009). doi:10.1073/pnas.0906850106

[55] Bird, D. K. et al. Metabolic mapping of MCF10A human breast cells via multiphoton fluorescence lifetime imaging of the coenzyme NADH. *Cancer Res.* 65, 8766-8773 (2005).

[56] Lakowicz, J. R., Szmacinski, H., Nowaczyk, K. & Johnson, M. L. Fluorescence lifetime imaging of free and protein-bound NADH. *Proc. Natl. Acad. Sci.* (1992). doi:10.1073/pnas.89.4.1271

[57] Skala, M. C. et al. In vivo multiphoton microscopy of NADH and FAD redox states, fluorescence lifetimes, and cellular morphology in precancerous epithelia. *Proc. Natl. Acad. Sci.* (2007). doi:10.1073/pnas.0708425104

[58] Sharick, J. T. et al. Protein-bound NAD(P)H Lifetime is Sensitive to Multiple Fates of Glucose Carbon. *Sci. Rep.* (2018). doi:10.1038/s41598-018-23691-x

[59] Stringari, C. et al. Phasor approach to fluorescence lifetime microscopy distinguishes different metabolic states of germ cells in a live tissue. *Proc. Natl. Acad. Sci.* 108, 13582-13587 (2011).

[60] Stringari, C. et al. Multicolor two-photon imaging of endogenous fluorophores in living tissues by wavelength mixing. *Sci. Rep.* (2017). doi:10.1038/s41598-017-03359-8

[61] Sun, Y. et al. Endoscopic fluorescence lifetime imaging for in vivo intraoperative diagnosis of oral carcinoma. in *Microscopy and Microanalysis* (2013). doi:10.1017/S1431927613001530

[62] Ghukasyan, V. V. & Kao, F. J. Monitoring cellular metabolism with fluorescence lifetime of reduced nicotinamide adenine dinucleotide. *J. Phys. Chem. C* (2009). doi:10.1021/jp810931u

[63] Walsh, A. J. et al. Quantitative optical imaging of primary tumor organoid metabolism predicts drug response in breast cancer. *Cancer Res.* (2014). doi:10.1158/0008-5472.CAN-14-0663

[64] Conklin, M. W., Provenzano, P. P., Eliceiri, K. W., Sullivan, R. & Keely, P. J. Fluorescence lifetime imaging of endogenous fluorophores in histopathology sections reveals differences between normal and tumor epithelium in carcinoma in situ of the breast. *Cell Biochem. Biophys.* (2009). doi:10.1007/s12013-009-9046-7

[65] Browne, A. W. et al. Structural and functional characterization of human stem-cell-derived retinal organoids by live imaging. *Investig. Ophthalmol. Vis. Sci.* (2017). doi:10.1167/iovs.16-20796

[66] Weissman, T. A. & Pan, Y. A. Brainbow: New resources and emerging biological applications for multicolor genetic labeling and analysis. Genetics 199, 293-306 (2015).

[67] Pan, Y. A., Livet, J., Sanes, J. R., Lichtman, J. W. & Schier, A. F. Multicolor brainbow imaging in Zebrafish. Cold Spring Harb. Protoc. 6, (2011).

[68] Raj, B. et al. Simultaneous single-cell profiling of lineages and cell types in the vertebrate brain. *Nat. Biotechnol.* 36, 442-450 (2018).

[69] Mahou, P. et al. Multicolor two-photon tissue imaging by wavelength mixing. *Nat. Methods* 9, 815-818 (2012).

[70] Loulier, K. et al. Multiplex Cell and Lineage Tracking with Combinatorial Labels. *Neuron* 81, 505-520 (2014).

[71] North, T. E. & Goessling, W. Haematopoietic stem cells show their true colours. *Nature Cell Biology* 19, 10-12 (2017).

[72] Chen, C. H. et al. Multicolor Cell Barcoding Technology for Long-Term Surveillance of Epithelial Regeneration in Zebrafish. *Dev. Cell* 36, 668-680 (2016).

[73] Vert, J., Tsuda, K. & Schölkopf, B. A primer on kernel methods. Kernel Methods Comput. Biol. 35-70 (2004). doi:10.1017/CBO9781107415324.004

[74] Bruton, D. {RGB} Values for visible wavelengths. (1996). Available at: http://www.physics.sfasu.edu/astro/color/spectra.html.

[75] Westerfield, M. The Zebrafish Book. *A Guide for the Laboratory Use of Zebrafish (Danio rerio)*, 4th Edition. book (2000).

[76] Huss, D. et al. A transgenic quail model that enables dynamic imaging of amniote embryogenesis. *Development* 142, 2850-2859 (2015).

[77] Holst, J., Vignali, K. M., Burton, A. R. & Vignali, D. A. A. Rapid analysis of T-cell selection in vivo using T cell-receptor retrogenic mice. *Nat. Methods* 3, 191-197 (2006).

[78] Kwan, K. M. et al. The Tol2kit: A multisite gateway-based construction Kit for Tol2 transposon transgenesis constructs. *Dev. Dyn.* 236, 3088-3099 (2007).

[79] Kawakami, K. et al. A transposon-mediated gene trap approach identifies developmentally regulated genes in zebrafish. *Dev. Cell* 7, 133-144 (2004).

[80] Urasaki, A., Morvan, G. & Kawakami, K. Functional dissection of the Tol2 transposable element identified the minimal cis-sequence and a highly repetitive sequence in the subterminal region essential for transposition. Genetics 174, 639-649 (2006).

[81] White, R. M. et al. Transparent Adult Zebrafish as a Tool for In Vivo Transplantation Analysis. *Cell Stem Cell* 2, 183-189 (2008).

[82] Arnesano, C., Santoro, Y. & Gratton, E. Digital parallel frequency-domain spectroscopy for tissue imaging. *J. Biomed. Opt.* 17, 0960141 (2012).

SUMMARY

An imaging system for denoising and/or color unmixing multiple overlapping spectra in a low signal-to-noise regime with a fast analysis time is disclosed. This imaging system may be a hyperspectral imaging system. A system may carry out Hyper-Spectral Phasors (HySP) calculations to effectively analyze hyper-spectral time-lapse data. For example, this system may carry out Hyper-Spectral Phasors (HySP) calculations to effectively analyze five-dimensional (5D) hyper-spectral time-lapse data. Advantages of this imaging system may include: (a) fast computational speed, (b) the ease of phasor analysis, and (c) a denoising algorithm to obtain minimally-acceptable signal-to-noise ratio (SNR). This imaging system may also generate an unmixed color image of a target. This imaging system may be used in diagnosis of a health condition.

The hyperspectral imaging system may include an optics system, an image forming system, or a combination thereof. For example, the hyperspectral imaging system may include an optics system and an image forming system. For example, the hyperspectral imaging system may include an image forming system.

The optics system may include at least one optical component. Examples of the at least one optical component are a detector ("optical detector"), a detector array ("optical detector array"), a source to illuminate the target ("illumination source"), a first optical lens, a second optical lens, a dispersive optic system, a dichroic mirror/beam splitter, a first optical filtering system, a second optical filtering system, or a combination thereof. For example, the at least one optical detector may include at least one optical detector. For example, the at least one optical detector may include at least one optical detector and at least one illumination source. A first optical filtering system may be placed between the target and the at least one optical detector. A second optical filtering system may be placed between the first optical filtering system and the at least one optical detector.

The optical system may include an optical microscope. The components of the optical system can form this optical microscope. Examples of the optical microscope may be a confocal fluorescence microscope, a two-photon fluorescence microscope, or a combination thereof.

The at least one optical detector may have a configuration that detects electromagnetic radiation absorbed, transmitted, refracted, reflected, and/or emitted ("target radiation") by at least one physical point on the target. The target radiation may include at least one wave ("target wave"). The target radiation may include at least two target waves. Each target wave may have an intensity and a different wavelength. The at least one optical detector may have a configuration that detects the intensity and the wavelength of each target wave. The at least one optical detector may have a configuration that transmits the detected intensity and wavelength of each target wave to the image forming system. The at least one optical detector may include a photomultiplier tube, a photomultiplier tube array, a digital camera, a hyperspectral camera, an electron multiplying charge coupled device, a Sci-CMOS, a digital camera, or a combination thereof.

The target radiation may include an electromagnetic radiation emitted by the target. The electromagnetic radiation emitted by the target may include luminescence, thermal radiation, or a combination thereof. The luminescence may include fluorescence, phosphorescence, or a combination thereof. For example, the electromagnetic radiation emitted by the target may include fluorescence, phosphorescence, thermal radiation, or a combination thereof.

The at least one optical detector may detect the electromagnetic radiation emitted by the target at a wavelength in the range of 300 nm to 800 nm. The at least one optical detector may detect the electromagnetic radiation emitted by the target at a wavelength in the range of 300 nm to 1,300 nm.

The hyperspectral imaging system may also form a detected image of the target using the target radiation comprising at least four wavelengths, wherein the at least four wavelengths with detected intensities form a spectrum. Color resolution of the image may thereby be increased.

The at least one illumination source may generate an electromagnetic radiation ("illumination source radiation"). The illumination source radiation may include at least one wave ("illumination wave"). The illumination source radiation may include at least two illumination waves. Each illumination wave may have a different wavelength. The at least one illumination source may directly illuminate the target. In this configuration, there is no optical component between the illumination source and the target. The at least one illumination source may indirectly illuminate the target. In this configuration, there is at least one optical component between the illumination source and the target. The illumination source may illuminate the target at each illumination wavelength by simultaneously transmitting all illumination waves. The illumination source may illuminate the target at each illumination wavelength by sequentially transmitting all illumination waves.

The illumination source may include a coherent electromagnetic radiation source. The coherent electromagnetic radiation source may include a laser, a diode, a two-photon excitation source, a three-photon excitation source, or a combination thereof.

The illumination source radiation may include an illumination wave with a wavelength in the range of 300 nm to 1,300 nm. The illumination source radiation may include an illumination wave with a wavelength in the range of 300 nm to 700 nm. The illumination source radiation may include an illumination wave with a wavelength in the range of 690 nm to 1,300 nm.

The image forming system may include a control system, a hardware processor, a memory, a display, or a combination thereof.

The image forming system may have a configuration that causes the optical detector to detect the target radiation and to transmit the detected intensity and wavelength of each target wave to the image forming system; acquires the detected target radiation comprising the at least two target waves; forms an image of the target using the detected target radiation ("target image"), wherein the target image includes at least two pixels, and wherein each pixel corresponds to one physical point on the target; forms at least one spectrum for each pixel using the detected intensity and wavelength of each target wave ("intensity spectrum"); transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one point on a phasor plane ("phasor point") for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. The image forming system may also have a configuration that displays the unmixed color image of the target on the image forming system's display.

The image forming system may have a configuration that uses at least one harmonic of the Fourier transform to generate the unmixed color image of the target. The image forming system may use at least a first harmonic of the Fourier transform to generate the unmixed color image of the target. The image forming system may use at least a second harmonic of the Fourier transform to generate the unmixed color image of the target. The image forming system may use at least a first harmonic and a second harmonic of the Fourier transform to generate the unmixed color image of the target The denoising filter may include a median filter.

The unmixed color image of the target may be formed at a signal-to-noise ratio of the at least one spectrum in the range of 1.2 to 50. The unmixed color image of the target may be formed at a signal-to-noise ratio of the at least one spectrum in the range of 2 to 50.

The target may be any target. The target may be any target that has a specific spectrum of color. For example, the target may be a tissue, a fluorescent genetic label, an inorganic target, or a combination thereof.

The hyperspectral imaging system may be calibrated by using a reference material to assign arbitrary colors to each pixel. The reference material may be any known reference material. For example, the reference may be any reference material wherein unmixed color image of the reference material is determined prior to the generation of unmixed color image of the target. For example, the reference material may be a physical structure, a chemical molecule, a biological molecule, a biological activity (e.g. physiological change) as a result of physical structural change and/or disease.

Any combination of above features/configurations is within the scope of the instant disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps. The colors disclosed in the following brief description of drawings and other parts of this disclosure refer to the color drawings and photos as originally filed with the U.S. provisional patent application 62/419,075, entitled "An Imaging System," filed Nov. 8, 2016; U.S. provisional patent application 62/799,647, entitled "A Hyperspectral Imaging System," filed Jan. 31, 2019; and U.S. Patent Application Publication No. 2019/0287222, published on Sep. 19, 2019. The entire contents of these patent applications are incorporated herein by reference. The patent application file contains these and additional drawings and photos executed in color. Copies of this patent application file with color drawings and photos will be provided by the United States Patent and Trademark Office upon request and payment of the necessary fee.

The following reference numerals are used for the system features disclosed in the following figures: a hyperspectral imaging system 10, an optics system 20, an image forming system 30, a control system 40, a hardware processor(s) 50, a memory system 60, a display 70, a fluorescence microscope 100, a multiple illumination wavelength microscope 200, a multiple wavelength detection microscope 300, a multiple wavelength detection device 400, a multiple illumination wavelength and multiple wavelength detection microscope 500, a multiple wavelength detection device 600, a multiple wavelength detection device 700, an illumination source 101, a dichroic mirror/beam splitter 102, a first optical lens 103, a second optical lens 104, a target (i.e. sample) 105, a (optical) detector 106, an illumination source radiation 107, an emitted target radiation 108, an illumination source radiation at a first wavelength 201, an illumination source radiation at a second wavelength 202, an emitted target radiation or reflected illumination source radiation at a first wavelength 203, an emitted target radiation or reflected illumination source radiation at a second wavelength 204, an emitted target radiation or reflected illumination source radiation 301, a dispersive optic 302, a spectrally dispersed target radiation 303, an optical detector array 304, a target image formation 401, a spectrum formation 402, a Fourier transformation 403, a real component of the Fourier function 404, an imaginary component of the Fourier function 405, a denoising filter 406, a plotting on phasor plane 407, a mapping back to target image 408, and a formation of unmixed color image of the target 409.

Figure 1A:
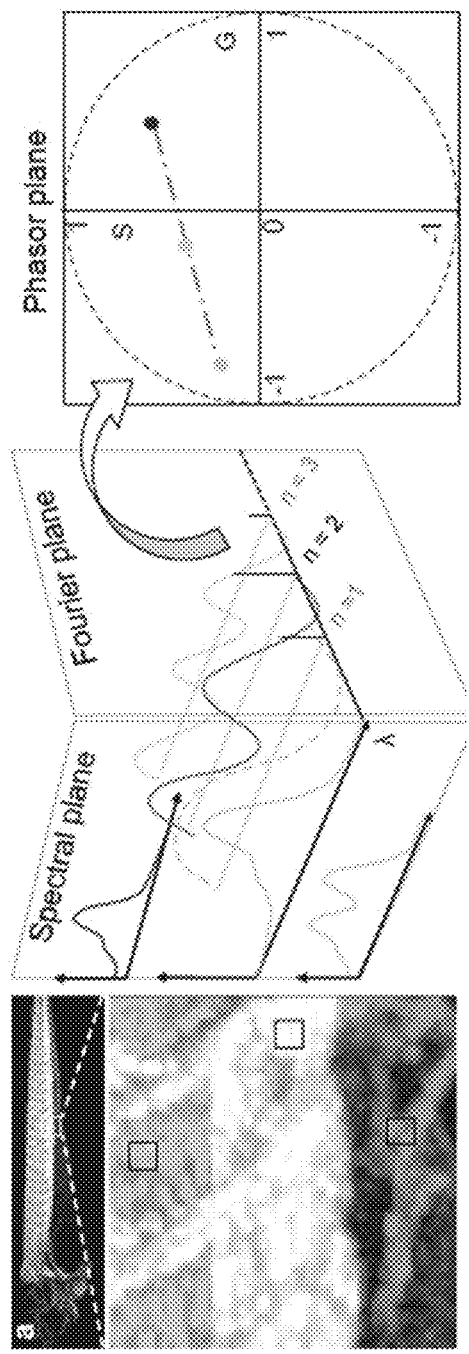
FIG. 1 Hyper-Spectral Phasor analysis. (a) Schematic principle of the HySP method. Spectra from every voxel in the multi-dimensional (x,y,z,λ) dataset are represented in terms of its Fourier coefficients (harmonics, n). Typically, n=2 is chosen and the corresponding coefficients are represented on the phasor plot (for other harmonics, see FIG. 5f). (b) Representative recordings of fluorescein (about 5 µM in ethanol) spectra at a fixed gain value (about 800) but varying laser power (about 1% to about 60%). The error bars denote the variation in intensity values over 10 measurements. Color coding represents intensities, blue for low-intensities and red for high-intensities. The inset shows that when normalized, emissions spectra overlap, provided recordings are made below the saturation limit of the detector. Imaging was done on Zeiss LSM780 equipped with QUASAR detector. (c) Scatter error ($\varepsilon_\sigma$) on phasor plot, resulting from the Poissonian noise in recording of a spectrum, is defined as the standard deviation of the scatter around expected phasor value ($z_e(n)$). Inset shows the 3D histogram of the distribution of phasor points around $z_e$. (d) Shifted-mean error ($\varepsilon_\mu$) on phasor plot result from changes in the shape of normalized spectrum that move the mean phasor point away from the true phasor coordinates corresponding to a given spectrum. (e) Scatter error, varies inversely with the number of total digital counts, being most sensitive to the detector gain. The legend is applicable to (e) and (f). (f) Normalized shifted-mean error remains nearly constant and below 5% over a large range of total digital counts form different imaging parameters. In an effort to understand which error is dominating, ratios of the two errors were plotted (inset). The ratio shows that scatter error ($\varepsilon_\sigma$) is almost an order of magnitude higher than the shifted-mean error ($\varepsilon_\mu$).

RFP(red) in double transgenic embryos, Tg(ubiq: membrane-Cerulean-2a-H2B-mCherry);Tg(kdrl:eGFP) (red, cyan and green respectively). The sample was excited sequentially at about 950 nm (b and d) and about 561 nm (c) yielding their autofluorescence as two separate signals (e) (purple and orange respectively). Time-lapse of 25 timepoints at about seven minute intervals were acquired with laser power at about 5% at about 950 nm and about 0.2% at about 561 nm.

FIG. 4 Errors on spectral phasor plot. (a) scatter error may scale inversely as the square root of the total digital counts. The legend is applicable to all parts of the figure. Scatter error may also depend on the Poissonian noise in the recording. R-squared statistical method may be used to confirm linearity with the reciprocal of square root of counts. The slope may be a function of the detector gain used in acquisition showing the counts-to-scatter error dynamic range is inversely proportional to the gain. Lower gains may produce smaller scatter error at lower intensity values. (b) Denoising in the phasor space may reduce the scatter error without affecting the location of expected values ($z_e(n)$) on the phasor plot. (c) Denoised scatter error may linearly depend on the scatter error without filtering, irrespective of the acquisition parameters. The slope may be determined by the filter size (3×3 here). (d) Denoising may not affect normalized shifted-mean errors since the locations of $z_e(n)$'s on the phasor plot remain unaltered due to filtering (d).

FIG. 5 Sensitivity of phasor point. (a,b,c) $|Z(n)|$ may remain nearly constant for different imaging parameters. Legend applies to (a,b,c,d,e). (d) Total digital counts as a function of laser power. (e) Proportionality constant in Equation 2 may depend on the gain. (f) Relative magnitudes of residuals ($R(n)$) on phasor plots shows that harmonics n=1 and 2 may be sufficient for unique representation of spectral signals.

FIG. 6 Phasor analysis for unmixing hyper-spectral fluorescent signals in vivo. (a) Schematic of the expression patterns of Citrine (skeletal muscles) and eGFP (endothelial tissue) in transgenic zebrafish lines Gt(desm-citrine)$^{ct122a/+}$ and Tg(kdrl:eGFP) respectively. (b) Conventional optical filter separation for Gt(desm-citrine)$^{ct122a/+}$ Tg(kdrl:eGFP). Using emission bands on detector of spectrally overlapping fluorophores (eGFP and citrine) may not overcome the problem of bleed-through of signal in respective channels. Arrows indicate erroneous detection of eGFP or Citrine expressions in the other channel. Scale bar, about 200 µm. (c) Phasor plots showing spectral fingerprints (scatter densities) for Citrine and eGFP in individually expressed embryo and double transgenic. The individual Citrine and eGFP spectral fingerprints may remain preserved in the double transgenic line. (d) Maximum intensity projection images reconstructed by mapping the scatter densities from phasor plot to the original volume. eGFP and Citrine fingerprints may cleanly distinguish the skeletal muscles from interspersed blood vessels (endothelial tissue), though within the same anatomical region of the embryo, in both single and double transgenic lines. Scale bar about 300 µm. Embryos imaged about 72 hours post fertilization. (e,f) HySP analysis may outperform optical separation and linear unmixing in distinguishing spectrally overlapping fluorophores in vivo. (e) Maximum intensity projection images of the region in Tg(kdrl:eGFP);Gt(desm-citrine)$^{ct122a/+}$ shown in (d) compares the signal for eGFP and Citrine detected by optical separation, linear unmixing and phasor analysis. (f) Corresponding normalized intensity profiles along the width (600 pixels, about 553.8 µm) of the image integrated over a height of 60 pixels. Correlation values (R) reported for the three cases show the lowest value for HySP analysis, as expected by the expressions of the two proteins.

Figure 7A:
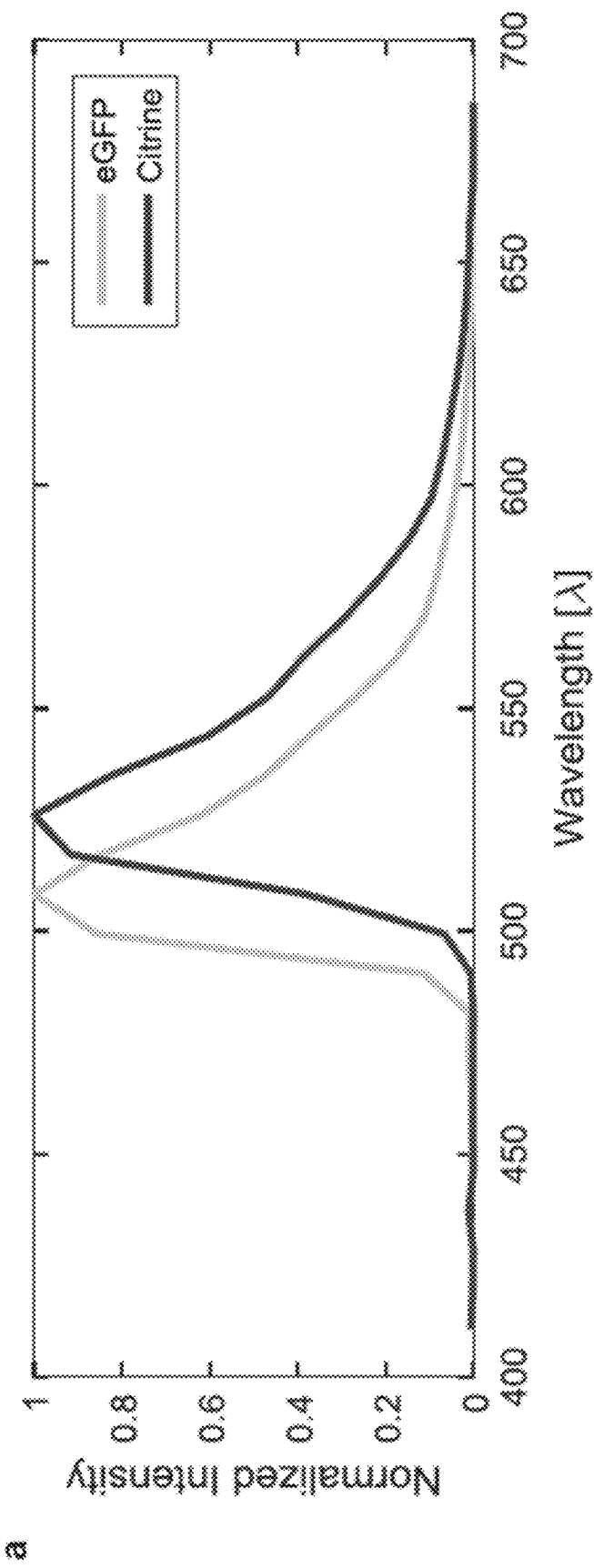
Figure 7B:
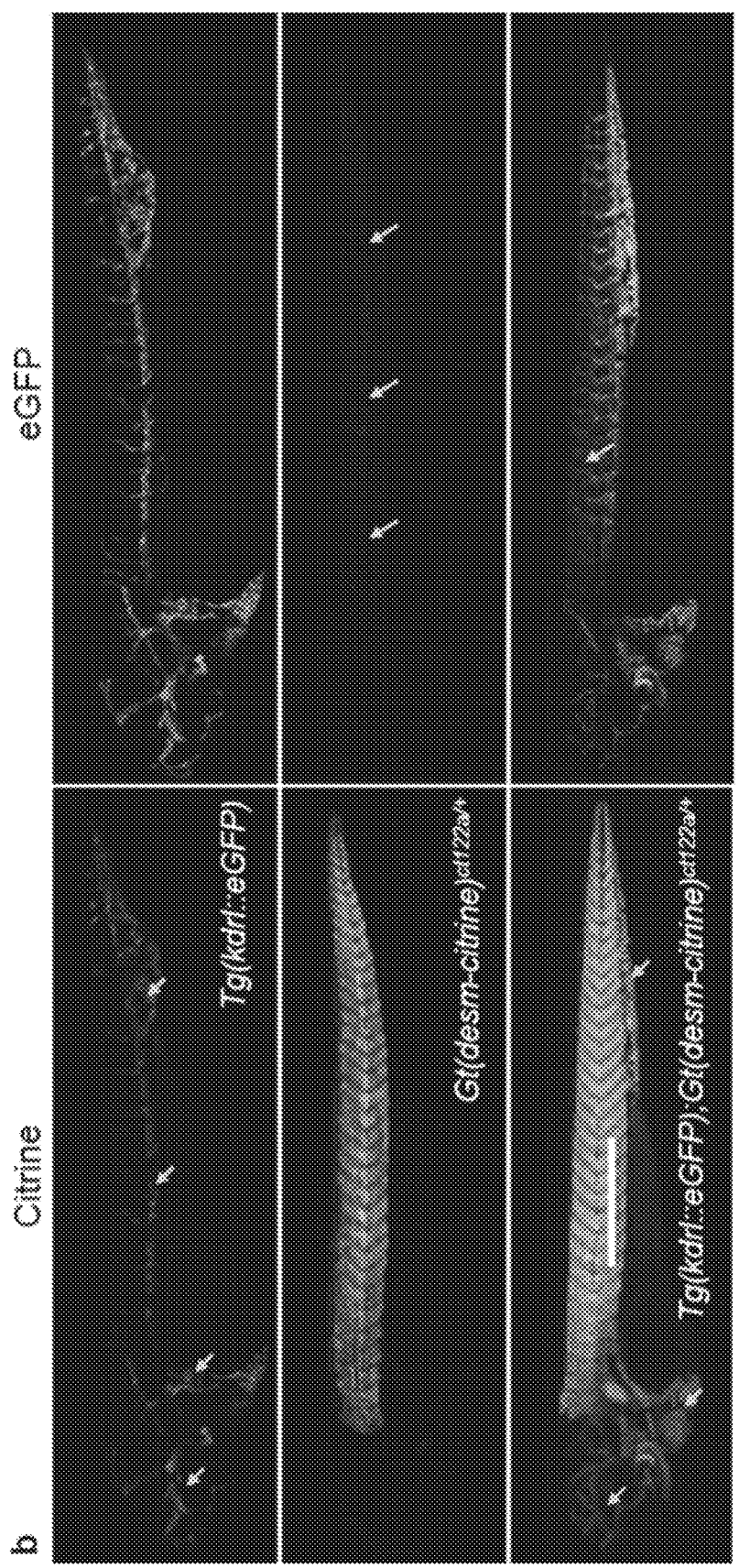
Figure 7C:
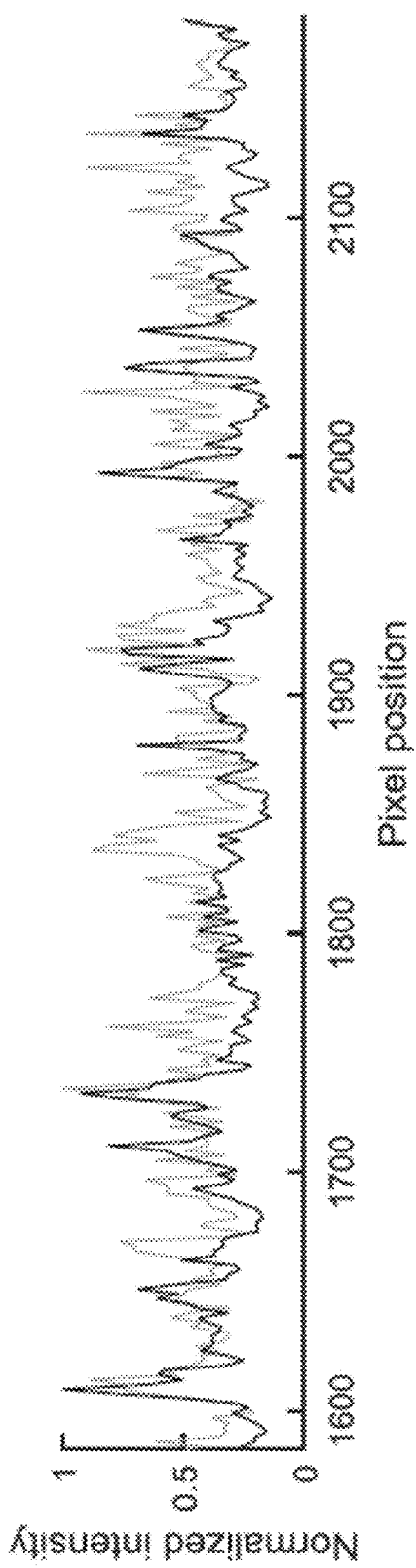

FIG. 7 Optical separation of eGFP and Citrine. (a) Spectra of citrine (peak emission about 529 nm, skeletal muscles) and eGFP (peak emission about 509 nm, endothelial tissue) measured using confocal multispectral lambda mode in transgenic zebrafish lines Gt(desm-citrine)$^{ct122a/+}$ and Tg(kdrl:eGFP) respectively. (b) Conventional optical separation (using emission bands on detector) of spectrally close fluorophores (eGFP and citrine) may not overcome the problem of bleed-through of signal in respective channels. Arrows indicate erroneous detection of eGFP or citrine expressions in the other channel. Scale bar about 300 µm. (c) Normalized intensity profiles along the length (600 pixels, about 553.8 µm) of the line in panel (a).

FIG. 8 Effect of phasor space denoising on Scatter Error and Shifted-Mean Error. (a) Scatter Error as a function of digital counts for different number of denoising filters with 3 by 3 mask. Data origin is fluorescein dataset acquired at gain of about 800. (b) Scatter Error as a function of number of denoising filters with 3 by 3 mask for different laser powers. (c) Shifted-Mean Error as a function of digital counts for different number of denoising filters with 3 by 3 mask. Data origin is fluorescein dataset acquired at gain of about 800. (d) Shifted-Mean Error as a function of number of filters with 3 by 3 mask for different laser powers. (e) Relative change of Scatter Error as a function of number of denoising filters applied for different mask sizes. (f) Relative change of Shifted-Mean Error as a function of number of filters applied for different mask sizes. "Filters" of this figure are denoising filters.

FIG. 9 Effect of phasor space denoising on image intensity. (a,b) HySP processed Citrine channel of a dual labeled eGFP-Citrine sample (132.71 um×132.71 um) before and after filtering in phasor space. (c,d) HySP processed eGFP channel of the sample in (a,b) before and after filtering in phasor space. (e) Total intensity profile of the green line highlighted in (a,b,c,d) for different number of denoising filters. Intensity values may not be changing. (f) eGFP channel intensity profile of green line highlighted in (a,b,c,d) for different number of denoising filters. (g) Citrine channel intensity profile of green line highlighted in (a,b,c,d) for different number of denoising filters. "Filters" of this figure are denoising filters.

FIG. 10 Autofluorescence identification and removal in phasor space. (a) Phasor plots showing spectral fingerprints (scatter densities) for citrine, eGFP and autofluorescence may allow simple identification of intrinsic signal. (b) Maximum intensity projection images reconstructed by mapping the scatter densities from phasor plot to the original volume. Autofluorescence may have a broad fingerprint that can effectively be treated as a channel. Embryos imaged about 72 hours post fertilization.

Figure 8A:
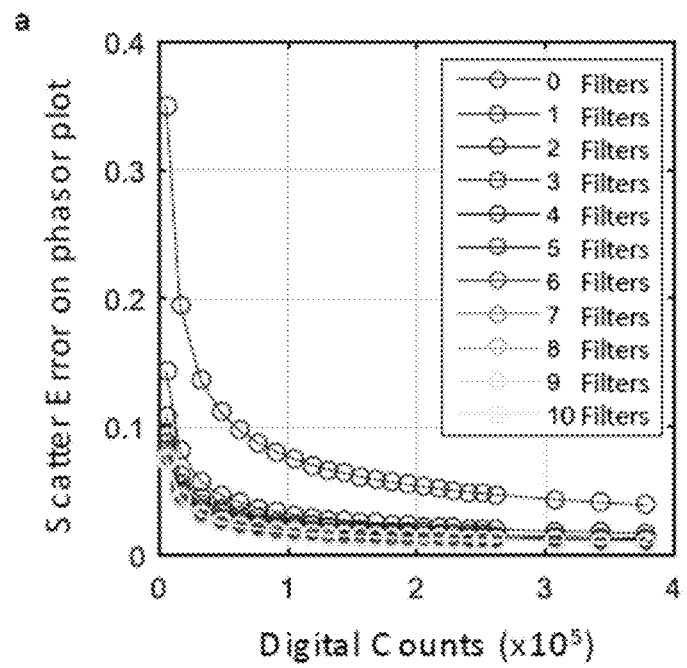
Figure 8B:
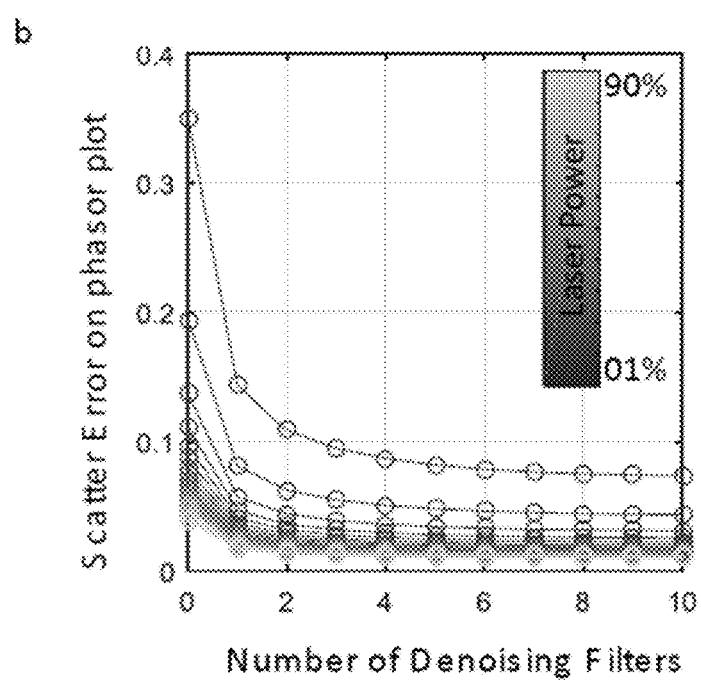
Figure 8C:
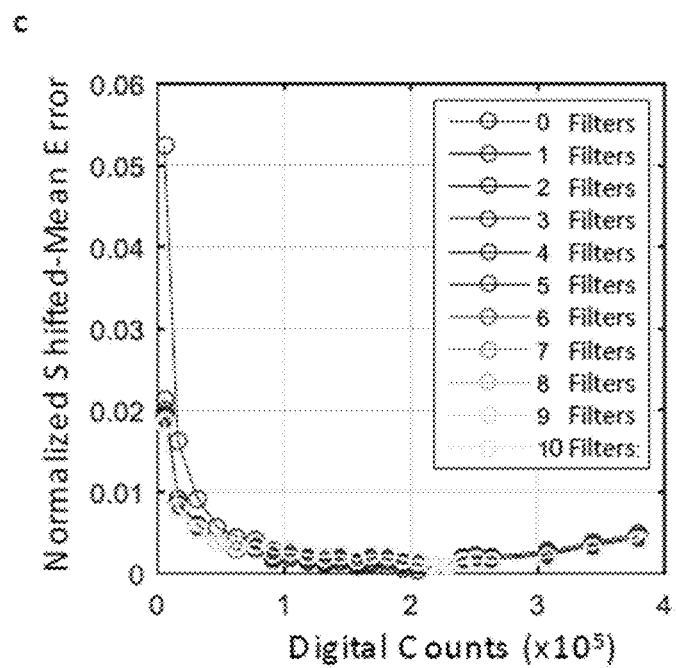
Figure 8D:
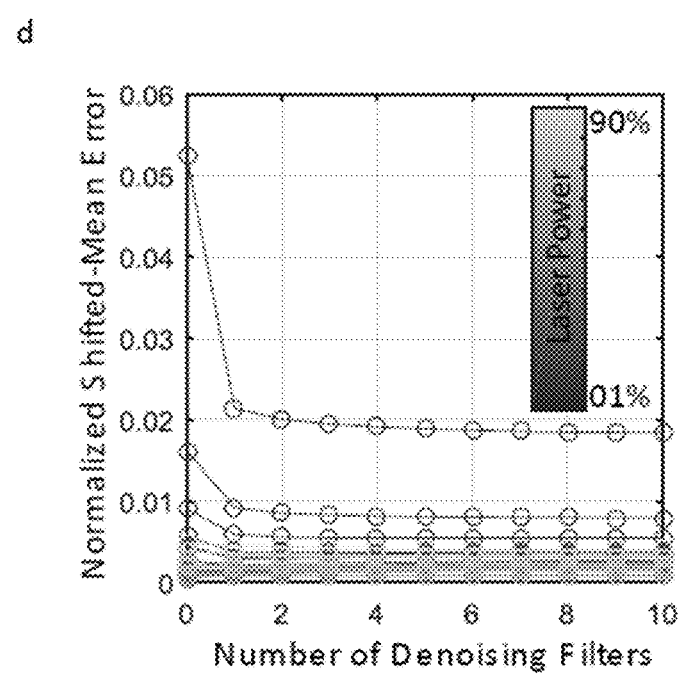
Figure 8E:
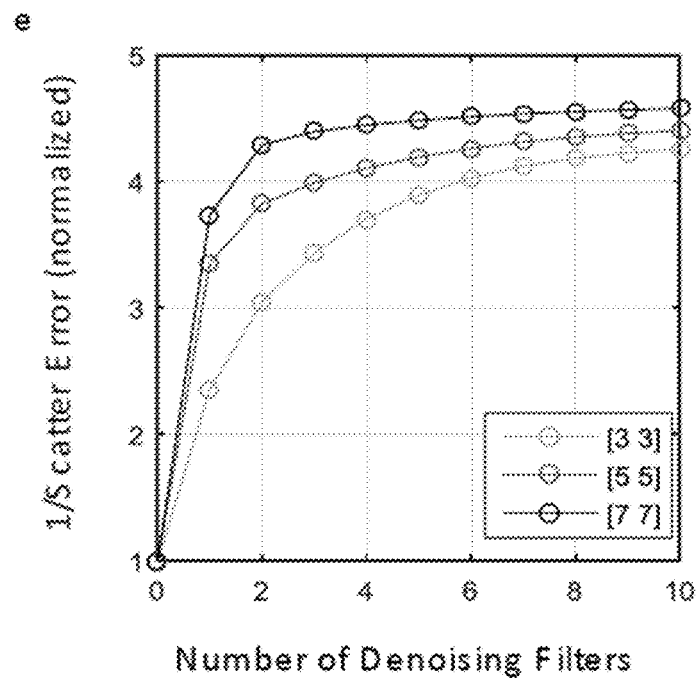
Figure 8F:
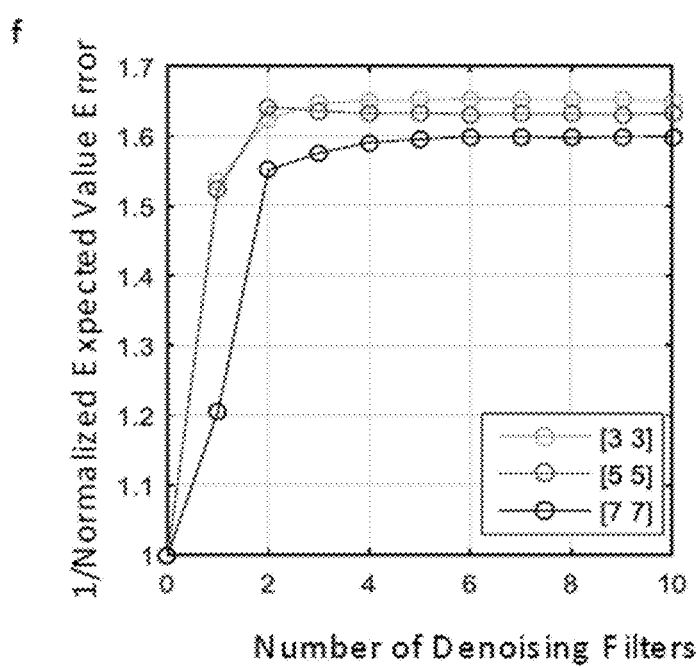
Figure 9A:
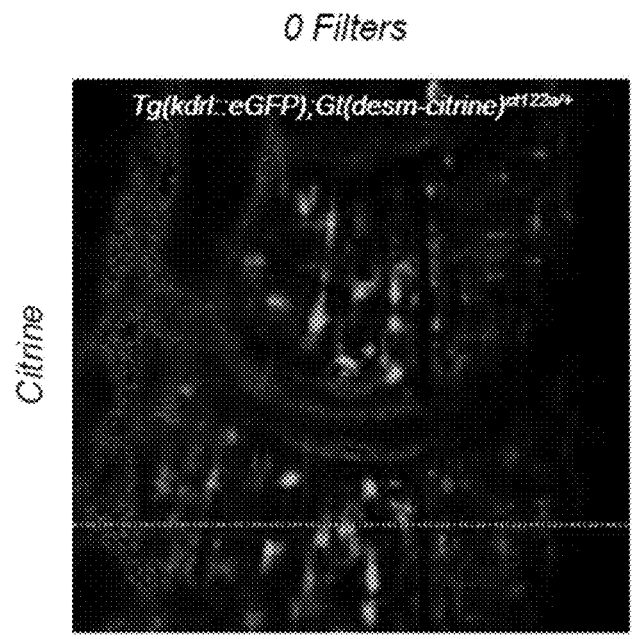
Figure 9B:
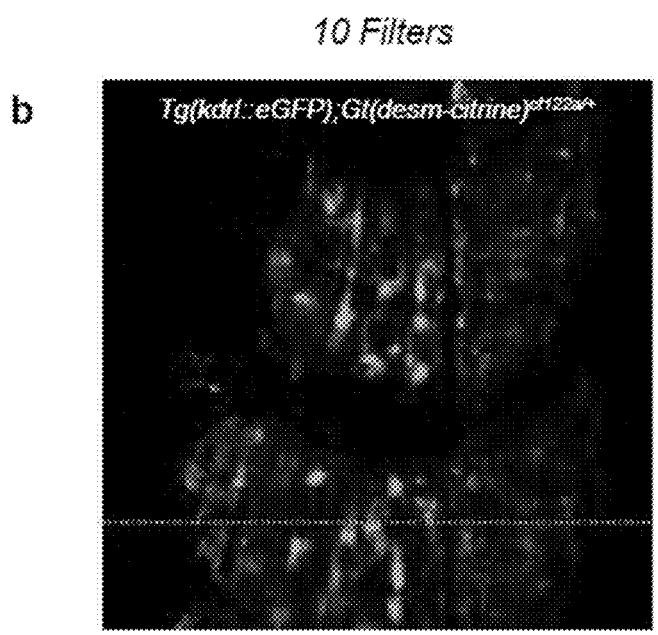
Figure 9C:
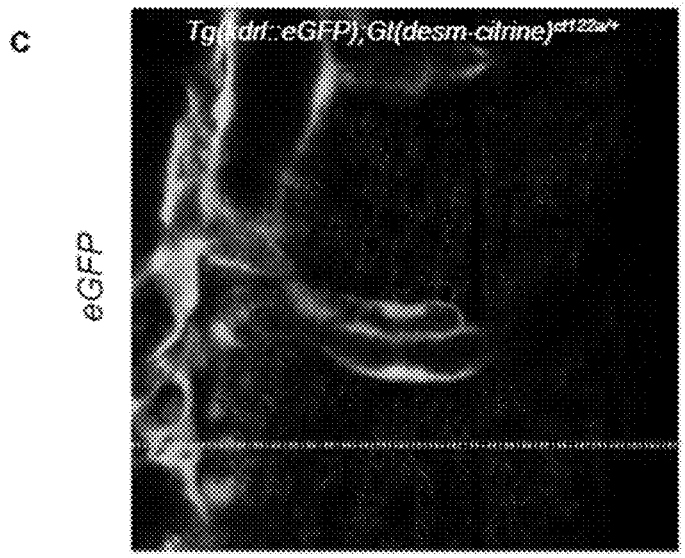
Figure 9D:
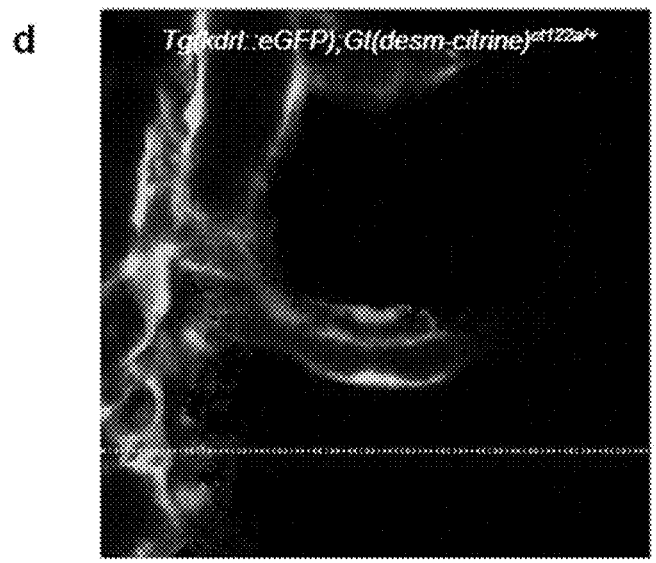
Figure 9E:
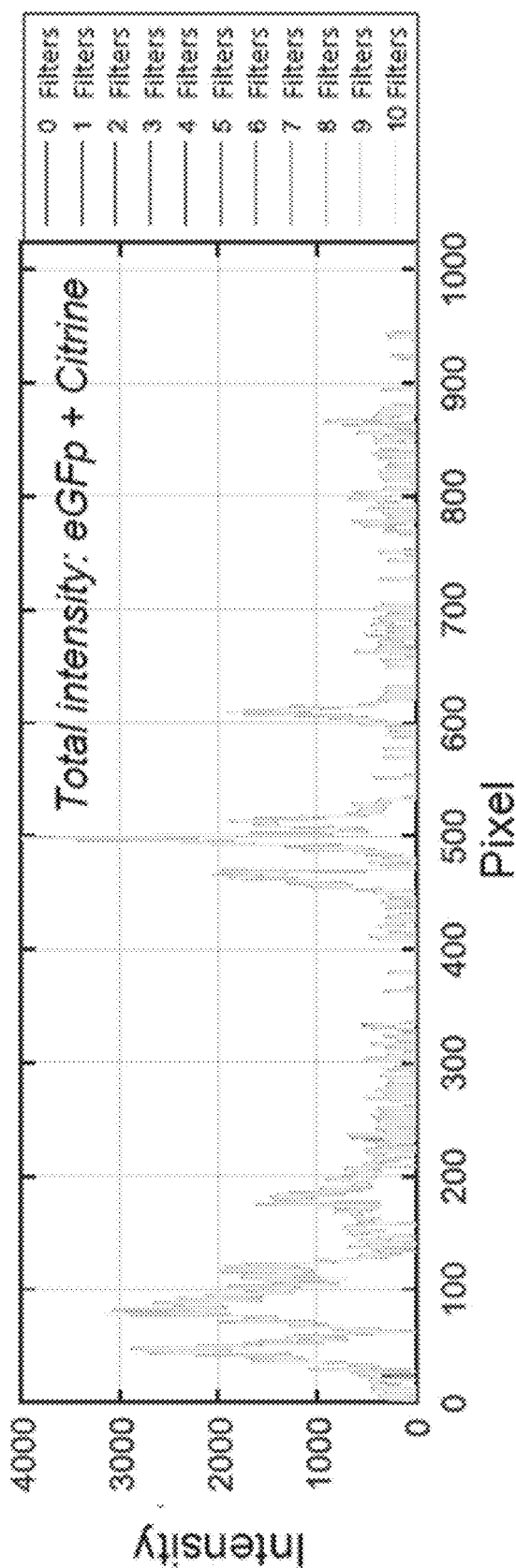
Figure 9F:
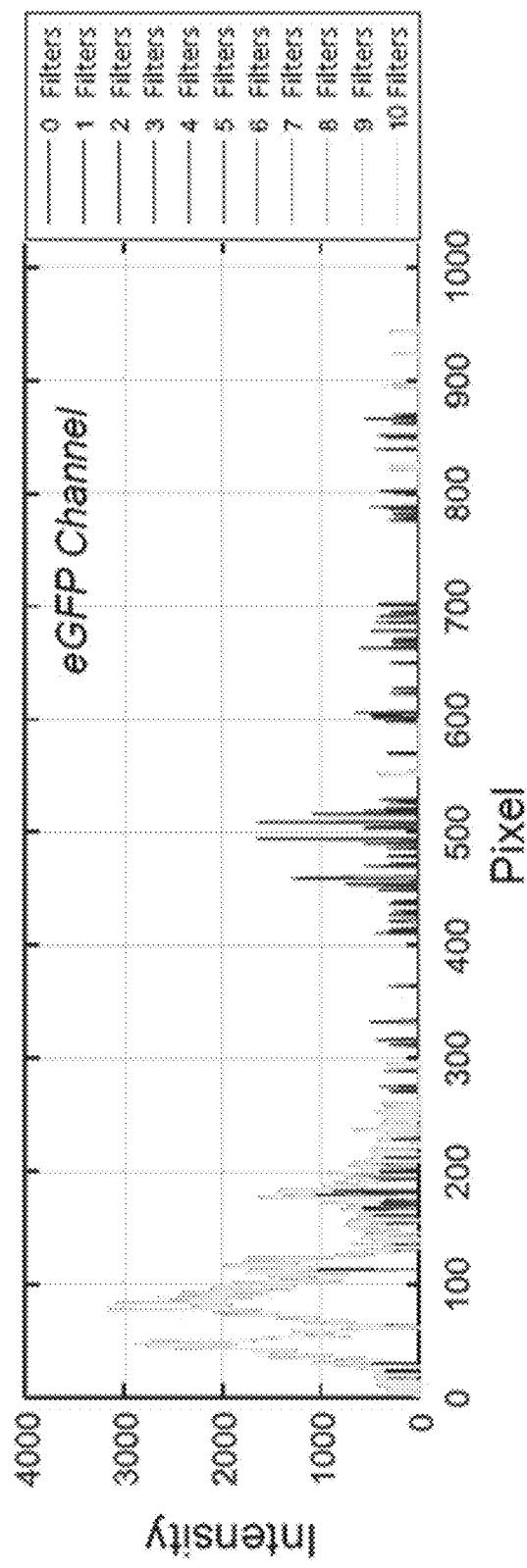
Figure 9G:
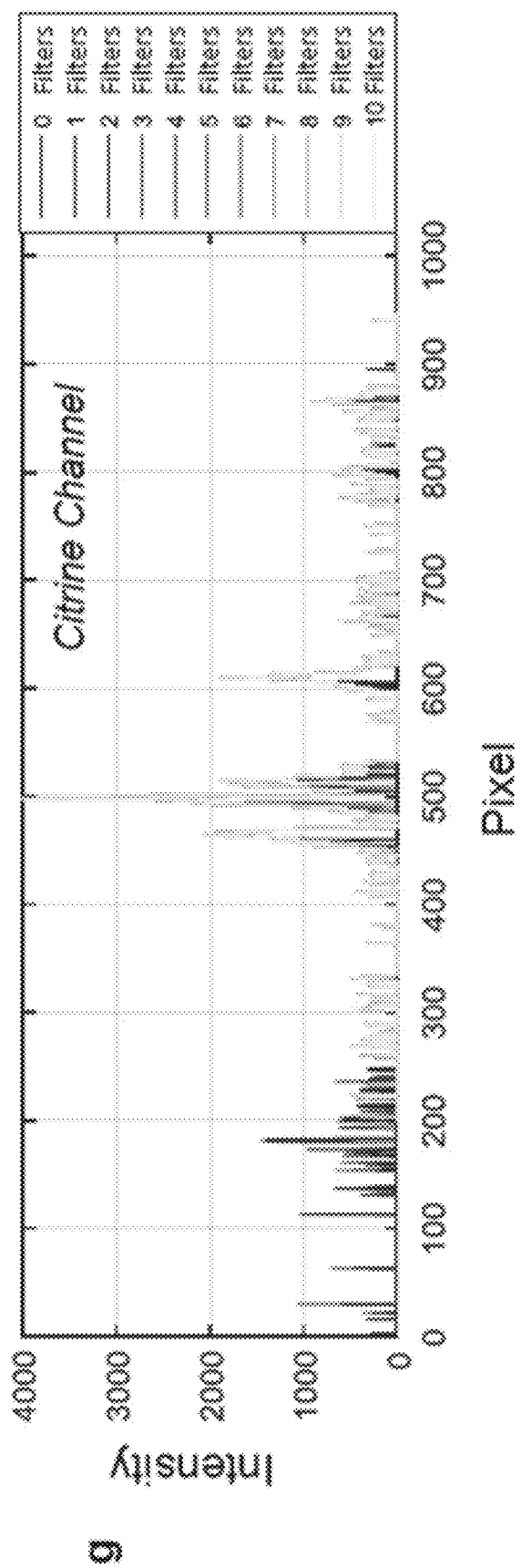
Figures 10A, 10B:
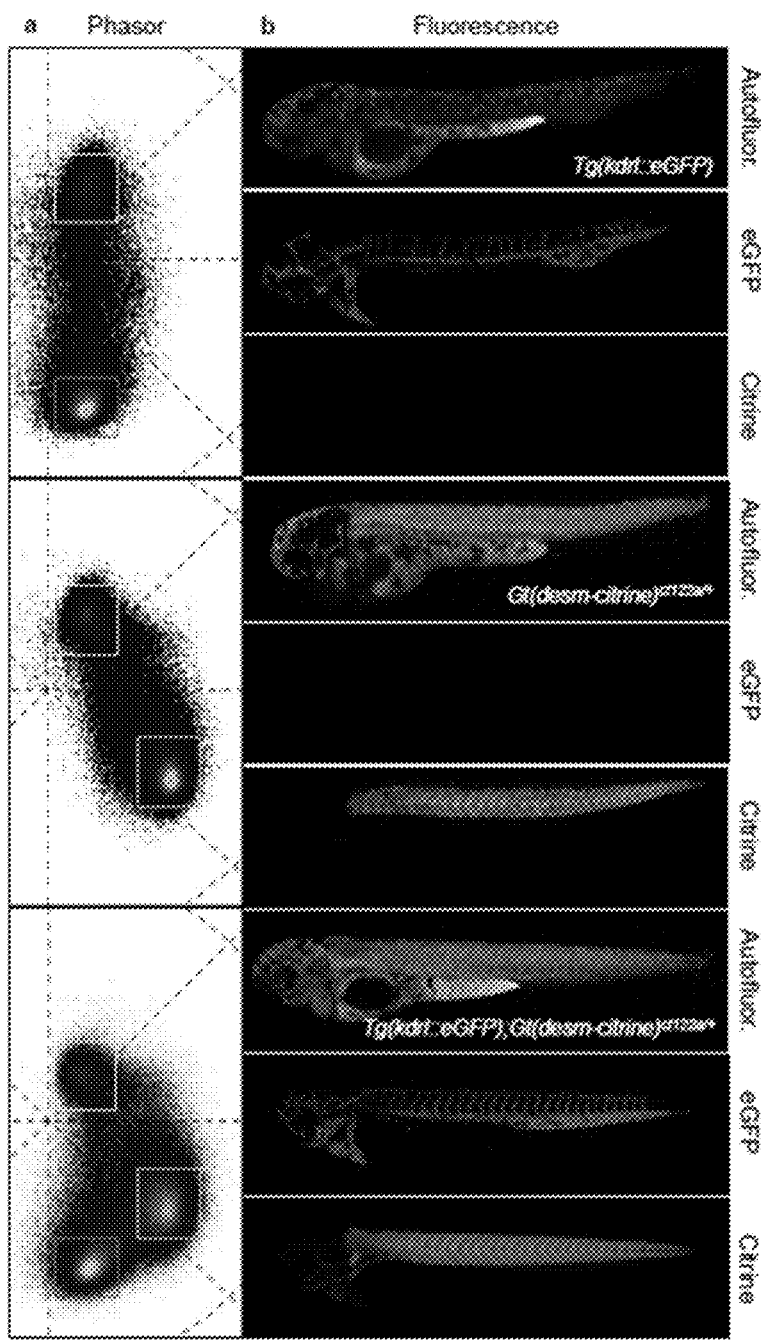
Figures 11A, 11B:
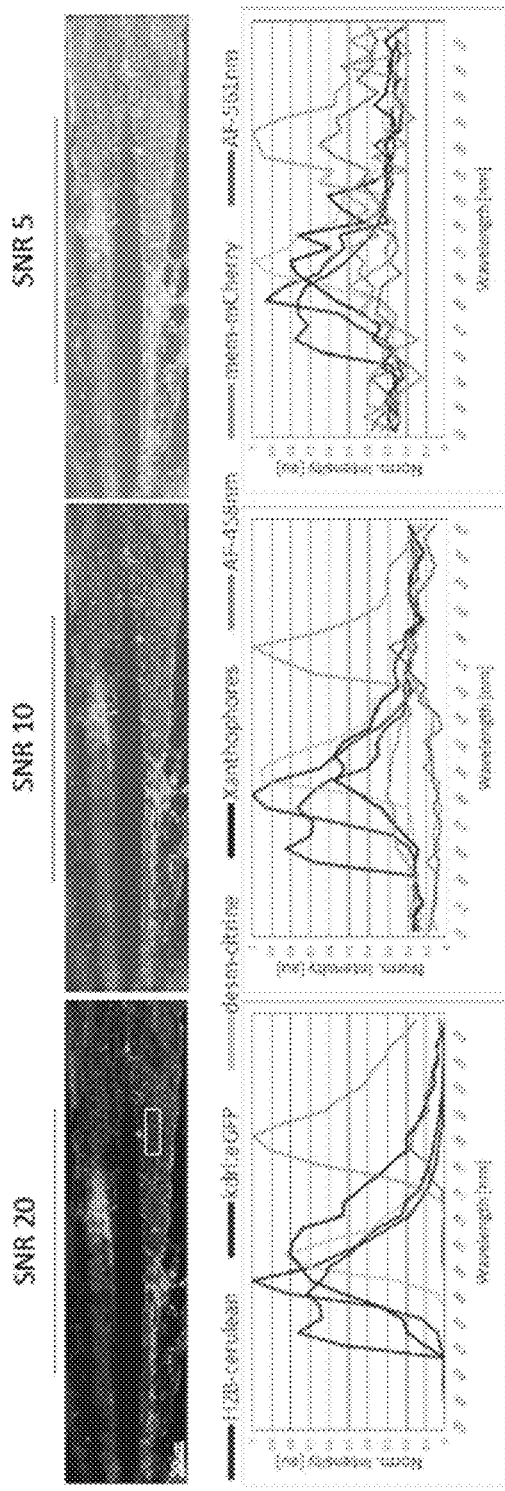
Figure 12A:
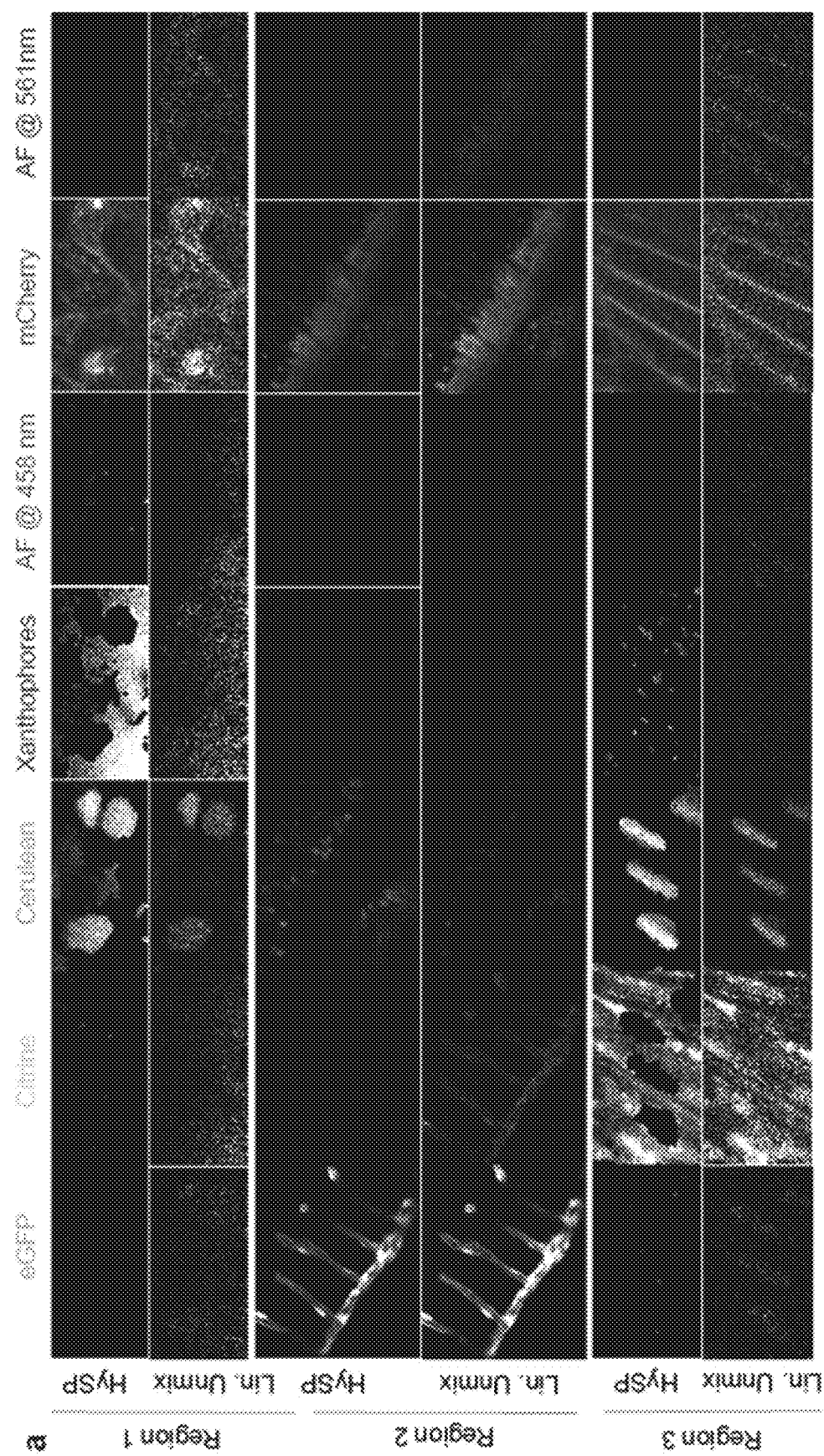
Figure 12B:
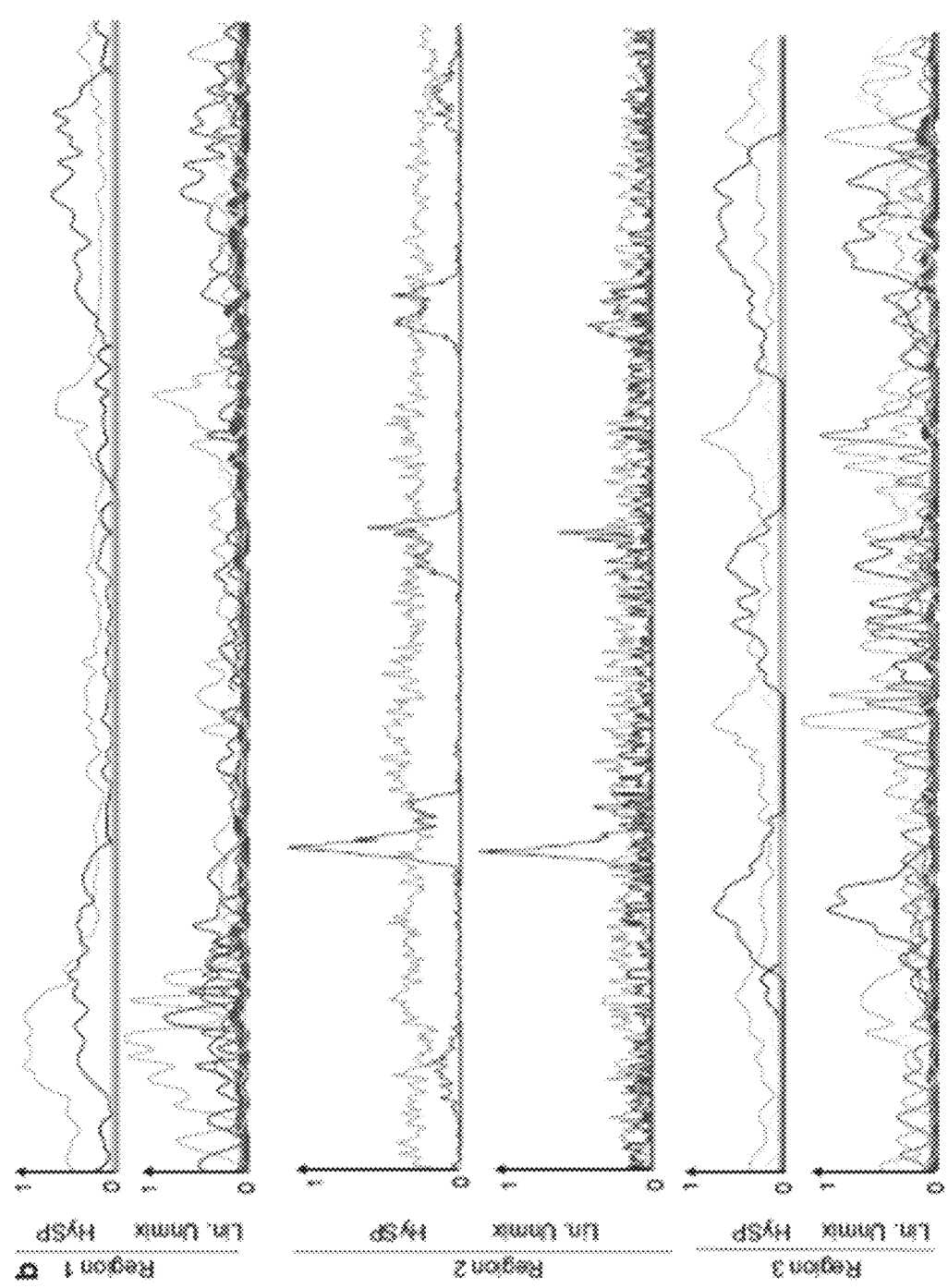

FIG. 11 Comparison of HySP and Linear unmixing under different Signal to Noise Ratio (SNR). (a) TrueColor images of 32 channel datasets of zebrafish labeled with H2B-cerulean, kdrl:eGFP, desm-citrine, Xanthophores, membrane-mCherry as well as Autofluorescence at about 458 nm and about 561 nm. The original dataset (SNR 20) was digitally degraded by adding noise and decreasing signal down to SNR 5. (b) Normalized spectra used for non-weighted linear unmixing. Spectra were identified on each sample from anatomical regions known to contain only the specific label. For example Xanthophore's spectrum was collected in dorsal area, nuclei's from fin, vasculature's intramuscularly. The chosen regions combinations were tested and corrected until optimal linear unmixing results were obtained. The same regions were then used for all three datasets. The same legend and color coding is used through the entire figure. (c) Processed zoomed-in region (box in (a)) for linear unmixing and HySP. The comparison shows three nuclei belonging to muscle fiber. At good SNR (20 and above) both linear unmixing and HySP results are accurate. Lowering SNR, however, affects the linear unmixing more than the phasor. This can improve unmixing of labels in volumetric imaging of biological samples, where generally SNR decreases with depth and explains the differences in FIG. 2e, f; FIG. 6e, f; FIG. 10 and FIG. 12. One advantage of HySP, in this SNR comparison, may be the spectral denoising in Fourier space. Spectral denoising may be performed by applying filters directly in phasor space. This may maintain the original image resolution but may improve spectral fingerprinting in the phasor plot. A median filter may be applied as the filter. However, other filtering approaches may also be possible. For any image of a given size (n×m pixels), S and G values may be obtained for every pixel, yielding 2 new 2D matrices, for S and G, with dimensions n×m. Since the initial S and G matrix entries may have the same indices as the pixels in the image, the filtered matrices S* and G*, therefore, may preserve the geometrical information. Effectively by using filtering in phasor space, S and G matrices may be treated as 2D images. First, this may reduce the scatter error, i.e. the localization precision on phasor plot increases (FIG. 8a-b), improving the spectral fingerprinting resolution while improving the already minimal Shifted-Mean Error (FIG. 8c-d). The effect on data may be an improved separation of distinct fluorescent proteins (FIG. 9a-d). Second, denoising in (G,S) coordinates may preserve both geometry, intensity profile as well as the original resolution at which the images were acquired (FIG. 9e-g). Effectively filtering in phasor space may affect the spectral dimension of the data achieving denoising of spectral noise without interfering with intensities. (d) Intensity profile (dashed arrow in (c)) comparison may show the improvement of HySP at low SNR. Under decreased SNR H2B-cerulean (cyan) and desm-citrine (yellow) (solid arrows in (c)) may consistently be identified in HySP while they may be partially mislabeled in linear unmixing. For example, some noisy may be identified as kdrl:eGFP (green) while, anatomically no vasculature is present in this region of interest.

FIG. 12 Comparison of HySP and Linear unmixing in resolving seven fluorescent signals. (a) Gray scale images from different optical sections, same as the ones used in FIG. 2 (Regions 1-3), comparing the performance of HySP analysis and linear unmixing. (b) Normalized intensity plots for comparison of HySP analysis and linear unmixing. Similar to the corresponding panels in FIG. 2f, the x-axes denote the normalized distance and y-axes in all graphs were normalized to the value of maximum signal intensity among the seven channels to allow relative comparison. The panels show all intensity profiles for seven channels in the respective images.

FIG. 13 Effect of binning on HySP analysis of seven in vivo fluorescent signals. The original dataset acquired with 32 channels may be computationally binned sequentially to 16, 8 and 4 channels to understand the limits of HySP in unmixing the selected fluorescence spectral signatures (a). The binning may not produce visible deterioration of the unmixing. White square area may be used for zoomed comparison of different bins. Spectral phasor plots at about 458 nm and about 561 nm excitation (b). Binning of data may result in shorter phasor distances between different fluorescent spectral fingerprints. Clusters, even if closer, may still be recognizable. Zoomed-in comparison of embryo trunk (box in (a)). Differences for HySP analysis for the same dataset at different binning values may still be subtle to the eye. One volume may be chosen for investigating intensity profiles (white dashed arrow) (c). Intensity profiles for kdrl:eGFP, H2B-cerulean, desm-citrine and Xanthophores at different binning for summed intensities of a volume of about 26.60 µm×about 0.27 µm×about 20.00 µm (white dashed arrow (c)) (d). The effects of binning may now be visible. For vasculature the unmixing may not be excessively deteriorated by the binning. Same result for nuclei. Desm and xanthophores may seem to be more affected by binning. This result may suggest that, in our case of zebrafish embryo with seven separate spectral fingerprints acquired sequentially using two different lasers, it is possible to use 4 bins at the expense of a deterioration of the unmixing.

Figure 14:
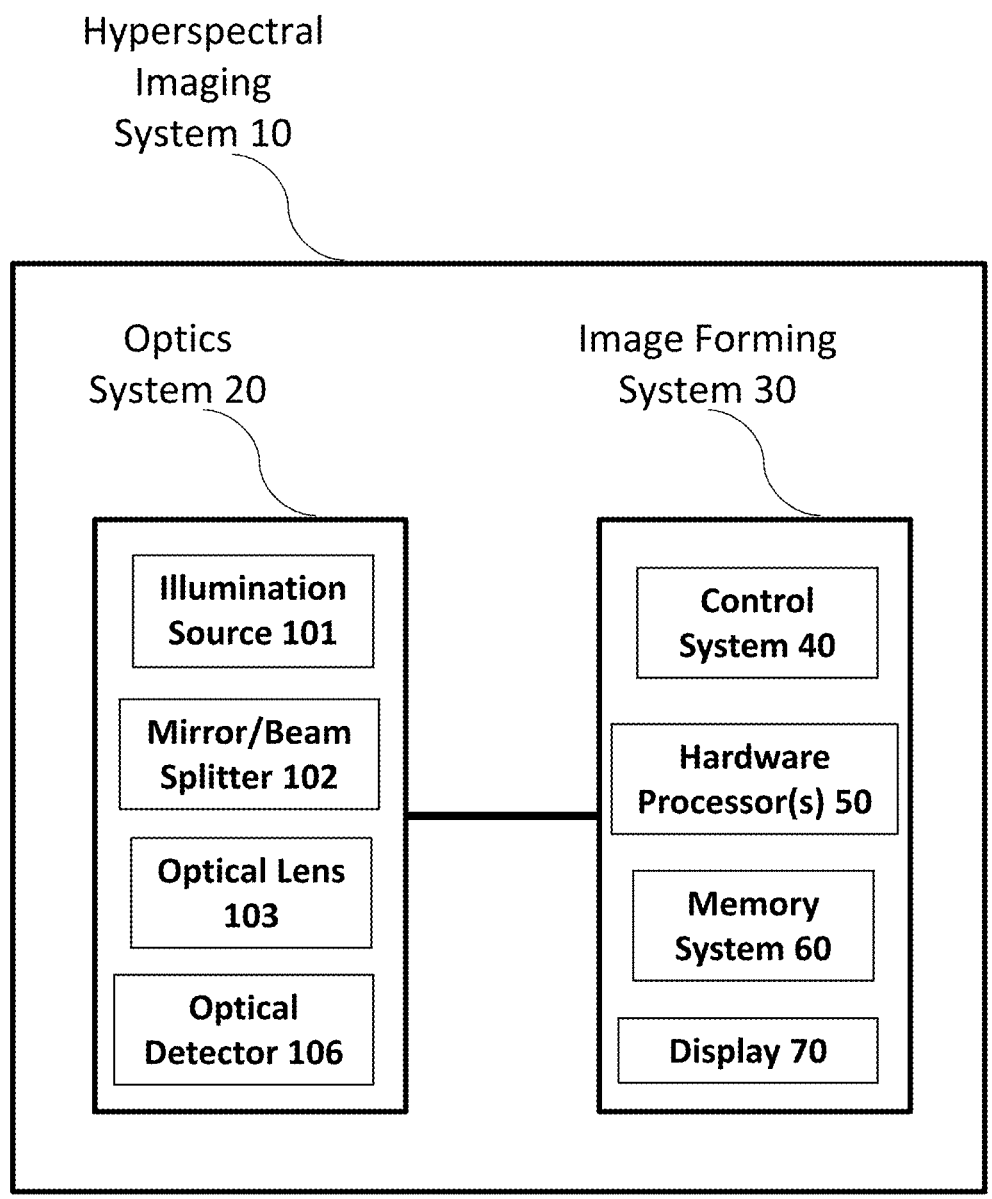

FIG. 14 An exemplary hyperspectral imaging system comprising an exemplary optics system and an exemplary image forming system.

Figure 15:
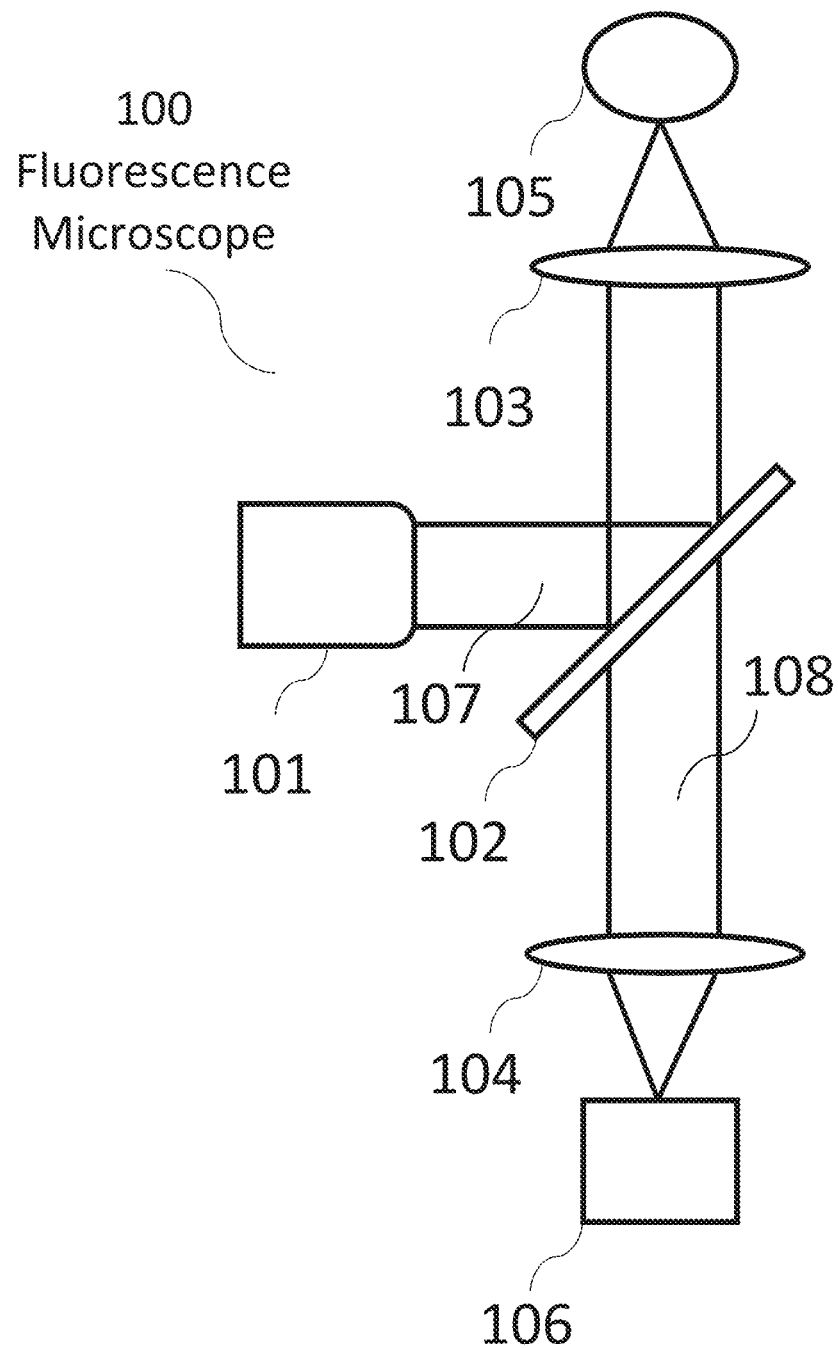

FIG. 15 An exemplary hyperspectral imaging system comprising an exemplary optics system, a fluorescence microscope. This system may generate an unmixed color image of a target by using an exemplary image forming system comprising features disclosed, for example in FIGS. 22-23.

Figure 16:
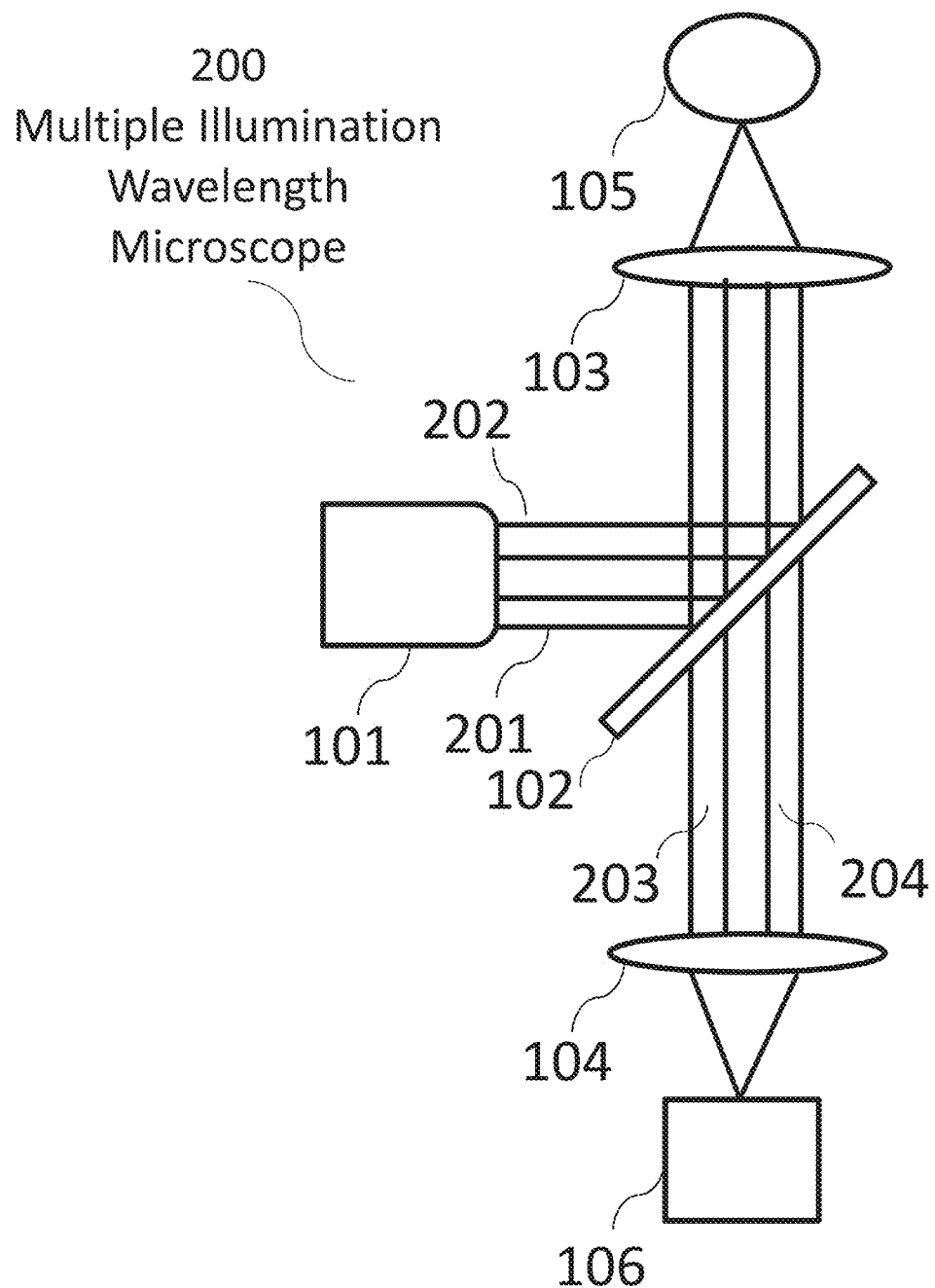

FIG. 16 An exemplary hyperspectral imaging system comprising an exemplary optics system, a multiple illumination wavelength microscope. This system may generate an unmixed color image of a target by using an exemplary image forming system comprising features disclosed, for example in FIGS. 22-23.

Figure 17:
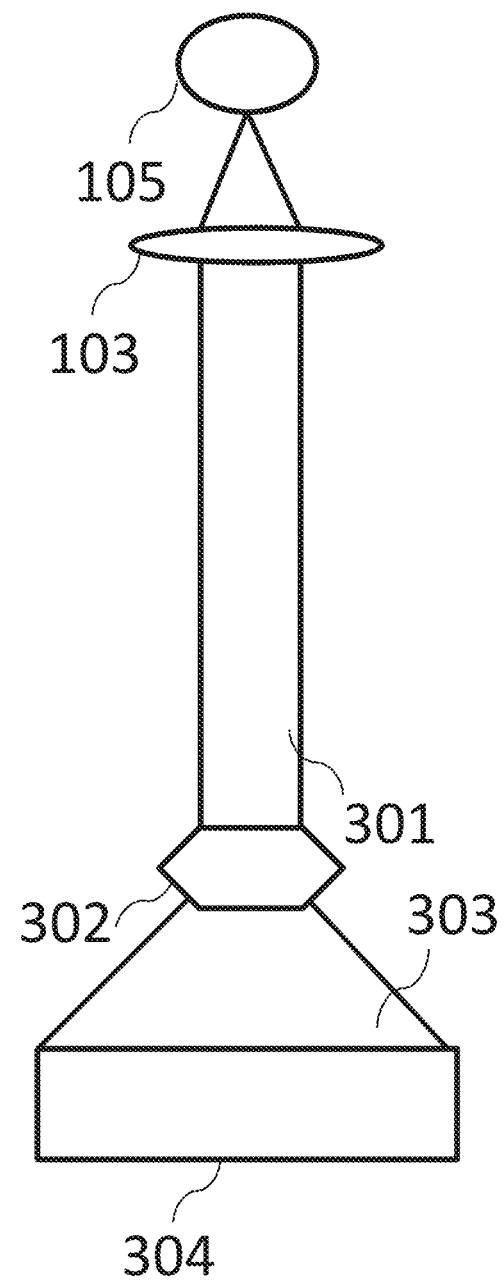

FIG. 17 An exemplary hyperspectral imaging system comprising an exemplary optics system, a multiple illumination wavelength device. This system may generate an unmixed color image of a target by using an exemplary image forming system comprising features disclosed, for example in FIGS. 22-23.

Figure 18:
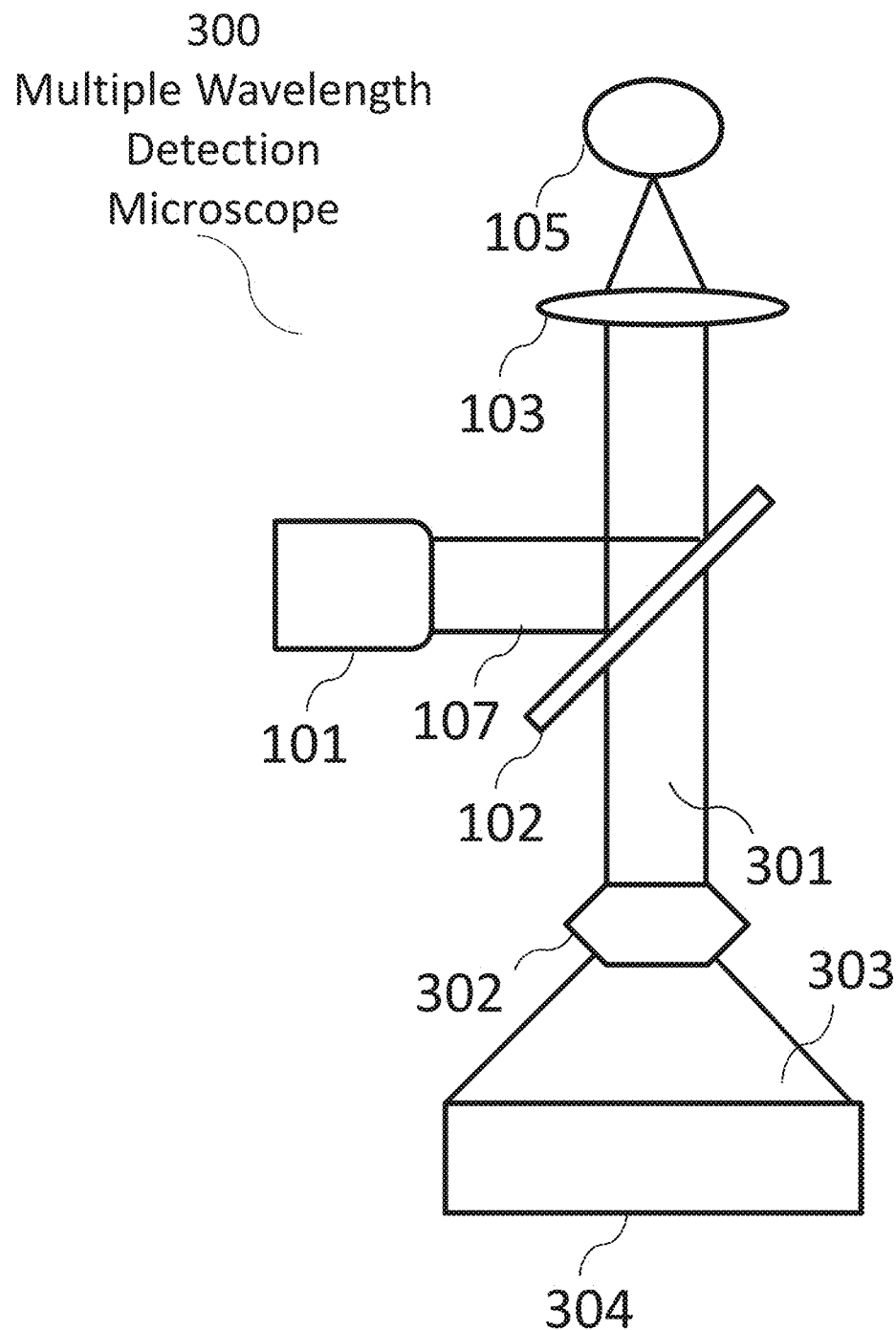

FIG. 18 An exemplary hyperspectral imaging system comprising an exemplary optics system, a multiple wavelength detection microscope. This system may generate an unmixed color image of a target by using an exemplary image forming system comprising features disclosed, for example in FIGS. 22-23.

Figure 19:
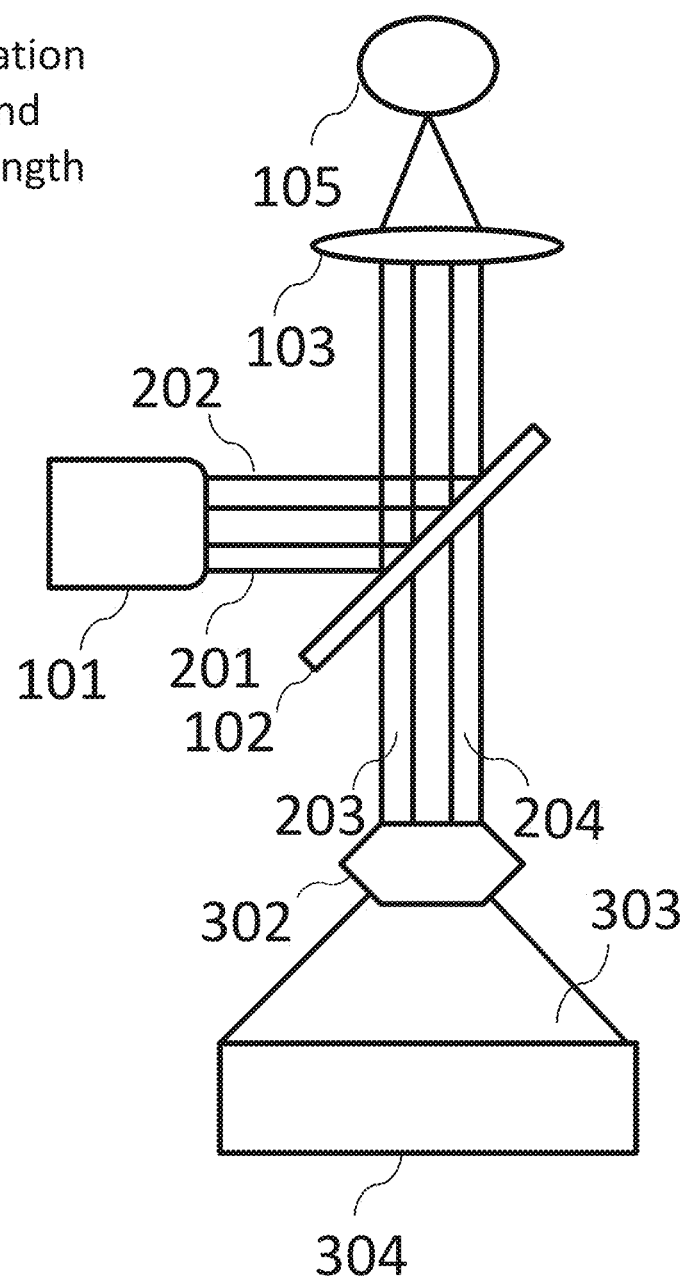

FIG. 19 An exemplary hyperspectral imaging system comprising an exemplary optics system, a multiple illumination wavelength and multiple wavelength detection microscope. This system may generate an unmixed color image of a target by using an exemplary image forming system comprising features disclosed, for example in FIGS. 22-23.

Figure 20:
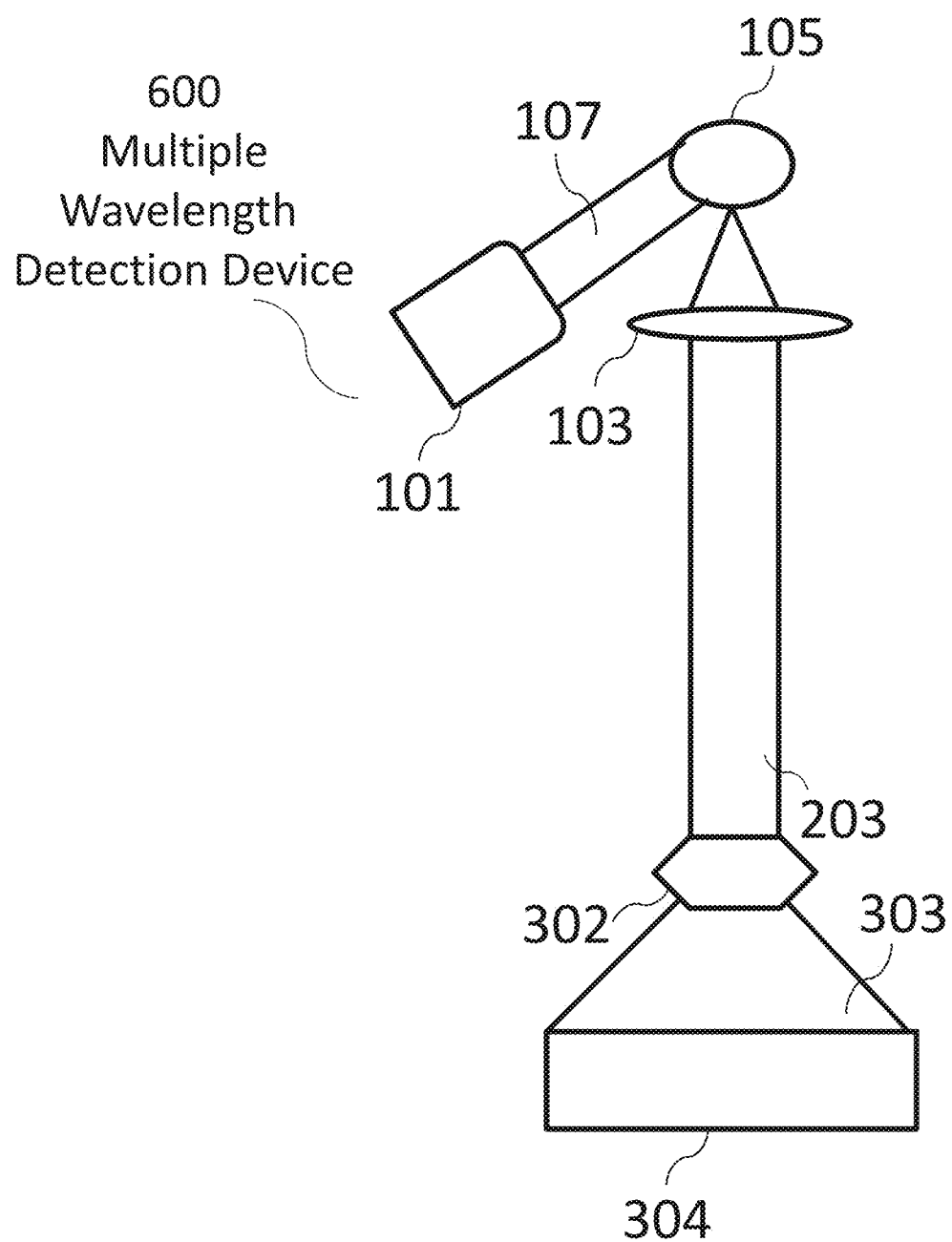

FIG. 20 An exemplary hyperspectral imaging system comprising an exemplary optics system, a multiple wavelength detection device. This system may generate an unmixed color image of a target by using an exemplary image forming system comprising features disclosed, for example in FIGS. 22-23.

Figure 21:
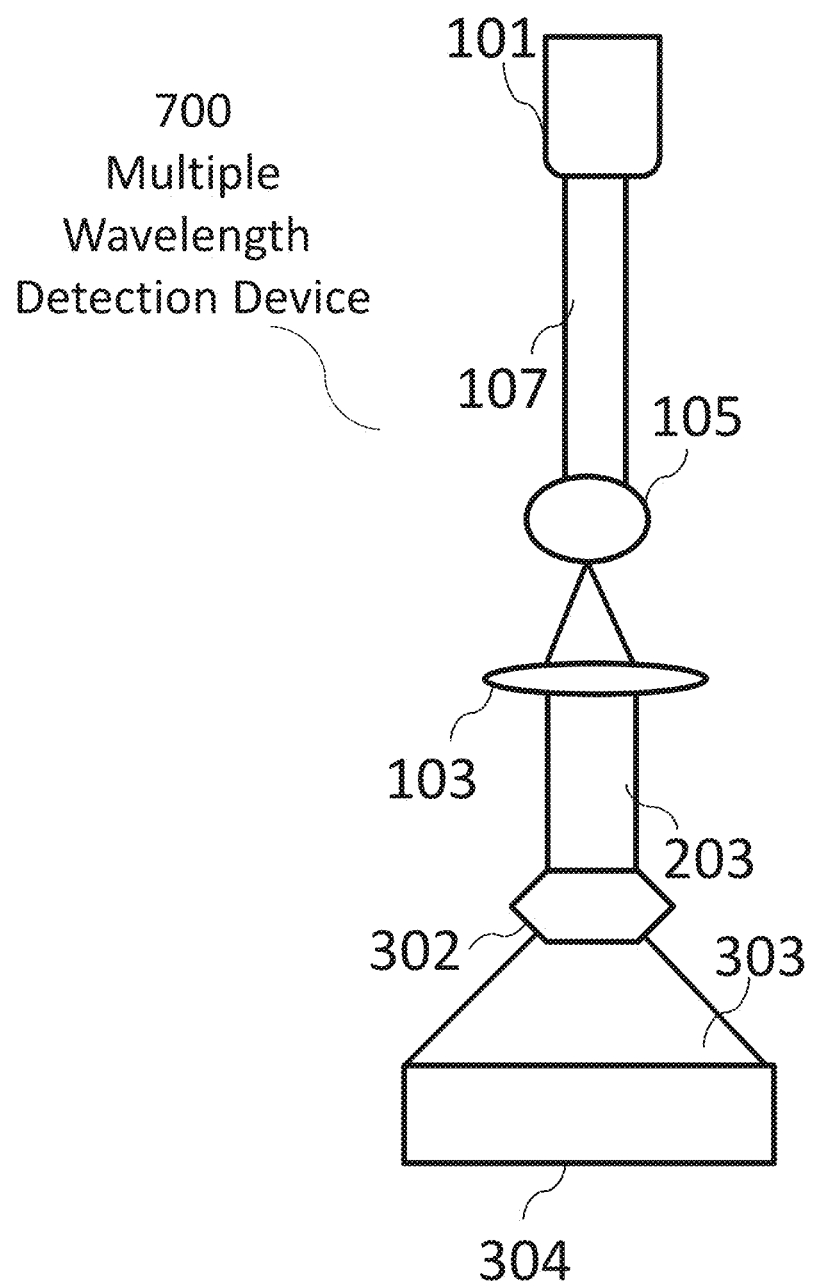

FIG. 21 An exemplary hyperspectral imaging system comprising an exemplary optics system, a multiple wavelength detection device. This system may generate an unmixed color image of a target by using an exemplary image forming system comprising features disclosed, for example in FIGS. 22-23.

Figure 22:
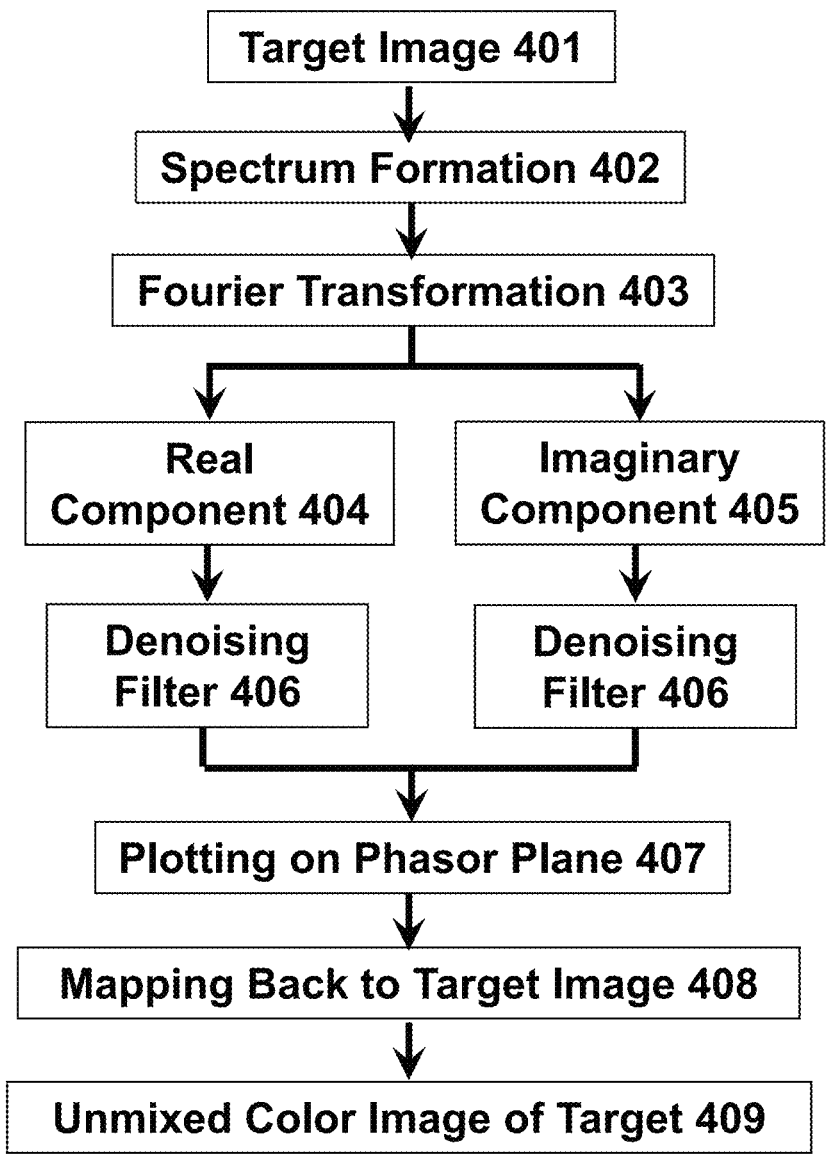

FIG. 22 Features of an exemplary image forming system that may be used to generate an unmixed color image of a target.

Figure 23:
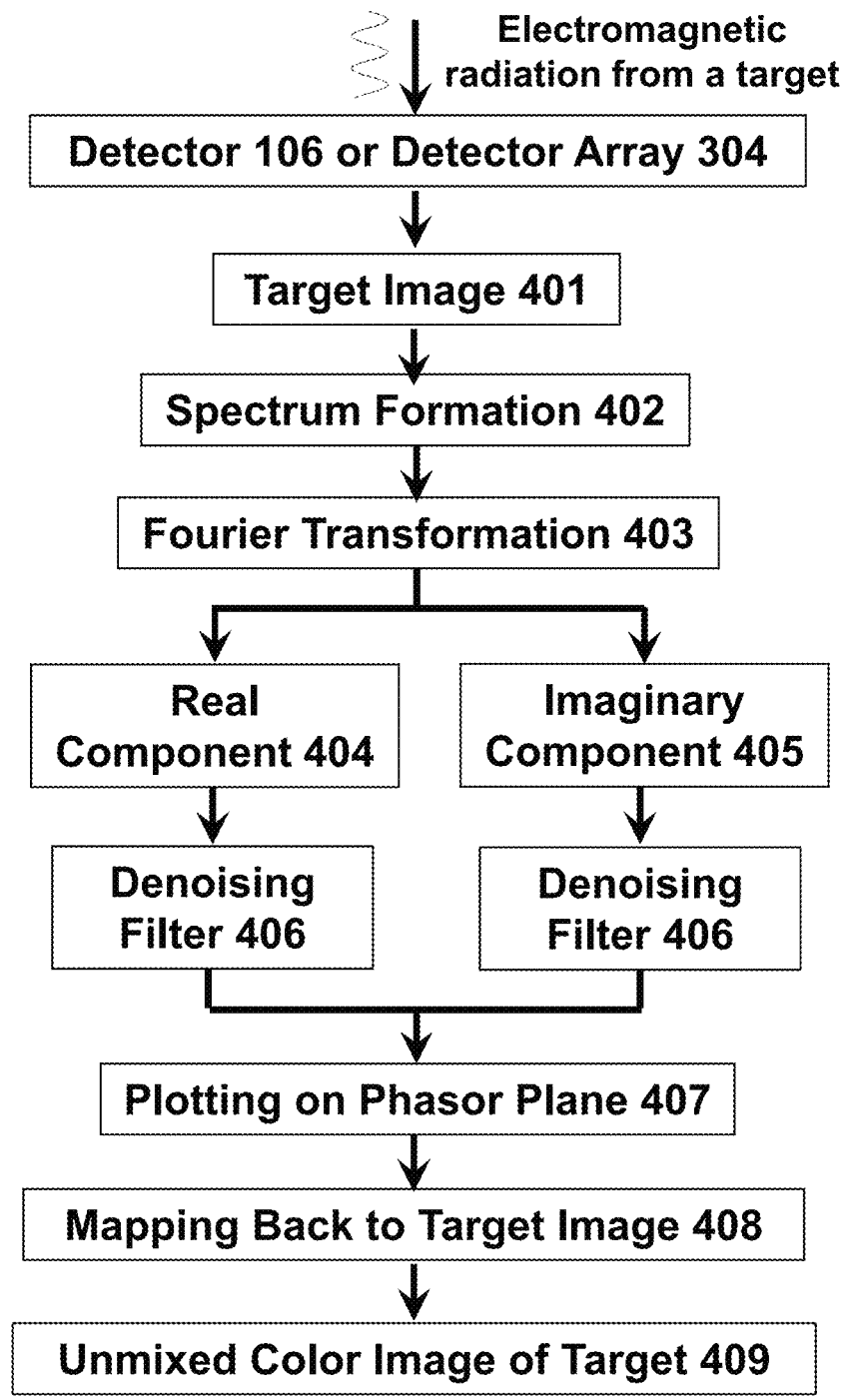

FIG. 23 Features of an exemplary image forming system that may be used to generate an unmixed color image of a target.

FIG. 24 Spectrally Encoded Enhanced Representations (SEER) conceptual representation. (a) Hyperspectral Fluorescence Image Data. A multispectral fluorescent dataset is acquired using a confocal instrument in spectral mode (32-channels). Here we show a Tg(ubi:Zebrabow) dataset where cells contain a stochastic combination of cyan, yellow and red fluorescent proteins. (b) Raw Spectra. Average spectra within six regions of interest (colored boxes in a) show the level of overlap resulting in the sample. (c) Standard Visualization. Standard multispectral visualization approaches have limited contrast for spectrally similar fluorescence. (d) Raw Phasor. Spectra for each voxel within the dataset are represented as a two-dimensional histogram of their Sine and Cosine Fourier coefficients S and G, known as the phasor plot. (e) Denoised Phasor. Spatially lossless spectral denoising is performed in phasor space to improve signal. (f) Reference Map. SEER provides a choice of several color reference maps that encode positions on the phasor into predetermined color palettes. The reference map used here (magenta selection) is designed to enhance smaller spectral differences in the dataset. (g) Contrast Modalities. Multiple contrast modalities allow for improved visualization of data based on the phasor spectra distribution, focusing the reference map on the most frequent spectrum, on the statistical spectral center of mass of the data (magenta selection), or scaling the map to the distribution. (h) Color Remapping. Color is assigned to the image utilizing the chosen SEER reference map and contrast modality. (i) Spectrally Encoded Enhanced Representations (SEER). Nearly indistinguishable spectra are depicted with improved contrast, while more separated spectra are still rendered distinctly.

FIG. 25 Spectrally Encoded Enhanced Representation (SEER) designs. A set of Standard Reference Maps and their corresponding result on a Simulated Hyperspectral Test Chart (SHTC) designed to provide a gradient of spectral overlaps between spectra. (a) The Standard phasor plot with corresponding average grayscale image provides the positional information of the spectra on the phasor plot. The phasor position is associated to a color in the rendering according to a set of Standard Reference Maps, each highlighting a different property of the dataset. (b) The angular map enhances spectral phase differences by linking color to changes in angle (in this case, with respect to origin). This map enhances changes in maximum emission wavelength, as phase position in the plot is most sensitive to this feature, and largely agnostic to changes in intensity. (c) The radial map, instead, focuses mainly on intensity changes, as a decrease in the signal to noise generally results in shifts towards the origin on the phasor plot. As a result, this map highlights spectral amplitude and magnitude, and is mostly insensitive to wavelength changes for the same spectrum. (d) The gradient ascent map enhances spectral differences, especially within the higher intensity regions in the specimen. This combination is achieved by adding a brightness component to the color palette. Darker hues are localized in the center of the map, where lower image intensities are plotted. (e) The gradient descent map improves the rendering of subtle differences in wavelength. Colorbars for b,c,d,e represent the main wavelength associated to one color in nanometers. (f) The tensor map provides insights in statistical changes of spectral populations in the image. This visualization acts as a spectral edge detection on the image and can simplify identification of spectrally different and infrequent areas of the sample such as the center of the SHTC. Colorbar represents the normalized relative gradient of counts.

FIG. 26 Enhanced contrast modalities. For each SEER standard reference map design, four different modes can provide improved contrast during visualization. As a reference we use the gradient descent map applied on a Simulated Hyperspectral Test Chart (SHTC). (a) Standard mode is the standard map reference. It covers the entire phasor plot circle, centering on the origin and anchoring on the circumference. The color palette is constant across samples, simplifying spectral comparisons between datasets (b) Scaled mode adapts the gradient descent map range to the values of the dataset, effectively performing a linear contrast stretching. In this process the extremities of the map are scaled to wrap around the phasor representation of the viewed dataset, resulting in the largest shift in the color palette for the phase and modulation range in a dataset. (c) Max Morph mode shifts the map center to the maximum of the phasor histogram. The boundaries of the reference map are kept anchored to the phasor circle, while the colors inside the plot are warped. The maximum of the phasor plot represents the most frequent spectrum in the dataset. This visualization modality remaps the color palette with respect to the most recurring spectrum, allowing insights on the distribution of spectra inside the sample. (d) Mass Morph mode, instead, uses the histogram counts to calculate a weighted average of the phasor coordinates and uses this color-frequency center of mass as a new center for the SEER map. The color palette now maximizes the palette color differences between spectra in the sample.

Figure 27D:
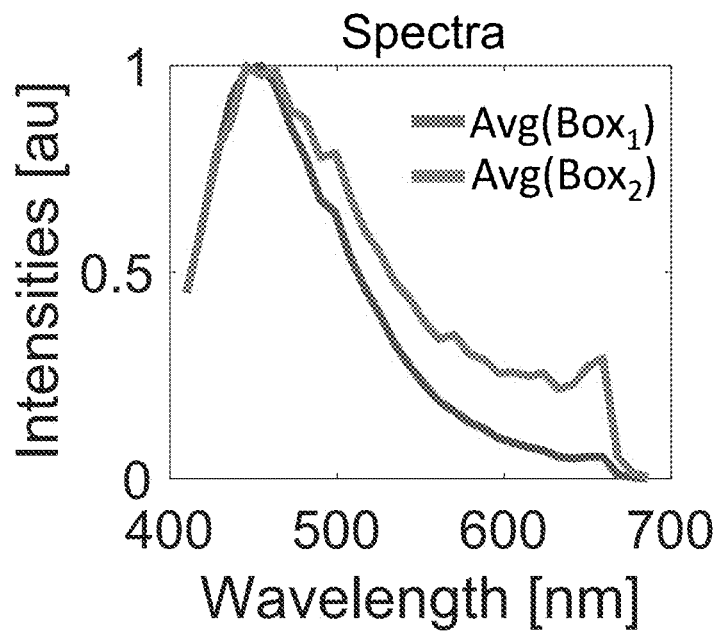
Figure 27E:
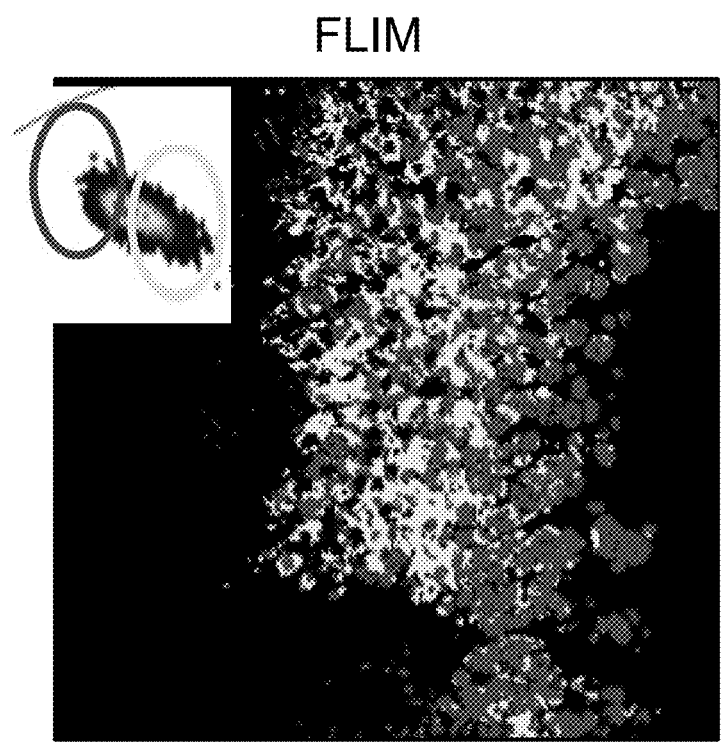

FIG. 27 Autofluorescence visualization comparison for unlabeled freshly isolated mouse tracheal explant. The sample was imaged using multi-spectral two-photon microscopy (740 nm excitation, 32 wavelength bins, 8.9 nm bandwidth, 410-695 nm detection) to collect the fluorescence of intrinsic molecules including folic acid, retinoids and NADH in its free and bound states. These intrinsic molecules have been used as reporters for metabolic activity in tissues by measuring their fluorescence lifetime, instead of wavelength, due to their closely overlapping emission spectra. This overlap increases the difficulty in distinguishing spectral changes when utilizing a (a) TrueColor image display (Zen Software, Zeiss, Germany) (b) The gradient descent morphed map shows differences between apical and basal layers, suggesting different metabolic activities of cells based on the distance from the tracheal airway. Cells on the apical and basal layer (dashed boxes) are rendered with distinct color groups. Colorbar represents the main wavelength associated to one color in nanometers. (c) The tensor map image provides an insight of statistics in the spectral dataset, associating image pixels' colors with corresponding gradient of phasor counts for pixels with similar spectra. The spectral counts gradients in this sample highlights the presence of fibers and edges of single cells. Colorbar represents the normalized relative gradient of counts. (d) Average spectra for the cells in dashed boxes (1 and 2 in panel c) show a blue spectral shift in the direction of the apical layer. (e) Fluorescence Lifetime Image Microscopy (FLIM) of the sample, acquired using a frequency domain detector validates the interpretation from panel b, Gradient Descent Map, where cells in the apical layer exhibit a more Oxidative Phosphorylation phenotype (longer lifetime in red) compared to cells in the basal layer (shorter lifetime in yellow) with a more Glycolytic phenotype. The selections correspond to areas selected in phasor FLIM analysis (e, top left inset, red and yellow selections) based on the relative phasor coordinates of NAD+/NADH lifetimes.

FIG. 28 Visualization of a single fluorescence label against multiple autofluorescences. Tg(fli1:mKO2) (pan-endothelial fluorescent protein label) zebrafish was imaged with intrinsic signal arising from the yolk and xanthophores (pigment cells). Live imaging was performed using a multi-spectral confocal (32 channels) fluorescence microscope with 488 nm excitation. The endothelial mKO2 signal is difficult to distinguish from intrinsic signals in a (a) maximum intensity projection TrueColor 32 channels Image display (Bitplane Imaris, Switzerland). The SEER angular map highlights changes in spectral phase, rendering them with different colors (reference map, bottom right of each panel). (b) Here we apply the angular map with scaled mode on the full volume. Previously indistinguishable spectral differences (boxes 1, 2, 3 in panel a) are now easy to visually separate. Colorbar represents the main wavelength associated to one color in nanometers. (c-h) Zoomed-in views of regions 1-3 (from a) visualized in TrueColor (c, e, g) and with SEER (d, f, h) highlight the differentiation of the pan-endothelial label (yellow) distinctly from pigment cells (magenta). The improved sensitivity of SEER further distinguishes different sources of autofluorescence arising from yolk (blue and cyan) and pigments.

FIG. 29 Triple label fluorescence visualization. Zebrafish embryo Tg(kdrl:eGFP); Gt(desmin-Citrine);Tg(ubiq:H2B-Cerulean) labelling respectively vasculature, muscle and nuclei. Live imaging with a multi-spectral confocal microscope (32-channels) using 458 nm excitation. Single plane slices of the tiled volume are rendered with TrueColor and SEER maps. (a) TrueColor image display (Zen, Zeiss, Germany). (b) Angular map in center of mass morph mode improves contrast by distinguishable colors. The resulting visualization enhances the spatial localization of fluorophores in the sample. (c) Gradient Descent map in max morph mode centers the color palette on the most frequent spectrum in the sample, highlighting the spectral changes relative to it. In this sample, the presence of skin pigment cells (green) is enhanced. 3D visualization of SEER maintains these enhancement properties. Colorbars represent the main wavelength associated to one color in nanometers. Here we show (d, e, f) TrueColor 32 channels Maximum Intensity Projections (MIP) of different sections of the specimen rendered in TrueColor, Angular map center of mass mode and Gradient Descent max mode. The selected views highlight SEER's performance in the (d) overview of somites, (e) zoom-in of somite boundary, and (f) lateral view of vascular system.

FIG. 30 Visualization of combinatorial expression on Zebrabow samples. Maximum Intensity Projection renderings of Tg(ubi:Zebrabow) muscle acquired live in multi-spectral confocal mode with 458 nm excitation. (a) The elicited signal (e.g. white arrows) is difficult to interpret in the TrueColor Image display (Zen Software, Zeiss, Germany). (b) Discerning spectral differences is increasingly simpler with Gradient Descent map scaled to intensities, while compromising on the brightness of the image. (c) Gradient Descent and (d) Gradient Ascent RGB Masks in scale mode show the color values assigned to each pixel and greatly improve the visual separation of recombined CFP, YFP and RFP labels. Colorbars represent the main wavelength associated to one color in nanometers.

Figures 31A, 31B:
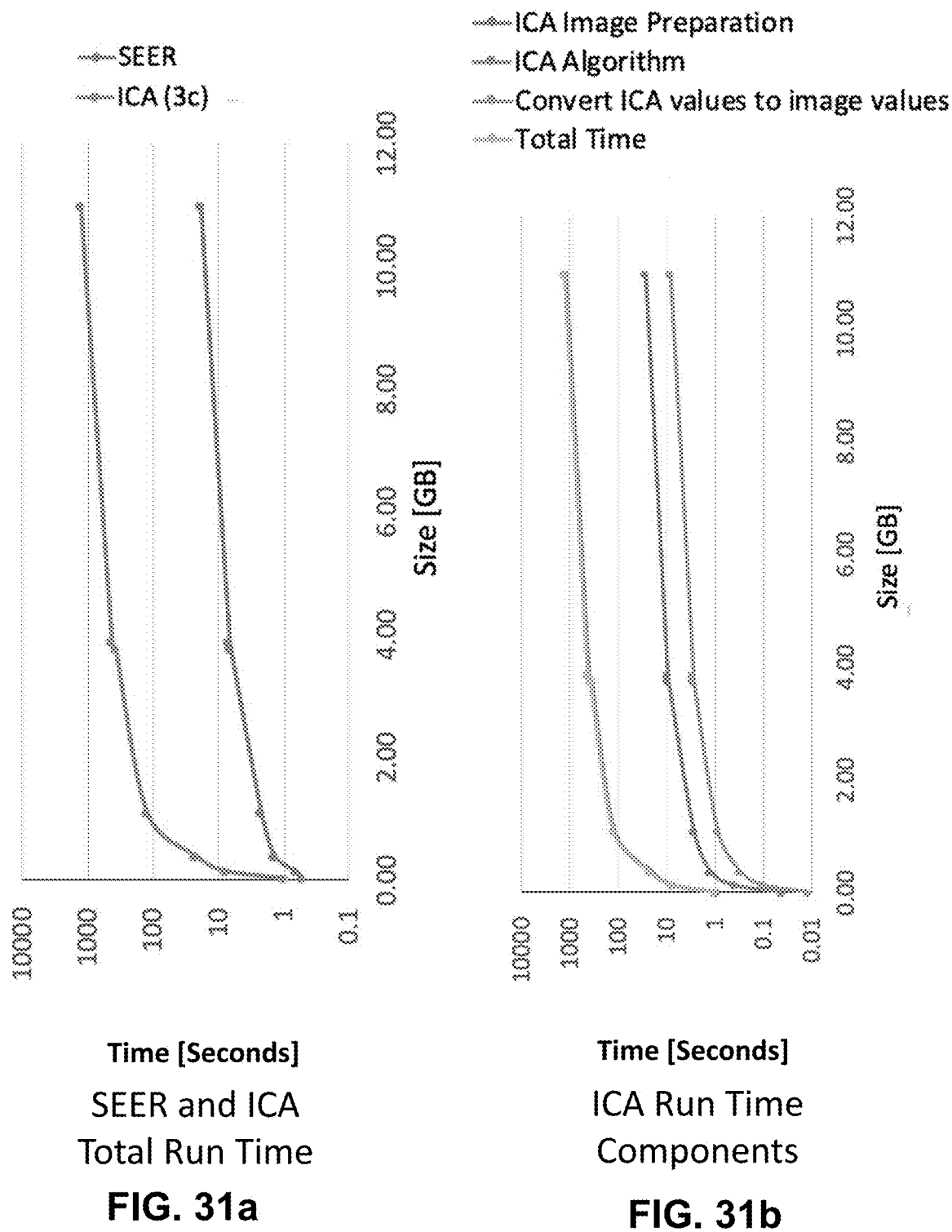
Figure 31C:
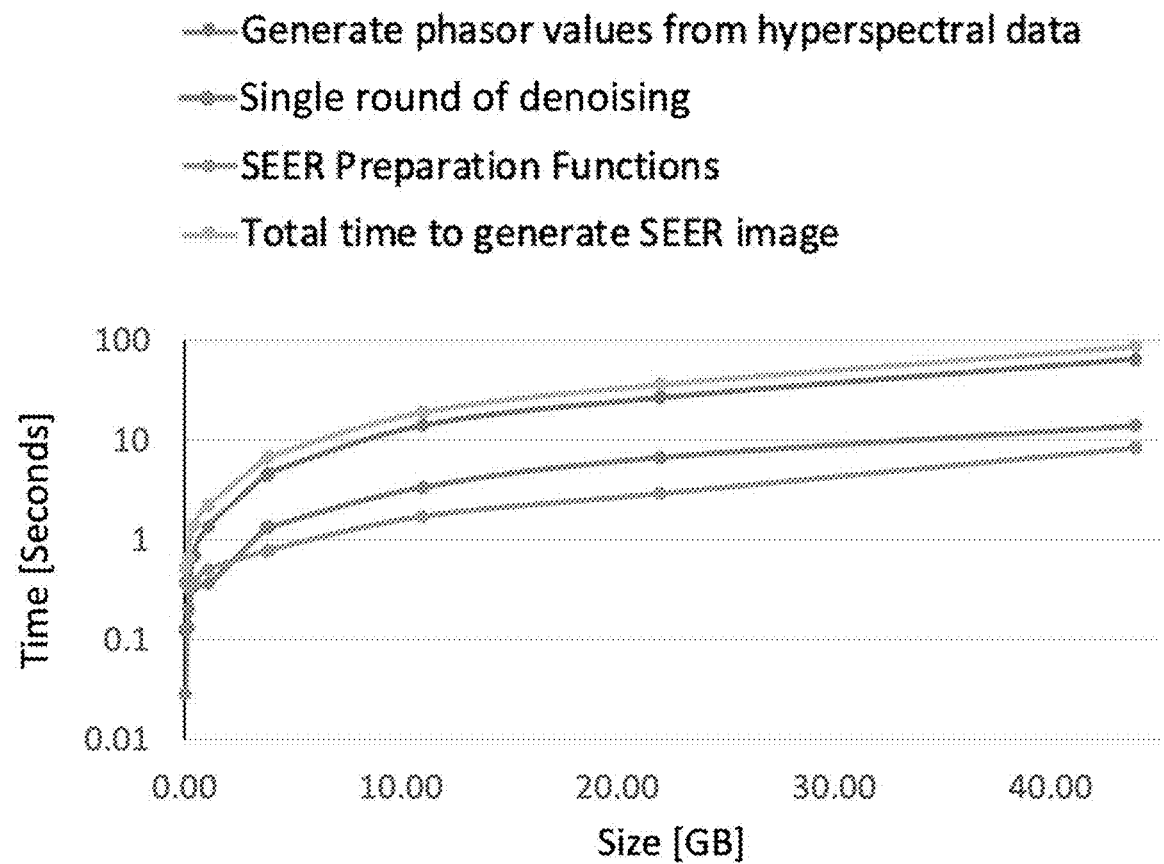

FIG. 31 Computational time comparison of SEER and ICA for different file sizes. (a) HySP and ICA run times (plot in log scale) were measured on a HP workstation with two 12 core CPUs, 128 GB RAM, and 1 TB SSD. SEER run times were measured within a modified version of the software. ICA run times were measured using a custom script and the FastICA submodule of the python module, scikit-learn. Timers using the perf_counter function within the python module, time, were placed around specific functions corresponding to the calculations required for the creation of SEER maps in HySP and extracting individual component outputs from the custom ICA script. Data size varies from 0.02-10.97 GB, with constant number of bands (32 bands, 410.5 nm to 694.9 nm with 8.9 nm bandwidth) corresponding to a range of $2.86 \cdot 10^5$-$1.83 \cdot 10^8$ spectra. ICA testing was limited to 10.97 GB maximum as for higher values the RAM requirements exceeded the 128 GB available on our workstation. (b) For the custom ICA script, timers were placed to measure the time to reshape the hyperspectral data for ICA input, to run the ICA algorithm, and to convert values of the ICA components into image intensity values, reaching minutes of computation at just 1.1 GB (plot in log scale). (c) For HySP, timers were placed to measure the generation of the phasor values from hyperspectral data, including initial calculations of the real and imaginary components (g and s) and creation of the phasor plot histogram. A timer was also placed around all preparatory functions required for on-the-fly creation of SEER maps. The more memory-efficient phasor process allowed us to compute datasets of size 0.02-43.9 GB, corresponding to a range of $2.86 \cdot 10^5$-$7.34 \cdot 10^8$ spectra (plot in log scale).

Figure 32A:
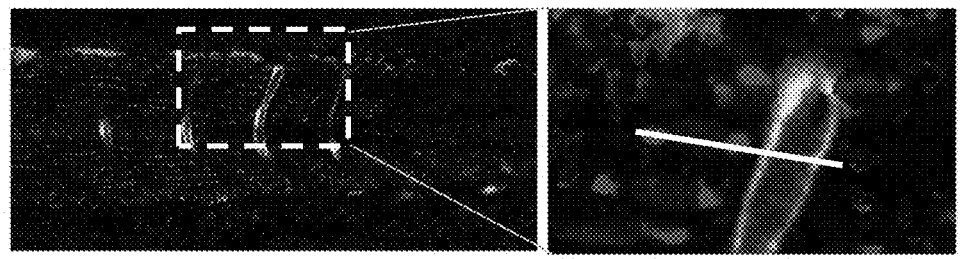
Figure 32D:
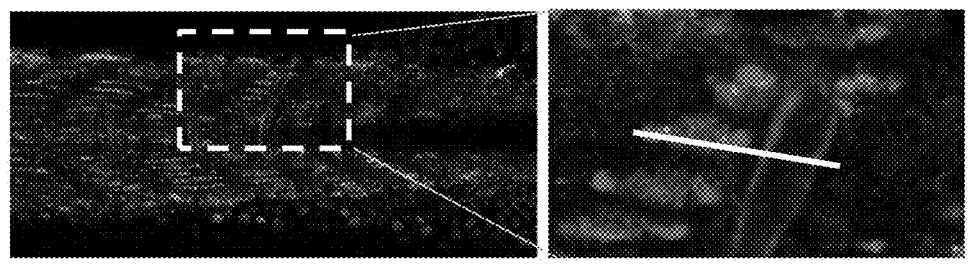
Figure 32G:
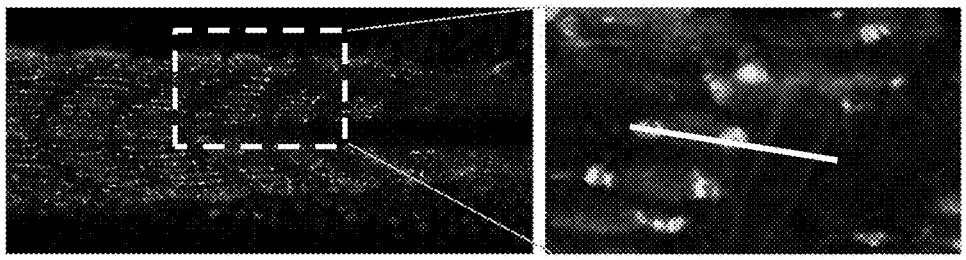

FIG. 32 Comparison of SEER with visualized HySP[1] results. Here we show a zebrafish embryo Tg(kdrl:eGFP); Gt(desmin-Citrine);Tg(ubiq:H2B-Cerulean) labelling respectively vasculature, muscle, and nuclei. Live imaging with a multi-spectral confocal microscope (32-channels) using 458 nm excitation. Single plane slices of the tiled volume are rendered with SEER maps (3 channel, RGB) and compared to rendering of the same dataset analyzed with HySP (here 5 channels). (a) Rendering of a 5 channel HySP analyzed dataset, the dashed box is expanded in the zoomed-in portion of panel a with its (b) line profile to the right along the solid line all 5 separate channels, eGFP, Citrine, Cerulean, Pigments and autofluorescence at 458 nm. (c) Visualization of the 5 channel dataset as a blended RGB, similarly to how it appears on a screen. The (d) morphed mode center of mass visualization shows patterns in accordance with HySP with a differently color coded (e) line profile along the solid line in panel d, which shows intensities in the 3 R,G,B channels of the image. The profiles of the single R,G,B do not match the unmixed HySP profiles in panel b. However, (f) color visualization of the same line plot (as R,G,B vectors), shows patterns in accordance to the on-screen visualization of HySP unmixed data. Similarly, (g) morphed mode max visualization shows an image in accordance to the rendered HySP analyzed data in panel a with its (h) line profile along the solid line of the zoomed-in portion of panel g being comparable to both the HySP 5 separate channels and the R,G,B profiles of the different morphed center of mass map in panel e. (i) The color on-display visualization of the RGB intensities in g reveals different color features as those of the HySP unmixed channels (panel b).

Figure 33:
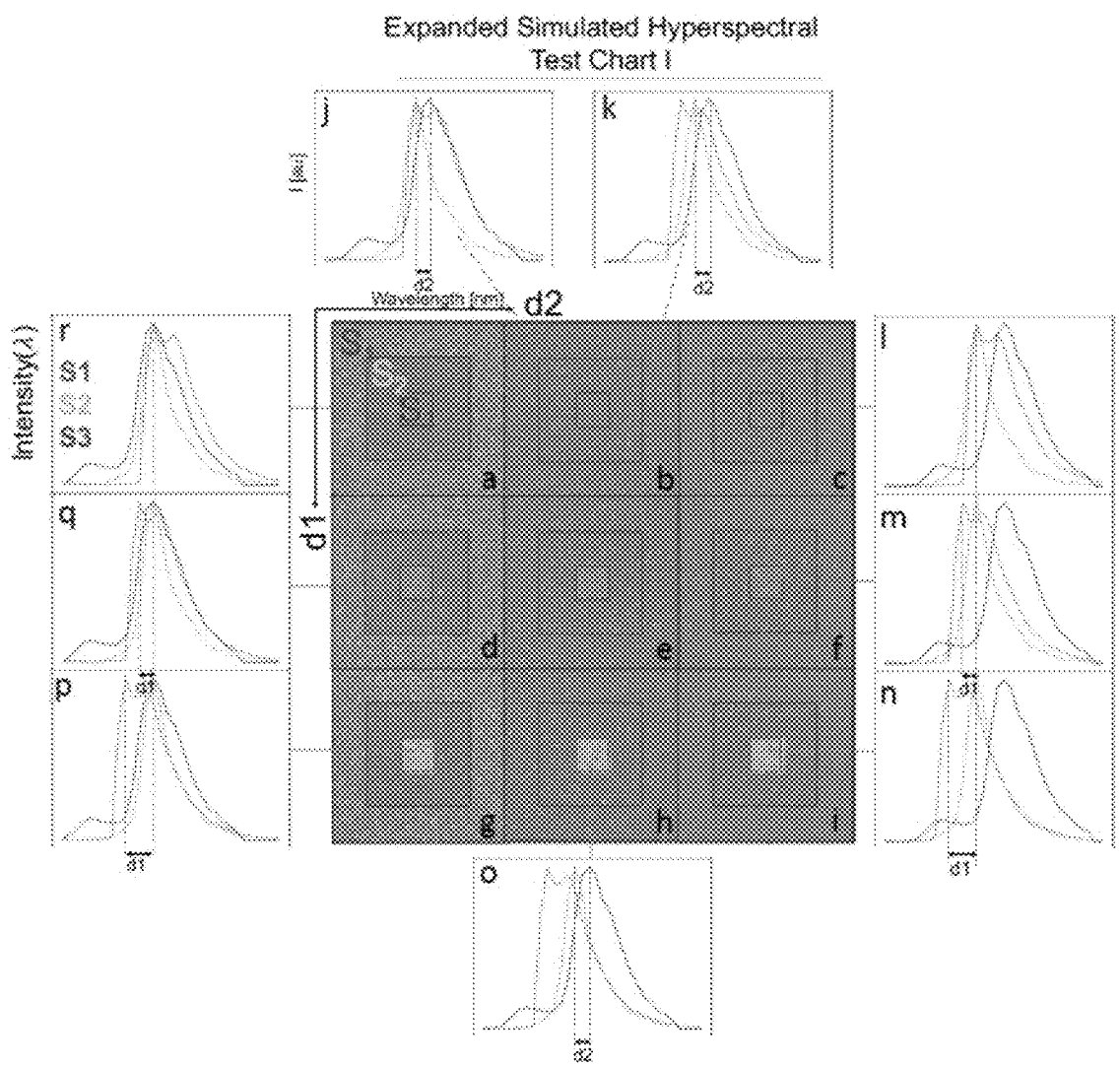
Figure 33S:
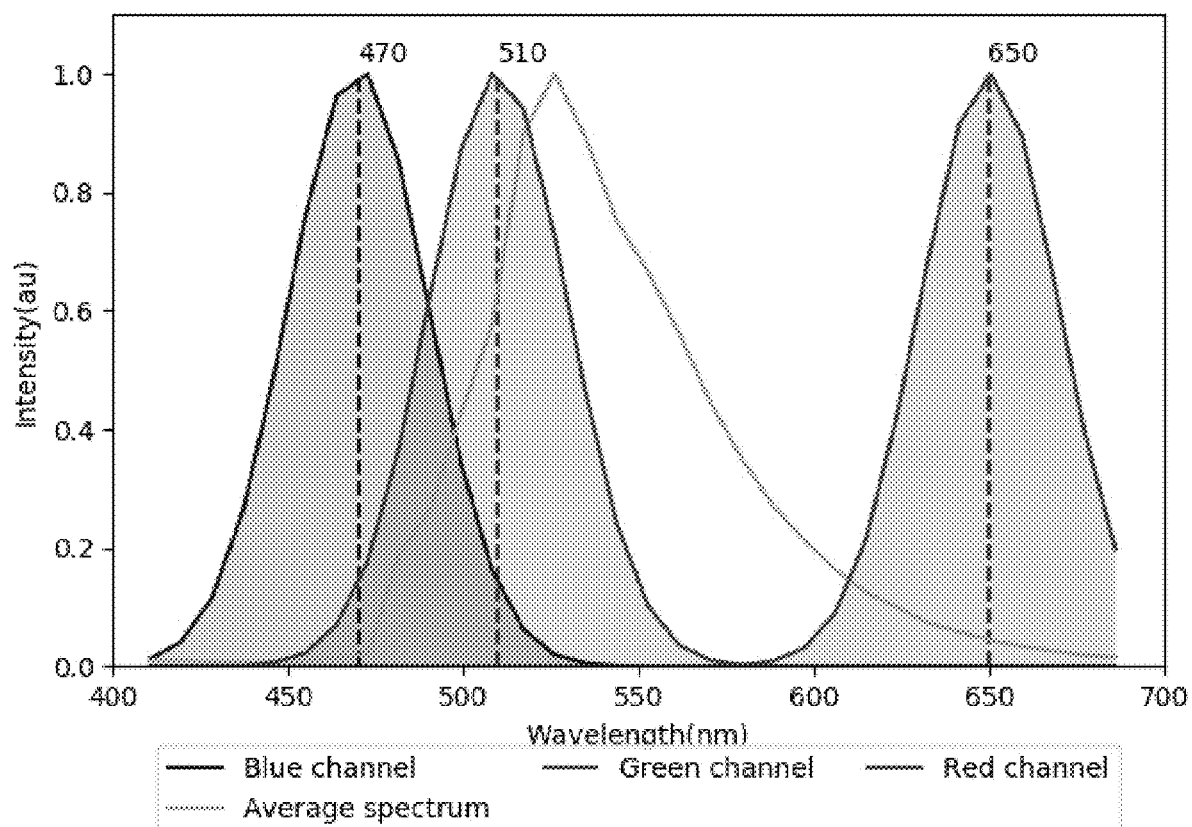

FIG. 33 Simulated Hyperspectral Test Chart I rendered in TrueColor shows nearly indistinguishable spectra. The simulation is represented here in "TrueColor RGB" (Methods). $S_1$, $S_2$, and $S_3$ spectra acquired respectively from CFP, YFP, RFP zebrafish embryos are used to generate a (a-i) 3-by-3 Simulated Hyperspectral Test Chart. In each panel (a-i) of the chart, three spectra ($S_1$ to $S_3$) are represented as concentric squares (see panel a) outer: S1—blue, intermediate: S2—yellow, middle: S3—red spectra respectively).

The spectrum $S_2$ (intermediate square in each panel) is kept unchanged in all panels. The maximum of spectrum $S_1$ is shifted by d1 (−2 wavelength bins, −17.8 nm steps) with respect to the fixed spectrum $S_2$ maximum. $S_3$ max value is shifted by d2 (2 wavelength bins, 17.8 nm steps) respect to $S_2$ maximum. The changes are applied for 2 steps along the vertical (d1) and horizontal (d2) axis of the center panel assembly (a-i), starting from d1=d2=0 (panel a). The spectra utilized in each panel (a-i) are represented in panels j-r. Each plot (j-r) represents the averaged normalized $S_1$-$S_3$ spectra as 32 wavelength bins, 8.9 nm bandwidth, 410-695 nm detection. Each panel has different visual contrast but is generally difficult to distinguish by eye due to significant overlap in spectra. (s) R,G,B channels used in the Gaussian Kernel for True color representation (red, green, blue lines) and average spectrum for panels (a-i) (yellow line) for reference.

Figure 34:
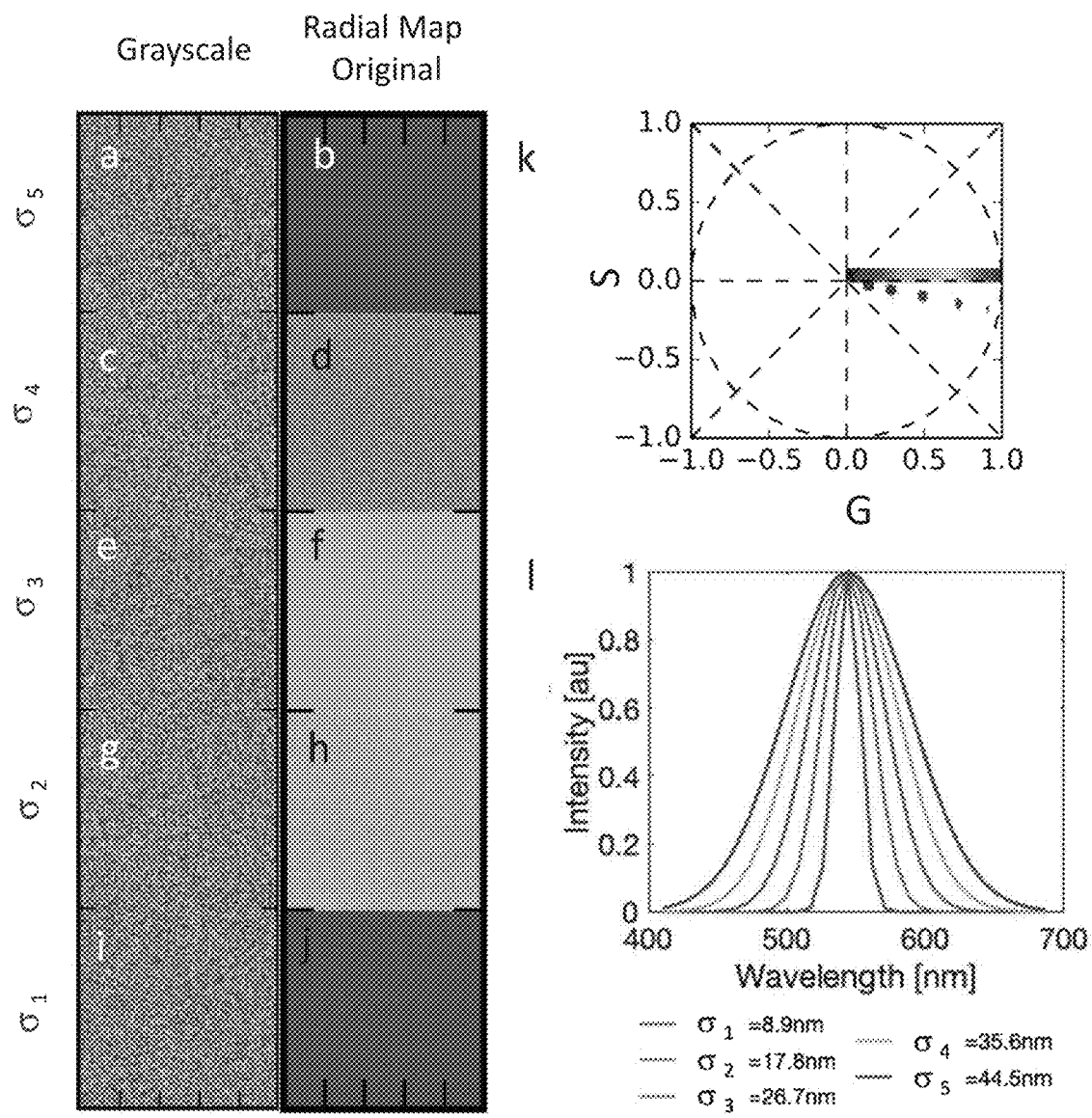

FIG. 34 Effect of spectral shape with constant intensities on radial map in absence of background. This simulation shows spectra with Gaussian shape and different standard deviations on using 32 wavelength bins, 8.9 nm bandwidth, and a 410-695 nm range in the absence of background. All spectra are centered on 543 nm (channel 16) and the integral of intensities is kept constant. (a-j) For each value of the standard deviation, a grayscale image and SEER visualization are presented. The map used is the Radial map (k) centered on the origin and extended to the border of the phasor plot. A color reference is added in the phasor plot (l). Clusters on the phasor plot are distributed along the radius, with distance from the origin inversely proportional to the standard deviation.

Figure 35:
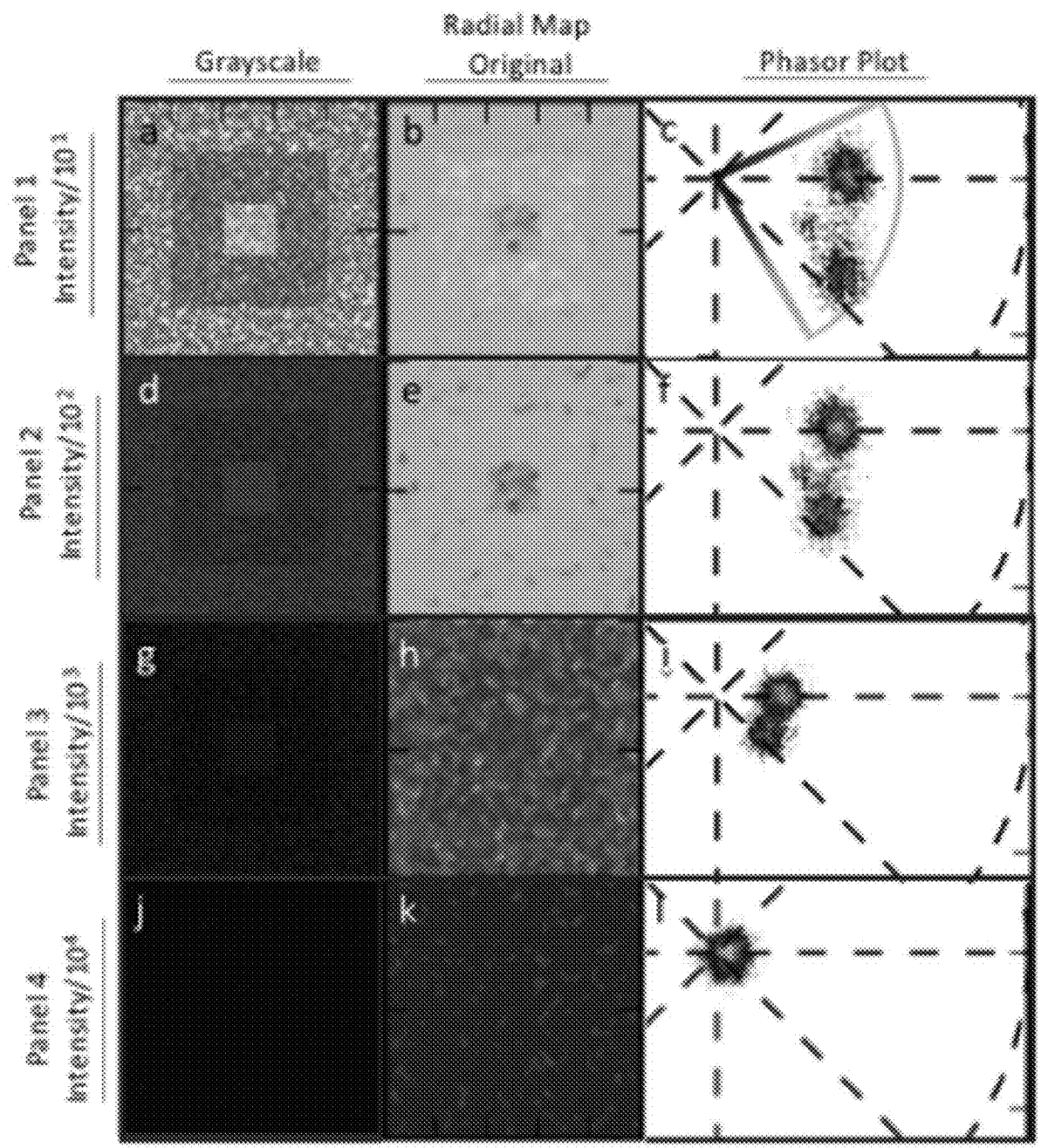
Figure 35M:
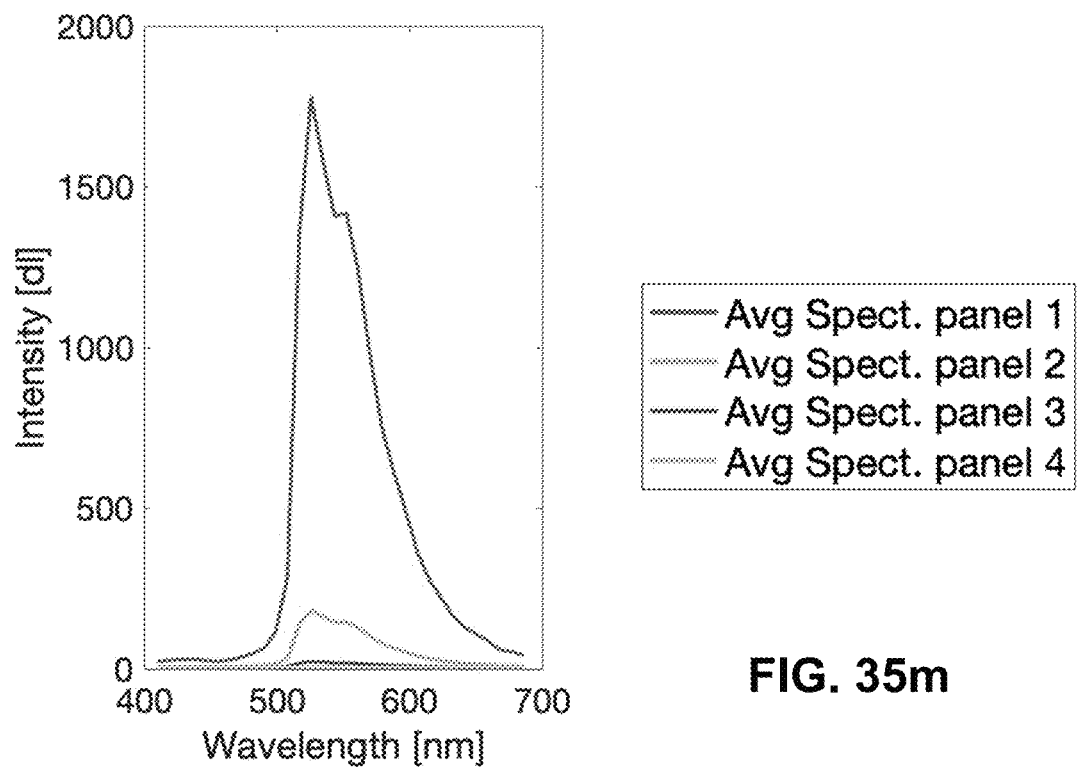
Figure 35N:
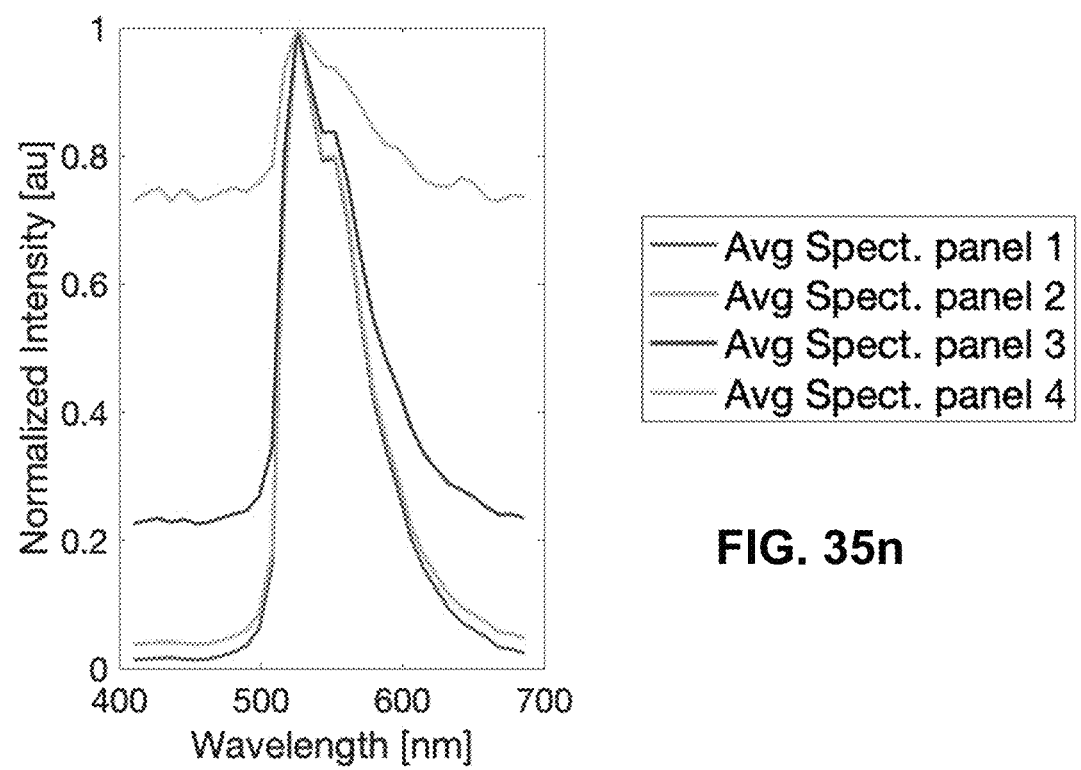

FIG. 35 Effect of spectrum intensity in presence of background on radial map. In this simulation, the first panel (top-left) of the Simulated Hyperspectral Test Chart (FIG. 33) is reduced in intensity by a factor of $10^1$-$10^4$ (panel 1-4 respectively) in the presence of a constant background. Background with an average intensity of 5 digital levels was generated in Matlab; poissonian noise was added using the poissrnd( ) function. Grayscale images (a,d,g,j) are scaled by (a) factor of 10, (d) factor of $10^2$, (g) factor of $10^3$, (j) factor of $10^4$. Radial map (original) visualization shows a shift of panel colors toward blue with the decreasing intensities (b,e,h,k). The phasor plots (c,f,i,l) (harmonic n=2) show a radial shift of the clusters toward the origin. Radial map reference is added in (c). (m) Absolute intensities plot shows the average spectrum for the four panels, maximum peak values are 1780, 182, 23, 7 digital levels (panel 1-4 respectively). The normalized intensity spectra (n) show an apparent broadening of the shape of spectra with the decreasing signal-to-noise.

Figure 36A:
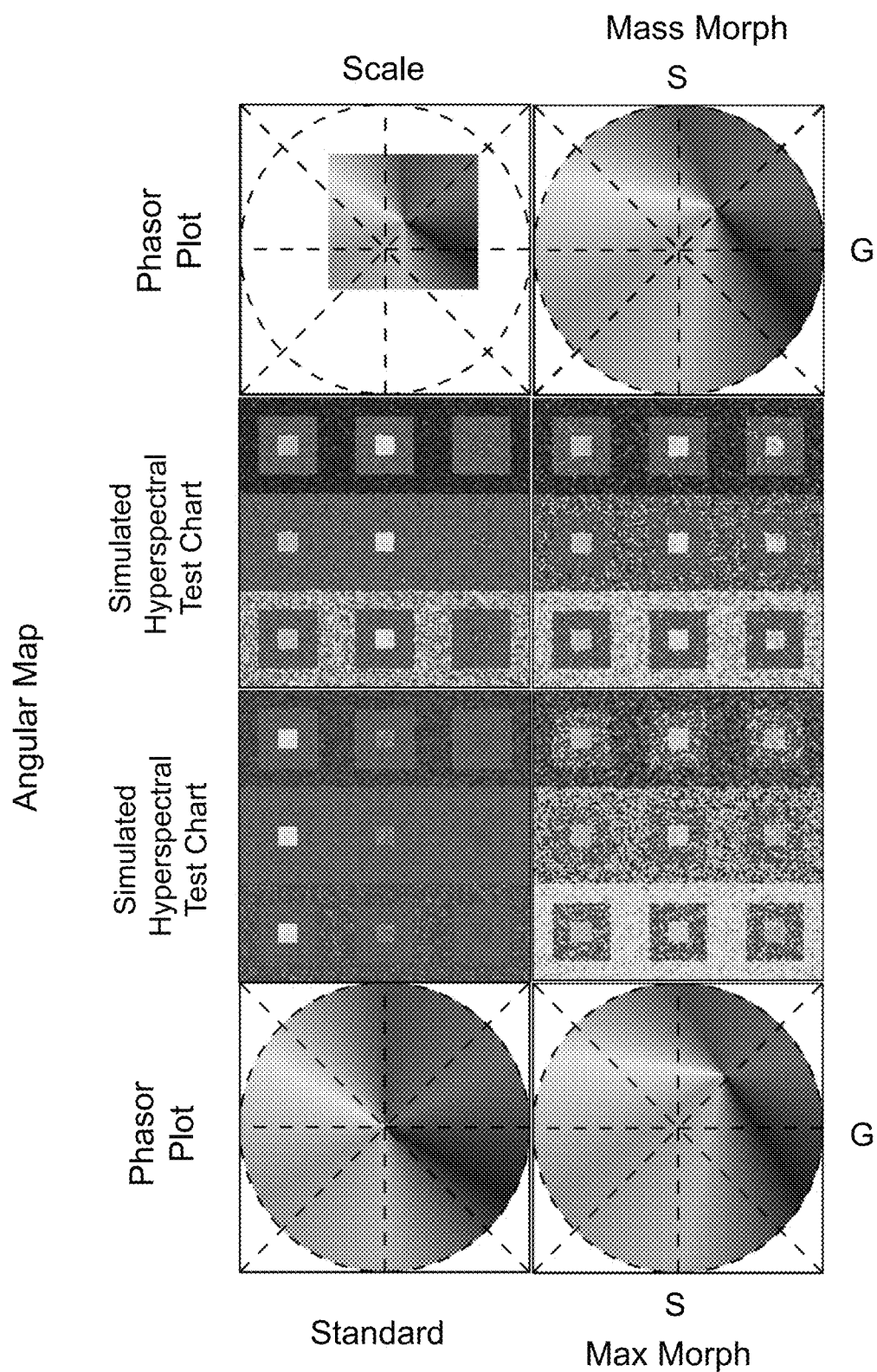
Figure 36B:
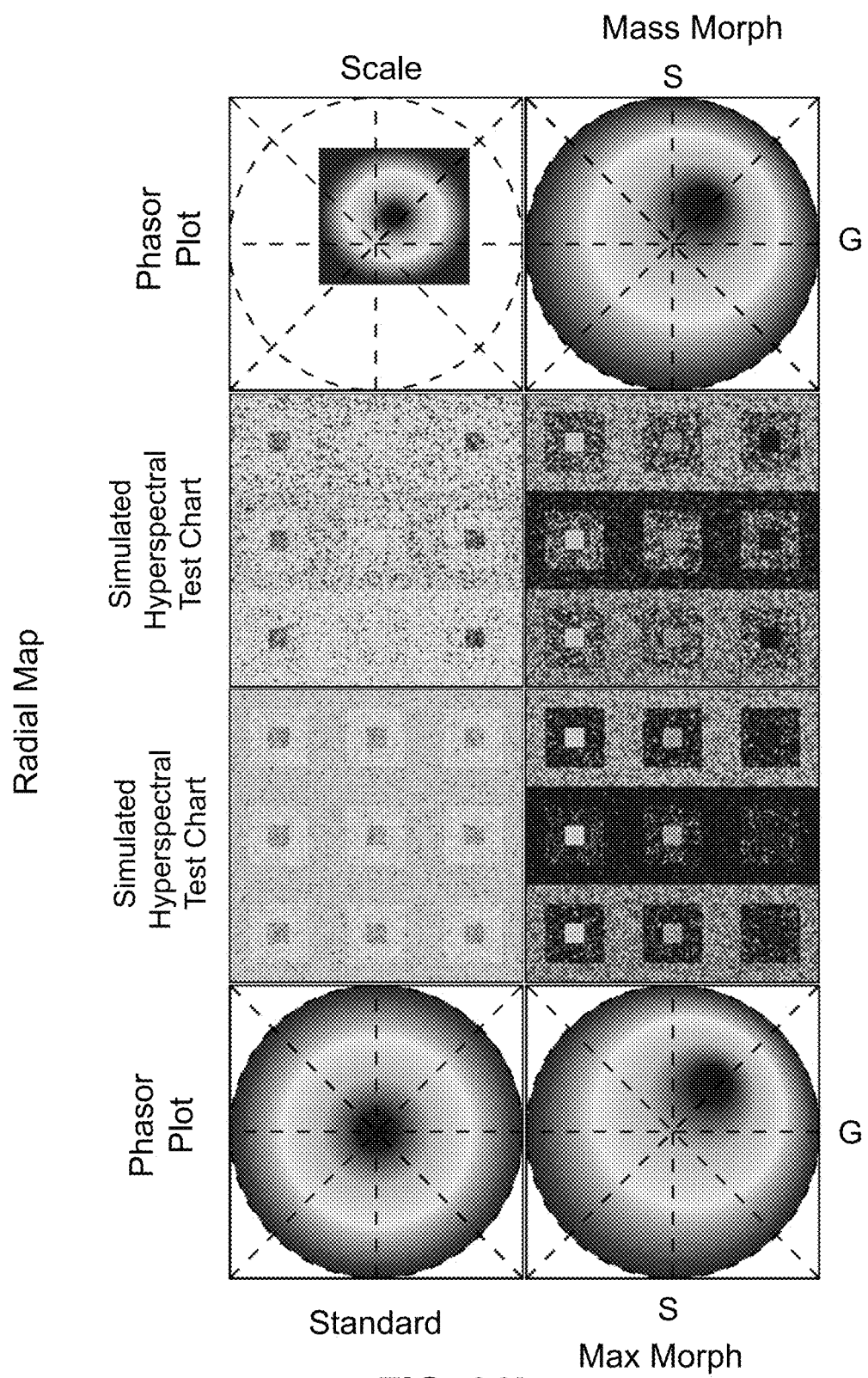

FIG. 36 Radial and Angular reference map designs and modes differentiate nearly indistinguishable spectra (Simulated Hyperspectral Test Chart 1) (FIG. 33). We present 4 different modes that can be applied for each map. Here second harmonic is utilized for the calculations. Angular map (a) and Radial map (b) in Standard mode, Scaled mode, Max Morph mode and Mass Morph mode. In Standard mode, the reference map is centered at the origin and limited by the phasor unit circle. In Scaled mode, the reference map adapts to the phasor plot histogram, changing its coordinates to wrap around the edges of the phasor clusters and enhancing contrast of the chosen map properties. In Max Morph mode, the map is centered on the spectrum with highest frequency of appearance in the phasor histogram. This mode improves sensitivity by using statistical frequency bias. In Mass Morph mode, the map is centered on the weighted center of the phasor, enhancing sensitivity for multiple small spectra. Visualizations are presented after 1× spectral denoising.

Figure 37A:
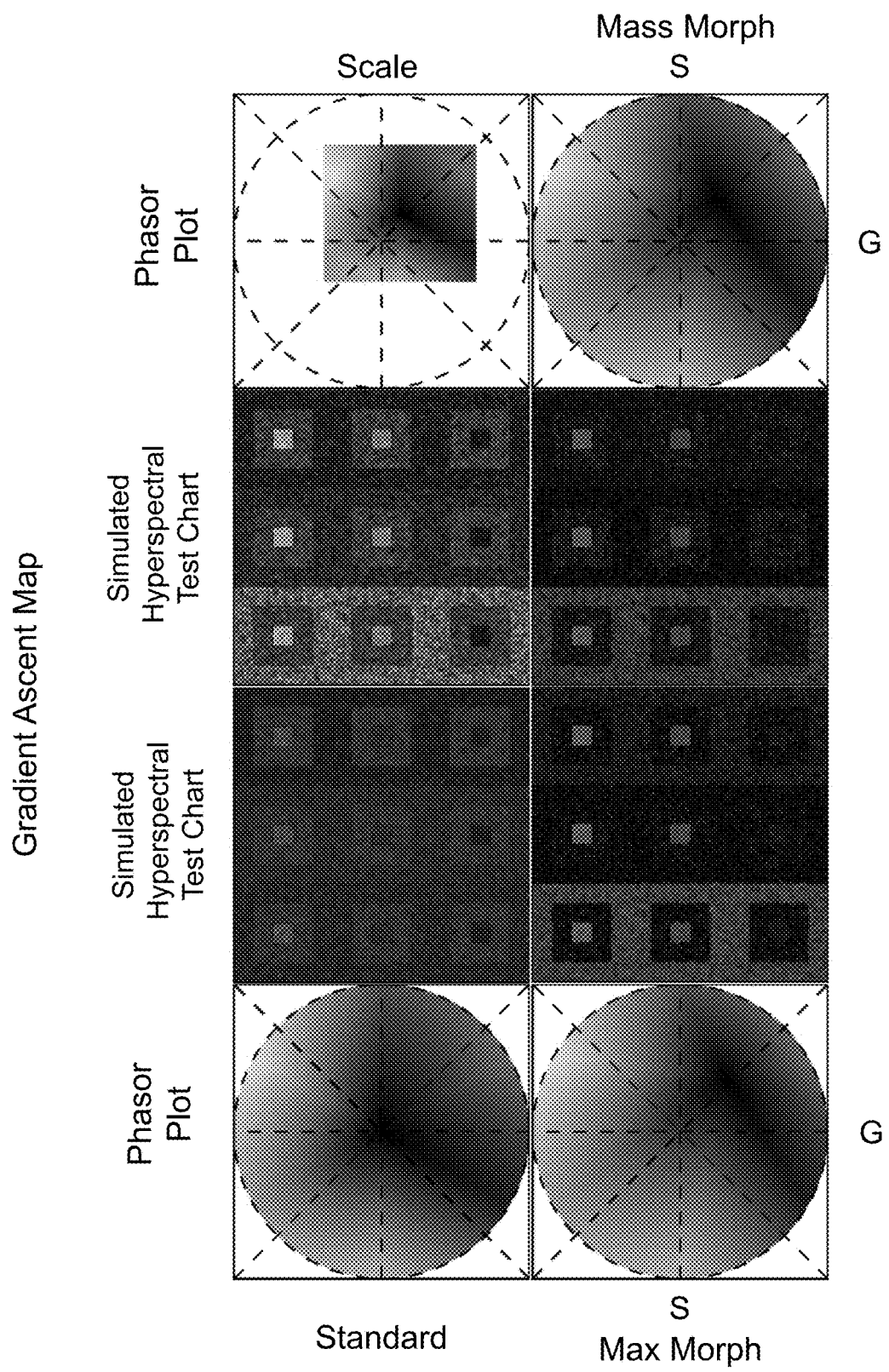
Figure 37B:
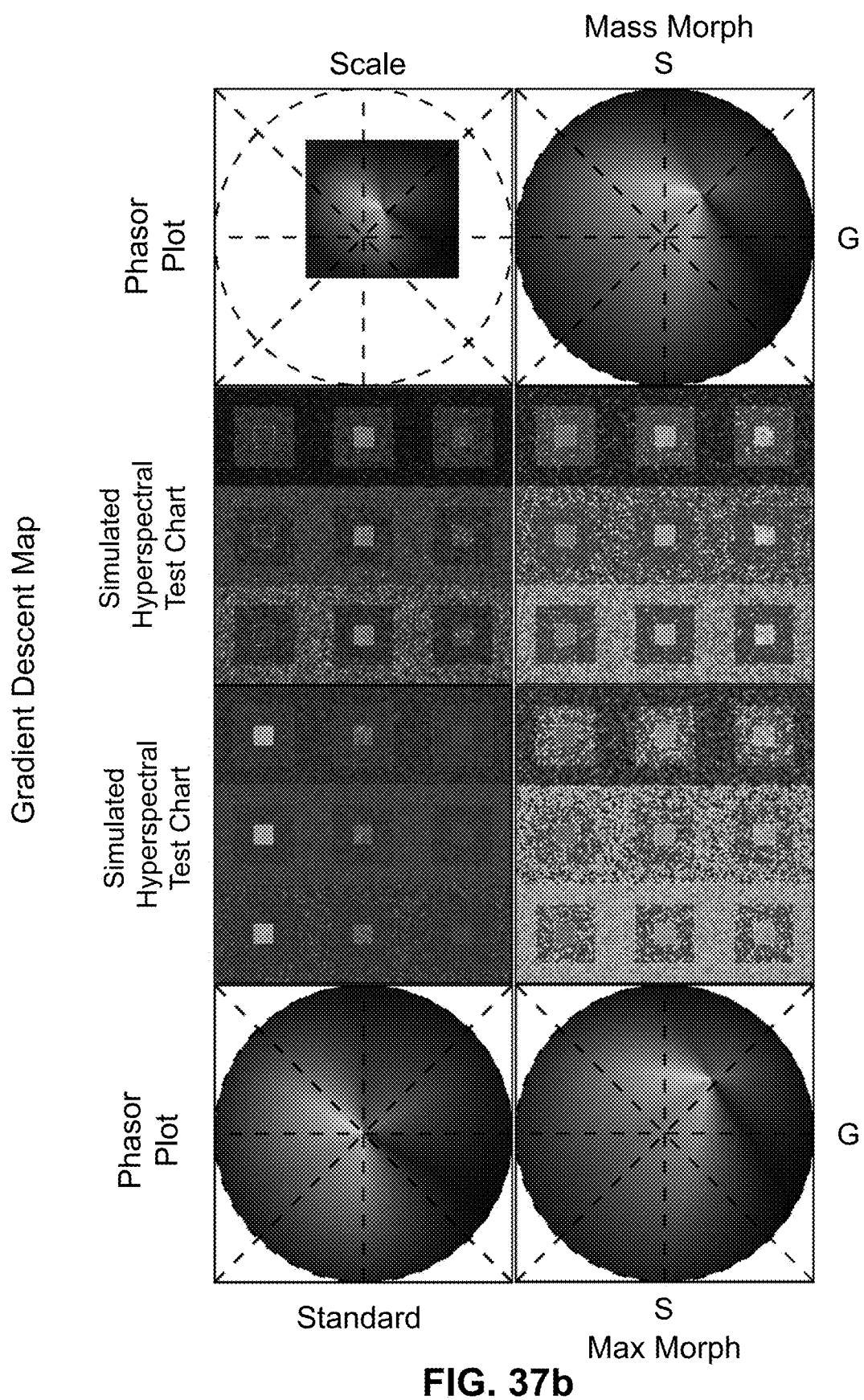

FIG. 37 Gradient Ascent and Descent reference map designs and modes differentiate nearly indistinguishable spectra (FIG. 33). Here second harmonic is utilized for SEER. Gradient Ascent map (a) and Gradient Descent map (b) in Standard mode, Scaled mode, Max Morph mode and Mass Morph mode. The two maps place a focus on very different (Ascent) and similar (Descent) spectra by fading the reference map to dark at the center and edges of the phasor plot unit circle respectively. Visualizations are presented after 1× spectral denoising.

Figure 38:
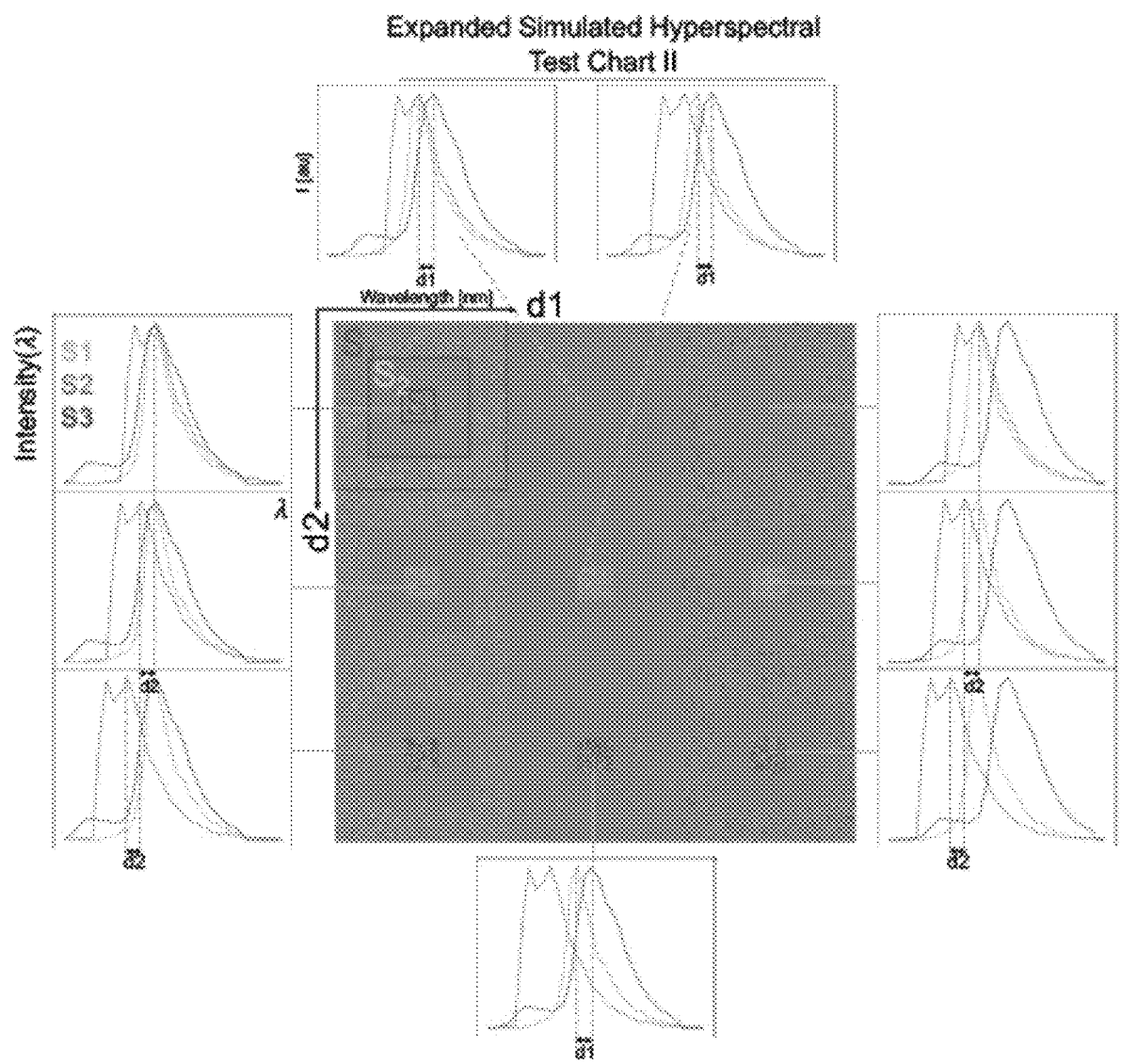

FIG. 38 Simulated Hyperspectral Test Chart II and its standard overlapping spectra. Simulated SHTC II was generated from the same zebrafish embryo datasets and same design used in SHTC1 (FIG. 33) utilizing CFP, YFP and RFP labeled samples and 3-by-3 block chart, with each block subdivided into 3 regions corresponding to spectra $S_1$, $S_2$, and $S_3$. The aim is to test scenarios with less overlapping spectra. We change the shifting distance in this simulation to be d1 (−3 wavelength bins, −26.7 nm steps) and d2 (3 wavelength bins, 26.7 nm steps). The channels used in the Gaussian Kernel for TrueColor RGB representation here were 650 nm, 510 nm, 470 nm which respectively represent R, G, B. The concentric squares in the lower right side of the simulation are separated by a peak-to-peak distance of 53.6 nm, with outer and inner concentric squares well separated by 106.8 nm. This distance is similar to the emission gap between CFP (475 nm EM) and tdTomato (581 nm). Under these spectral conditions most methods are expected to perform well.

Figure 39A:
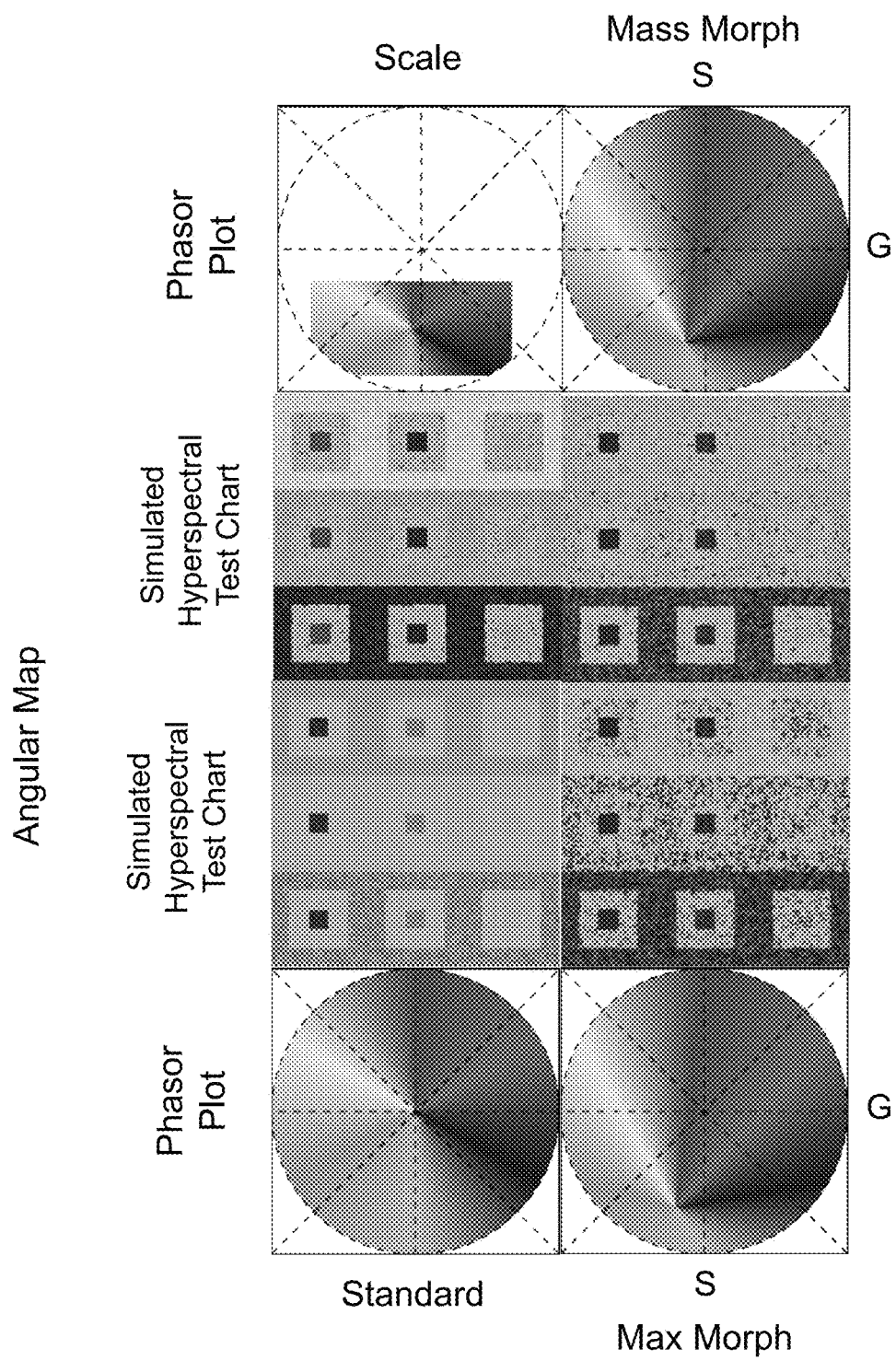
Figure 39B:
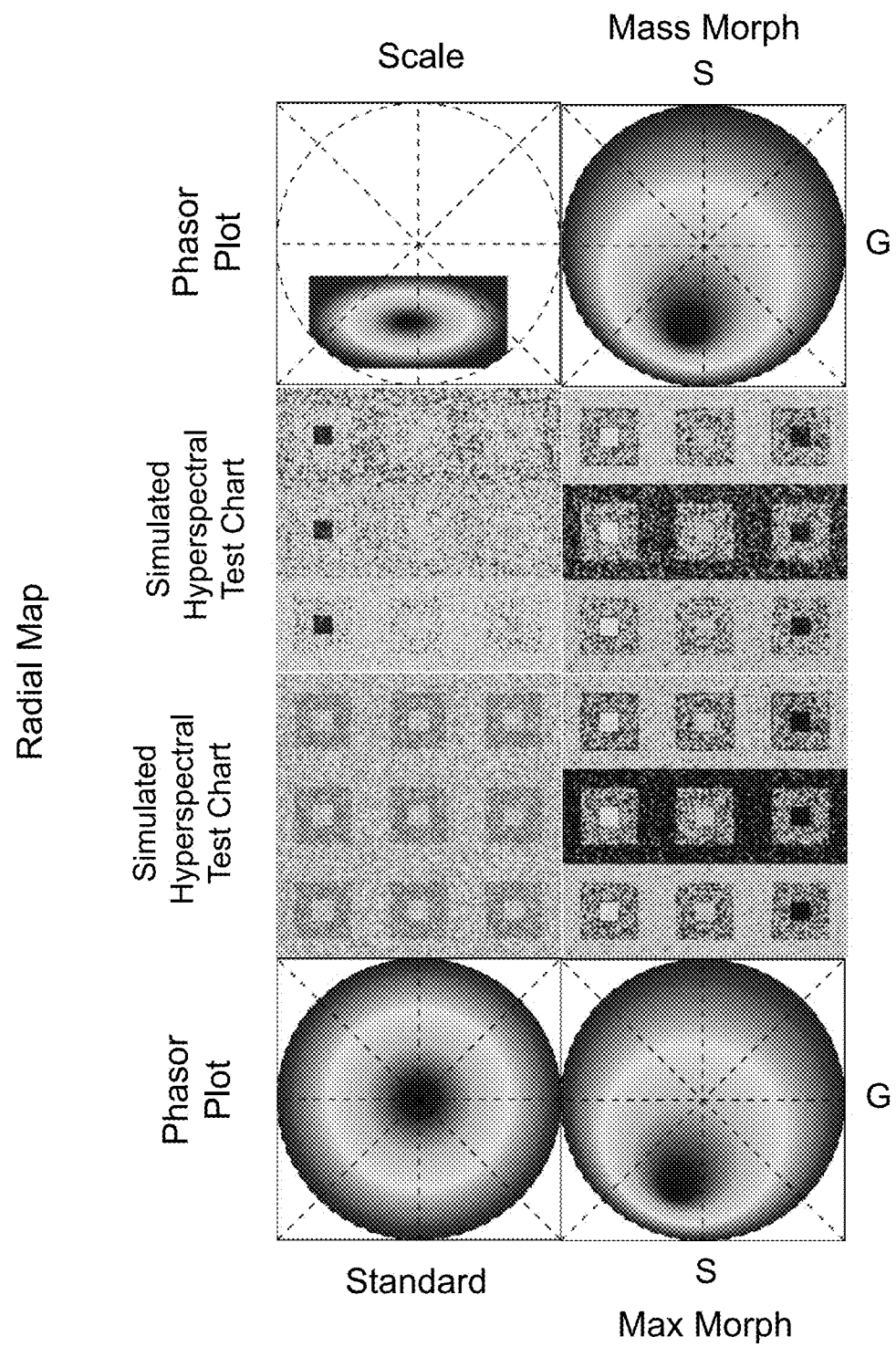

FIG. 39 Radial and Angular reference map designs and modes rendering standard overlapping spectra (Simulated Hyperspectral Test Chart II) (FIG. 32). Here first harmonic is utilized for SEER Angular map (a) and Radial map (b) in Standard mode, Scaled mode, Max Morph mode and Mass Morph mode are here applied to the standard overlapping spectra simulation. The reference maps show improved contrast consistently among different modalities. Visualizations are presented after 1× spectral denoising.

Figure 40A:
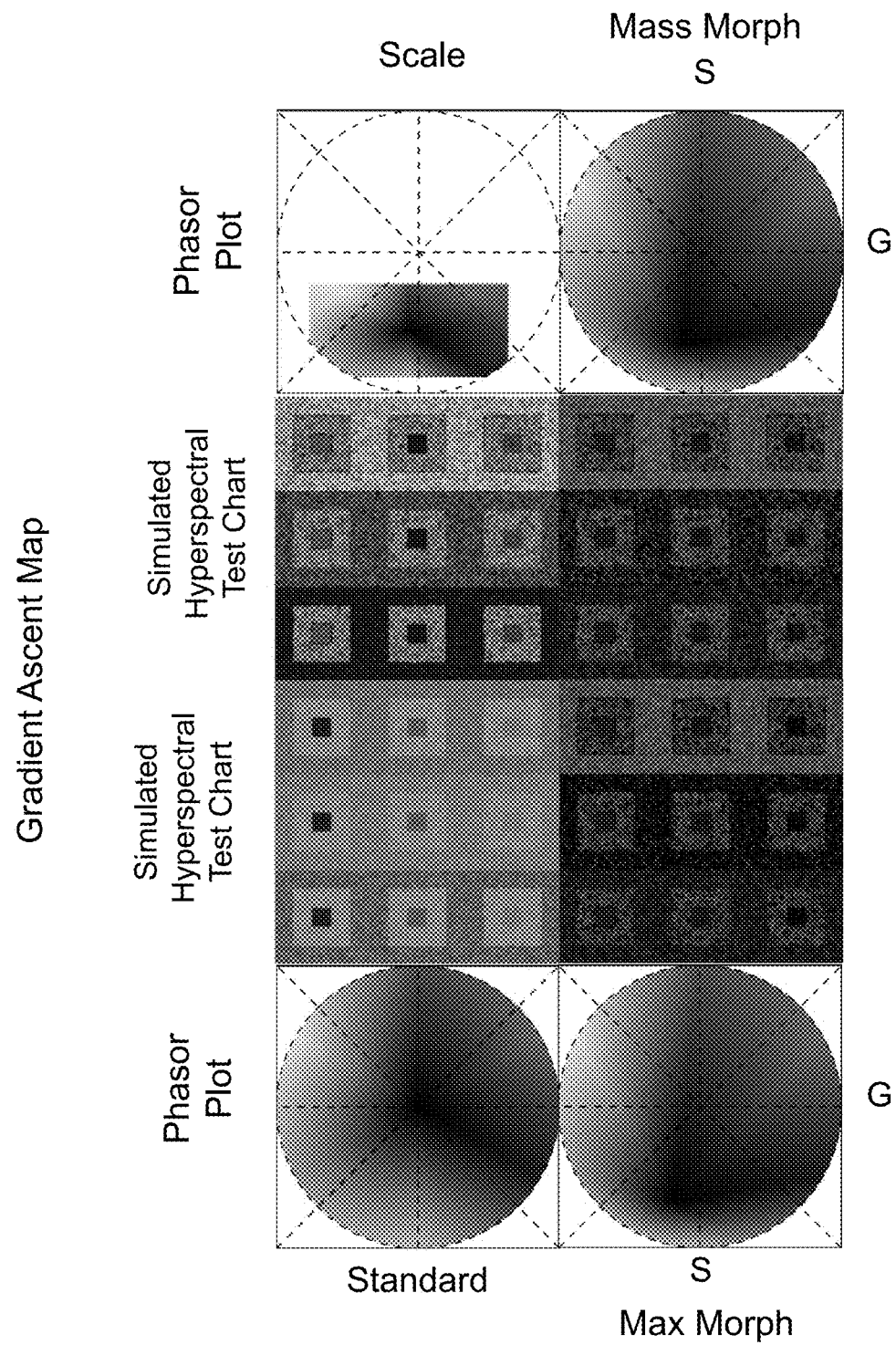
Figure 40B:
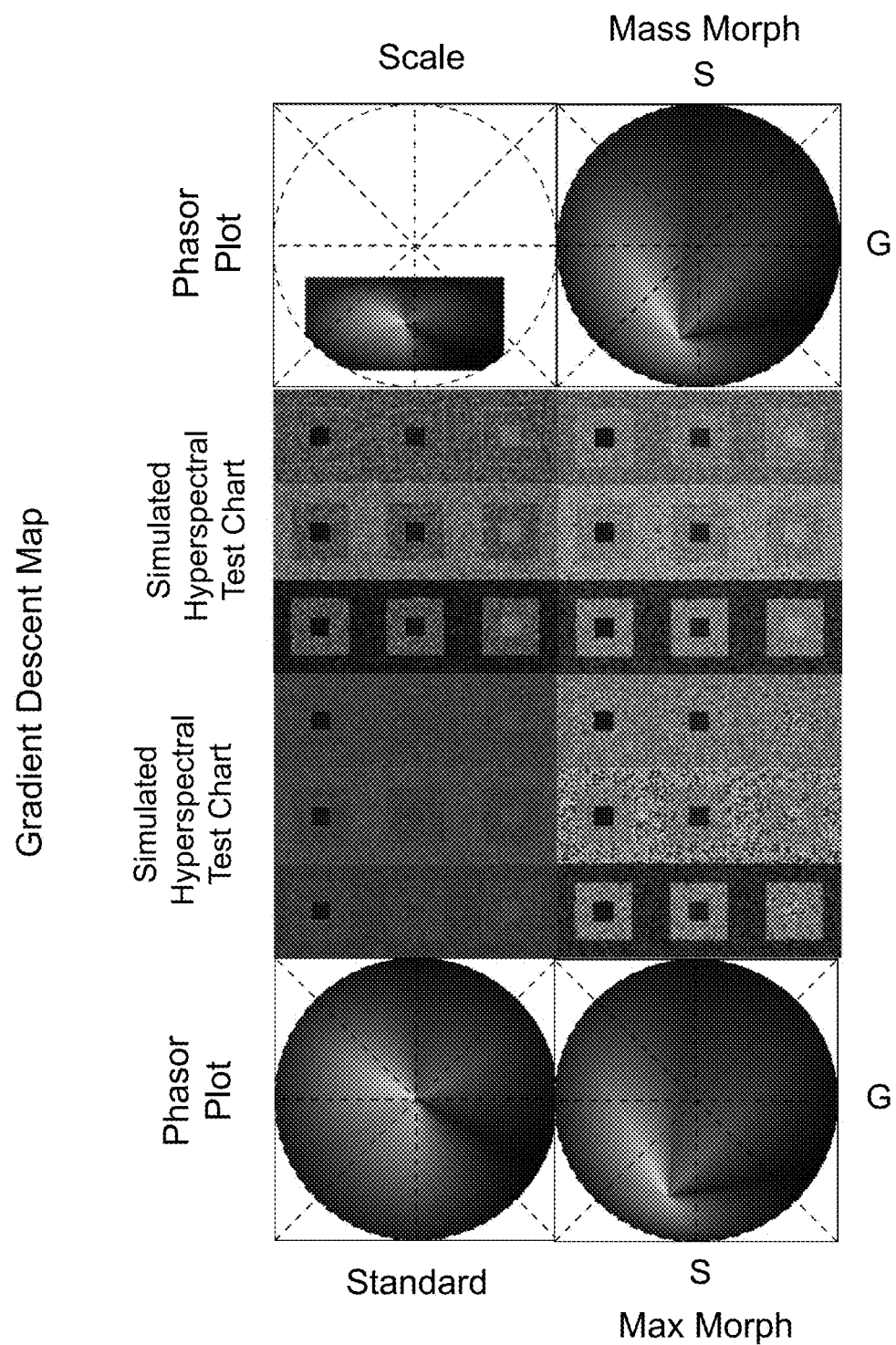
Figure 43A:
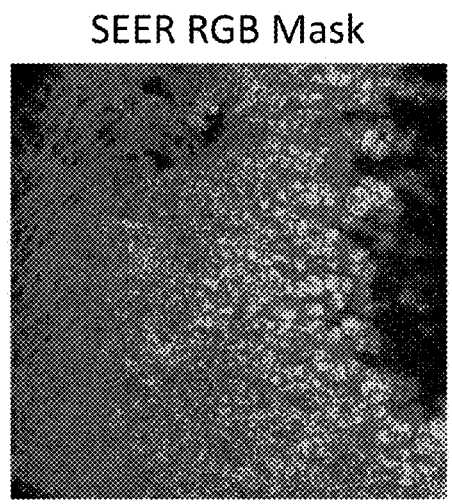
Figure 43B:
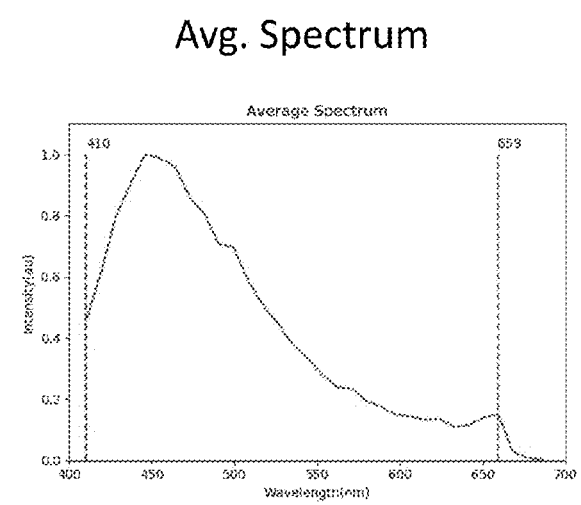
Figure 43C:
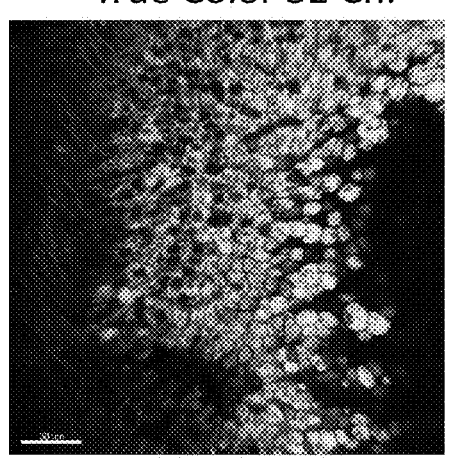
Figure 43D:
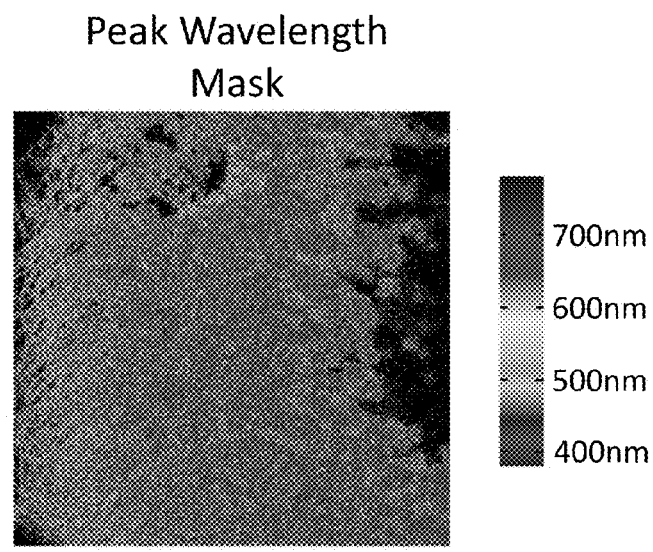
Figure 43E:
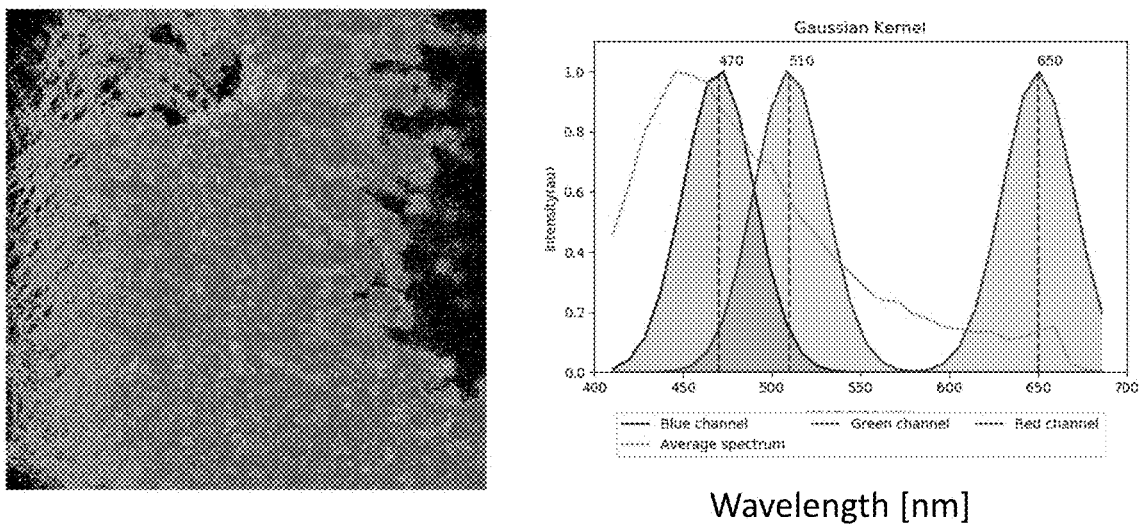
Figure 43F:
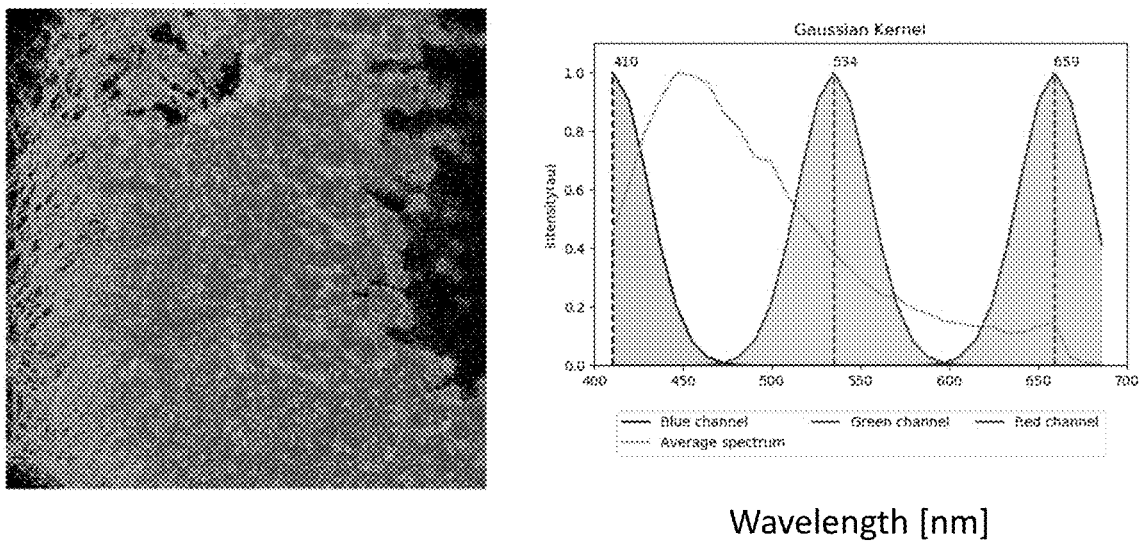
Figures 43I, 43J, 43K, 43L, 43M:
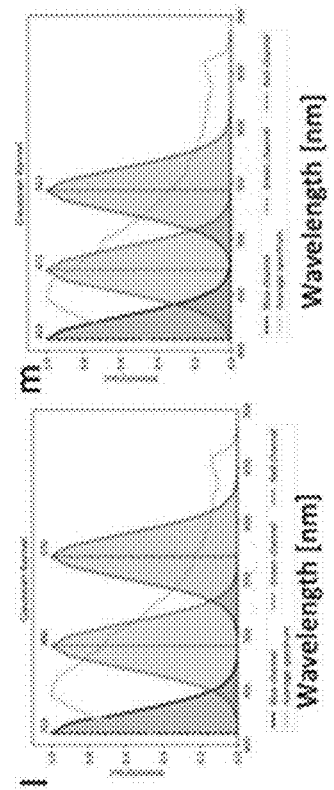

FIG. 40 Gradient ascent and descent reference map designs and modes differentiation of standard overlapping spectra (Simulated Hyperspectral Test Chart II). Here first harmonic is utilized for SEER Gradient Ascent map (a) and Gradient Descent map (b) in Standard mode, Scaled mode, Max Morph mode and Mass Morph mode. The reference maps provide enhanced visualization even in the scenario of spectra overlapping at similar level to commonly used fluorescent proteins. Visualizations are presented after 1× spectral denoising.

FIG. 41 Spectral denoising effect on Angular and Radial maps visualization of standard overlapping spectra (Simulated Hyperspectral Test Chart II, FIG. 38). Phasor spectral denoising affects the quality of data along the spectral dimension, without changing intensities. Here second harmonic is utilized for calculations. Noisy data appears as a spread cluster on the phasor, here shown overlaid with the (a) Angular map and (b) Radial map, with the overlaid visualization exhibiting salt and pepper noise. (c, d) When denoising is applied on the phasor, the cluster spread is reduced, providing greater smoothing and less noise in the simulated chart. (e, f) Increasing the number of denoising filters results in a clearer distinction between the three spectrally different areas in each block of the simulation. (a, c, e) In Max Morph Mode, each denoising filter introduces a shift of the apex of the map, changing the reference center of the color palette (b, d, f) In Scale Mode, the less scattered phasor cluster makes maximum use of the reference maps, enhancing the contrast (d, f) of the rendered SHTC.

FIG. 42 Spectral denoising effect on Gradient Ascent and Descent maps visualization of standard overlapping spectra (Simulated Hyperspectral Test Chart II, FIG. 38). The phasor spectral denoising principle described in (FIG. 41) applies to different reference maps. In this case (a) Gradient Ascent map in Scaled mode and (b) Gradient Descent in Mass Morph mode are overlaid to the scattered phasor representation of a standard overlapping spectrum SHTC. The denoising filter removes outliers along the spectral dimension while preserving intensities. (c, d) The phasor cluster spread is reduced after filtering, resulting in spectral smoothing of the images affected by noise. Due to the changes in phasor cluster spread after filtering, the map reference for the Gradient Ascent map has an increased brightness in comparison to its non-filtered representation (chart panel in a and b). (e, f) The rendered SHTC after multiple denoising passes has higher intensity, which simplifies distinction of subtle differences in spectra. (b, d, f) The denoising filter does not change the clusters' center of mass, therefore the apex of the reference map remains unchanged after filtering. However, the filters play a role in reducing Poisson noise in the dataset, converging to a stable value after 5× filtering. The representation shows more uniformity in the concentric squared areas of within each block, which are simulated using the same spectrum. The edges of these squares are now more sharp and easier to detect, suggesting the combination of SEER and phasor denoising can play an important role in simplifying image segmentation.

FIG. 43 Visualization comparison for autofluorescence with other RGB standard visualizations. The visualization of unlabeled freshly isolated mouse tracheal explant (FIG. 27) is shown here with different standard approaches. Details for these visualizations are reported above. (a) SEER RGB mask obtained using gradient descent morphed map; this mask shows the colors associated by SEER to each pixel, without considering intensity. (b) Average spectrum for the entire dataset. (c) TrueColor 32 channels maximum intensity projection (d) Peak wavelength RGB mask. (e) Gaussian Default Kernel with RGB centered respectively at 650 nm, 510 nm and 470 nm. (f) Gaussian Kernel at 10% threshold, RGB values centered at 659 nm, 534 nm and 410 nm. (g) Gaussian Kernel at 20% threshold, RGB values centered at 570 nm, 490 nm and 410 nm. (h) Gaussian kernel at 30% threshold, RGB values centered at 543 nm, 472 nm and 410 nm. (i) wavelength-to-RGB color representation for Peak Wavelength mask in panel d. A representation of the RGB visualization parameters is reported in (j) kernel used for panel e, average spectrum of the dataset (yellow plot), (k) kernel used for panel f, average spectrum of the dataset (yellow plot), (l) kernel used for panel g, average spectrum of the dataset (yellow plot), (m) kernel used for panel h, average spectrum of the dataset (yellow plot).

Figure 44A:
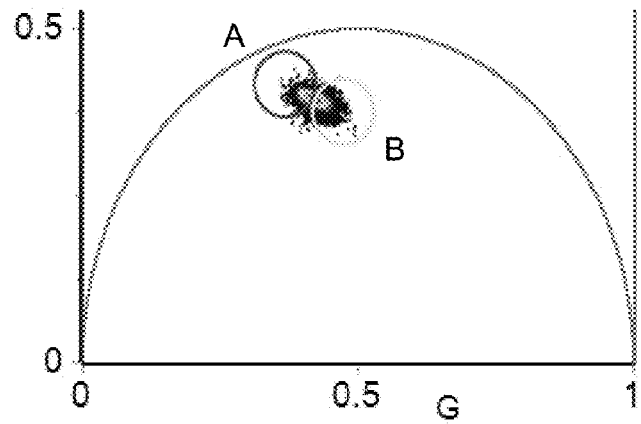
Figure 44B:
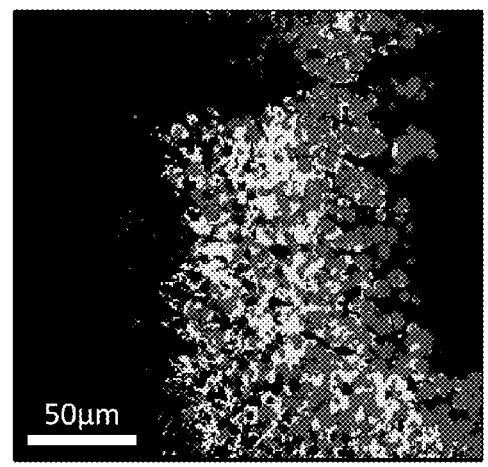
Figure 44C:
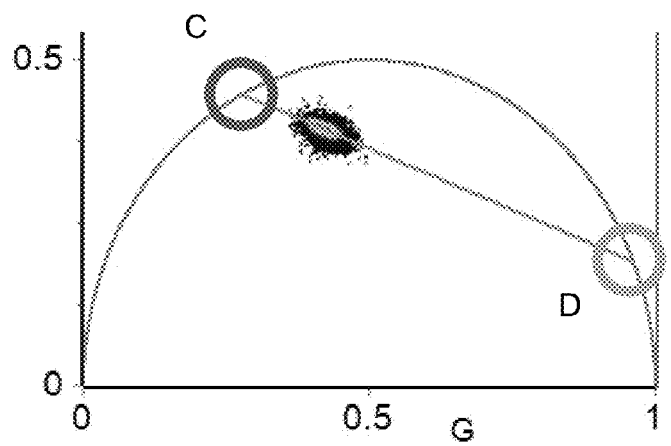

FIG. 44 Phasor Fluorescence Lifetime Imaging Microscopy (FLIM) of unlabeled freshly isolated mouse tracheal explant. (a) Phasor FLIM representation of fluorescence lifetime data for unlabeled freshly isolated mouse tracheal explant acquired in frequency domain utilizing a 2-photon fluorescence microscope (LSM 780, Zeiss, Jena) tuned at 740 nm, coupled with an acquisition unit with Hybrid Detectors (FLIM Box, ISS, Urbana-Champaign). The selected regions correspond to more Oxidative Phosphorylation phenotype (red circle) more Glycolytic phenotype (yellow circle). (b) FLIM segmented image corresponding to the selection performed on phasor (a) where cells in apical layer exhibit Oxidative Phosphorylation phenotype compared to cells in basal layer with a Glycolytic phenotype. (c) The line joining free and bound NADH in the phasor plot is known as the "metabolic trajectory", and a shift in the free NADH direction is representative of a more reducing condition and a glycolytic metabolism, while a shift towards more bound NADH is indicative of more oxidizing conditions and more oxidative phosphorylation, as described in previous studies. The extremes of the metabolic trajectory are the lifetimes for NADH free and bound. The parameters for lifetime (τ phase and modulation) are in line with those reported in literature (0.4 ns free and 1.0-3.4 ns bound).

Figure 45:
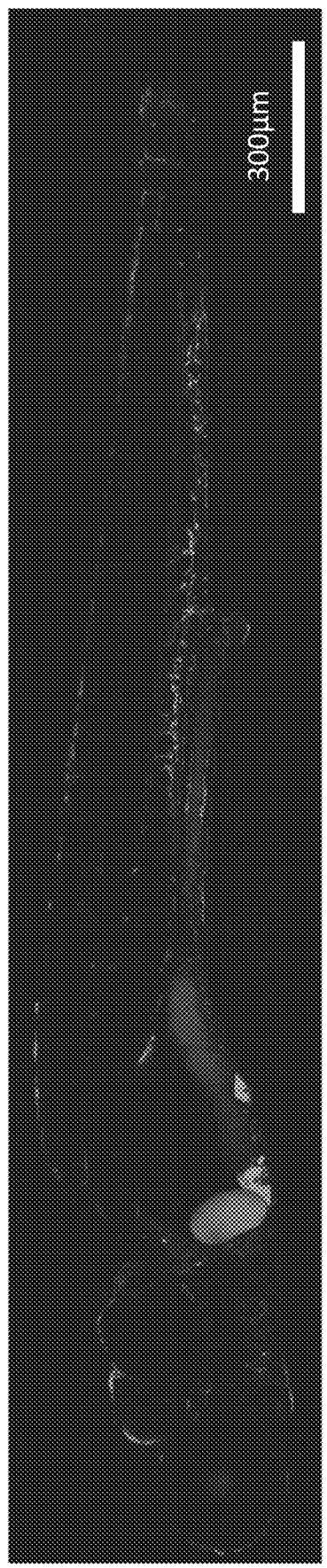

FIG. 45 Gray scale visualization of a single fluorescence label against multiple autofluorescences. Monochrome representation of the average spectral intensity for a single optical section of Tg(fli1:mKO2) (pan-endothelial fluorescent protein label) zebrafish presenting intrinsic signal arising from the yolk and xanthophores (pigment cells). Dataset was acquired using a confocal microscope in multi-spectral mode (LSM 780, Zeiss, Jena) with 488 nm excitation. Average intensity was calculated along the spectral dimension and then represented in grayscale.

Figure 46:
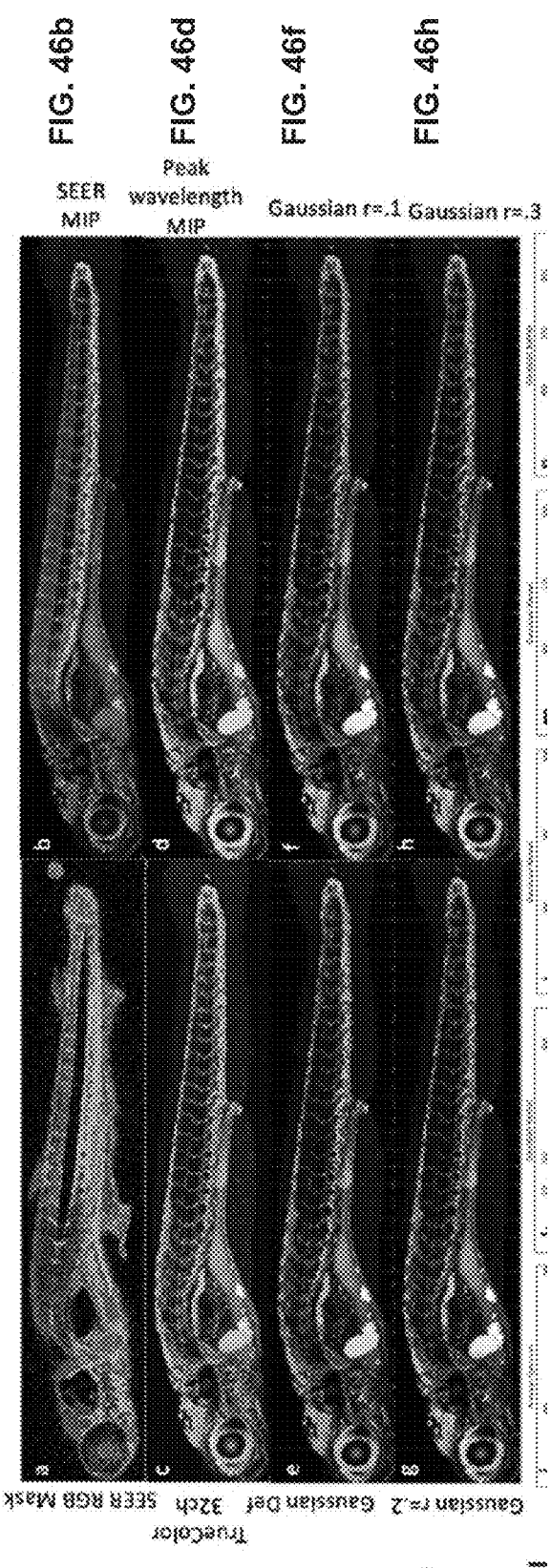

FIG. 46 Visualization comparison for single fluorescent label with other RGB standard visualizations in presence of autofluorescence. Visualization of Tg(fli1:mKO2) (pan-endothelial fluorescent protein label) zebrafish with intrinsic signal arising from the yolk and xanthophores (pigment cells) (FIG. 28) is here shown with different standard approaches. Details for these visualization are reported above. (a) SEER RGB mask for a single z-plane, obtained using gradient angular map in scaled mode, this mask shows the colors associated by SEER to each pixel, without considering intensity. (b) SEER maximum intensity projection (MIP) for the entire volume (c) TrueColor 32 channels volume MIP (d) Peak wavelength volume MIP. (e) Gaussian Default Kernel with RGB centered respectively at 650 nm, 510 nm and 470 nm. (f) Gaussian Kernel at 10% threshold, RGB values centered at 686 nm, 588 nm and 499 nm. (g) Gaussian Kernel at 20% threshold, RGB values centered at 668 nm, 579 nm and 499 nm. (h) Gaussian kernel at 30% threshold, RGB values centered at 641 nm, 570 nm and 499 nm. (i) wavelength-to-RGB color representation for Peak Wavelength mask in panel d. A representation of the RGB visualization parameters is reported in (j) Average spectrum (blue plot) for the entire dataset with boundaries used for TrueColor 32ch MIP in panel c. (k) Kernel used for panel e, average spectrum of the dataset (yellow plot), (l) kernel used for panel f, average spectrum of the dataset (yellow plot), (m) kernel used for panel g, average spectrum of the dataset (yellow plot), (n) kernel used for panel h, average spectrum of the dataset (yellow plot).

Figure 47:
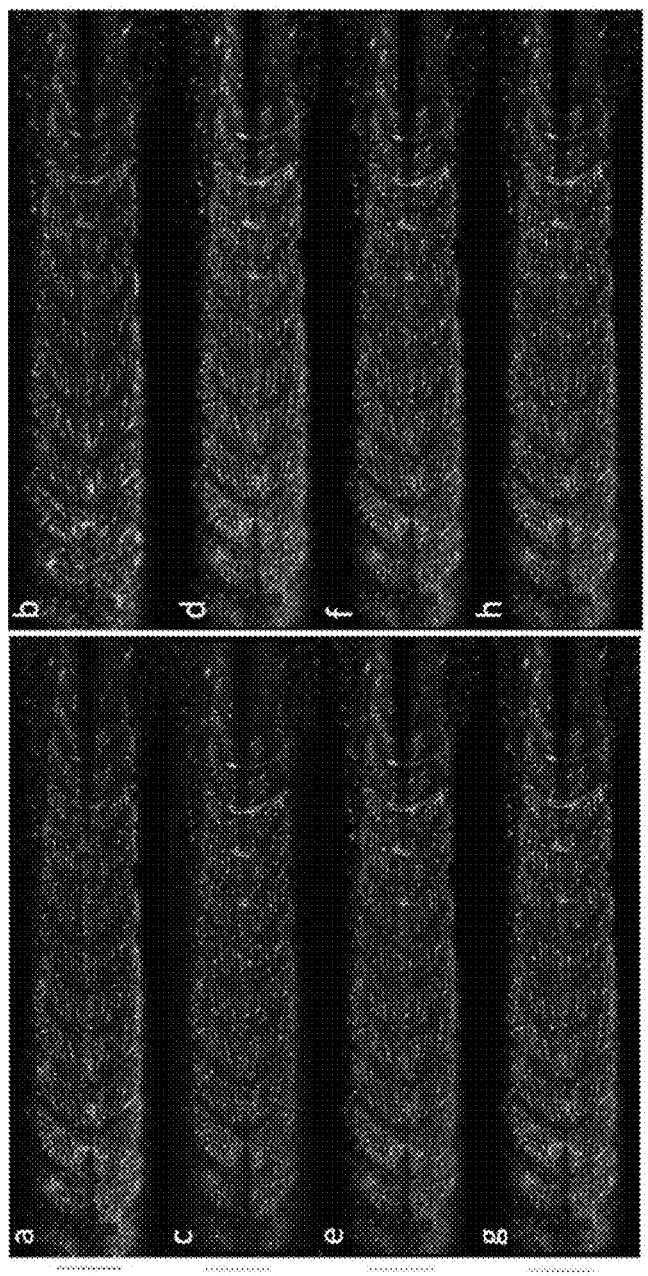
Figure 48D:
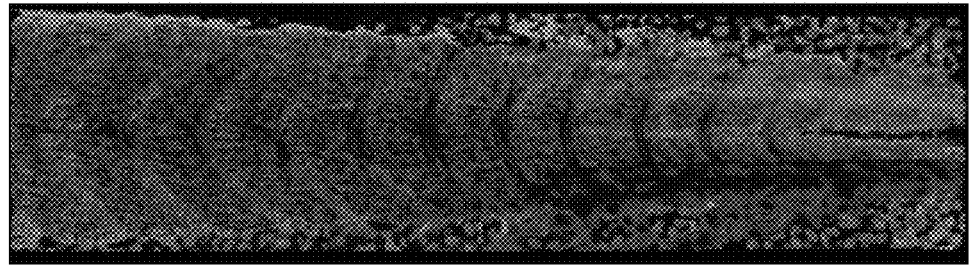
Figure 48C:
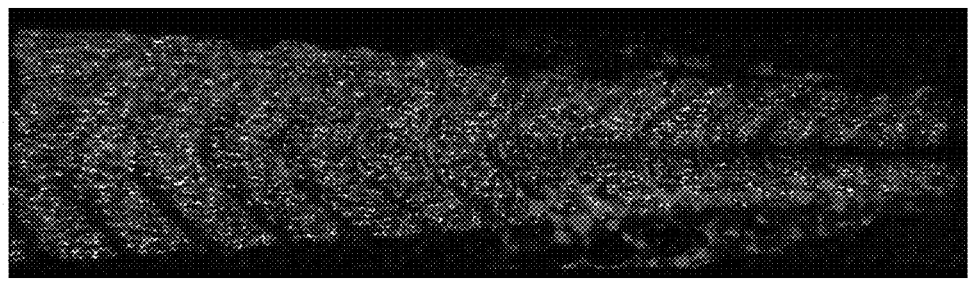
Figure 48B:
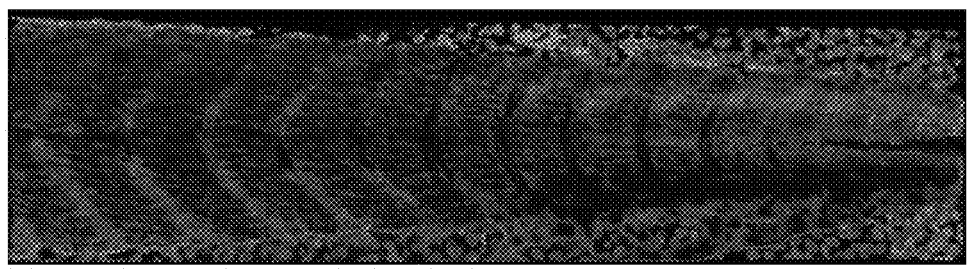
Figure 48A:
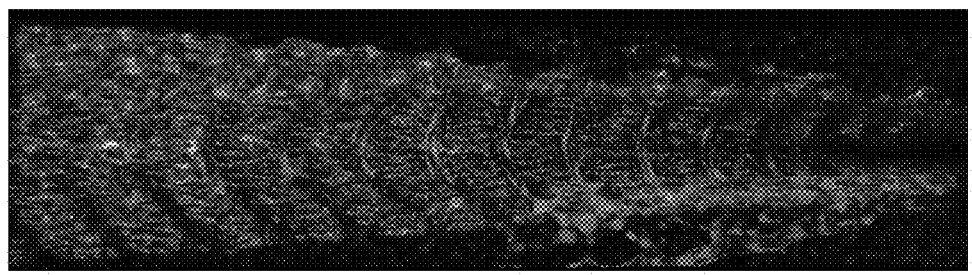
Figure 49E:
Figure 49J:
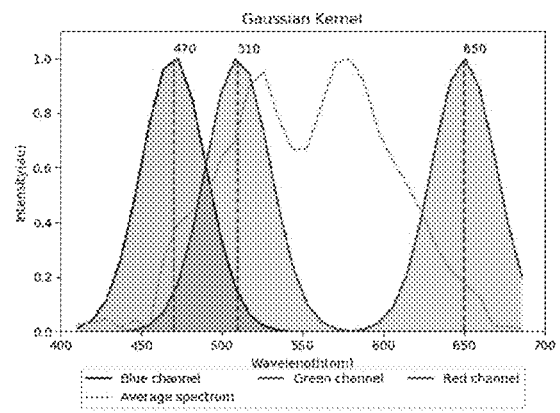
Figure 49F:
Figure 49K:
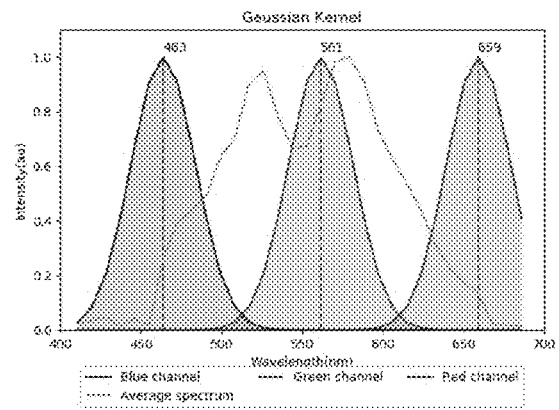
Figure 49G:
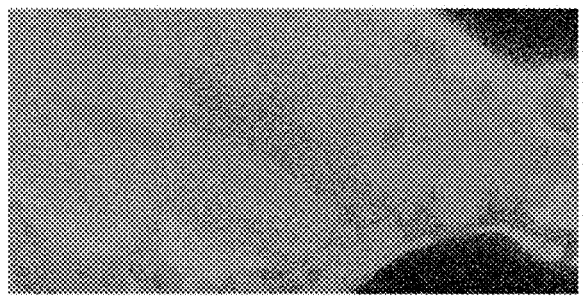
Figure 49L:
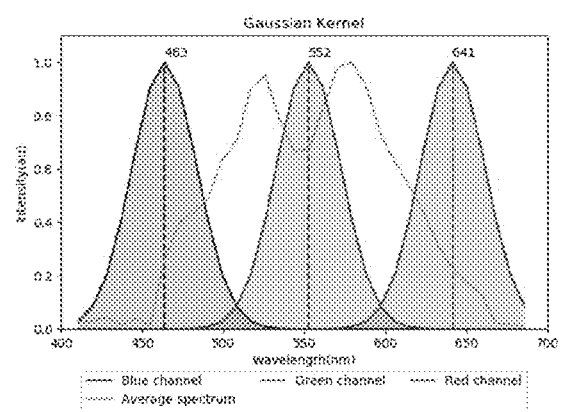
Figure 49H:
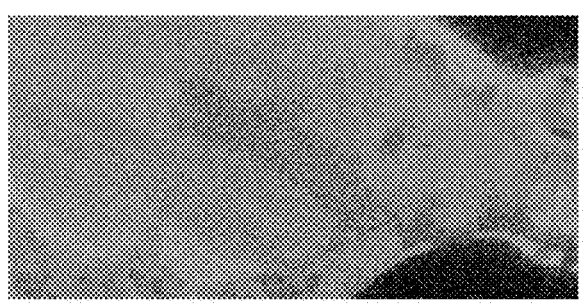
Figure 49M:
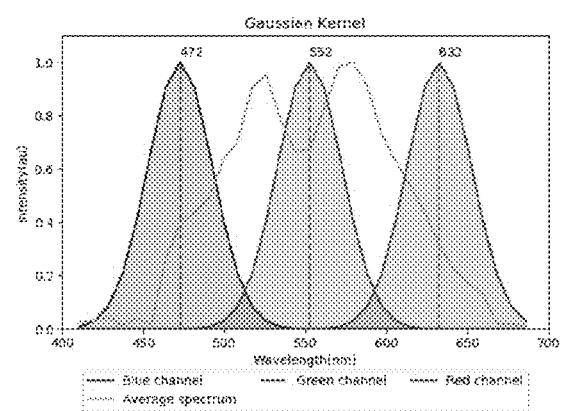
Figure 50G:
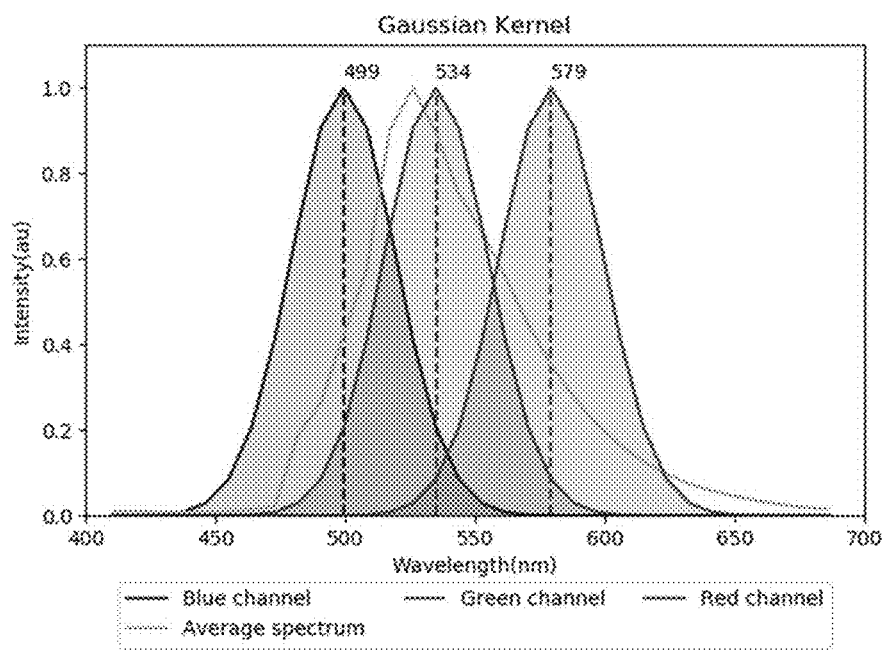
Figure 50H:
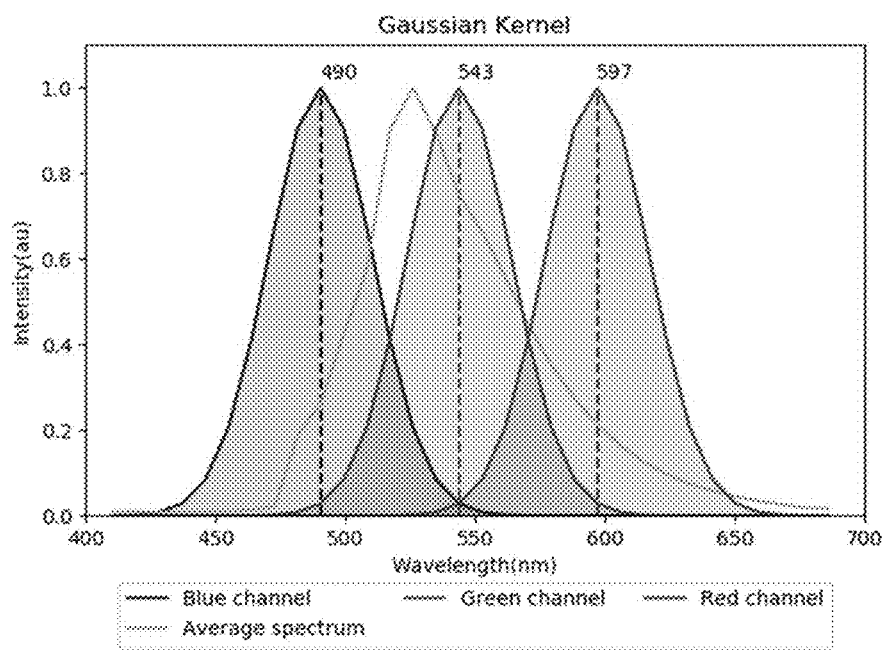
Figure 50I:
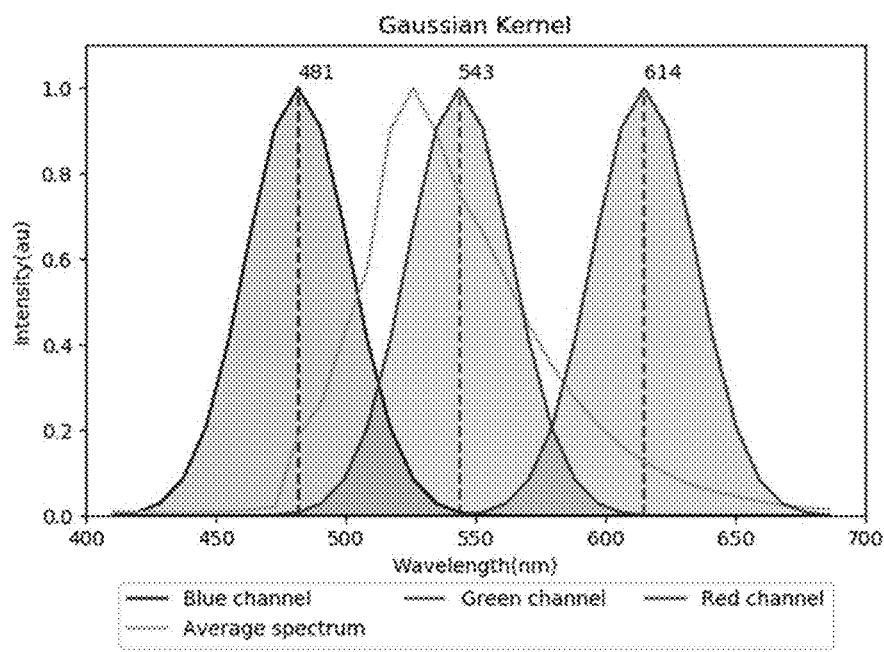
Figure 50J:
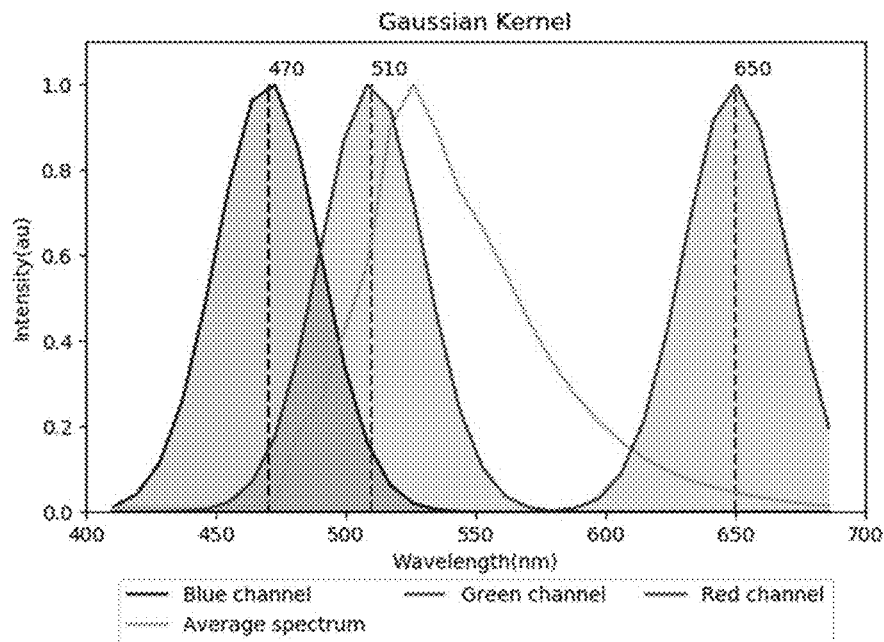
Figure 51A:
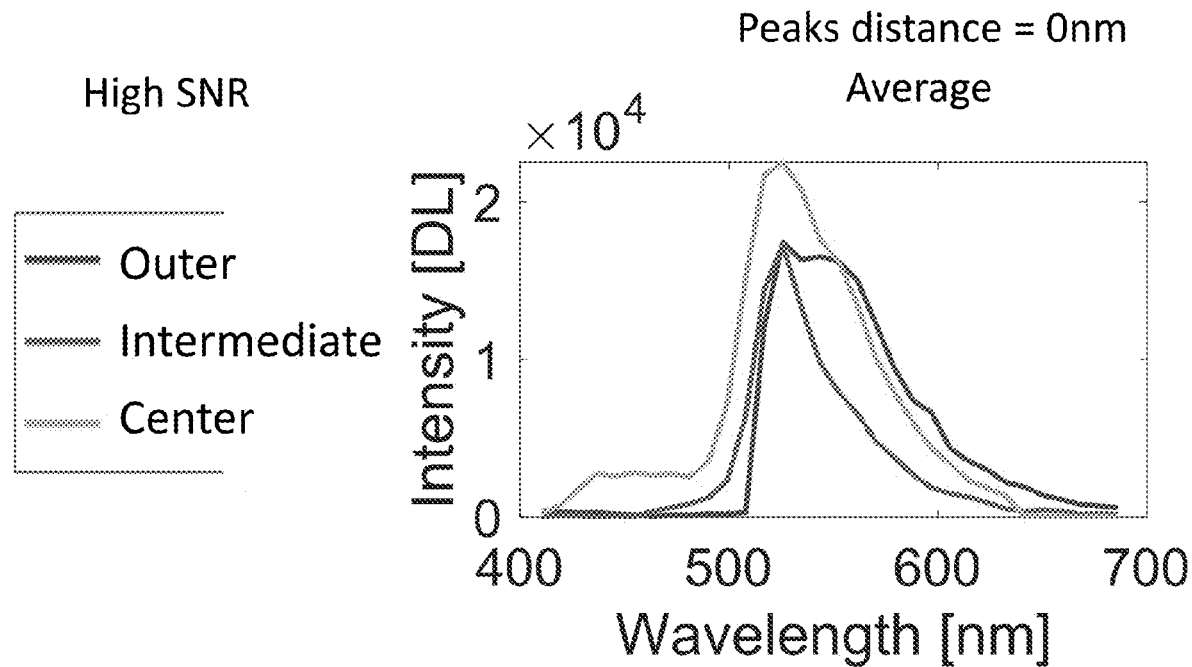
Figure 51B:
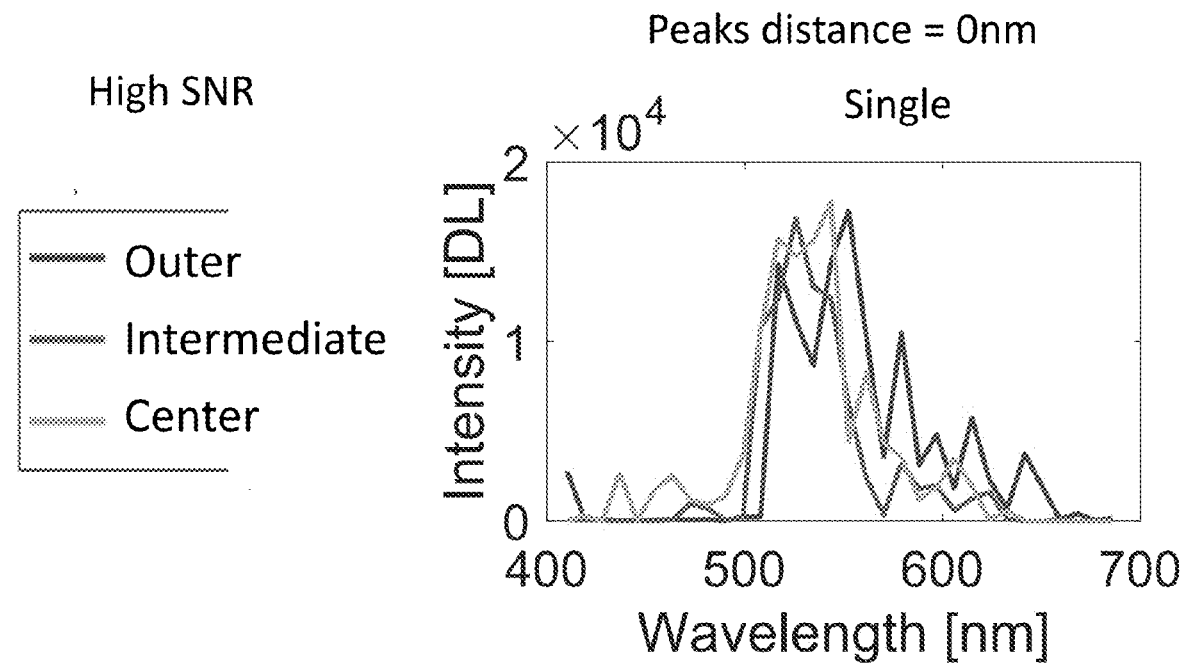
Figure 51C:
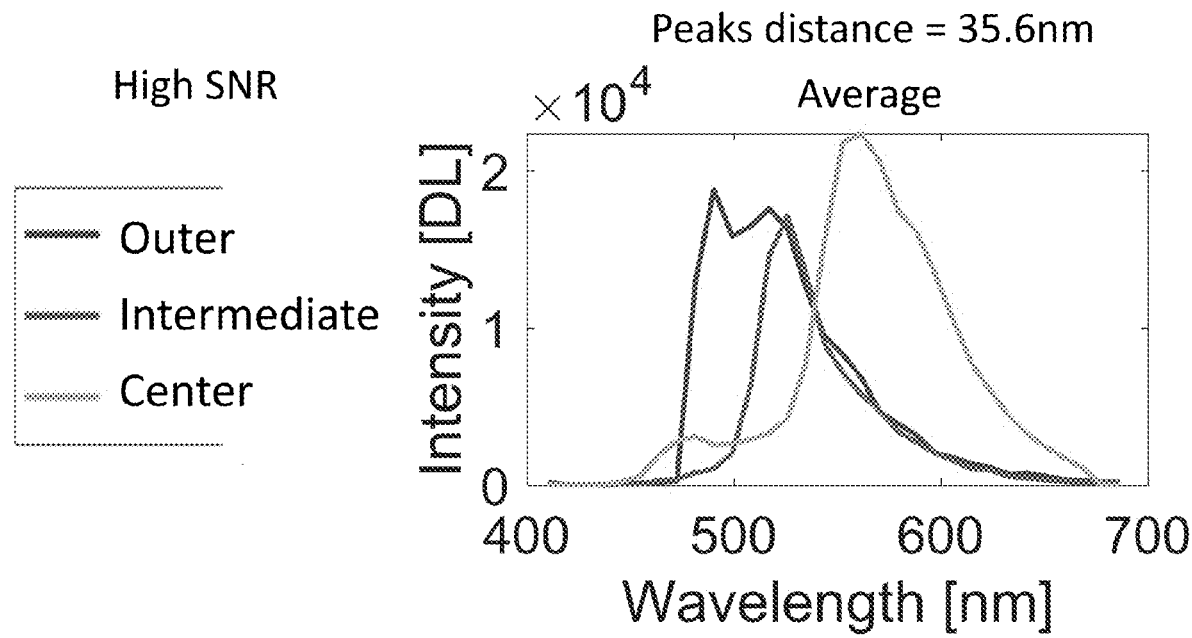
Figure 51D:
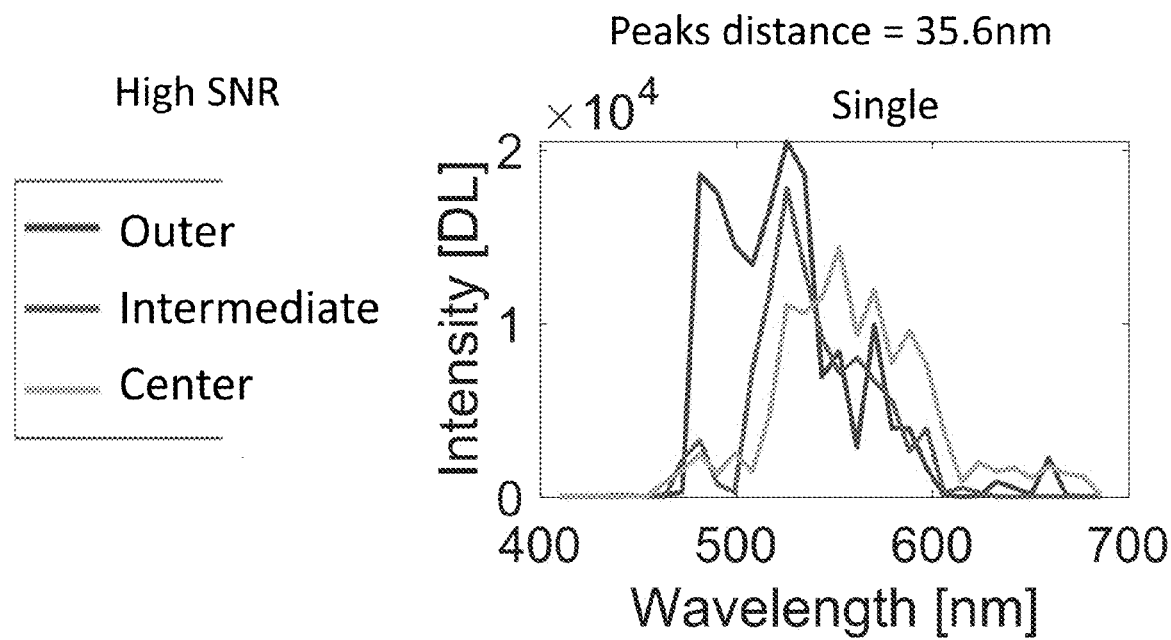
Figure 51E:
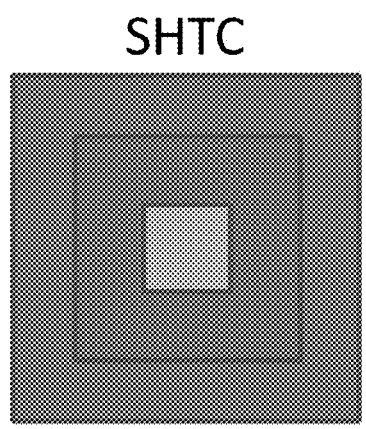
Figure 51F:
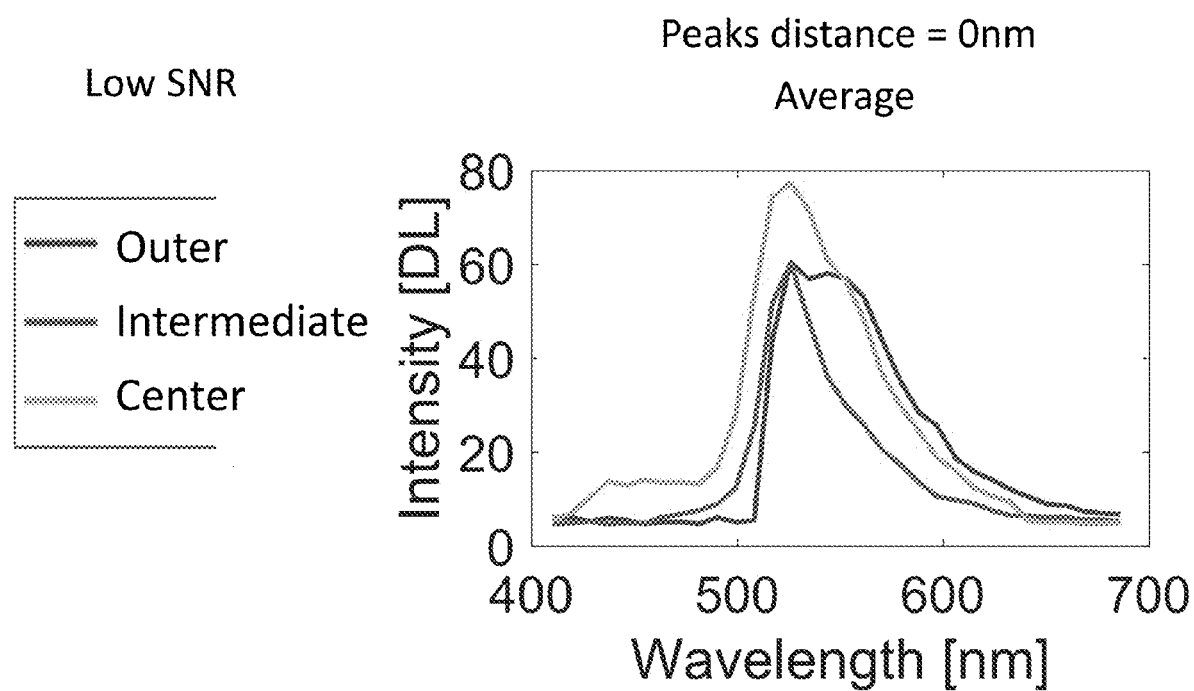
Figure 51G:
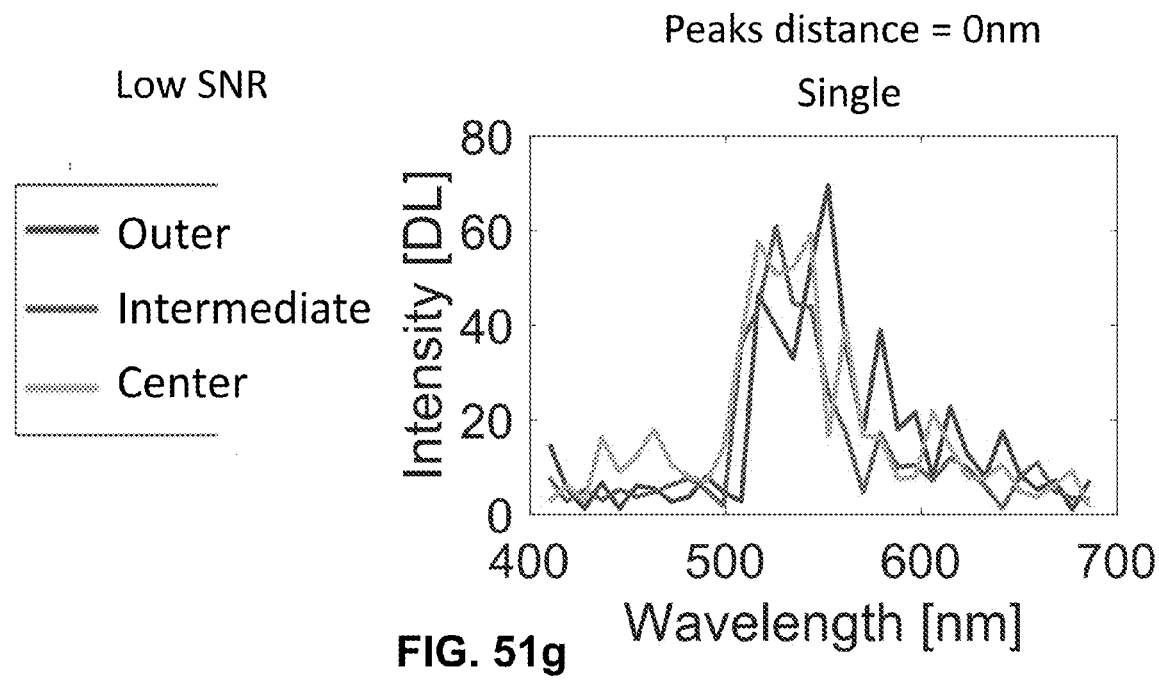
Figure 51H:
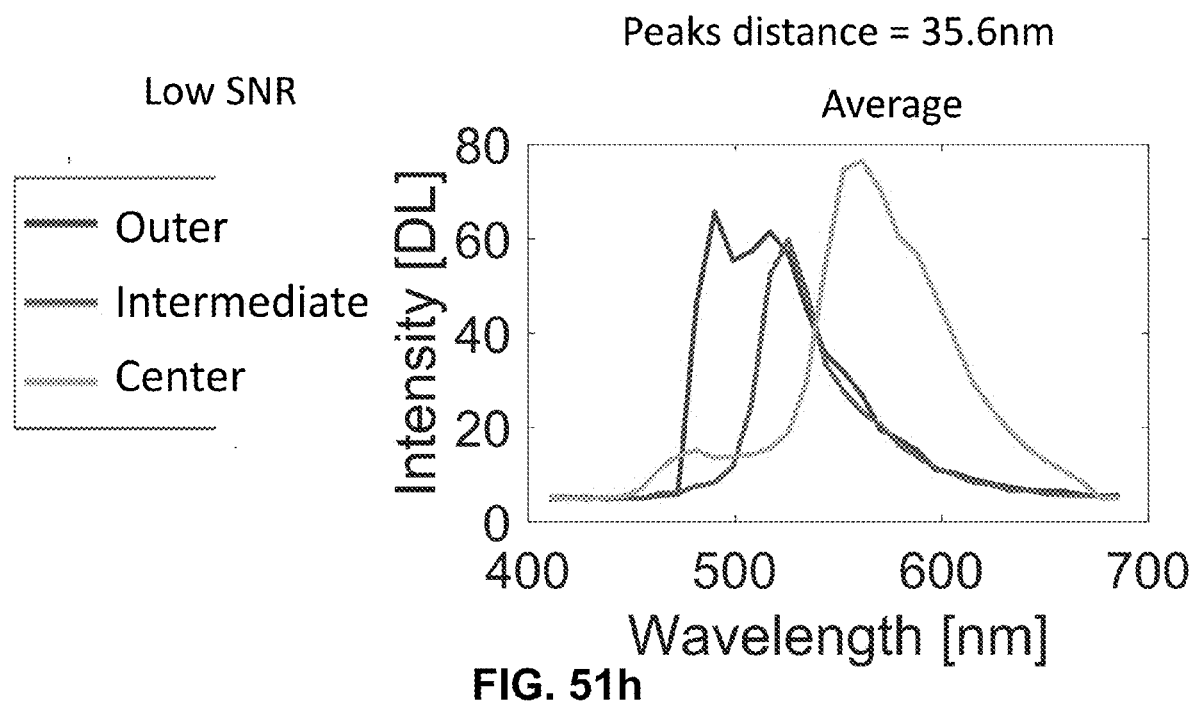
Figure 51I:
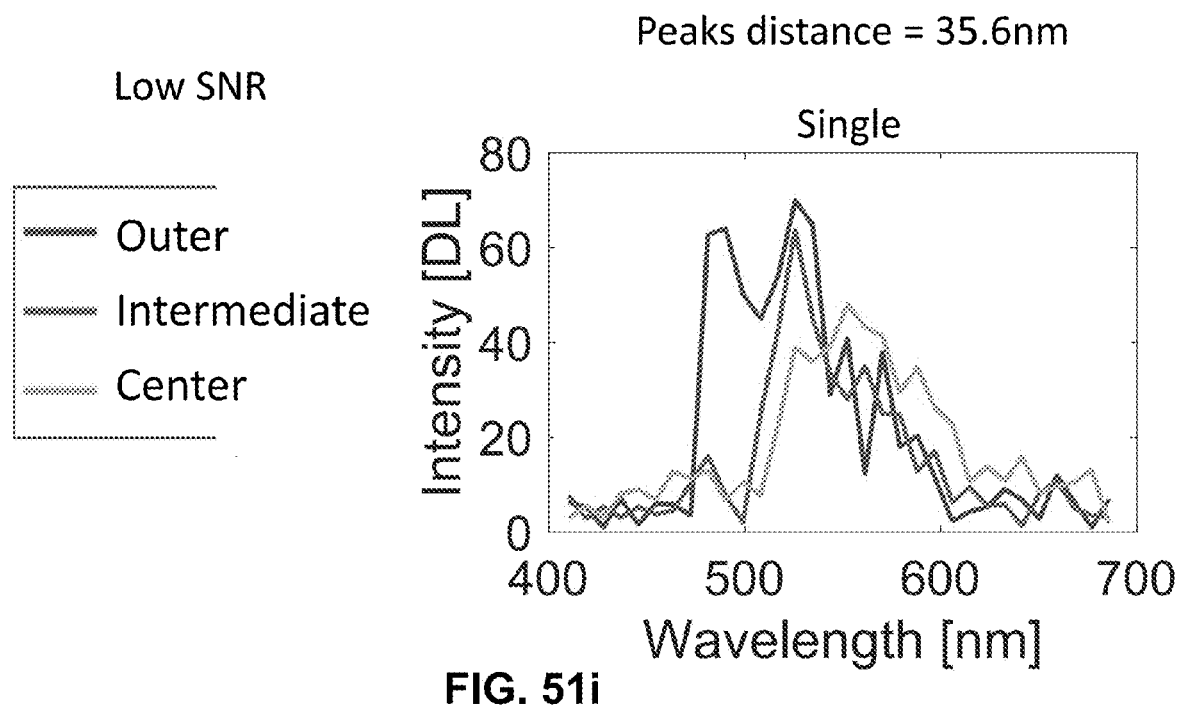
Figure 52A:
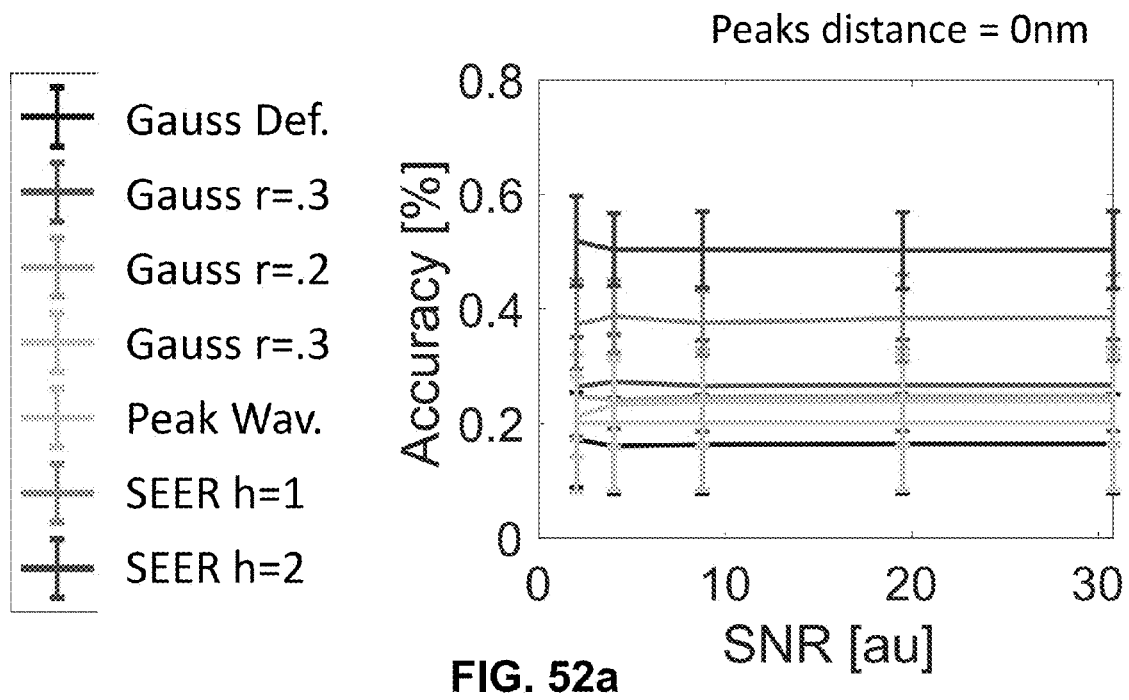
Figure 52B:
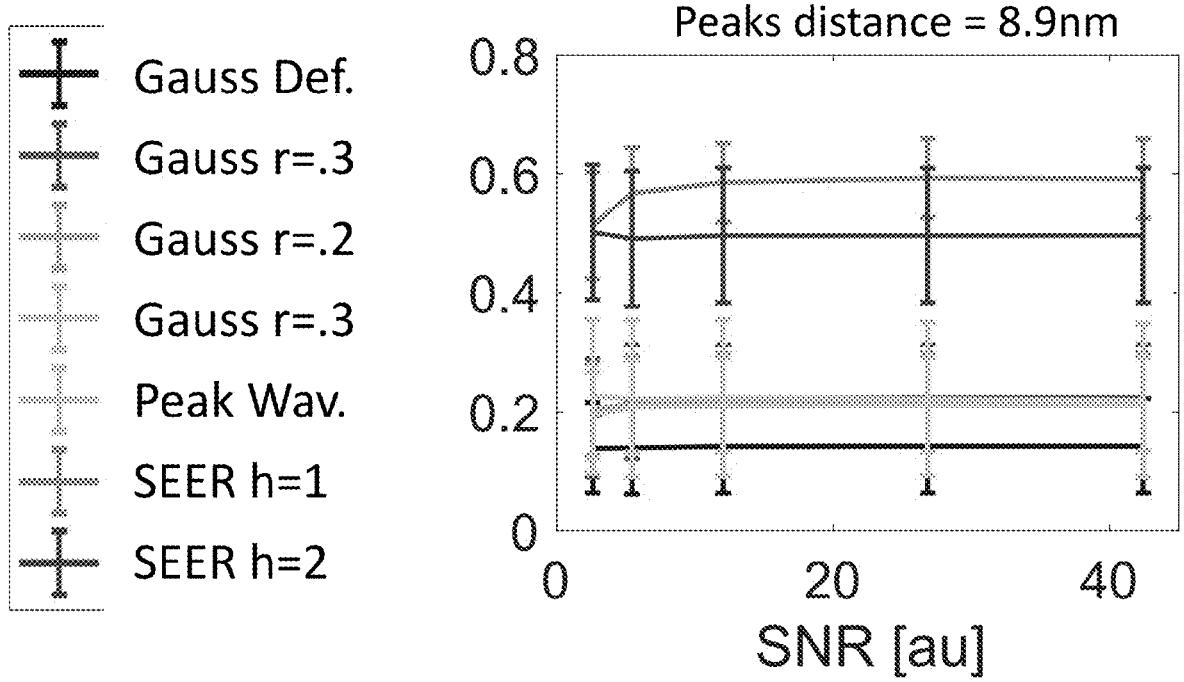
Figure 52C:
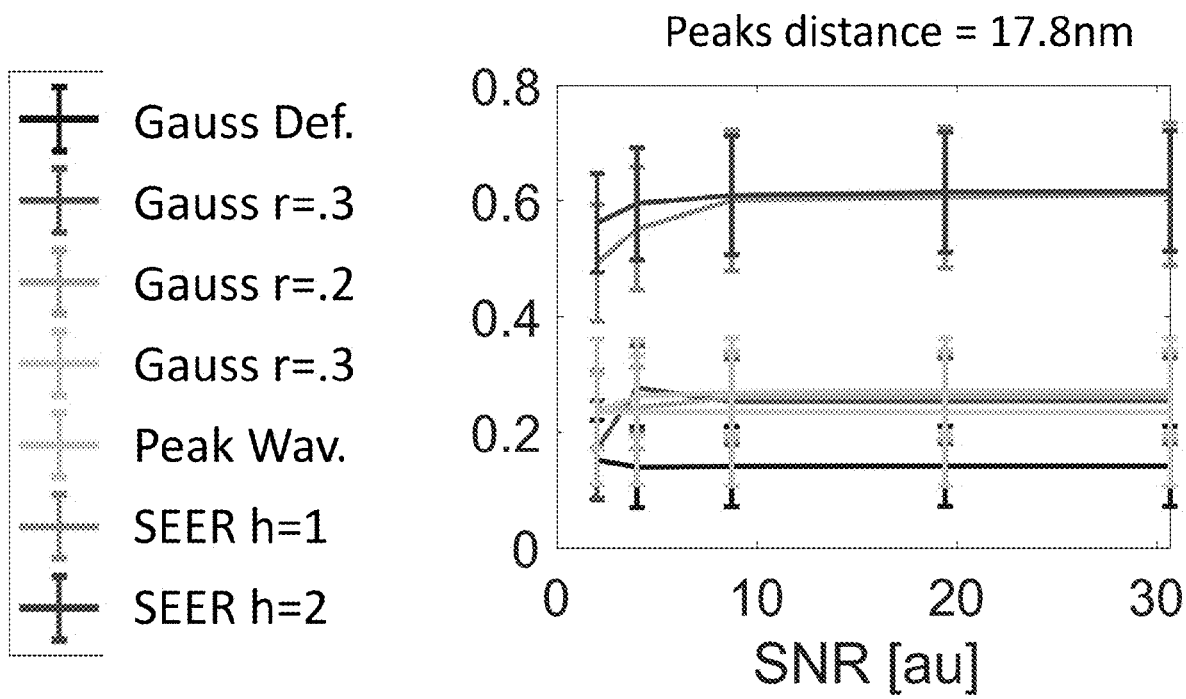
Figure 52D:
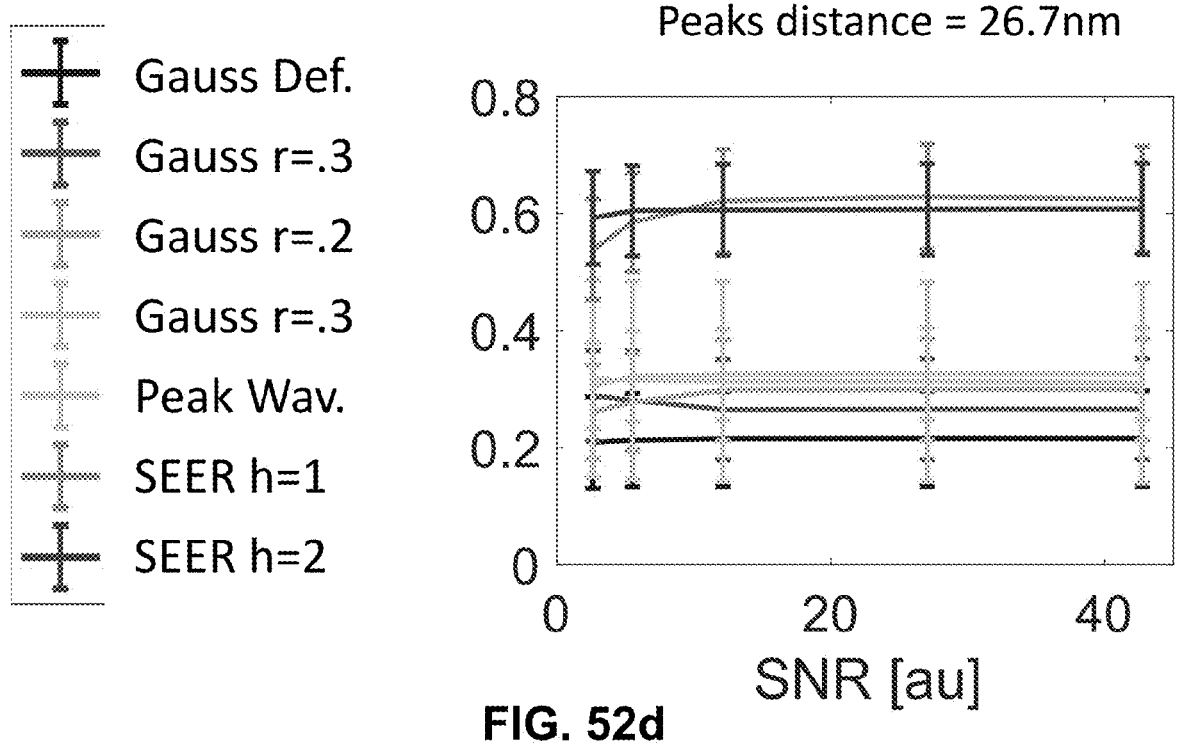
Figure 52E:
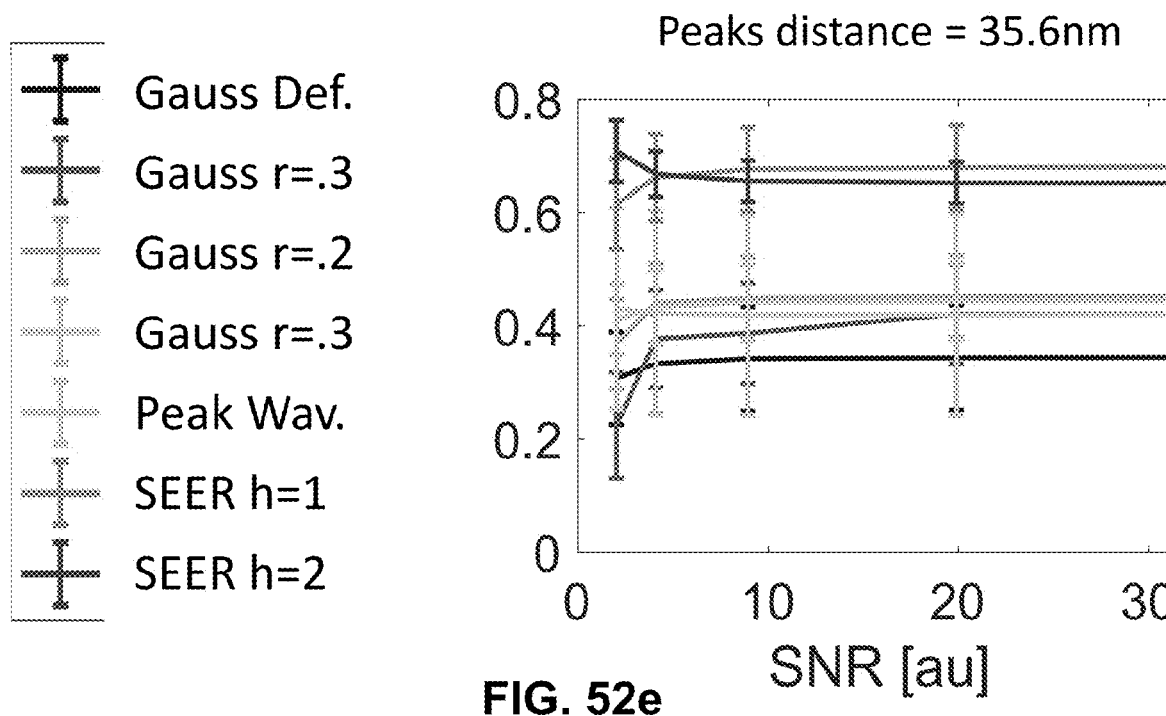
Figure 53F:
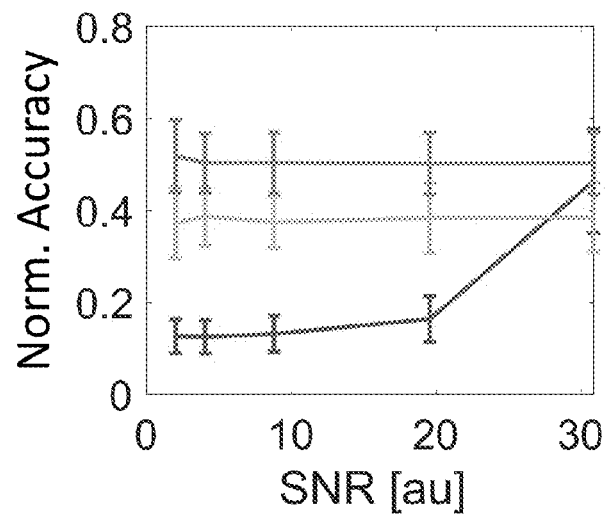
Figure 53G:
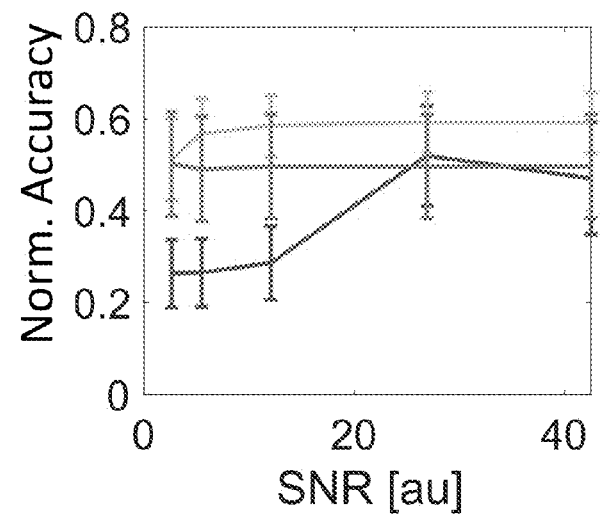
Figure 53H:
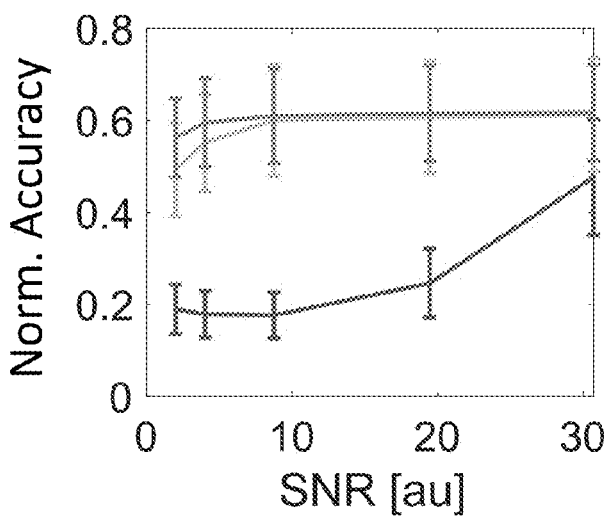
Figure 53I:
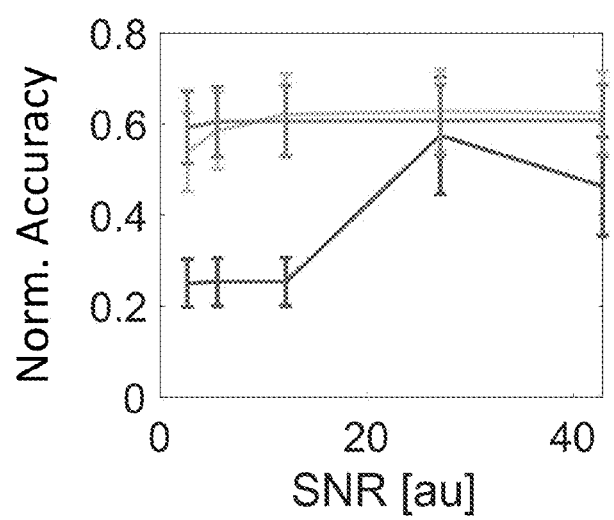
Figure 53J:
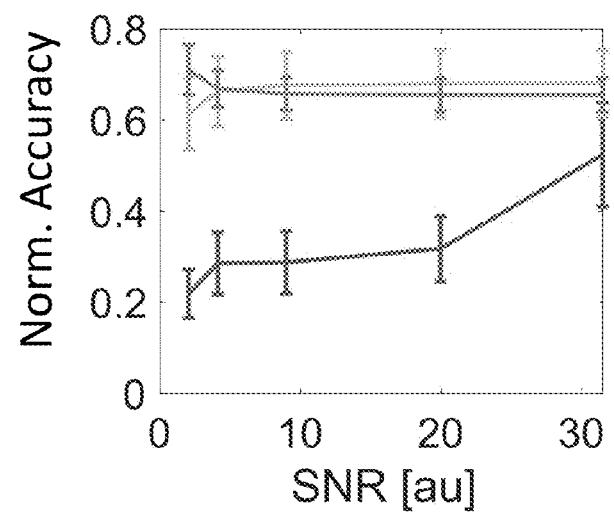

FIG. 47 Visualization comparison for triple label fluorescence with other RGB standard approaches. Visualization of Tg(kdrl:eGFP); Gt(desmin-Citrine); Tg(ubiq:H2B-Cerulean) labelling respectively vasculature, muscle, and nuclei (FIG. 29) is shown here with different standard approaches. Details for these visualizations are reported above. The same slice (here z=3) is shown as a maximum intensity projection (MIP) using: (a) SEER gradient descent map in max morph mode, (b) SEER MIP angular map mass morph mode, (c) TrueColor 32 channels, (d) Peak wavelength, (e) Gaussian Default Kernel with RGB centered respectively at 650 nm, 510 nm and 470 nm. (f) Gaussian Kernel at 10% threshold, RGB values centered at 597 nm, 526 nm and 463 nm (g) Gaussian Kernel at 20% threshold, RGB values centered at 579 nm, 517 and 463 nm (h) Gaussian kernel at 30% threshold, RGB values centered at 561 nm, 526 nm and 490 nm. A representation of the RGB visualization parameters is reported in (i) wavelength-to-RGB color representation for Peak Wavelength mask in panel d, (j) Average spectrum (blue plot) for the entire dataset with boundaries used for TrueColor 32ch MIP in panel c. (k) kernel used for panel e, average spectrum of the dataset (yellow plot), (l) kernel used for panel f, average spectrum of the dataset (yellow plot), (m) kernel used for panel g, average spectrum of the dataset (yellow plot), (n) kernel used for panel h, average spectrum of the dataset (yellow plot).

FIG. 48 SEER of zebrafish volumes in Maximum Intensity Projection (MIP) and Shadow Projection. The capability of SEER to improve visualization of spectral datasets is translatable to 3D visualizations with different visualization modalities. Here we show a zebrafish embryo Tg(kdrl: eGFP); Gt(desmin-Citrine);Tg(ubiq:H2B-Cerulean) labelling respectively vasculature, muscle, and nuclei. (a) MIP of an Angular map volume with Mass Morph mode. (b) The same combination of map and mode is shown using shadow projection. While the volume rendering approaches are different, the spatial distinction between fluorescent labels is maintained. The Gradient Descent map in Max Morph mode is here applied on the same dataset using (c) MIP and (d) shadow projection. With the Gradient Descent map (c) MIP improves contrast for determining spatial distinction between fluorophores. (d) Shadow projection further enhances the location of skin pigments (green).

FIG. 49 Visualization comparison for combinatorial expression with other RGB standard approaches. Visualization of ubi:Zebrabow muscle (FIG. 30) with different standard approaches. Details for these visualization are reported above. The same slice is shown as an RGB mask which represents the color associated to each pixel, independent from the intensity, or as a maximum intensity projection (MIP) using: (a) SEER gradient descent map mask in scaled mode, (b) Average spectrum (blue plot) for the entire dataset with boundaries used for TrueColor 32ch MIP in panel c. (c) TrueColor 32 channels, (d) Peak wavelength mask, (e) Gaussian Default Kernel with RGB centered respectively at 650 nm, 510 nm and 470 nm. (f) Gaussian Kernel at 10% threshold, RGB values centered at 659 nm, 561 nm and 463 nm. (g) Gaussian Kernel at 20% threshold, RGB values centered at 641 nm, 552 nm and 463 nm. (h) Gaussian kernel at 30% threshold, RGB values centered at 632 nm, 552 nm and 472 nm. (i) wavelength-to-RGB color representation for Peak Wavelength mask in panel d. A representation of the RGB visualization parameters is reported in (j) kernel used for panel e, average spectrum of the dataset (yellow plot), (k) kernel used for panel f, average spectrum of the dataset (yellow plot), (l) kernel used for panel g, average spectrum of the dataset (yellow plot), (m) kernel used for panel h, average spectrum of the dataset (yellow plot).

FIG. 50 RGB Visualization with multiple modalities under different spectral overlap and SNR conditions. In this simulation, the first panel (top-left) of the Simulated Hyperspectral Test Chart (SHTC, FIG. 33) is reduced in intensity by a factor of $(0.5*10)^1$-$(0.5*10)^4$ (panel 1-5 respectively) in the presence of a constant background. Background with average intensity 5 was generated in Matlab, poissonian noise was added using the poissrnd( ) function obtaining 5 different levels of SNR. (a,b,c,d,e) Peak-to-peak distance for the spectra in the middle and outer concentric squares in the SHTC is shifted by units of 8.9 nm with respect to the peak of the average spectrum in the intermediate square, which is kept constant in this simulation (similarly to FIG. 33) starting from distance 0 (a) to 35.6 nm (e). For each level of spectral overlap (a-e), seven different RGB visualization modalities are presented here for comparison at five different level of SNR. In order from the top row, SEER at harmonic 2 (SEER h=2) and harmonic 1 (SEER h=1), peak wavelength selected (Peak Wav.), Gaussian kernel set at 30% of the spectrum (Gauss r=0.3), set at 20% (Gauss r=0.2) and at 10% (Gauss r=0.1), finally Gaussian kernel set at 650 nm, 510 nm, 470 nm for RGB respectively (Gauss. Def.). (f) the wavelength-to-RGB conversion map used for the peak wavelength visualization. (g) center wavelength for the R=579 nm, G=534 nm, B=499 nm channels of Gauss r=0.3. Average spectrum (yellow) (h) center wavelength for the R=597 nm, G=543 nm, B=490 nm channels of Gauss r=0.2. Average spectrum (yellow). (i) center wavelength for the R=614 nm, G=543 nm, B=481 nm channels of Gauss r=0.1. Average spectrum (yellow). (j) center wavelength for the R=650, G=510 nm, B=470 nm channels of Gauss. Def. Average spectrum (yellow). The maps utilized here for SEER were gradient descent in scale mode (a, b, c, d), and center of mass mode (e). Visualization with SEER shows a reasonably constant contrast and color for the different spectra in the simulation at different SNR.

FIG. 51 Spectra of extreme conditions in SNR-Overlap simulation. The extremes of the simulation utilized in FIG. 50 are reported here as spectra for comparison. For high signal-to-noise ratio (a) average spectrum for spectra with peak-maxima distance set to zero and (b) example single spectra from each concentric square region of the simulation (digital levels, DL). (c) Average and (d) single spectra at high SNR for simulation with spectra separated with a peak-to-peak distance of 35.6 nm. (e) Reference Simulated Hyperspectral Test Chart with color coded concentric squares. The low SNR simulation spectra are reported here for a peak distance of zero as (f) average and (g) single and for a peak distance of 35.6 nm as (h) average and (i) single.

FIG. 52 Spectral separation accuracy of SEER under different spectral overlap and SNR conditions. Accuracy was calculated for different signal-to-noise ratios and spectral maxima separation (a) aligned, (b) 8.9 nm, (c) 17.8 nm, (d) 26.7 nm, (e) 35.6 nm, starting from the visualizations in FIG. 50 and corresponding spectra in FIG. 51. The accuracy is calculated here as the sum of the Euclidean distance of the RGB vectors between pairs of the concentric squares of the simulation, in ratio to the largest color separation (red to green, red to blue, blue to green). A thorough description of accuracy calculation is reported in the Methods section. Each value in the plots represents the average distance of $200^2$ pixels; error bars are the standard deviation of normalized accuracy value across all pixels. The average accuracies over multiple SNR conditions for each spectral maxima separation: (a) with highly overlapping spectra SEER provides on average 38.0% for harmonic 1, 50.6% for harmonic 2, while the best performing other comparison here is Gaussian r=0.3 with an average 26.7%. (b) With a 8.9 nm peak-to-peak separation SEER h=1 averages 57.0%, SEER h=2 49.6%, other best performing here is Peak Wavelength with 22.2%; (c) with 17.8 nm separation SEER h=1 averages 57.2%, SEER h=2 60.0±2.3%, other best Gauss r=0.3 with 26.2% (d) with 26.7 nm separation SEER h=1 averages 59.9%, SEER h=2 60.4%, other best Gauss r=0.3 with 32.1%; (e) with well separated spectra 35.6 nm apart, SEER h=1 averages 66.3%, SEER h=2 66.7%, with other best Gauss r=0.3 scoring 43.5% in average.

FIG. 53 Comparison of SEER and ICA spectral image visualization (RGB) under different spectral overlap and SNR conditions. The same simulation used in FIG. 50, which changes parameters for the Simulated Hyperspectral Test Chart obtaining different values of peak-to-peak spectral overlap and signal to noise, is used here to compute the accuracy for Independent Component Analysis using Python package Scikit-Learn function, sklearn.decomposition.FastICA, with 3 independent components (ICs) without optimization for this specific dataset. (a,b,c,d,e). The three ICs are utilized as R, G, B channels for creating a color image for each simulation parameter (ICA=3 line) and are shown here next to SEER harmonic 1 and 2 (SEER h=1 and SEER h=2 respectively). Error bars are the standard deviation. (f,g,h,i,j) The parameters of accuracy described in the methods section are applied here to the SEER and ICA results. Each value in the plots represents the average distance of $200^2$ pixels and error bars are the standard deviation of normalized accuracy value across all pixels. Accuracy of ICA, as calculated here, for multiple overlap values at high SNR (over 30) is in average 48.0% comparable to SEER, 57.9% h=1 and 57.6% h=2, but is reduced at low SNR (below 10) where it averages 21.0%, with SEER at 50.6% and 57.7% respectively for the first and second harmonic. (f) average accuracy ICA 20.2%, SEER 38.0% for harmonic 1, 50.6% for harmonic 2; (g) average accuracy ICA 36.1%, SEER h=1 57.0%, SEER h=2 49.6%; (h) average accuracy ICA 25.3%, SEER h=1 57.2%, SEER h=2 60.0%; (i) average accuracy ICA 35.9%, SEER h=1 59.9%, SEER h=2 60.4%; (j) average accuracy ICA 32.6%, SEER h=1 66.3%, SEER h=2 66.7%.

Figure 54:
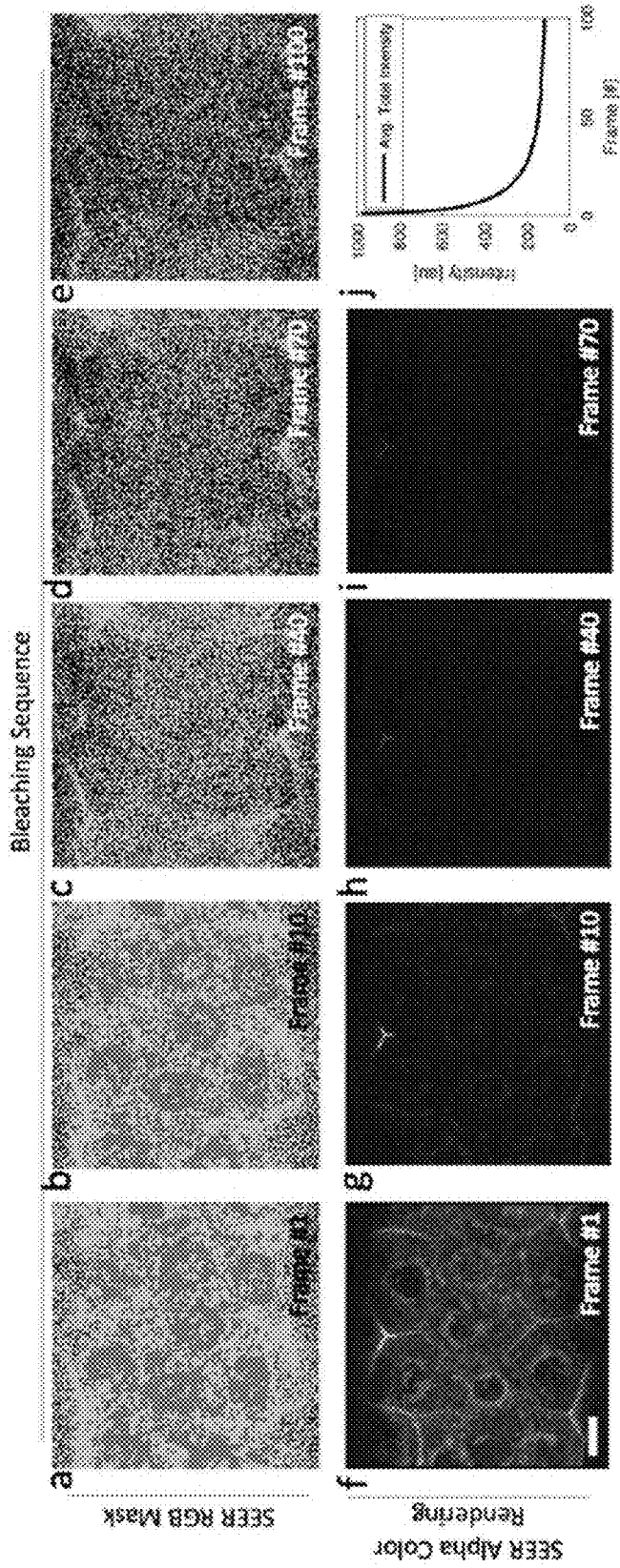

FIG. 54 Visualization of photobleaching with SEER. Photo-bleaching experiments were performed on a 24 hpf zebrafish embryo Gt(cltca-citrine); Tg(fli1:mKO2); Tg(ubiq:memTdTomato), labeling clathrin, pan-endothelial and membrane respectively. The experiments were performed utilizing the "bleaching" modality in the Zeiss Zen 780 inverted confocal, where single z positions were acquired in lambda mode. Frames are acquired every 13.7 sec, with 5 intermediate bleaching frames (not acquired) at high laser power until image intensity reached 90% bleaching. The SEER RGB mask represents the values of colors associated to each pixel, independent from the intensity values. The map used here is Radial map in Center of Mass mode. In this modality the map will adjust its position on the shifting center of mass of the phasor clusters, visually compensating for the decrease in intensity. (a) In the initial frame the cltca-citrine is associated to a magenta color, membrane to cerulean, pan-endothelial is not in frame and background to yellow. (b) Frame 10 shows consistent colors with the initial bleaching; the colors are maintained (c) at frame 40 and (d) frame 70 where most of the signal has bleached and most colors have switched to yellow (here, background). (e) Final frame shows the 90% bleached sample. The Alpha Color rendering adds the information of intensity to the image visualization. Here we show for comparison (f) frame 1, (g) frame 10, (h) frame 40 and (i) frame 70. Scale bar 10 µm. (j) Average total intensity plot as a function of frame, calculated from the sum of 32 channels, shows evident bleaching in the sample.

Figure 55:
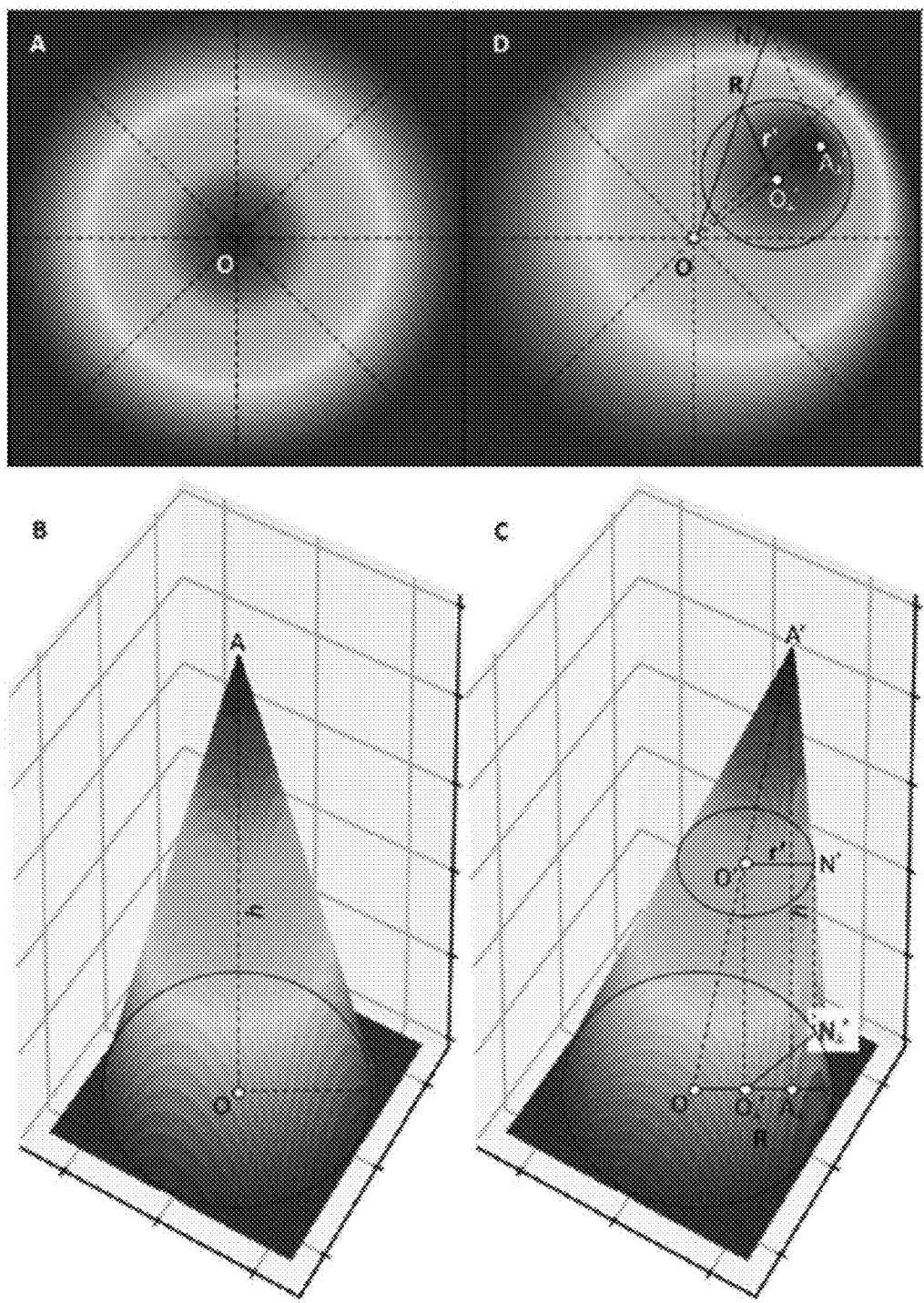

FIG. 55 Morph mode algorithm pictorial abstraction. (a) A Radial map in standard mode centered at the origin O can be abstracted as a (b) 3D Conic shape with height h and apex A. (c) Upon shifting the apex of the cone from A to A', the map reference center translates from origin O to the projection A⊥'. During this shift, the edges of the cone base are anchored on the phasor unit circle. (c-d) If we consider a plane cutting the oblique cone horizontally, the resulting section is a circle with center O' and radius r'. The projection of this circle is centered on O⊥' which lies on the line OA⊥', adjoining the fixed center O and new apex projection A⊥/and has the same radius r'. As a result, (d) all of the points in each of these projected circles are shifted along the vector OO⊥' on the phasor plot.

FIG. 56 Autofluorescence visualization in volumetric data of unlabeled freshly isolated mouse tracheal explant. A tiled z-stack (x,y,z) imaged with multi-spectral two photon microscopy (740 nm excitation, 32 wavelength bins, 8.9 nm bandwidth, 410-695 nm detection) is here visualized as a single (x,y) z-slice SEER RGB Gradient Descent Max Morph mask at (a) 43 µm, (b) 59 µm, (c) 65 µm depth. Color differences between basal and apical layer cells are maintained at different depths, with consistent hue for each of the cell layers. Colorbar represents the main wavelength associated to one color in nanometers. Volume renderings presented as SEER Alpha Color renderings for (d) top-down (x,y) view, (e) Lateral (y,z) view and (f) zoomed-in lateral (y,z) view show the shape and the 98 µm thickness of the unlabeled tissue sample.

Figure 57A:
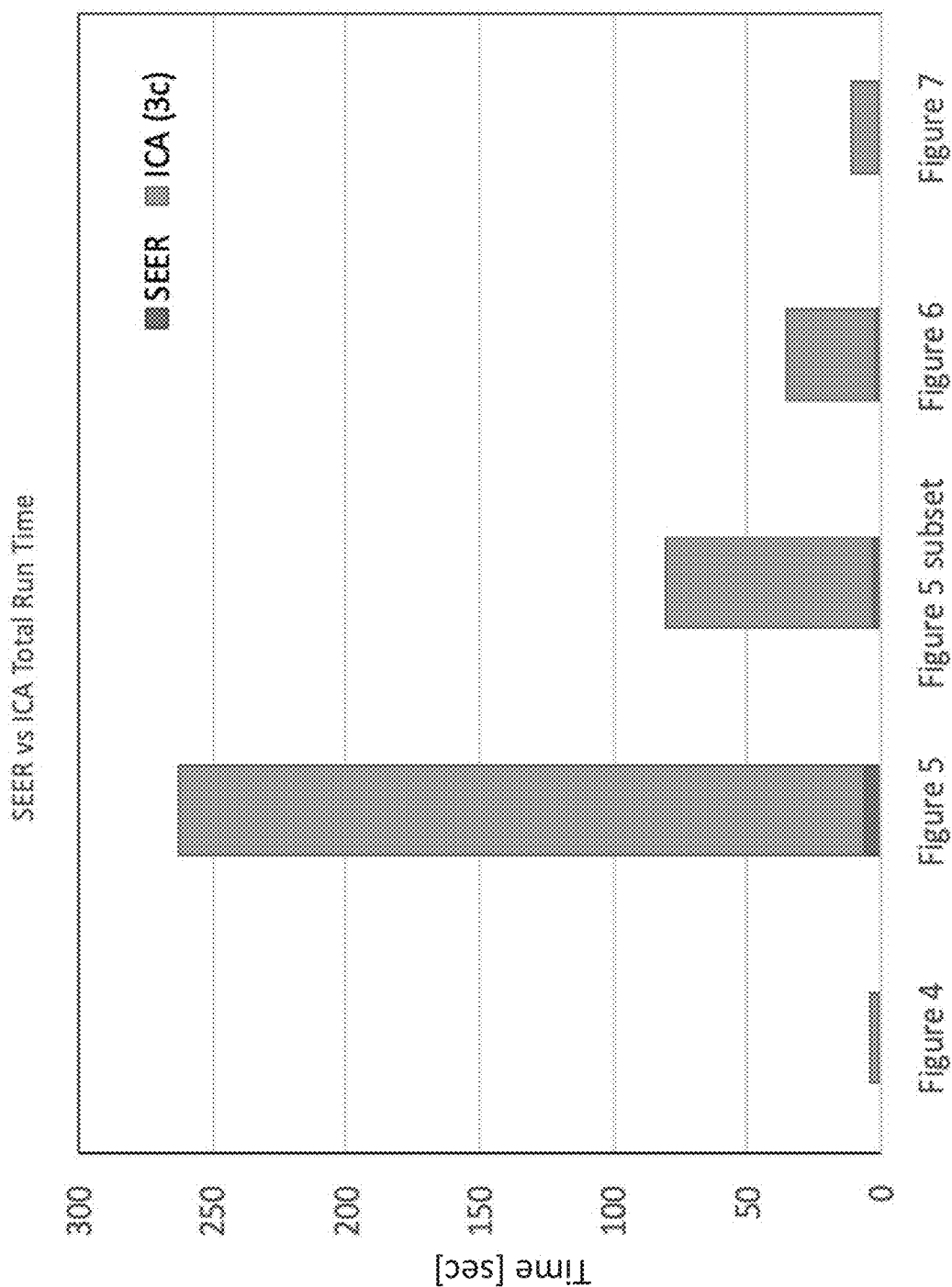
Figure 57B:
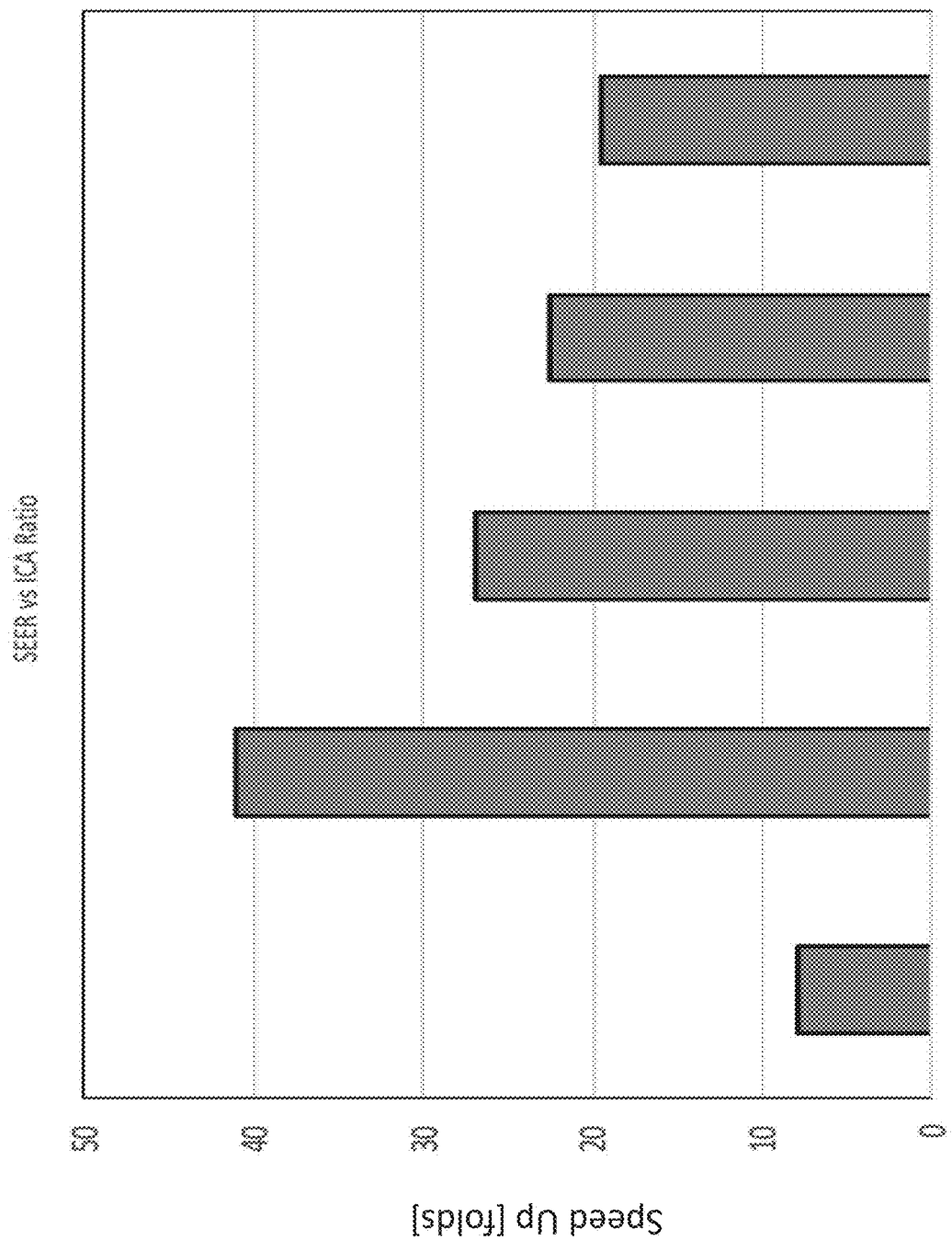

FIG. 57 Processing speed comparison SEER vs Independent Component Analysis for the datasets of FIGS. 27-30. Here we compare the processing time between SEER and the FastICA submodule of the python module, scikit-learn. With the same measurement strategy used in FIG. 31, timers using the perf_counter function within the python module, time, were placed around specific functions corresponding to the calculations required for the creation of SEER maps in HySP and with FastICA. (a) Run time for SEER (magenta) was considerably lower than ICA (3 components) (cyan) in all figures and their subsets. (b) The speed up was higher for larger z-stack spectral datasets (FIG. 28, 41-fold improvement) and reduced for smaller, single spectral images (FIG. 27, 7.9-fold improvement). Numerical values for these plots are reported in Table 4.

Figure 58A:
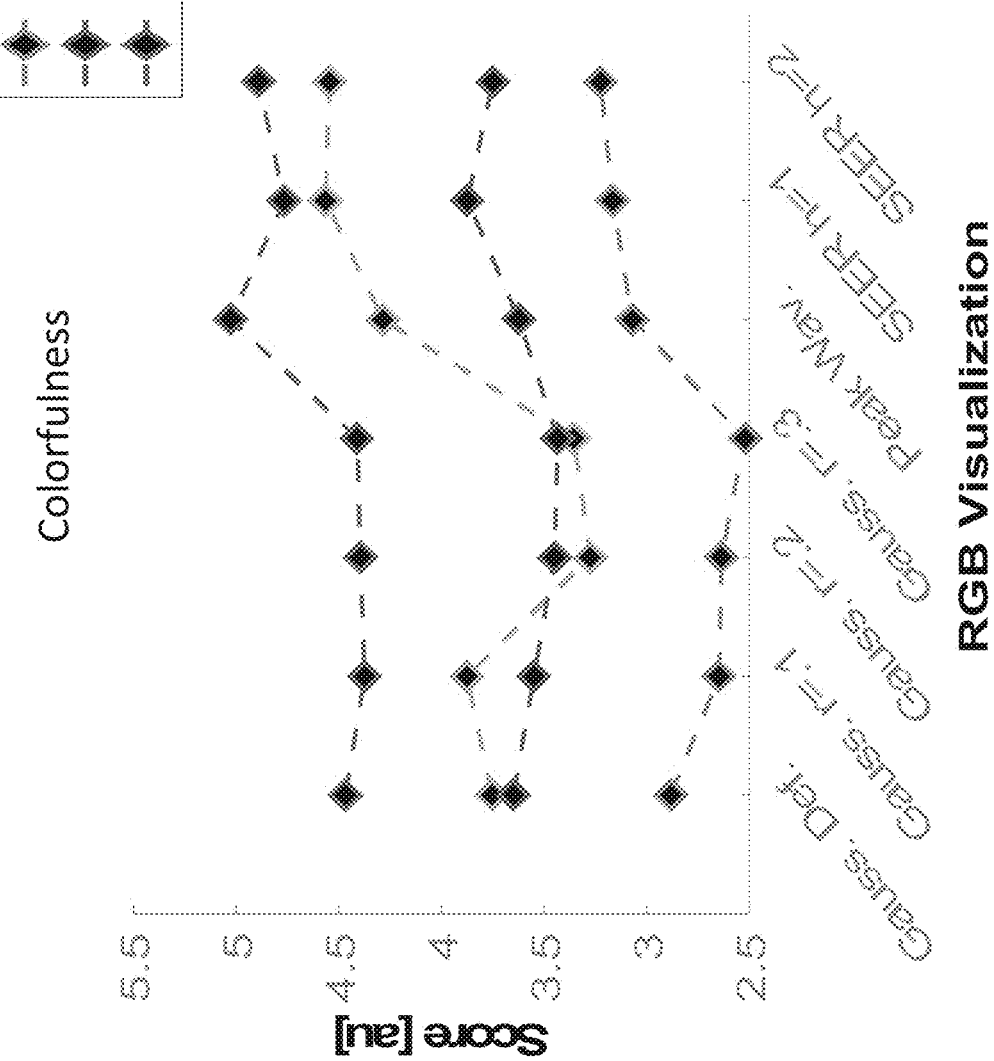
Figure 58B:
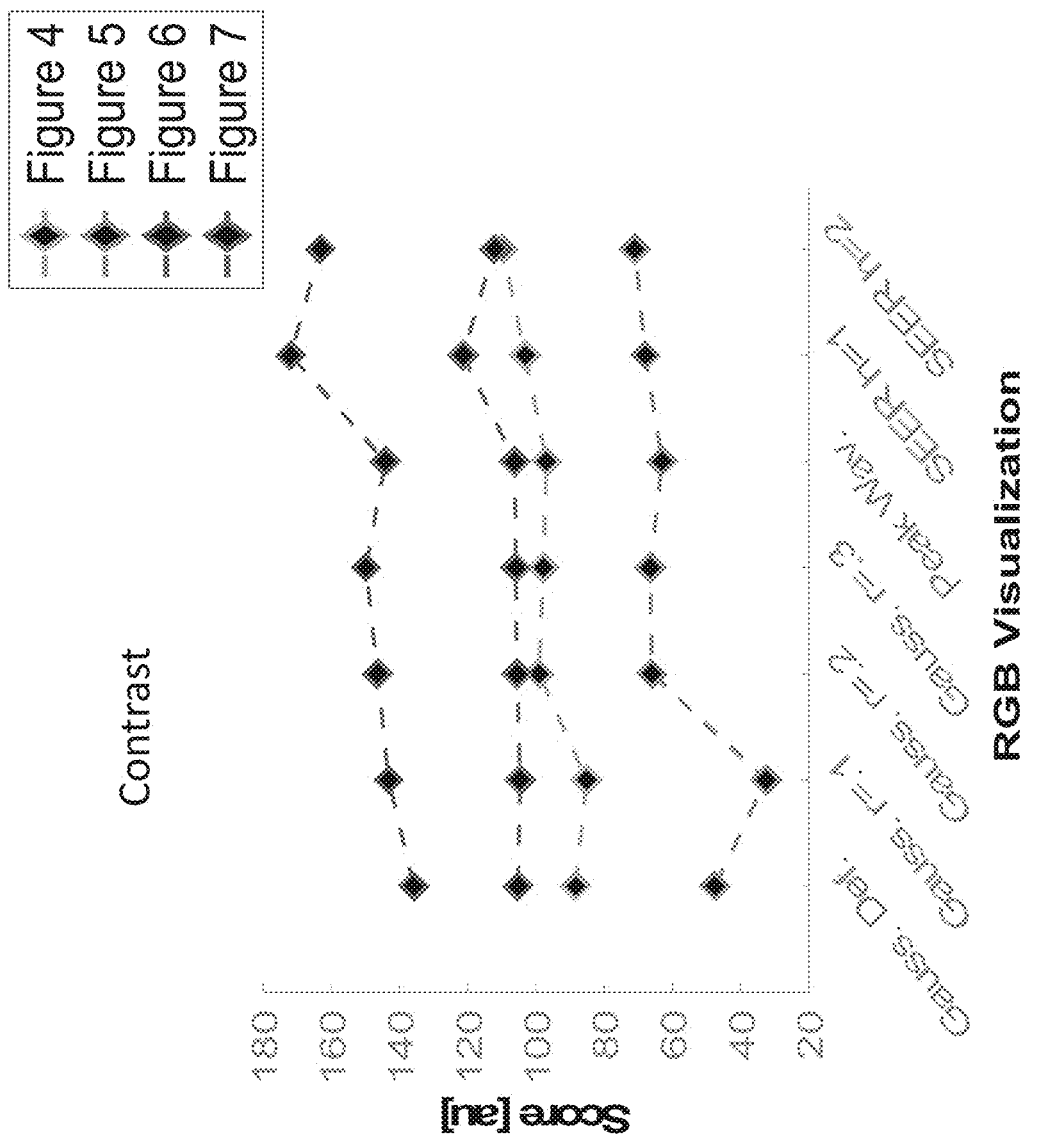
Figure 58D:
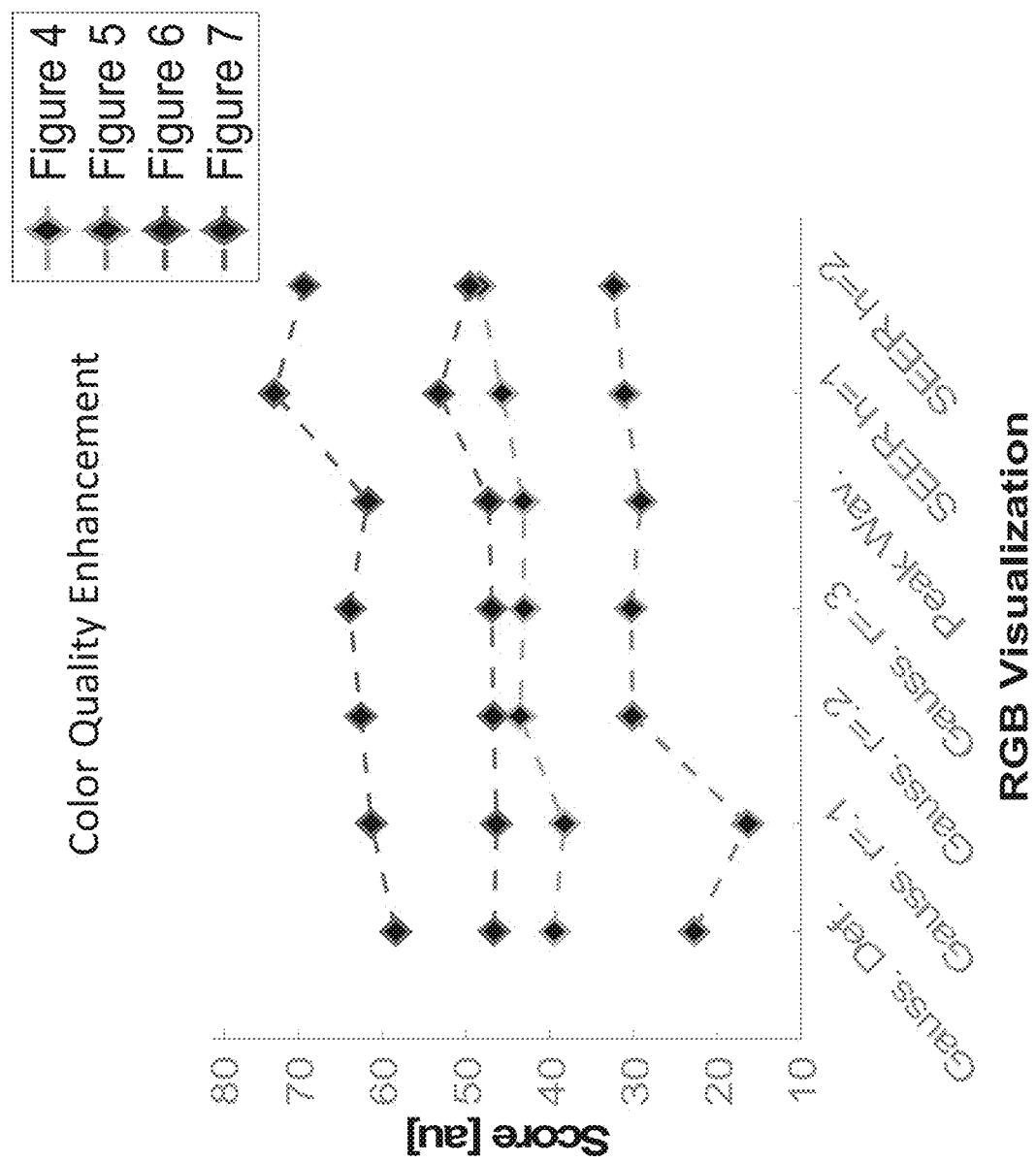

FIG. 58 Quantification of enhancement for FIGS. 27-30. The scores of (a) colorfulness, (b) contrast, (c) sharpness and (d) Color Quality Enhancement (CQE) are calculated according to Methods section for multiple visualization strategies. Average values are reported in Table 4 and 5. (a) Colorfulness values for SEER were generally higher than other approaches, made exception for FIG. 7 Peak Wavelength visualization (reported in Supplementary FIG. 19d), owing to a very low average intensity in the red channel (<IR>=840), and an almost double average green to blue intensity (<IG>/<IB>=1.7), which makes the β parameter used in colorfulness small in average and the denominator of the second logarithm in the colorfulness equation (Methods) approximately equal to 1, producing a factor of 10 larger than usual ratio of variance β to average β. This combination of intensities results in a colorfulness 1.03-fold higher than the SEER h=2, however in this case the value of colorfulness does not correspond to human observation (FIG. 49d) suggesting this score could be an outlier due to a special combination of intensities. The values of (b) contrast, (c) Sharpness show higher performance for SEER. (d) The CQE score of SEER was higher than the standard, with improvement of 11%-26% for FIG. 4, 7%-98% for FIG. 5, 14%-25% for FIG. 6 and 12%-15% for FIG. 7.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Following acronyms are used.
2D: Two dimensional
5D: Five dimensional.
HySP: Hyper-Spectral Phasors
IACUC: Institutional Animal Care and Use Committee
N: Number of acquired photons
n: Harmonic number
PMT: Photomultiplier tube
PTU: 1-phenyl-2-thiourea
SBR: Signal-to-background ratios
SEER: Spectrally Encoded Enhanced Representation
SNR: signal to noise
SP: Spectral Phasor
USC: University of Southern California This disclosure relates to a hyperspectral imaging system. This disclosure further relates to a hyperspectral imaging system that generates an unmixed color image of a target. This imaging system may be used for denoising and/or color unmixing multiple overlapping spectra in a low signal-to-noise regime with a fast analysis time. The unmixed color image of the target may be used in diagnosing a health condition.

The hyperspectral imaging system may carry out Hyper-Spectral Phasor (HySP) calculations to effectively analyze hyper-spectral time-lapse data. For example, this system may carry out HySP calculations to effectively analyze five-dimensional (5D) hyper-spectral time-lapse data. The main advantages of this system may include: (a) fast computational speed, (b) the ease of phasor analysis, and (c) a denoising system to obtain the minimally-acceptable signal-to-noise ratio (SNR), as demonstrated by way of example in FIG. 1.

This hyperspectral imaging system may efficiently reduce spectral noise, remove autofluorescence, and distinguish multiple spectrally-overlapping fluorophores within biological samples. This system may improve in vivo imaging, both by expanding the fluorophore palette choice and by reducing the contribution from background autofluorescence. In an example below, the robustness of HySP is demonstrated by imaging developing zebrafish embryos with seven colors during light-sensitive stages of development (FIGS. 2-3).

The hyperspectral imaging system 10 may include an optics system 20, an image forming system 30, or a combination thereof. For example, the hyperspectral imaging system may include and an optics system and an image forming system. For example, the hyperspectral imaging system may include an image forming system. One example of the exemplary hyperspectral imaging system comprising an optics system and an image forming system is schematically shown in FIG. 14. Exemplary optics systems are shown in FIGS. 15-21. An exemplary configuration of the image forming system is shown in FIG. 22. An exemplary configuration of the hyperspectral imaging system is shown in FIG. 23.

In this disclosure, the optics system may include at least one optical component. Examples of the at least one optical component are a detector ("optical detector"), a detector array ("optical detector array"), a source to illuminate the target ("illumination source"), a first optical lens, a second optical lens, an optical filter, a dispersive optic system, a dichroic mirror/beam splitter, a first optical filtering system placed between the target and the at least one optical detector, a second optical filtering system placed between the first optical filtering system and the at least one optical detector, or a combination thereof. For example, the at least one optical component may include at least one optical detector. For example, the at least one optical component may include at least one optical detector and at least one illumination source. For example, the at least one optical component may include at least one optical detector, at least one illumination source, at least one optical lens, at least one optical filter, and at least one dispersive optic system. For example, the at least one optical component may include at least one optical detector, at least one illumination source, a first optical lens, a second optical lens, and a dichroic mirror/beam splitter. For example, the at least one optical component may include at least one optical detector, at least one illumination source, an optical lens, a dispersive optic; and wherein at least one optical detector is an optical detector array. For example, the at least one optical component may include at least one optical detector, at least one illumination source, an optical lens, a dispersive optic, a dichroic mirror/beam splitter; and wherein at least one optical detector is an optical detector array. For example, the at least one optical component may include at least one optical detector, at least one illumination source, an optical lens, a dispersive optic, a dichroic mirror/beam splitter; wherein at least one optical detector is an optical detector array; and wherein the illumination source directly illuminates the target. These optical components may form, for example, the exemplary optics systems shown in FIGS. 15-21.

In this disclosure, the optical system may include an optical microscope. Examples of the optical microscope may be a confocal fluorescence microscope, a two-photon fluorescence microscope, or a combination thereof.

In this disclosure, the at least one optical detector may have a configuration that detects electromagnetic radiation absorbed, transmitted, refracted, reflected, and/or emitted ("target radiation") by at least one physical point on the target. The target radiation may include at least one wave ("target wave"). The target radiation may include at least two target waves. Each target wave may have an intensity and a different wavelength. The at least one optical detector may have a configuration that detects the intensity and the wavelength of each target wave. The at least one optical detector may have a configuration that transmits the detected target radiation to the image forming system. The at least one optical detector may have a configuration that transmits the detected intensity and wavelength of each target wave to the image forming system. The at least one optical detector may have any combination of these configurations.

The at least one optical detector may include a photomultiplier tube, a photomultiplier tube array, a digital camera, a hyperspectral camera, an electron multiplying charge coupled device, a Sci-CMOS, a digital camera, or a combination thereof. The digital camera may be any digital camera. The digital camera may be used together with an active filter for detection of the target radiation. The digital camera may also be used together with an active filter for detection of the target radiation, for example, comprising, luminescence, thermal radiation, or a combination thereof.

In this disclosure, the target radiation may include an electromagnetic radiation emitted by the target. The electromagnetic radiation emitted by the target may include luminescence, thermal radiation, or a combination thereof. The luminescence may include fluorescence, phosphorescence, or a combination thereof. For example, the electromagnetic radiation emitted by the target may include fluorescence, phosphorescence, thermal radiation, or a combination thereof. For example, the electromagnetic radiation emitted by the target may include fluorescence. The at least one optical component may further include a first optical filtering system. The at least one optical component may further include a first optical filtering system and a second optical filtering system. The first optical filtering system may be placed between the target and the at least one optical detector. The second optical filtering system may be placed between the first optical filtering system and the at least one optical detector. The first optical filtering system may include a dichroic filter, a beam splitter type filter, or a combination thereof. The second optical filtering system may include a notch filter, an active filter, or a combination thereof. The active filter may include an adaptive optical system, an acousto-optic tunable filter, a liquid crystal tunable bandpass filter, a Fabry-Perot interferometric filter, or a combination thereof.

In this disclosure, the at least one optical detector may detect the target radiation at a wavelength in the range of 300 nm to 800 nm. The at least one optical detector may detect the target radiation at a wavelength in the range of 300 nm to 1,300 nm.

In this disclosure, the at least one illumination source may generate an electromagnetic radiation ("illumination source radiation"). The illumination source radiation may include at least one wave ("illumination wave"). The illumination source radiation may include at least two illumination waves. Each illumination wave may have a different wavelength. The at least one illumination source may directly illuminate the target. In this configuration, there is no optical component between the illumination source and the target. The at least one illumination source may indirectly illuminate the target. In this configuration, there is at least one optical component between the illumination source and the target. The illumination source may illuminate the target at each illumination wavelength by simultaneously transmitting all illumination waves. The illumination source may illuminate the target at each illumination wavelength by sequentially transmitting all illumination waves.

In this disclosure, the illumination source may include a coherent electromagnetic radiation source. The coherent electromagnetic radiation source may include a laser, a diode, a two-photon excitation source, a three-photon excitation source, or a combination thereof.

In this disclosure, the illumination source radiation may include an illumination wave with a wavelength in the range of 300 nm to 1,300 nm. The illumination source radiation may include an illumination wave with a wavelength in the range of 300 nm to 700 nm. The illumination source radiation may include an illumination wave with a wavelength in the range of 690 nm to 1,300 nm. For example, the illumination source may be a one-photon excitation source that is capable of generating electromagnetic radiation in the range of 300 to 700 nm. For example, such one-photon excitation source may generate an electromagnetic radiation that may include a wave with a wavelength of about 405 nm, about 458 nm, about 488 nm, about 514 nm, about 554 nm, about 561 nm, about 592 nm, about 630 nm, or a combination thereof. In another example, the source may be a two-photon excitation source that is capable of generating electromagnetic radiation in the range of 690 nm to 1,300 nm. Such excitation source may be a tunable laser. Yet in another example, the source may a one-photon excitation source and a two-photon excitation source that is capable of generating electromagnetic radiation in the range of 300 nm to 1,300 nm. For example, such one-photon excitation source may generate an electromagnetic radiation that may include a wave with a wavelength of about 405 nm, about 458 nm, about 488 nm, about 514 nm, about 554 nm, about 561 nm, about 592 nm, about 630 nm, or a combination thereof. For example, such two-photon excitation source may be capable of generating electromagnetic radiation in the range of 690 nm to 1,300 nm. Such two-photon excitation source may be a tunable laser.

In this disclosure, the intensity of the illumination source radiation may not be higher than a certain level such that when the target is illuminated the target is not damaged by the illumination source radiation.

In this disclosure, the hyperspectral imaging system may include a microscope. The microscope may be any microscope. For example, the microscope may be an optical microscope. Any optical microscope may be suitable for the system. Examples of an optical microscope may be a two-photon microscope, a one-photon confocal microscope, or a combination thereof. Examples of the two-photon microscopes are disclosed in Alberto Diaspro "Confocal and Two-Photon Microscopy: Foundations, Applications and Advances" Wiley-Liss, New York, November 2001; and Greenfield Sluder and David E. Wolf "Digital Microscopy" 4th Edition, Academic Press, Aug. 20, 2013. The entire content of each of these publications is incorporated herein by reference.

An exemplary optics system comprising a fluorescence microscope 100 is shown in FIG. 15. This exemplary optics system may include at least one optical component. In this system, optical components may include an illumination source 101, a dichroic mirror/beam splitter 102, a first optical lens 103, a second optical lens 104, and a detector 106. These optical components may form a fluorescence microscope 100. This exemplary system may be suitable to form an image of a target 105. The source may generate an illumination source radiation 107. The dichroic mirror/beam splitter 102 may reflect the illumination wave to illuminate the target 105. The target, as a result, may emit an electromagnetic radiation (e.g. fluorescence) 108 and reflect back the illumination source radiation 107. The dichroic mirror/beam splitter 102 may filter the illumination source radiation from the target and may substantially prevent the illumination source radiation reflected from the target reaching the detector. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

An exemplary optics system comprising a multiple illumination wavelength microscope 200 is shown in FIG. 16. This exemplary optics system may include at least one optical component. In this system, the optical components may include an illumination source 101, a dichroic mirror/beam splitter 102, a first optical lens 103, a second optical lens 104, and a detector 106. These optical components may form a hyperspectral imaging system comprising a fluorescence microscope, a reflectance microscope, or a combination thereof. This exemplary system may be suitable to form an image of a target 105. The illumination source may generate an illumination source radiation comprising multiple waves wherein each wave may have a different wavelength. For example, the illumination source in this example may generate an illumination source radiation comprising two waves each having a different wavelength, 201 and 202. The source may sequentially illuminate the target at each wavelength. The dichroic mirror/beam splitter 102 may reflect the illumination source radiation to illuminate the target 105. The target, as a result, may emit and/or may reflect back a wave of the electromagnetic radiation. In one example, the dichroic mirror/beam splitter 102 may filter the electromagnetic radiation from the target and may substantially allow emitted radiation to reach the detector and substantially prevent the illumination source radiation reflected from the target reaching the detector. In another example, the dichroic mirror/beam splitter 102 may transmit only the reflected waves from the target, but substantially filter emitted waves from the target, thereby allowing only the reflected waves from the target to reach the detector. Yet in another example, the dichroic mirror/beam splitter 102 may transmit both the reflected radiation and emitted radiation from the target, thereby allowing both the reflected radiation and the reflected radiation from the target to reach the detector. In this example, multiple waves may reach the detector, each having a different wavelength. For example, the electromagnetic radiation reaching the detector may have two waves 203 and 204, each having a different wavelength. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Another exemplary hyperspectral imaging system comprising a multiple wavelength detection microscope 300 is shown in FIG. 17. This exemplary hyperspectral imaging system may include at least one optical component. In this system, the optical components may include a first optical lens 103, a dispersive optic 302, and a detector array 304. These optical components may form a hyperspectral imaging system comprising a fluorescence device, a reflectance device, or a combination thereof. This exemplary system may be suitable to form an image of a target 105. The target may emit and/or may reflect a wave 301 of an electromagnetic radiation. In this example, at least one wave or at least two waves may reach the detector array. Each wave may have a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Another exemplary hyperspectral imaging system comprising a multiple wavelength detection microscope 400 is shown in FIG. 18. This exemplary hyperspectral imaging system may include at least one optical component. In this system, the optical components may include an illumination source 101, a dichroic mirror/beam splitter 102, a first optical lens 103, a dispersive optic 302, and a detector array 304. These optical components may form a hyperspectral imaging system comprising a fluorescence device. This exemplary system may be suitable to form an image of a target 105. The illumination source may generate an illumination source radiation comprising at least one wave 107. Each wave may have a different wavelength. The source may sequentially illuminate the target at each wavelength. The dichroic mirror/beam splitter 102 may reflect the illumination wave to illuminate the target 105. The target, as a result, may emit a wave of the electromagnetic radiation. The dichroic mirror/beam splitter 102 may substantially allow the emitted wave 301 to reach the detector array, but may filter the target radiation and thereby substantially prevent the waves reflected from the target to reach the detector array. In this example, the emitted radiation reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features disclosed above. For example, this unmixed color image of the target may be generated by using any of the system features schematically shown in FIGS. 22-23.

Another exemplary hyperspectral imaging system comprising a multiple illumination wavelength and multiple wavelength detection device 500 is shown in FIG. 19. This exemplary hyperspectral imaging system may include at least one optical component. In this system, the optical components may include an illumination source 101, a dichroic mirror/beam splitter 102, a first optical lens 103, a dispersive optic 302, and a detector array 304. These optical components may form a hyperspectral imaging system comprising a fluorescence microscope, a reflectance microscope, or a combination thereof. This exemplary system may be suitable to form an image of a target 105. The source may generate an illumination wave comprising multiple waves wherein each wave may have a different wavelength. For example, the illumination source in this example may generate an illumination source radiation comprising two waves each having a different wavelength, 201 and 202. The illumination source may sequentially illuminate the target at each wavelength. The dichroic mirror/beam splitter 102 may reflect the illumination radiation to illuminate the target 105. The target, as a result, may emit and/or may reflect back the electromagnetic radiation. In one example, the dichroic mirror/beam splitter 102 may filter the radiation from the target substantially allowing only emitted radiation reaching the detector array, but substantially preventing the radiation reflected from the target to reach the detector array. In another example, the dichroic mirror/beam splitter 102 may transmit only the reflected waves from the target, but substantially filter emitted waves from the target, thereby substantially allowing only the reflected waves from the target to reach the detector array. Yet in another example, the dichroic mirror/beam splitter 102 may substantially transmit both the reflected waves and emitted waves from the target, thereby allowing both the reflected waves and the reflected beams from the target to reach the detector array. In this example, the beam reaching detector array may have multiple waves, each having a different wavelength. For example, the beam reaching the detector array may have two waves 203 and 204, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Another exemplary optical system comprising a multiple wavelength detection device 600 is shown in FIG. 20. This exemplary optical system may include at least one optical component. In this system, the optical components may include an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, reflect, refract, and/or absorb a beam 203 of the electromagnetic radiation. In this example, the emitted, reflected, refracted, and/or absorbed beam reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Another exemplary optics system comprising a multiple wavelength detection device 700 is shown in FIG. 21. This optics system may include at least one optical component. In this system, the optical components may include an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, transmit, refract, and/or absorb a beam 203 of the electromagnetic radiation. In this example, the emitted, transmitted, refracted, and/or absorbed electromagnetic radiation reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

In this disclosure, the image forming system 30 may include a control system 40, a hardware processor 50, a memory system 60, a display 70, or a combination thereof. An exemplary image forming system is shown in FIG. 14. The control system may be any control system. For example, the control system may control the optics system. For example, the control system may control at least one optical component of the optics system. For example, the control system may control the at least one optical detector to detect target radiation, detect the intensity and the wavelength of each target wave, transmit the detected intensity and wavelength of each target wave to the image forming system, and display the unmixed color image of the target. For example, the control system may control motions of the optical components, for example, opening and closure of optical shutters, motions of mirrors, and the like. The hardware processor can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. In an embodiment, all of the processing discussed herein is performed by the one or more hardware processor(s). For example, the hardware processor may form the target image, perform phasor analysis, perform the Fourier transform of the intensity spectrum, apply the denoising filter, form the phasor plane, map back the phasor point(s), assigns the arbitrary color(s), generate the unmixed color image of the target, the like, or a combination of such configurations thereof. The memory system may be any memory system. For example, the memory system may receive and store inputs from the hardware processor. These inputs, for example, may be the target image, the target radiation, the intensity spectrum, the phasor plane, the unmixed color image of the target, the like, or a combination of such configurations. For example, the memory system may provide outputs to other components of the image forming system, for example, to the processor and/or the display. These outputs, for example, may be the target image, the target radiation, the intensity spectrum, the phasor plane, the unmixed color image of the target, the like, or a combination of such configurations. The display may be any display. For example, the display may display the target image, the intensity spectrum, the phasor plane, the unmixed color image of the target, the like, or a combination of such configurations. The image forming system 30 may be connected with the optics system 20 via a network. In some instances the image forming system 30 may be located on a server that is remote from the optics system 20.

In this disclosure, the image forming system may have a configuration that causes the optical detector to detect the target radiation and to transmit the detected intensity and wavelength of each target wave to the image forming system.

In this disclosure, the image forming system may have a configuration that acquires the detected target radiation comprising the at least two target waves.

In this disclosure, the image forming system may have a configuration that acquires a target radiation comprising at least two target waves, each wave having an intensity and a different wavelength.

In this disclosure, the image forming system may have a configuration that acquires a target image, wherein the target image includes at least two pixels, and wherein each pixel corresponds to one physical point on the target.

In this disclosure, the image forming system may have a configuration that forms an image of the target using the detected target radiation ("target image"). The target image may include at least one pixel. The target image may include at least two pixels. Each pixel corresponds to one physical point on the target.

In this disclosure, the target image may be formed/acquired in any form. For example, the target image may have a visual form and/or a digital form. For example, the formed/acquired target image may be a stored data. For example, the formed/acquired target image may be stored in the memory system as data. For example, the formed/acquired target image may be displayed on the image forming system's display. For example, the formed/acquired target image may be an image printed on a paper or any similar media.

In this disclosure, the image forming system may have a configuration that forms at least one spectrum for each pixel using the detected intensity and wavelength of each target wave ("intensity spectrum").

In this disclosure, the image forming system may have a configuration that acquires at least one intensity spectrum for each pixel, wherein the intensity spectrum includes at least two intensity points.

In this disclosure, the intensity spectrum may be formed/acquired in any form. For example, the intensity spectrum may have a visual form and/or a digital form. For example, the formed/acquired intensity spectrum may be a stored data. For example, the formed/acquired intensity spectrum may be stored in the memory system as data. For example, the formed/acquired intensity spectrum may be displayed on the image forming system's display. For example, the formed/acquired intensity spectrum may be an image printed on a paper or any similar media.

In this disclosure, the image forming system may have a configuration that transforms the formed intensity spectrum of each pixel using a Fourier transform into a complex-valued function based on the intensity spectrum of each pixel, wherein each complex-valued function has at least one real component and at least one imaginary component.

In this disclosure, the image forming system may have a configuration that applies a denoising filter on both the real component and the imaginary component of each complex-valued function at least once so as to produce a denoised real value and a denoised imaginary value for each pixel.

In this disclosure, the image forming system may have a configuration that forms one point on a phasor plane ("phasor point") for each pixel by plotting the denoised real value against the denoised imaginary value of each pixel. The image forming system may form the phasor plane, for example, by using its hardware components, for example, the control system, the hardware processor, the memory or a combination thereof. The image forming system may display the phasor plane.

In this disclosure, the phasor point and/or phasor plane may be formed/acquired in any form. For example, the phasor point and/or phasor plane may have a visual form and/or a digital form. For example, the formed/acquired phasor point and/or phasor plane may be a stored data. For example, the formed/acquired phasor point and/or phasor plane may be stored in the memory system as data. For example, the formed/acquired phasor point and/or phasor plane may be displayed on the image forming system's display. For example, the formed/acquired phasor point and/or phasor plane may be an image printed on a paper or any similar media.

In this disclosure, the image forming system may have a configuration that maps back the phasor point to a corresponding pixel on the target image based on the phasor point's geometric position on the phasor plane. In this disclosure, the image forming system may have a configuration that maps back the phasor plane to the corresponding target image based on each phasor point's geometric position on the phasor plane. The image forming system may map back the phasor point, for example, by using its hardware components, for example, the control system, the hardware processor, the memory or a combination thereof.

In this disclosure, the phasor point and/or phasor plane may be mapped back in any form. For example, the mapped back phasor point and/or phasor plane may have a visual form and/or a digital form. For example, the mapped back phasor point and/or phasor plane may be a stored data. For example, the mapped back phasor point and/or phasor plane may be stored in the memory system as data. For example, the mapped back phasor point and/or phasor plane may be displayed on the image forming system's display. For example, the mapped back phasor point and/or phasor plane may be an image printed on a paper or any similar media.

In this disclosure, the image forming system may have a configuration that assigns an arbitrary color to the corresponding pixel based on the geometric position of the phasor point on the phasor plane.

In this disclosure, the image forming system may have a configuration that generates an unmixed color image of the target based on the assigned arbitrary color.

In this disclosure, the unmixed color image may be formed in any form. For example, the unmixed color image may have a visual form and/or a digital form. For example, the unmixed color image may be a stored data. For example, the unmixed color image may be stored in the memory system as data. For example, the unmixed color image may be displayed on the image forming system's display. For example, the unmixed color image may be an image printed on a paper or any similar media.

In this disclosure, the image forming system may have a configuration that displays the unmixed color image of the target on the image forming system's display.

In this disclosure, the image forming system may have any combination of above configurations.

In this disclosure, the image forming system may use at least one harmonic of the Fourier transform to generate the unmixed color image of the target. The image forming system may use at least a first harmonic of the Fourier transform to generate the unmixed color image of the target. The image forming system may use at least a second harmonic of the Fourier transform to generate the unmixed color image of the target. The image forming system may use at least a first harmonic and a second harmonic of the Fourier transform to generate the unmixed color image of the target.

In this disclosure, the denoising filter may be any denoising filter. For example, the denoising filter may be a denoising filter such that when the denoising filter is applied, the image quality is not compromised. For example, when the denoising filter is applied, the detected electromagnetic radiation intensity at each pixel in the image may not change. An example of a suitable denoising filter may include a median filter.

In this disclosure, the unmixed color image of the target may be formed at a signal-to-noise ratio of the at least one spectrum in the range of 1.2 to 50. The unmixed color image of the target may be formed at a signal-to-noise ratio of the at least one spectrum in the range of 2 to 50.

In one example, a hyperspectral imaging system for generating an unmixed color image of a target may include an optics system and an image forming system. The optics system may include at least one optical component. The at least one optical component may include at least one optical detector. The at least one optical detector may have a configuration that detects electromagnetic radiation absorbed, transmitted, refracted, reflected, and/or emitted ("target radiation") by at least one physical point on the target, the target radiation includes at least two waves ("target waves"), each wave having an intensity and a different wavelength; detects the intensity and the wavelength of each target wave; and transmits the detected target radiation, and each target wave's detected intensity and wavelength to the image forming system. The image forming system may include a control system, a hardware processor, a memory, and a display. The image forming system may have a configuration that forms an image of the target using the detected target radiation ("target image"), wherein the target image includes at least two pixels, and wherein each pixel corresponds to one physical point on the target; forms at least one spectrum for each pixel using the detected intensity and wavelength of each target wave ("intensity spectrum"); transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one point on a phasor plane ("phasor point") for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; generates an unmixed color image of the target based on the assigned arbitrary color; and displays the unmixed color image of the target on the image forming system's display.

In one example, the image forming system may have a configuration that causes the optical detector to detect the target radiation and to transmit the detected intensity and wavelength of each target wave to the image forming system. This image forming system may acquire the detected target radiation comprising the at least two target waves; form an image of the target using the detected target radiation ("target image"), wherein the target image includes at least two pixels, and wherein each pixel corresponds to one physical point on the target; forms at least one spectrum for each pixel using the detected intensity and wavelength of each target wave ("intensity spectrum"); transform the formed intensity spectrum of each pixel using a Fourier transform into a complex-valued function based on the intensity spectrum of each pixel, wherein each complex-valued function has at least one real component and at least one imaginary component; apply a denoising filter on both the real component and the imaginary component of each complex-valued function at least once so as to produce a denoised real value and a denoised imaginary value for each pixel; form one point on a phasor plane ("phasor point") for each pixel by plotting the denoised real value against the denoised imaginary value of each pixel; map back the phasor point to a corresponding pixel on the target image based on the phasor point's geometric position on the phasor plane; assign an arbitrary color to the corresponding pixel based on the geometric position of the phasor point on the phasor plane; and generate an unmixed color image of the target based on the assigned arbitrary color. This image forming system may have a further configuration that displays the unmixed color image of the target on the image forming system's display.

In another example, the image forming system may have a configuration that acquires a target radiation comprising at least two target waves, each wave having an intensity and a different wavelength; forms a target image, wherein the target image includes at least two pixels, and wherein each pixel corresponds to one physical point on the target; forms at least one intensity spectrum for each pixel using the intensity and the wavelength of each target wave; transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one phasor point for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. This exemplary image forming system may have a further configuration that displays the unmixed color image of the target on the image forming system's display.

In another example, the image forming system may have a configuration that acquires a target image, wherein the target image includes at least two pixels, and wherein each pixel corresponds to one physical point on the target; acquires at least one intensity spectrum for each pixel, wherein the intensity spectrum includes at least two intensity points; transforms the intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one phasor point for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. This exemplary image forming system may have a further configuration that displays the unmixed color image of the target on the image forming system's display.

One example of the hyperspectral imaging system is schematically shown in FIG. 22. In this example, the imaging system may obtain an image of a target 401. The image may include at least two waves and at least two pixels. The system may form an image of the target using intensities of each wave ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. The system may thereby obtain a denoised real value and a denoised imaginary value for each pixel. The system may plot the denoised real value against the denoised imaginary value for each pixel. The system may thereby form a point on a phasor plane 407. The system may form at least one additional point on the phasor plane by using at least one more pixel of the image. The system may select at least one point on the phasor plane, based on its geometric position on the phasor plane. The system may map back 408 the selected point on the phasor plane to corresponding pixel on the image of the target and may assign a color to the corresponding pixel, and wherein the color is assigned based on the geometric position of the point on the phasor plane. As a result, the system may thereby generate an unmixed color image of the target 409.

Another example of the hyperspectral imaging system is schematically shown in FIG. 23. In this example, the hyperspectral imaging system further includes at least one detector 106 or a detector array 304. This imaging system may form an image of a target 401 by using the detector or the detector array. The image may include at least two waves and at least two pixels. The system may form an image of the target using intensities of each wave ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. The system may thereby obtain a denoised real value and a denoised imaginary value for each pixel. The system may plot the denoised real value against the denoised imaginary value for each pixel. The system may thereby form a point on a phasor plane 407. The system may form at least one additional point on the phasor plane by using at least one more pixel of the image. The system may select at least one point on the phasor plane, based on its geometric position on the phasor plane. The system may map back 408 the selected point on the phasor plane to corresponding pixel on the image of the target and may assign a color to the corresponding pixel, and wherein the color is assigned based on the geometric position of the point on the phasor plane. As a result, the system may thereby generate an unmixed color image of the target 409.

In this disclosure, the target may be any target. The target may be any target that has a specific spectrum of color. For example, the target may be a tissue, a fluorescent genetic label, an inorganic target, or a combination thereof.

In this disclosure, the system may be calibrated by using a reference to assign colors to each pixel. The reference may be any known reference. For example, the reference may be any reference wherein unmixed color image of the reference is determined prior to the generation of unmixed color image of the target. For example, the reference may be a physical structure, a chemical molecule, a biological molecule, a biological activity (e.g. physiological change) as a result of physical structural change and/or disease.

In this disclosure, the target radiation may include fluorescence. The hyperspectral imaging system suitable for fluorescence detection may include an optical filtering system. Examples of the optical filtering system are: a first optical filter to substantially decrease the intensity of the source radiation reaching to the detector. The first optical filter may be placed between the target and the detector. The first optical filter may be any optical filter. Examples of the first optical filter may be dichroic filter, a beam splitter type filter, or a combination thereof.

In this disclosure, the hyperspectral imaging system suitable for fluorescence detection may further include a second optical filter. The second optical filter may be placed between the first optical filter and the detector to further decrease the intensity of the source radiation reaching the detector. The second optical filter may be any optical filter. Examples of the second optical filter may be a notch filter, an active filter, or a combination thereof. Examples of the active filter may be an adaptive optical system, an acousto-optic tunable filter, a liquid crystal tunable bandpass filter, a Fabry-Perot interferometric filter, or a combination thereof.

In this disclosure, the hyperspectral imaging system may be calibrated by using a reference material to assign colors to each pixel. The reference material may be any known reference material. For example, the reference material may be any reference material wherein unmixed color image of the reference material is determined prior to the generation of unmixed color image of the target. For example, the reference material may be a physical structure, a chemical molecule (i.e. compound), a biological activity (e.g. physiological change) as a result of physical structural change and/or disease. The chemical compound may be any chemical compound. For example, the chemical compound may be a biological molecule (i.e. compound).

In this disclosure, the hyperspectral imaging system may be used to diagnose any health condition. For example, the hyperspectral imaging system may be used to diagnose any health condition of any mammal. For example, the hyperspectral imaging system may be used to diagnose any health condition of a human. Examples of the health condition may include a disease, a congenital malformation, a disorder, a wound, an injury, an ulcer, an abscess, or the like. The health condition may be related to a tissue. The tissue may be any tissue. For example, the tissue may include a skin. Examples of a health condition related to a skin or tissue may be a skin lesion. The skin lesion may be any skin lesion. Examples of the skin lesion may be a skin cancer, a scar, an acne formation, a wart, a wound, an ulcer, or the like. Other examples of a health condition of a skin or tissue may be a makeup of a tissue or a skin, for example, the tissue or the skin's moisture level, oiliness, collagen content, hair content, or the like.

In this disclosure, the target may include a tissue. The hyperspectral imaging system may display an unmixed color image of the tissue. The health condition may cause differentiation of chemical composition of the tissue. This chemical composition may be related to chemical compounds such as hemoglobin, melanin, a protein (e.g. collagen), oxygen water, the like, or a combination thereof. Due to the differentiation of the tissue's chemical composition, color of the tissue that is affected by the health condition may appear to be different than that of the tissue that is not affected by the health condition. Because of such color differentiation, the health condition of the tissue may be diagnosed. The hyperspectral imaging system may therefore allow a user to diagnose, for example, a skin condition, regardless of room lighting and skin pigmentation level.

For example, an illumination source radiation delivered to a biological tissue may undergo multiple scattering from inhomogeneity of biological structures and absorption by chemical compounds such as hemoglobin, melanin, and water present in the tissue as the electromagnetic radiation propagates through the tissue. For example, absorption, fluorescence, and scattering characteristics of the tissue may change during the progression of a disease. For example, therefore, the reflected, fluorescent, and transmitted light from tissue detected by the optical detector of the hyperspectral imaging of this disclosure may carry quantitative diagnostic information about tissue pathology.

The diagnosis of the health condition may be performed by any user, including a physician, a medical staff, or a consumer.

The diagnostic information, obtained by using the hyperspectral imaging system, may determine the health condition of the tissue. As such, this diagnostic information may enhance a patient's clinical outcome, for example, before, during, and/or after surgery or treatment. This hyperspectral imaging system, for example, may be used to track a patient's evolution of health over time by determining the health condition of, for example, the tissue of the patient. In this disclosure, the patient may be any mammal. For example, the mammal may be a human.

In this disclosure, the reference material disclosed above may be used in the diagnosis of the health condition.

In this disclosure, the hyperspectral imaging system comprising HySP may apply Fourier transform to convert all photons collected across spectrum into one point in the two dimensional (2D) phasor plot ("density plot"). The reduced dimensionality may perform well in low SNR regime compared to linear unmixing method, where each channel's error may contribute to the fitting result. In any imaging system, the number of photons emitted by a dye during a time interval may be a stochastic (Poissonian) process, where the signal (total digital counts) may scale as the average number of acquired photons, N; and the noise may scale as square-root of N, √N. Such Poissonian noise of the fluorescence emission and the detector readout noise may become more significant at lower light levels. First, the error on HySP plots may be quantitatively assessed. Then, this information may be used to develop a noise reduction approach to demonstrate that the hyperspectral imaging system comprising HySP is a robust system for resolving time-lapse hyperspectral fluorescent signals in vivo in a low SNR regime.

The following features are also within the scope of this disclosure.

For each pixel in a dataset, the Fourier coefficients of its normalized spectra may define the coordinates of its phasor point (z(n)), with n the harmonic number (Equation 1, below). The Sine and Cosine transforms here may be used to guarantee that two normalized identical spectra yield identical phasor points (FIG. 1b, inset). When these transforms are applied to real data, the system (for example, the system comprising a microscope) may have multiple sources of noise that might affect the exact coordinates of the phasor point. Poissonian and detector noise in each spectral bin may cause a scatter of points on phasor plot, which is called scatter error, (std{z(n)}) hereafter. In addition, compromised SNR and signal saturation may alter the mean position of the scatter distribution itself, which is called shifted-mean error hereafter.

Figure 1B:
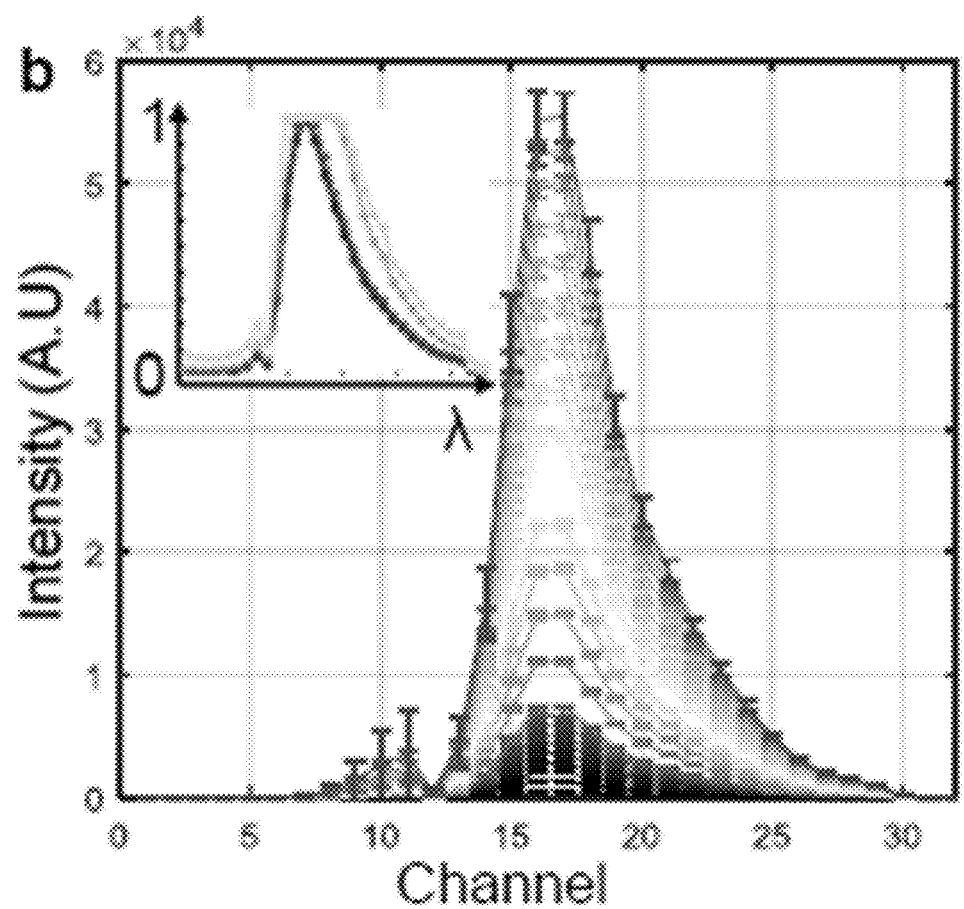
Figure 1C:
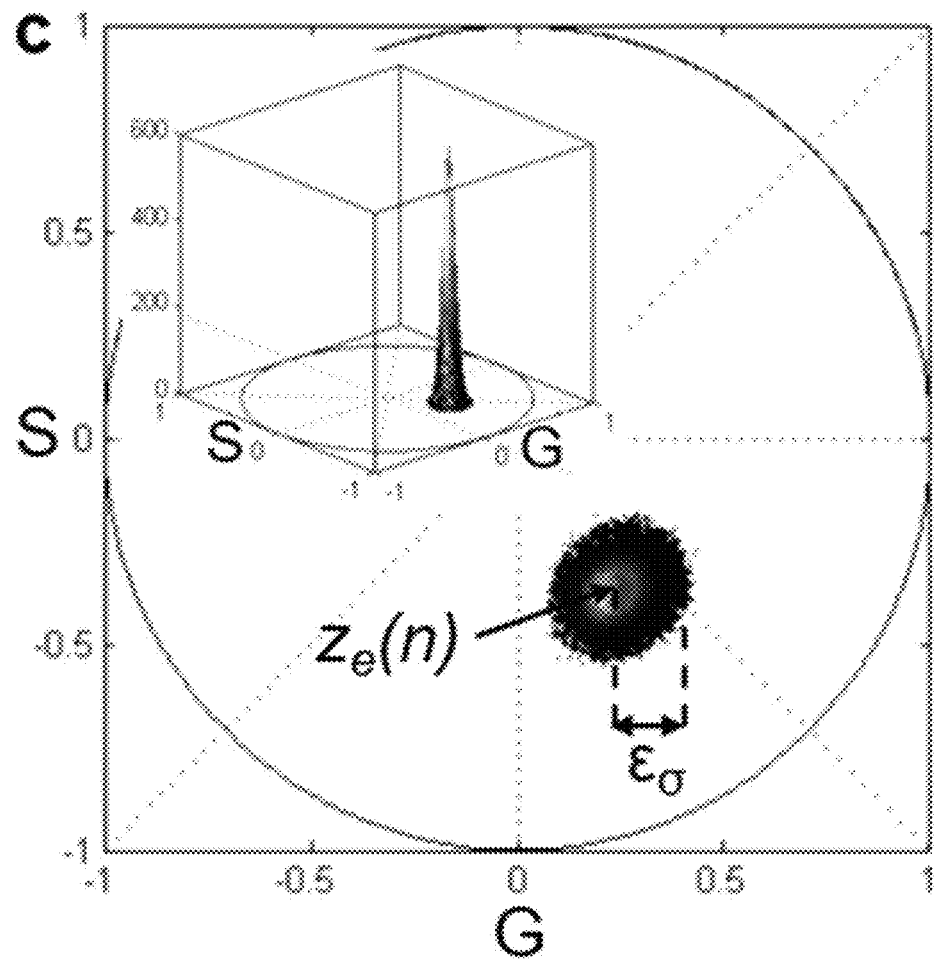
Figure 1D:
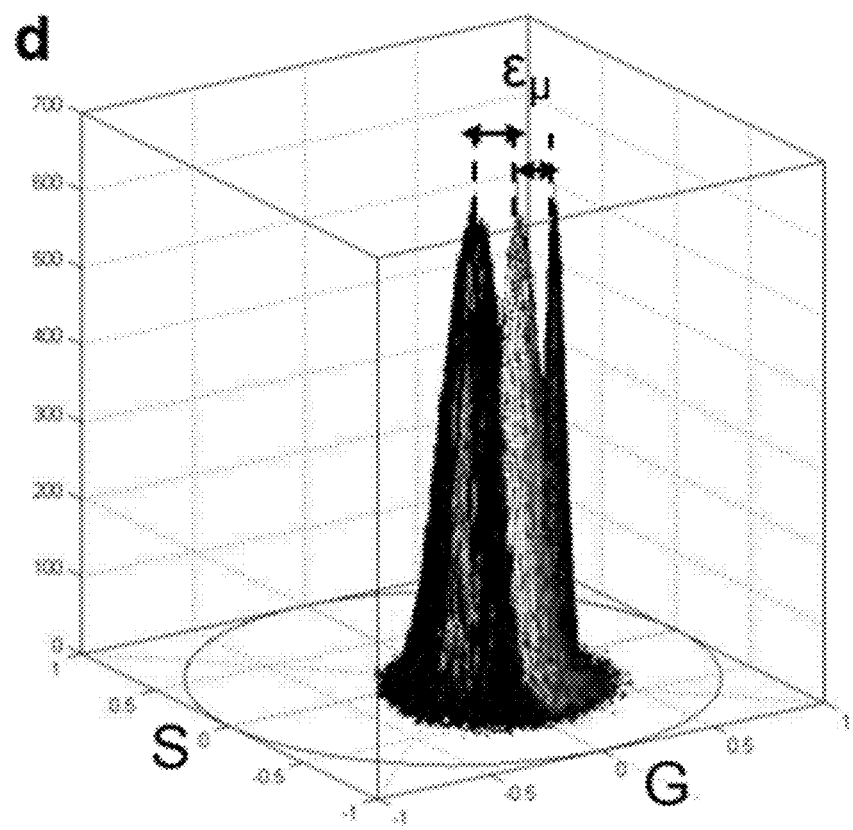

Scatter error may be observed around the expected fingerprint $z_e(n)$ of a spectrum when multiple measurements of the same fluorophore are represented on the phasor plot, and may be viewed as the standard deviation of phasor points around $z_e(n)$ (FIG. 1c). Shifted-mean error may be the result of degraded spectral shape from reduced SNR, inappropriate black-level settings, or inappropriate gain settings (saturation). Depending upon settings of the system, the average fingerprint position on the phasor plot may be shifted from its expected position $z_e(n)$ by the amount of the shifted-mean error (FIG. 1d). Combined, these two errors may disperse the points around the correct position on the phasor-plot $z_e(n)$.

Photon counting in an experiment may help quantify estimation of the bounds on either form of error. The detectors on most microscopes, and commercial multispectral confocal systems in particular, may record analog signals rather than photon counts. For the systems comprising such microscopes, quantitative estimates of these errors, in terms of recorded intensity values in the analog mode may be achieved.

To develop an experimental approach for estimating the contributions of both sources of error on the phasor plot, the emission spectra of fluorescein on a commercial confocal microscope equipped with parallel multi-channel spectral detector, at different acquisition parameters (Table 1, shown below) were recorded.

TABLE 1

Parameters for Fluorescein imaging.

| | Gain (A.U.) | 488 nm laser power (%) | Pixel dwell time (μs) |
|---|---|---|---|
| Experiment 1 | 500-1250 in steps of 25 | 2 | 6.3 |
| Experiment 2 | 700 | 1-60 in steps of 3 | 6.3 |
| Experiment 3 | 750 | 1-60 in steps of 3 | 6.3 |
| Experiment 4 | 800 | 1-21 in steps of 3 | 6.3 |
| Experiment 5 | 850 | 1-21 in steps of 3 | 6.3 |
| Experiment 6 | 900 | 1-21 in steps of 3 | 6.3 |
| Experiment 7 | 950 | 1-21 in steps of 3 | 6.3 |
| Experiment 8 | 850 | 21 | 2.55-177.32 in steps dictated by controlling software |

Figure 1E:
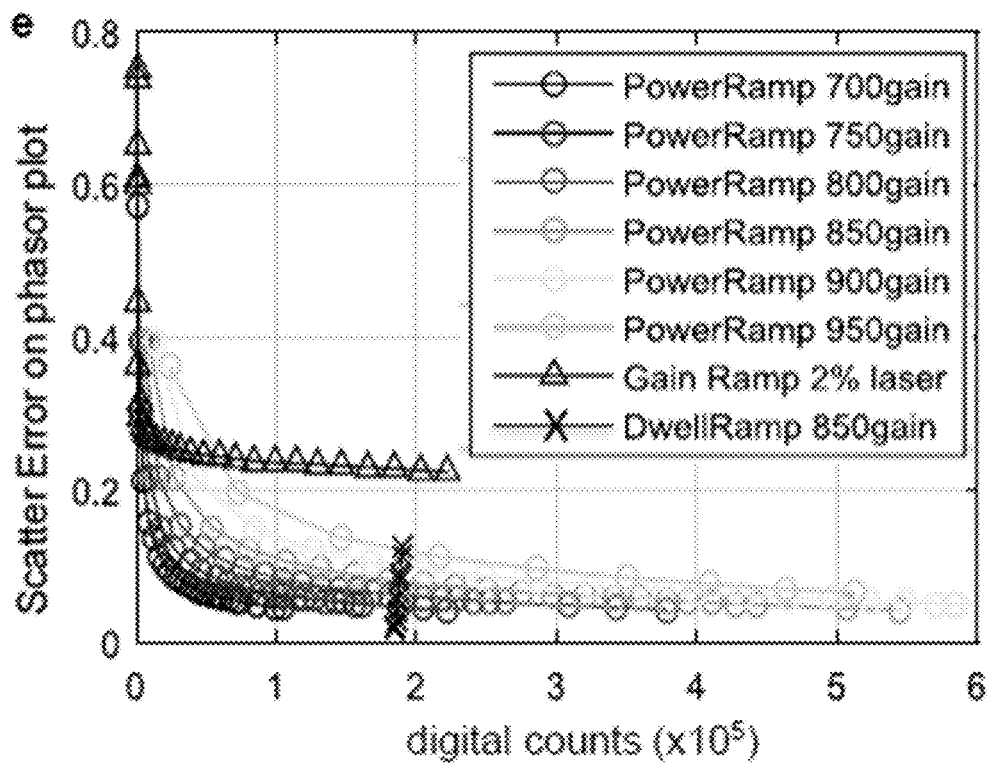
Figure 4A:
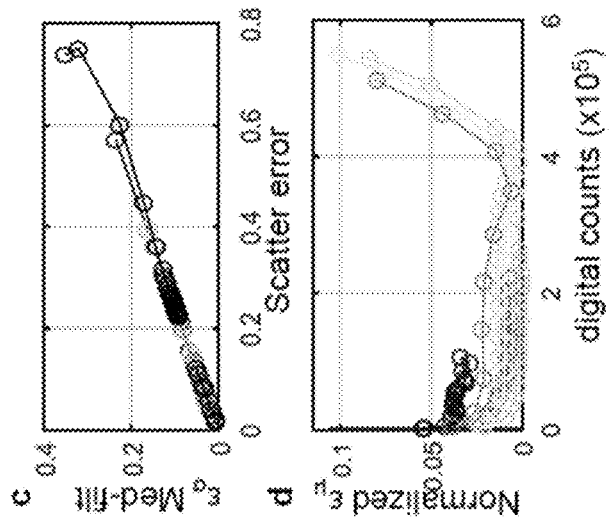

Based on the transform used in this disclosure and by propagation of statistical errors, scatter error, std{z(n)} may be derived. It may scale inversely as the square root of the total digital counts N (Equation 2, below). Experimental data confirm that scatter error scales inversely as √N for different acquisition parameters within the standard range of microscope settings (FIG. 1e, FIG. 4a). Furthermore, the constant of proportionality in Equation 2, depends on the detector gain used in the acquisition (FIG. 5e and Table 2, shown below).

TABLE 2

Proportionality constant for curves to calculate scatter error on phasor plot.

| Gain (A.U.) | Slope | |z(n)| | Proportionality constant |
|---|---|---|---|
| 700 | 1.35 | 0.43 | 3.14 |
| 750 | 1.8 | 0.437 | 4.12 |
| 800 | 2.34 | 0.437 | 5.36 |
| 850 | 3.03 | 0.443 | 6.83 |
| 900 | 3.89 | 0.446 | 8.72 |
| 950 | 4.79 | 0.45 | 10.65 |

Figures 5A, 5B, 5C:
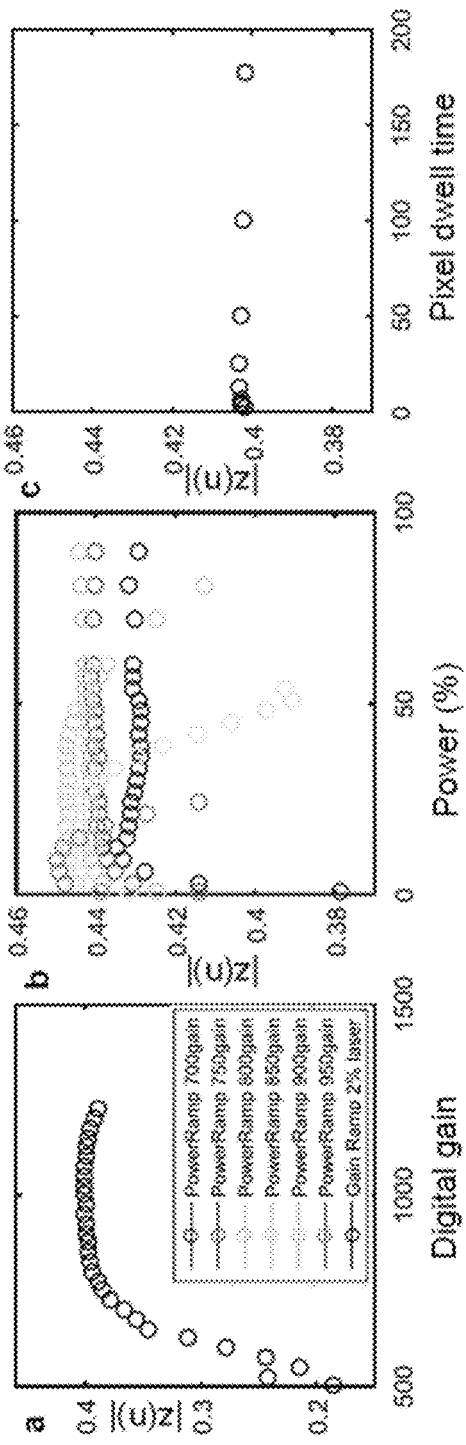

Detector shot noise may be proportional to gain [22], and scatter error empirically shows this characteristic (FIG. 5d-e). Given identical normalized spectra measured with different microscope settings, the one with higher gain value may have higher scatter error. However, the expected position of the spectral fingerprint $|z_e(n)|$ may remain constant over a large range of total digital counts for different imaging parameters (FIG. 5a-c).

Figure 4B:
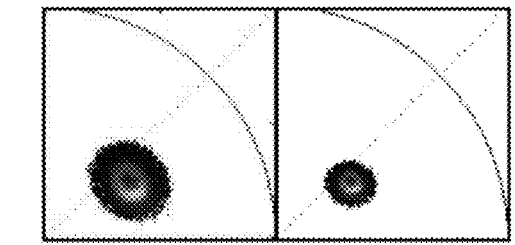
Figure 4C:
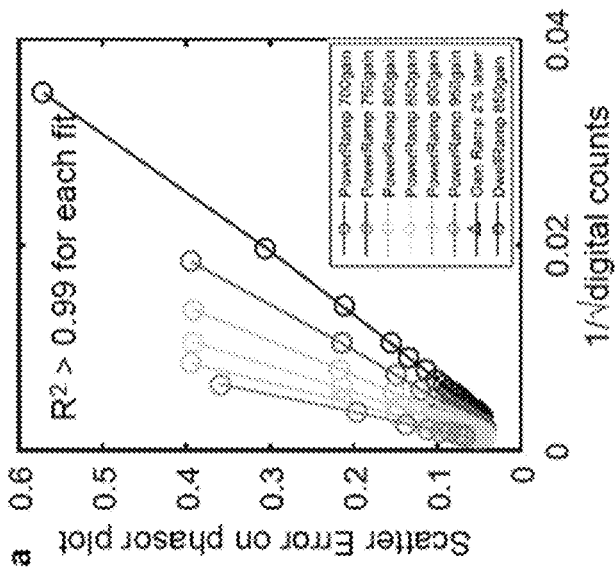

Changes in Shifted-Mean of a spectrum. Phasor plot may rely on normalized spectrum of a pixel to determine the coordinates. However, both the saturation of signal and very low photon counts (low signal to noise ratio (SNR)) may result in non-identical normalized spectra (FIG. 1b, inset). This may change the values of |z(n)| at the extreme values of total digital counts (FIG. 4a-c). At low SNR the signal may be indistinguishable from noise. At very high SNR, identical intensity values for several wavelengths, corresponding to saturation value on detector (FIG. 1b, inset), may render the spectrum non-informative again. In either cases, the phasor point may move to be closer to origin leading to low values of |z(n)|. Within the constant regime (FIG. 4a-e), the values of |z(n)| may be most sensitive to changes in the values of detector gain among the three parameters—namely detector gain, power and pixel dwell time (FIG. 4a-c).

The type of detect use for measures may affect the error on phasor. In any imaging system, the number of photons emitted by a dye during a time interval may be a stochastic (Poissonian) process, where the signal may scale as the average number of acquired photons N, and the noise may scale as $\sqrt{N}$. Typically the source of noise may include of shot noise resulting from (i) signal light (ii) background light and (iii) dark current.

In experiments, analog detectors were used for all measures. A typical Photomultiplier Tube (PMT) may measure the pulse of electrons at the anode resulting from a photon striking at its photocathode. These pulses may be counted both individually and as an averaged photocurrent in a given interval, thereby allowing both digital (photon-counting) and analog modes of operation respectively. While the noise (Poissonian) from signal and background light may remain the same for both analog and digital counts, shot noise from dark currents may vary in the two modes. The dark current may consist of thermal electrons with a typical pulse height distribution that, in photon-counting, may be discriminated robustly from the signal using a pulse height discriminator and thus eliminated. In analog mode, the averaged pulse may also incorporate the dark current leading to a higher noise. Signal to noise ratio (SNR) in the digital mode may improve compared to analog mode. Additionally, photon-counting mode may better perform at low signal levels, so as to avoid simultaneous arrival of two photons. Analog mode may operate over a wide range of photon levels.

For the purpose of HySP, the Fourier transforms may convert all photons collected across spectrum into one point in the phasor plot. In the photon-counting mode, HySP performance may be expected to be further enhanced due to the improved SNR compared to analog mode at low signal levels.

Figure 1F:
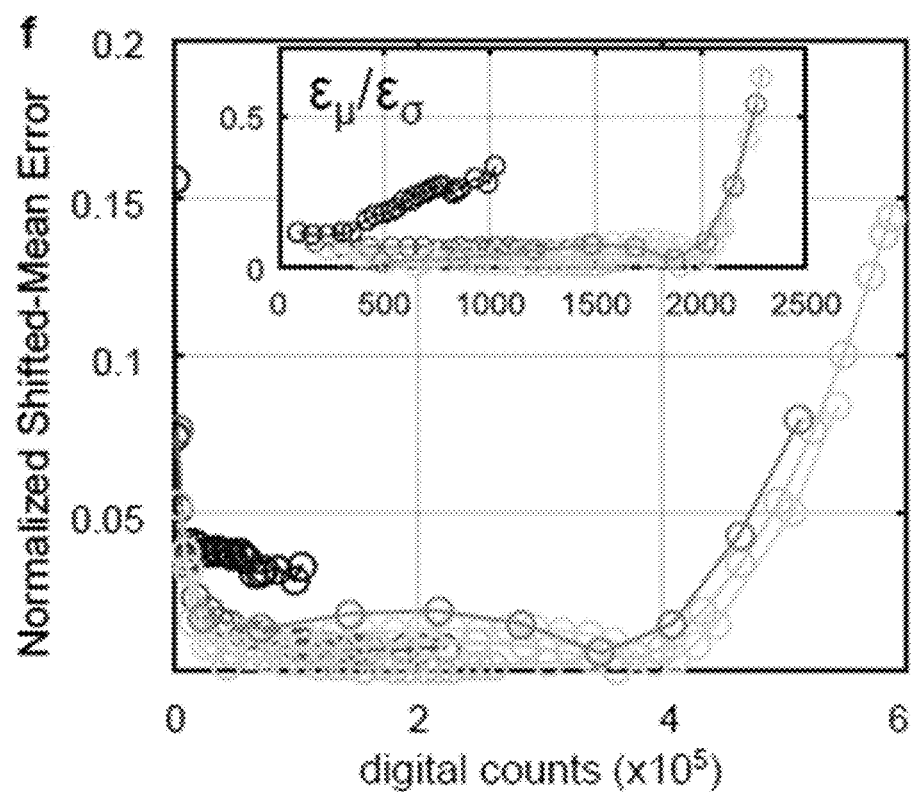

The repeatability of the spectral fingerprint may have two major effects on the shifted-mean error, a measure for the quality of fingerprinting. First, since it may be a function of $|z_e(n)|$, this error may remain below 5% over a large range of digital counts except for extreme counts values (FIG. 1f). Similar to scatter error, within reasonable range, it may only slightly sensitive to changes in detector gain. Second, comparison of the magnitudes of the two errors may show that scatter error may be dominant in phasor analysis (FIG. 1f, inset). Thus, any shift in the phasor point due to suboptimal imaging parameters may be likely to be buried within the scatter.

Because scatter error may dominate the error on HySP plot, and the phasor plot may reduce spectral dimensionality from 32 to 2, it may be possible to denoise the spectral images without altering the intensity data by directly applying filters in phasor space to reduce scatter error. Here, a denoising filter in phasor space was applied to reduce scatter error in the data, and significant recovery of fingerprint position $|z_e(n)|$ was observed, especially at low signal values. The plots show that denoising may not alter the location of the expected values ($z_e(n)$) (FIG. 4b-d), yet scatter error may be reduced (FIG. 4c). Repeated applications of a denoising filter may lead to a plateau of improvement that may typically occur after five iterations. Since the filter may be applied in phasor space, it may not affect the intensity profile of the image (FIGS. 9 and 10).

Spectral denoising in phasor space. Spectral denoising may be performed by applying filters directly in phasor space. This may maintain the original image resolution but may improve spectral fingerprinting in the phasor plot. The filter here applied may be a median filter. However, other approaches may also be possible. For any image of a given size (n×m pixels), S and G values may be obtained for every pixel, yielding 2 new 2D matrices, for S and G, with dimensions n×m. Since the initial S and G matrix entries may have the same indices as the pixels in the image, the filtered matrices S* and G*, therefore, may preserve the geometrical information. Effectively by using filtering in phasor space, S and G matrices may be treated as 2D images. First, this may reduce the scatter error, i.e. the localization precision on phasor plot increases (FIG. 8a-b), improving the spectral fingerprinting resolution while improving the already minimal Shifted-Mean Error (FIG. 8c-d). The effect on data may be an improved separation of distinct fluorescent proteins (FIG. 9a-d). Second, denoising in (G,S) coordinates may preserve both geometry, intensity profile as well as the original resolution at which the images were acquired (FIG. 9e-g). Effectively filtering in phasor space may affect the spectral dimension of the data achieving denoising of spectral noise without interfering with intensities.

Improved signal collection (FIG. 11) and reduced uncertainty may appear to make HySP an appealing technique for in vivo imaging. Studies of cellular and tissue interactions may often involve use of multiple fluorescent markers within the same anatomical region of developing embryos or other biological samples. Furthermore, dataset sizes for multi-(hyper) spectral fluorescence may be up to n times larger than standard confocal, with n equal to the number of bandwidths acquired (e.g. 32).

Four-dimensional (x,y,z,λ) data were acquired for whole-mount zebrafish embryos and represented spectral information from all pixels in a HySP plot to identify fluorophore fingerprints (Table 3), ranging from tissue to subcellular scale.

TABLE 3

Parameters for in vivo imaging. All data points are 16 bits integers.

| | Stage (hpf) | Imaged volume (xyzλt) (pixels) | Lateral pixel (x, y resolution) (μm) | Axial section (z resolution) (μm) | Pixel dwell time (μs) | Pinhole size (μm) | Laser Power (%) |
|---|---|---|---|---|---|---|---|
| FIGS. 1a; 6b, d; 7b; 10b (Tg(kdrl::eGFP); Gt (desmcitrine)$^{ct122a/+}$) | 72 | 3584 × 768 × 45 × 32 | 0.92 | 5.0 | 5.09 | 180 | 0.3 @ 488 nm |
| FIGS. 6d; 7b; 10b (Gt (desmcitrine)$^{ct122a/+}$) | 72 | 1408 × 384 × 39 × 32 | 1.84 | 5.0 | 5.09 | 180 | 0.5 @ 488 nm |

TABLE 3-continued

Parameters for in vivo imaging. All data points are 16 bits integers.

Figure 2A:
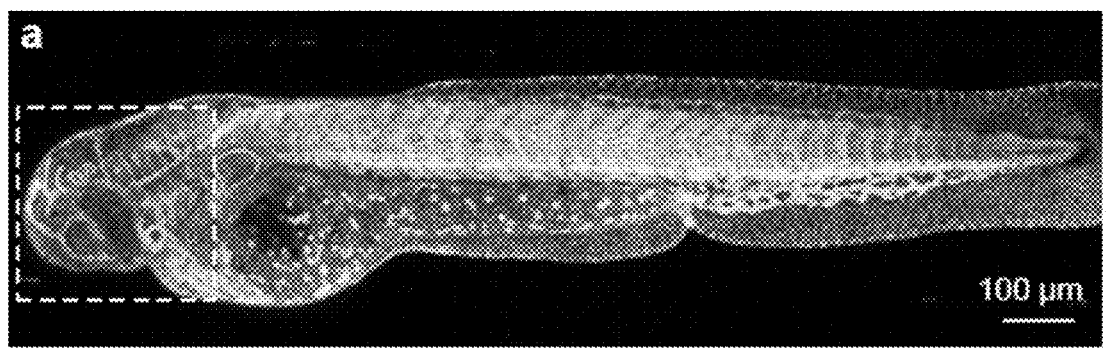
FIG. 2 Phasor analysis for multiplexing hyper-spectral fluorescent signals in vivo. (a) Maximum intensity projection image showing seven unmixed signals in vivo in a 72 hpf zebrafish embryo. Multiplexed staining was obtained by injecting mRNA encoding H2B-cerulean (cyan) and membrane-mCherry (red) in double transgenic embryos Gt(desm-citrine)$^{ct122a/+}$;Tg(kdrl:eGFP) (yellow and green respectively) with Xanthophores (blue). The sample was excited sequentially at about 458 nm and about 561 nm yielding their autofluorescence as two separate signals (magenta and grey respectively). Images were reconstructed by mapping the scatter densities from phasor plots (d) to the original volume in the 32-channel raw data. (b) Emission spectra of different fluorophores obtained by plotting normalized signal intensities from their respective regions of expression in the raw data. (c) Zoomed-in view of the head region of the embryo (box in (a)). Boxes labeled 1-3 denote sub-regions of this image used for comparing HySP with linear unmixing in (e-f). (d) Phasor plots showing the relative positions of pixels assigned to different fluorophores. Polygons denote the sub-set of pixels assigned to a particular fluorophore. (e) Zoomed-in views of Regions 1-3 (from (c)) reconstructed via both HySP analysis and linear unmixing of the same 32-channel signal. Arrows indicate the line along which normalized intensities obtained by the two techniques are plotted in (f) for comparison. By visual inspection itself it is evident that HySP analysis outperforms linear unmixing in distinguishing highly multiplexed signals in vivo. (f) Normalized intensity plots comparison of HySP analysis and linear unmixing. The x-axes denote the normalized distance along the arrows drawn in (e). y-axes in all graphs were normalized to the value of maximum signal intensity among the seven channels to allow relative comparison. Different panels show different set of channels (fluorophores) for clarity.
Figure 2B:
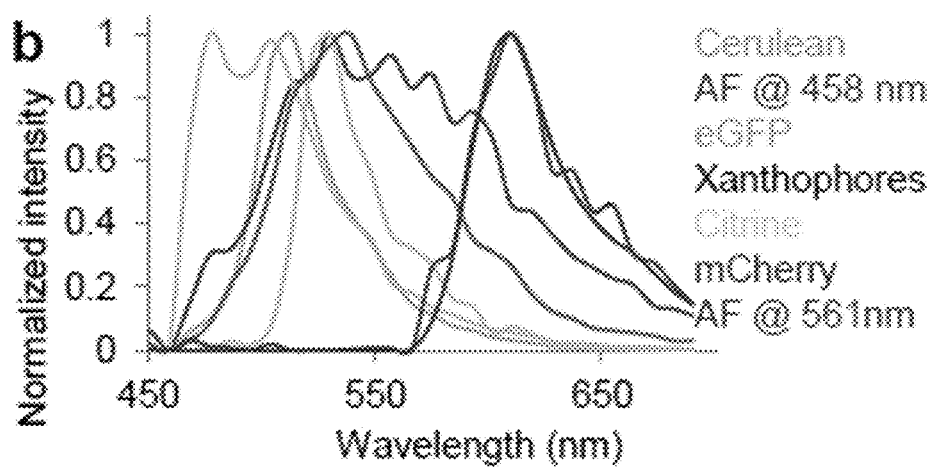
Figure 2C:
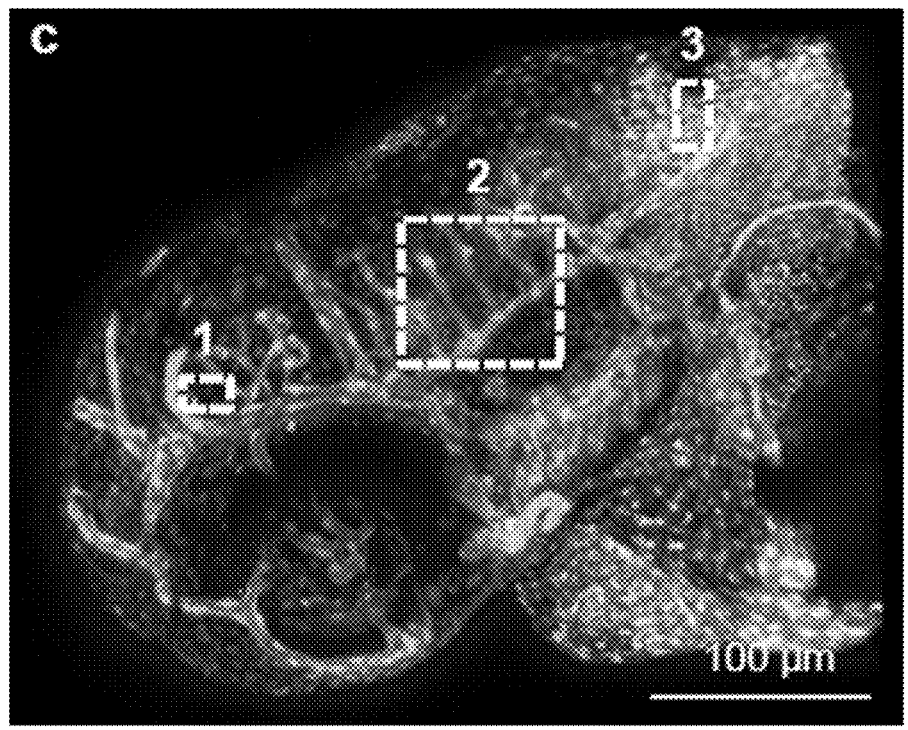
Figure 2D:
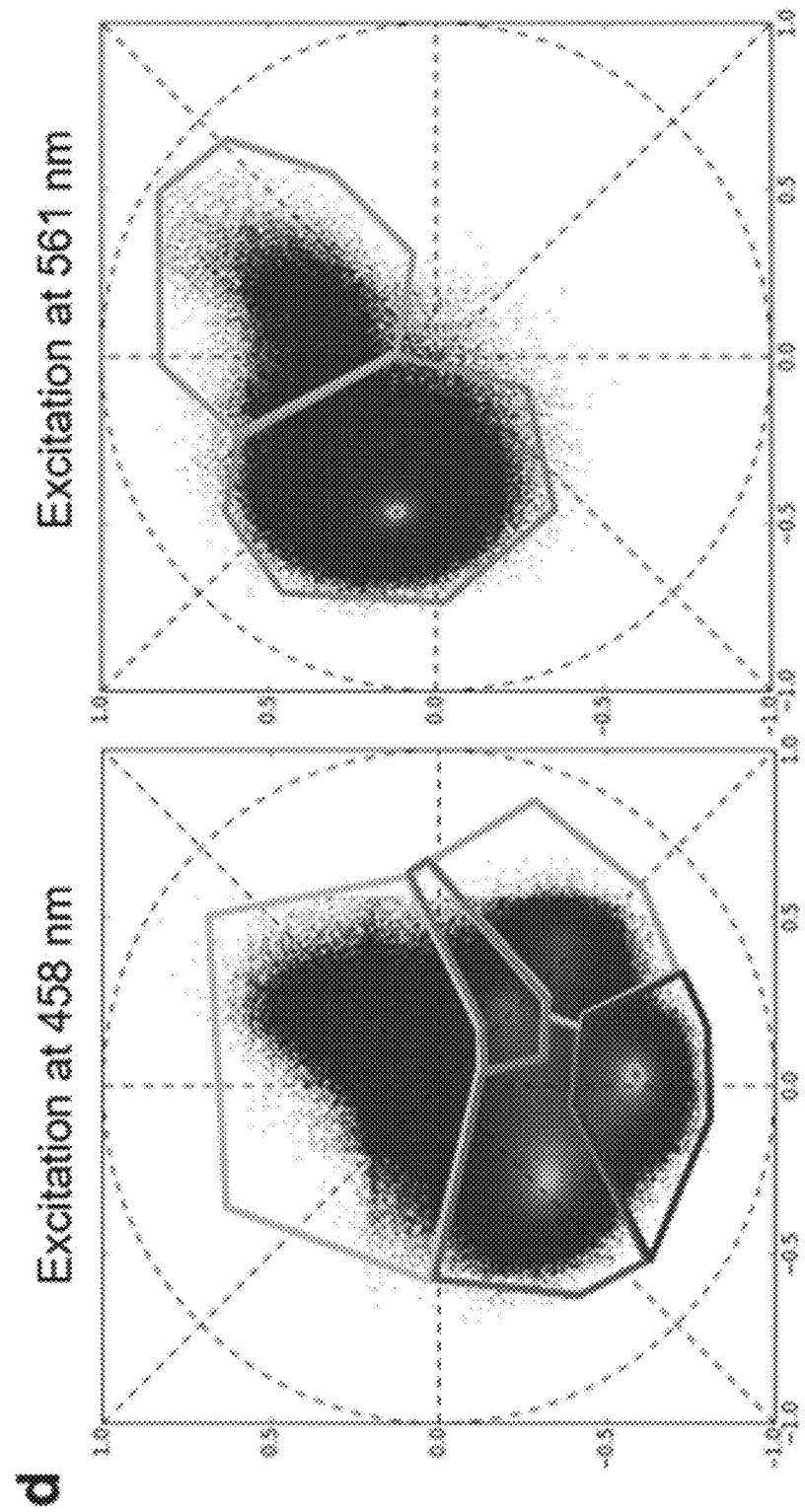
Figure 2E:
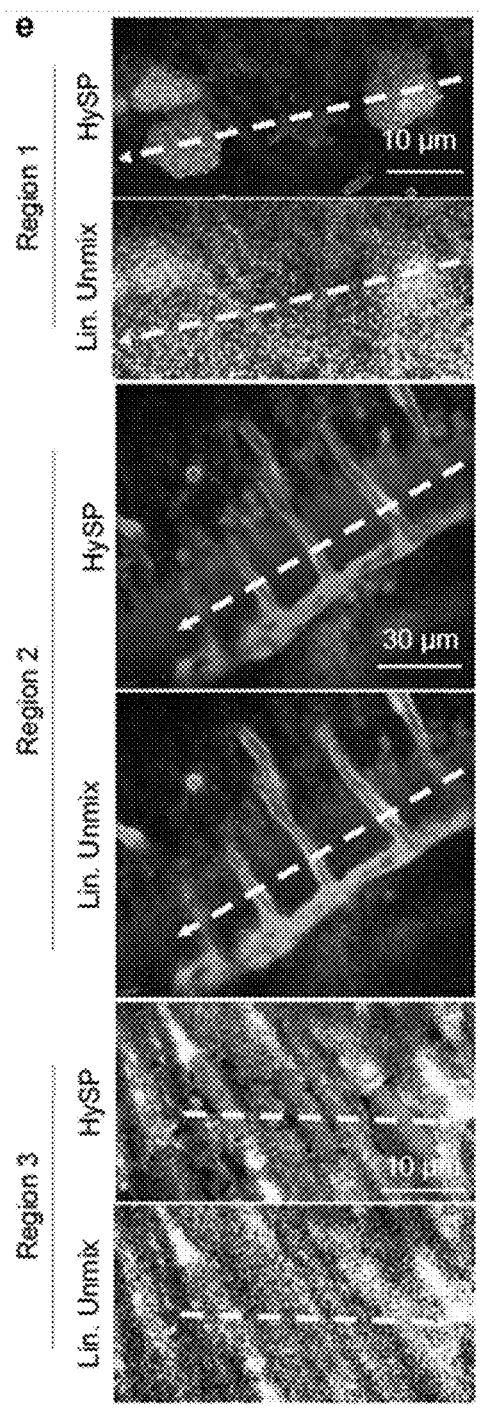
Figure 2F:
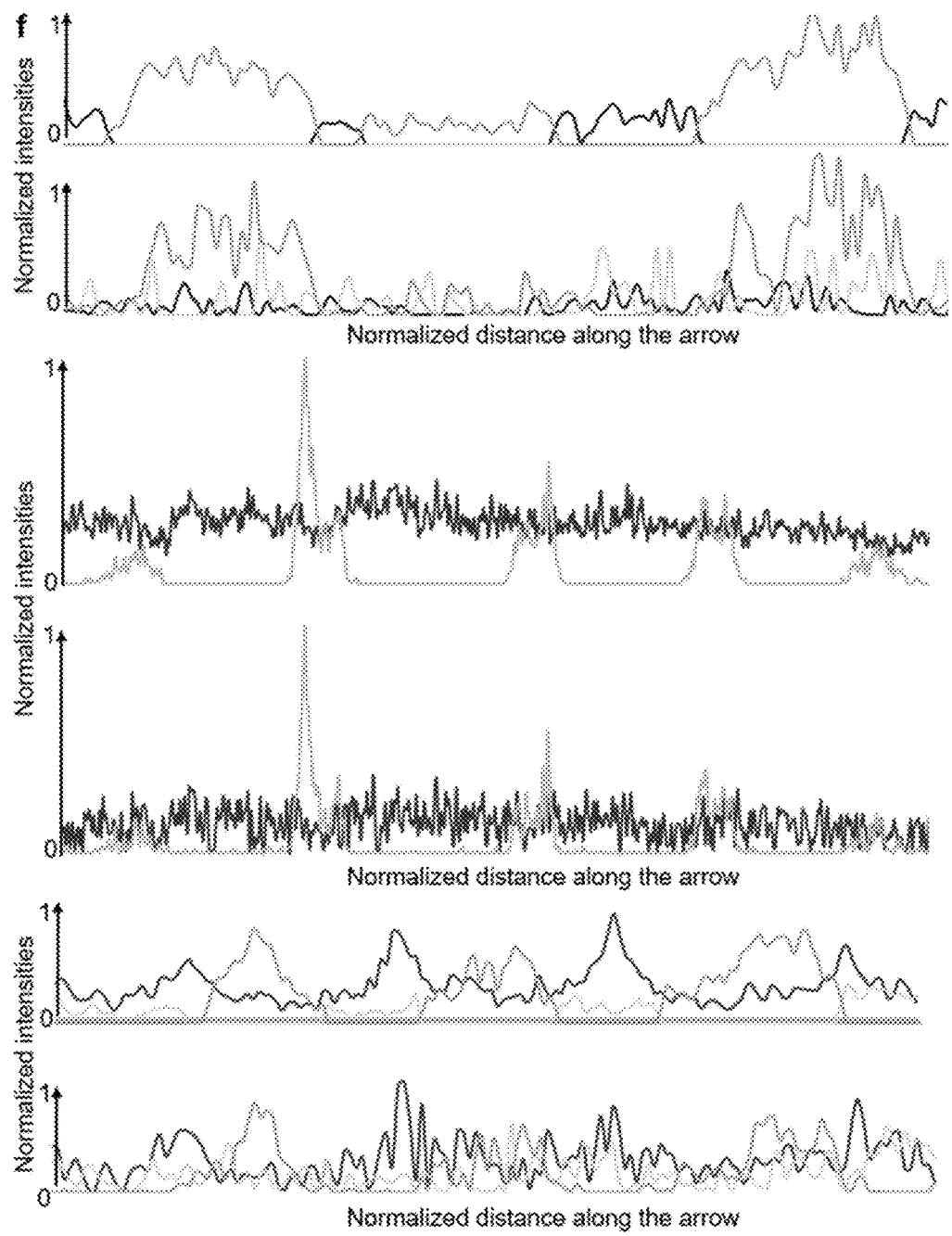
Figure 3A:
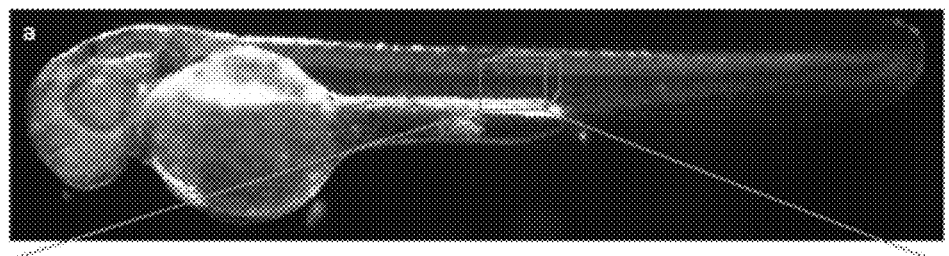
FIG. 3 Low laser power in vivo volumetric hyper-spectral time-lapse of zebrafish. (a) Brightfield image of zebrafish embryo about 12 hours post imaging (36 hpf). HySP improved performance at lower Signal to Noise Ratio allows for multi-color volumetric time-lapses with reduced phototoxicity. (b, c, d) Maximum intensity projection image showing eight unmixed signals in vivo in a zebrafish embryo starting at 24 hpf. Multiplexed staining was obtained by injecting mRNA encoding Rab9-YFP (yellow) and Rab11-
Figures 3B, 3C, 3D, 3E:
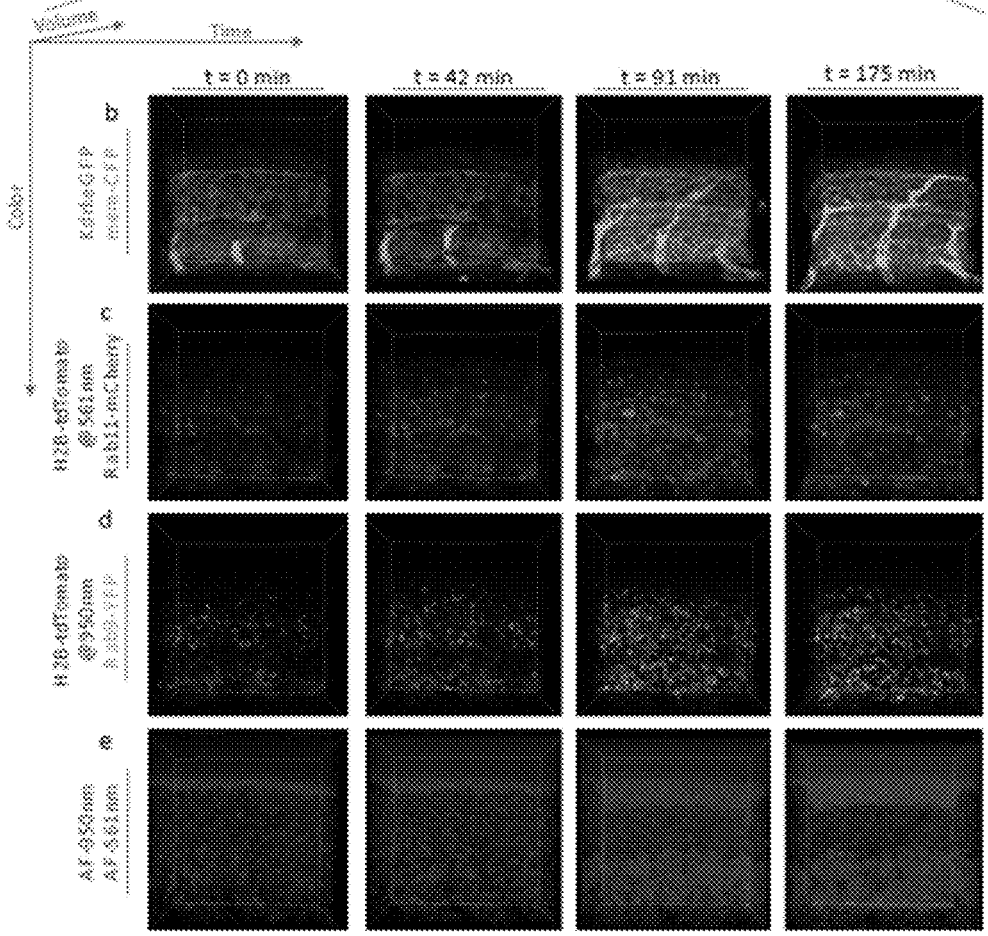

|  | Stage (hpf) | Imaged volume (xyzλt) (pixels) | Lateral pixel (x, y resolution) (μm) | Axial section (z resolution) (μm) | Pixel dwell time (μs) | Pinhole size (μm) | Laser Power (%) |
|---|---|---|---|---|---|---|---|
| FIGS. 6d; 7b; 10b (Tg(kdrl::eGFP)) | 72 | 1408 × 384 × 40 × 32 | 1.84 | 5.0 | 5.09 | 180 | 0.9 @ 488 nm |
| FIG. 6e, f | 72 | 600 × 60 × 45 × 32 | 0.95 | 5.0 | 5.09 | 180 | 0.3 @ 488 nm |
| FIGS. 2c; 12 | 74 | 2560 × 2048 × 29 × 32 | 0.277 | 5.0 | 3.15 | 186 | 3.0 @ 458 nm |
| FIGS. 2c; 12 | 74 | 2560 × 2048 × 29 × 32 | 0.277 | 5.0 | 3.15 | 186 | 0.3 @ 561 nm |
| FIG. 9a-d | 72 | 1024 × 1024 × 1 × 32 | 0.13 | 1.4 | 3.15 | 70 | 1.0 @ 488 nm |
| FIGS. 2A, 13 | 72 | 1664 × 512 × 55 × 32 | 2.076 | 5.0 | 6.50 | 186 | 3.0-5.0 @ 458 nm |
| FIGS. 2A, 13 | 72 | 1664 × 512 × 55 × 32 | 2.076 | 5.0 | 6.50 | 186 | 0.18 @ 561 nm |
| FIG. 3b, c, d, e | 24 | 512 × 512 × (25-40) × 32 × 25 | 0.277 | 2.0 | 2.55 | 601 | 5 @ 950 nm |
| FIG. 3b, c, d, e | 24 | 512 × 512 × (25-40) × 32 × 25 | 0.277 | 2.0 | 2.55 | 601 | 0.2 @ 561 nm |

Points selected in phasor space were re-mapped in the original volume and rendered as Maximum Intensity Projections. This successfully captured the unique spectral fingerprints of citrine (skeletal muscles) and eGFP (endothelial tissue) in transgenic zebrafish embryos, Gt(desm-citrine)$^{ct122a/+}$ and Tg(kdrl:eGFP) respectively [23,24] (FIG. 6a, 7a). On a tissue scale. the method may preserve the individual spectral fingerprints (scatter densities) for citrine and eGFP even in the double transgenic Gt(desm-citrine)$^{ct122a/+}$;Tg(kdrl:eGFP) embryos, which may feature co-expression within the same anatomical regions (FIG. 6d). The two easily separable scatter densities in phasor space (FIG. 6c) may cleanly distinguish the label in the skeletal muscles from that in the interdigitated blood vessels (endothelial tissue). Additionally, autofluorescence may clearly be separated by treating it as an independent HySP fingerprint (FIG. 10).

Autofluorescence in phasor space for in vivo imaging. Hyperspectral phasor may allow intuitive identification of fingerprints for fluorescent proteins. This may be shown for Citrine and eGFP but may be valid also for autofluorescence. Intracellular intrinsic fluorescence may be a known and common issue in in vivo biological imaging. Its spectral signature may be different from that of Citrine and eGFP. When represented on phasor plot as a scatter density, autofluorescence may have different (S,G) coordinates compared to fluorescent proteins and may create cluster regions in different area of the plot (FIG. 10a).

Effectively, phasor plot may identify autofluorescence as a separate spectral fingerprint allowing it to be treated as an independent imaging channel (FIG. 10b).

The gap from tissue to sub-cellular scale may be bridged by expanding the color palette with nuclear H2B-cerulean and membrane localized mCherry in the same double transgenic embryo. HySP analysis may allow fast identification and separation of signal from Cerulean, eGFP and Citrine from the intrinsic signals of xanthophores and tissue autofluorescence at about 458 nm excitation. Similarly, it may separate mCherry from background autofluorescence at about 561 nm excitation (FIG. 2).

Finally, the multi-dimensionality may be expanded to include time obtaining five-dimensional (5D) datasets (x,y,z,t,λ) and the challenges of photo-damaging and bleaching in time-lapse imaging may be tackled by fully exploiting the advantages of HySP improved signal collection. New vessel sprouts in double transgenic zebrafish embryos (Tg(ubiq:membrane-Cerulea-2a-H2B-tdTomato);Tg(kdrl:eGFP) expressing fusion proteins of the endosome components, Rab9 and Rab11 (YFP and mCherry respectively), and autofluorescence for each laser line (FIGS. 3a-3e) may be imaged. The low laser power used (about 5% at about 950 nm, about 0.15% at about 561 nm) may not affect development over multiple samples (n=3), while allowing the simultaneous study of at least seven clearly distinctive components without affecting light-sensitive development. Increasing laser power to improve fluorescence signal caused increased photo-toxicity that blocked vessel sprouting.

Multispectral volumetric time-lapse in vivo imaging with phasor. Hyperspectral phasor may allow reduced photo-damage when performing multispectral volumetric time-lapses in vivo. The improved unmixing efficiency at decreased Signal to Noise Ratio (FIG. 11) may play a role in tackling issues related to excess photons.

Generally, when multiple fluorophores are present in the sample, each fluorophore may have an optimal excitation wavelength. It may however be complicated to use multiple wavelengths which are too close (e.g. about 458 nm-about 488 nm-about 514 nm for CFP, GFP, YFP respectively) for excitation without considerably affecting the emission spectra. One solution may be to sequentially excite a volume with each wavelength. Sequential excitation, while optimal to prevent overlapping of emission spectral, may require an extended scanning time and may result in increased photo-damage and bleaching. Additionally, extended scanning time may result in motion artifacts due to sample development. An alternative option may be to excite with a single wavelength multiple fluorophores. The disadvantage in this approach may be the excitation efficiency of the lowest wavelength fluorophore will be higher than the other fluorophores in the sample. For example, at about 458 nm the excitation efficiency of CFP is about 93%, while GFP is about 62% and YFP is about 10%. There is a series of factors that affect the actual number of photons emitted by each fluorophores, such as Quantum Yield, Brightness, pH and concentration. However, in general, we may observe a stronger signal from one fluorescent protein and a weak signal from another. One may want to increase laser power in an attempt to extract more photons from the weaker signal. The effects of increasing laser power above 10% for about 950 nm (n=2) or above 10% for about 458 nm (n=3), in experiments, resulted in halted development of vasculature due to photo-toxicity. The opposite solution may be to deal with lower noisier signals, allowing for correct development of the sample.

The Hyperspectral Phasor method may allow for improved performance at lower SNR, hence overcoming the issue of the weaker signals. This advantage may consequently carry over to 2-photon imaging where excitation efficiency is lower than 1-photon and changing laser wavelength may require a few seconds.

As a consequence, the number of volumes necessary to be acquired may be reduced from 3 to 1 in the 3-fluorophore example described above.

The same approach may be applied on different color-clusters of proteins, for example one "blue" cluster CFP-GFP-YFP (excited at about 458 nm), a second "red" cluster mCherry-tdTomato-RFP (excited at about 561 nm), a third cluster with the multiple iRFPs (excited at about 630 nm).

We show two-photon multicolor volumetric time-lapse imaging of multiple samples as an example of potential application with two color-clusters.

As a result of these 5D measurements, different behaviors of Rab9 and Rab11 in relationship to endothelial cells (kdrl positive) and muscle tissue were observed. In particular, Rab11 positive vesicles were detected at the leading of kdrl positive cells, while this behavior was not observed with rab9 proteins. This example showed how HySP may enable increasingly complex multi-color experiments to interrogate molecular network interactions in vivo.

HySP may outperform other conventional multispectral approaches: optical filter separation and linear unmixing [4,6]. Conventional optical separation, due to the problem of signal bleed-through (FIGS. 6b,e,f; and 7), may yield low signal-to-background ratios (SBR). Linear unmixing may improve SBR significantly. However, HySP may offer superior performance especially in separating multiple colors within the same sample from multiple intrinsic signals (FIGS. 2, 3, 6e,f and 9) at lower SNR (FIG. 11). The reduced amount of signal required may allow for lower laser power and reduced photo-damage in time-lapse imaging. Furthermore, the analysis time for this about 10 Gigabytes dataset (FIG. 2a, Table 3) was about 10 minutes using HySP compared to about 2.5 hours using linear unmixing on the same computer. The simplicity and robustness of phasor approach may provide the potential of using HySP analysis post-acquisition of large samples. The HySP approach may well be poised to be used in the context of live imaging of biological processes in vivo as a solution for analysis of mosaic fluorescent protein expression systems [25-27] with the capability to handle multi-dimensional (x,y,z,λ,t) datasets with computational time in the order of minutes.

This analysis shows the robustness, speed, denoising capability and simplicity of the Hyper-Spectral Phasor representation. It may allow for a robust distinction of spectra, within the bounds of accuracy dictated primarily by the Poissonian noise in data acquisition. Because median filtering may be used to process the spectral data in phasor space without altering the intensity data, it may provide denoised images with substantially uncompromised resolution. The hyperspectral imaging system may be substantially oblivious to the mode of imaging as long as sufficient wavelength bins are available for calculating the Fourier coefficients of the spectral phasor (FIGS. 13a-13d). These advantages may make HySP applicable in a variety of contexts ranging from time-lapse imaging to cell lineage analysis, from fluorescence microscopy to cultural heritage reflectance imaging, and from emission to excitation multi-spectral data.

Other examples of this disclosure are as follows.

EXAMPLES

Example 1. Zebrafish Lines

Adult fish were raised and maintained as described in [28] and in strict accordance with the recommendations in the *Guide for the Care and Use of Laboratory Animals* by University of Southern California, where the protocol was approved by the Institutional Animal Care and Use Committee (IACUC) (Permit Number: 12007 USC). Transgenic FlipTrap Gt(desm-citrine)$^{ct122a/+}$ line was obtained from a previously described screen in the lab [23], Tg(kdrl:eGFP)$^{s843}$ line [24] was provided by the Stainier lab, and Tg(ubiq:membrane-Cerulean-2a-H2B-tdTomato) line was generated by injecting a construct containing tol2 transposable elements flanking the ubiquitin promoter, coding sequence for membrane localized cerulean, a short sequence encoding the ribosome-skipping peptide of Thosea asigna virus (2a) followed by H2B-tdTomato. Upon crossing appropriate adult lines, the embryos obtained were raised in Egg Water (about 60 µg/ml of Instant Ocean and about 75 µg/ml of $CaSO_4$ in Milli-Q water) at about 28.5° C. with addition of about 0.003% (w/v) 1-phenyl-2-thiourea (PTU) about 18 hpf to reduce pigment formation [28].

Example 2. Sample Preparation and Imaging

About 5 µM fluorescein (F1300, Invitrogen, Carlsbad, CA) solution in ethanol was prepared. For imaging, the solution was transferred into a sealed 10 mm glass bottom dish (P35G-1.5-10-c, MatTek Corporation, Ashland, MA, USA) and mounted in an inverted confocal microscope. Imaging was performed on a Zeiss LSM780 inverted confocal microscope with QUASAR detector (Carl Zeiss, Jena, Germany). A typical dataset consists of 32 images, each of dimensions 512×512 pixels, corresponding to different wavelengths from about 410.5 nm to about 694.9 nm with about 8.9 nm bandwidth. The measurement is repeated 10 times using C-Apochromat 40×/1.20 W Korr Zeiss objective at any given imaging parameter. Fluorescein was imaged with about 488 nm laser at different acquisition parameters (Table 1).

For in vivo imaging 5-6 zebrafish embryos at appropriate stage were placed into about 1% agarose (Catalog No. 16500-100, Invitrogen™) moulds created in an imaging dish with #1.5 coverglass bottom, (Catalog No. D5040P, WillCo Wells) using a custom designed negative plastic mould [29]. Embryos were immobilized by adding about 2 ml of about 1% UltraPure™ Low Melting Point Agarose (Catalog No. 16520-050, Invitrogen™) solution prepared in about 30% Danieau (about 17.4 mM NaCl, about 210 µM KCl, about 120 µM $MgSO_4.7H_2O$, about 180 µM $Ca(NO_3)_2$, about 1.5 mM HEPES buffer in water, pH about 7.6) with about 0.003% PTU and about 0.01% tricaine. This solution was then added on top of the embryos already placed in the mold. Following solidification of agarose at room temperature (1-2 minutes), the imaging dish was filled with about 30% Danieau solution and about 0.01% Tricaine, at about 28.5° C. Subsequent imaging was performed on an inverted confocal microscope by positioning the petridish appropriately on the microscope stage. Samples were obtained by crossing Gt(desm-citrine)$^{ct122a/+}$ with Tg(kdrl:eGFP) fish for two color imaging. Samples with four fluorescent proteins result from same crossing followed by injection of about 100 pg per embryo of mRNA encoding H2B-cerulean and membrane-mCherry. Samples of Gt(desm-citrine)$^{ct122a/+}$;Tg(kdrl:eGFP) were imaged with about 488 nm laser to excite both Citrine and eGFP and a narrow about 488 nm dichroic to separate excitation and fluorescence emission. Samples of Gt(desm-citrine)$^{ct122a/+}$;Tg(kdrl:eGFP) with H2B-cerulean and membrane-mCherry labels were imaged with about 458 nm laser to excite Cerulean, eGFP and Citrine with a narrow about 488 nm dichroic, following an about 561 nm laser to excite mCherry with an about 458-561 nm dichroic.

For in vivo time-lapse imaging 5-6 zebrafish at appropriate stage were immobilized in an imaging dish with #1.5 coverglass bottom using about 0.5% Low Melting Point Agarose agarose (same as above) to allow for development and with about 0.003% PTU and about 0.01% tricaine. Subsequent imaging was performed on the same confocal-two photon inverted microscope at about 28.5° C. A solution of Egg Water was added every hour to the imaging dish to ensure proper hydration of the sample. Samples with five fluorescent proteins were obtained by crossing Tg(kdrl:eGFP) with Tg(ubiq:membrane-Cerulean-2a-H2B-tdTomato) zebrafish followed by injection of about 120 pg and about 30 pg per embryo of mRNA encoding Rab9-YFP and Rab11-mCherry, respectively. Volumetric data was acquired using about 950 nm to excite Cerulean, eGFP, YFP and (weakly) tdTomato with a 760+ bandpass filter, following an about 561 nm laser to excite mCherry and tdTomato with an about 458-561 nm dichroic.

Table 3 provides the detailed description of the imaging parameters used for all images presented in this work.

Example 3. Phasor Analysis

Transform:
For each pixel in a dataset, the Fourier coefficients of its normalized spectra define the coordinates of its phasor point (z(n)):

$$z(n) = G(n) + iS(n), \quad \text{Equation (1)}$$

$$\text{where } G(n) = \frac{\sum_{\lambda_s}^{\lambda_f} I(\lambda)\cos(n\omega\lambda)\Delta\lambda}{\sum_{\lambda_s}^{\lambda_f} I(\lambda)\Delta\lambda} \text{ and}$$

$$S(n) = \frac{\sum_{\lambda_s}^{\lambda_f} I(\lambda)\sin(n\omega\lambda)\Delta\lambda}{\sum_{\lambda_s}^{\lambda_f} I(\lambda)\Delta\lambda}$$

where $\lambda s$ and $\lambda f$ are starting and ending wavelengths respectively; I is the intensity; $\omega = 2\pi/\tau s$ with $\tau s$ = number of spectral channels (e.g. 32) and n is the harmonic (e.g. 2).

Scatter Error on Phasor Plot:
Scatter error is inversely proportional to square root of number of photons N:

$$std\{z(n)\} \propto \frac{|z(n)|}{\sqrt{N}} \quad \text{Equation (2)}$$

This proportionality has been derived as follows. We define the recorded total signal intensity (digital counts, obtained by area under the spectral curve) as a measure of N with the assumption that the number of digital levels detected in confocal analog mode is proportional to the number of photons collected [20]. This implies:

$$\Sigma_{\lambda_s}^{\lambda_f} I(\lambda)\Delta\lambda \propto N. \quad \text{Equation (3)}$$

Based on Equation 1 and by propagation of statistical errors we know that, $$std\{G(n)\} = G(n)\sqrt{\frac{\text{Var}\{\sum_{\lambda_s}^{\lambda_f} I(\lambda)\cos(n\omega\lambda)\Delta\lambda\}}{[\sum_{\lambda_s}^{\lambda_f} I(\lambda)\cos(n\omega\lambda)\Delta\lambda]^2} + \frac{\text{Var}\{\sum_{\lambda_s}^{\lambda_f} I(\lambda)\Delta\lambda\}}{[\sum_{\lambda_s}^{\lambda_f} I(\lambda)\cos\Delta\lambda]^2}} \quad \text{Equation (4)}$$

where std and Var denote standard deviation and variance respectively. This can be further simplified as:

$$std\{G(n)\} \propto G(n)\sqrt{\frac{\sum_{\lambda_s}^{\lambda_f} \text{Var}\{I(\lambda)\}\cos^2(n\omega\lambda)}{G(n)N^2} + \frac{N}{N^2}} ; \quad \text{Equation (5)}$$

as std{digital counts} $\propto \sqrt{N}$:

$$std\{G(n)\} \propto \sqrt{\frac{\sum_{\lambda_s}^{\lambda_f} \text{Var}\{I(\lambda)\}\cos^2(n\omega\lambda)}{N^2} + \frac{G(n)^2}{N}} \quad \text{Equation (6)}$$

From the above, we can see that the second term dominates and therefore we have:

$$std\{G(n)\} \propto \frac{G(n)}{\sqrt{N}} \quad \text{Equation (7)}$$

Similarly:

$$std\{S(n)\} \propto \frac{S(n)}{\sqrt{N}} \quad \text{Equation (8)}$$

Therefore:

$$std\{z(n)\} \propto \frac{|z(n)|}{\sqrt{N}} \quad \text{Equation (9)}$$

Shifted-Mean Error on Phasor Plot:
Based on the expected value ($z_e(n)$) and the true representation of a spectrum ($z_0(n)$), we can write:

$$|z_e - z_0| = \sqrt{|\langle G_e \rangle - \langle G_o \rangle|^2 + |\langle S_e \rangle - \langle S_o \rangle|^2} \quad \text{Equation (10)}$$

where $\langle . \rangle$ denotes the average values used to compute the respective quantities. This expression is defined as shifted-mean error. Further:

$$|z_e - z_0| = \sqrt{|z_e|^2 + |z_0|^2 - 2|z_e||z_0|\cos(\Delta\varphi)} = \quad \text{Equation (11)}$$

$$|z_0|\sqrt{1 + \frac{|z_e|^2}{|z_o|^2} - 2\frac{|z_e|}{|z_o|}\cos(\Delta\varphi)}$$

where $\Delta\varphi$ is the phase difference between the two phasor points. It can be seen from above that the shifted-mean error remains bound as:

$$||z_e|-|z_0|| \leq |z_e-z_0| \leq \sqrt{|z_e|^2+|z_0|^2} \quad \text{Equation (12)}$$

Further we can also define a normalized shifted-mean error as defined as follows:

$$\frac{|z_e - z_0|}{z_0} = \sqrt{1 + \frac{|z_e|^2}{|z_0|^2} - 2\frac{|z_e|}{|z_0|}\cos(\Delta\varphi)} \quad \text{Equation (13)}$$

In this analysis the dataset is acquired with about 177 μs pixel dwell time at about 850 gain and about 21% laser power as the true representation of Fluorescein spectrum owing to its low value of scatter error. However, the general conclusions about the behavior of shifted-mean error remains the same irrespective of the value of $z_0(n)$.

Harmonic Number in Phasor Analysis:

Typically, phasor plots have been limited to using the first harmonic or the second harmonic of the Fourier representation of the spectral profile to determine the spectral signatures. This may be due to the presence of branch points in the Riemannian surfaces in complex plane corresponding to representations of harmonics greater than 2 that may not be easy to visualize. Based on Equation 1 we calculated residuals ($\rho(n)$) as the ratio of the absolute sum of all Fourier coefficients except the one corresponding to the harmonic number (n) of choice, to the absolute value of the $n^{th}$ Fourier coefficient. Therefore:

$$\rho(n) = \frac{\sum_{i=0, i \neq n}^{N} \left(\langle S_i \rangle^2 + \langle G_i \rangle^2\right)}{\langle S_n \rangle^2 + \langle G_n \rangle^2} \quad \text{Equation (14)}$$

For typical fluorescent spectra, such as the Fluorescein emission spectrum here, 1 and 2 remain the dominant harmonic numbers, as the residuals for these are at least an order of magnitude smaller than the residuals for other harmonics (FIG. 5f). Further the fluctuations in residual values may be dependent on the exact nature of the spectrum being analyzed. However, such an approach may be easy to implement every time phasor analysis is done and may allow a quick verification of the choice of the harmonic number used for any recorded spectrum.

Example 4. Denoising

For any image of a given size (n×m pixels), S and G values are obtained for every pixel, yielding 2 new 2D matrices, for S and G, with dimensions n×m. Upon filtering of these two matrices, with new values S* and G*, may be obtained for every pixel. Since the initial S and G matrices had the same indices as the pixels in the image, the filtered matrices S* and G*, therefore, preserve the geometrical information.

Fluorescein data were analyzed using Matlab scripts utilizing the equations disclosed above. Large zebrafish microscopy datasets were recorded by using the hyperspectral imaging system as disclosed above. Linear Unmixing was done by using Zen Software (Zeiss, Jena, Germany).

Example 5. Spectrally Encoded Enhanced Representations (SEER)

In this example, we present Spectrally Encoded Enhanced Representations (SEER), an approach for improved and computationally efficient simultaneous color visualization of multiple spectral components of hyperspectral (fluorescence) images. Exploiting the mathematical properties of the phasor method, we transform the wavelength space into information-rich color maps for RGB display visualization.

We present multiple biological fluorescent samples and highlight SEER's enhancement of specific and subtle spectral differences, providing a fast, intuitive and quantitative way to interpret hyperspectral images during collection, pre-processing and analysis.

Our approach is based on the belief that preserving most spectral information and enhancing the distinction of spectral properties between relevant pixels, will provide an ideal platform for understanding biological systems. The challenge is to develop tools that allow efficient visualization of multi-dimensional datasets without the need for computationally demanding dimensionality reduction, such as ICA, prior to analysis.

In this work, we build maps based on Phasors (Phase Vectors). The Phasor approach has multiple advantages deriving from its properties. After transforming the spectrum at each pixel into its Fourier components, the resulting complex value is represented as a 2-dimensional histogram where the axes represent the real and imaginary components. Such histogram has the advantage of providing a representative display of the statistics and distributions of pixels in the image from a spectral perspective, simplifying identification of independent fluorophores. Pixels in the image with similar spectra generate a cluster on the phasor plot. While this representation is cumulative across the entire image, each single point on the phasor plot is easily remapped to the original fluorescent image.

Exploiting the advantages of the phasor approach, Hyper-Spectral Phasors (HySP) has enabled analysis of 5D hyperspectral time-lapse data semi-automatically as similarly colored regions cluster on the phasor plot. These clusters have been characterized and exploited for simplifying interpretation and spatially lossless denoising of data, improving both collection and analysis in low-signal conditions. Phasor analysis generally explores the 2d-histogram of spectral fingerprints by means of geometrical selectors, which is an effective strategy but requires user involvement. While capable of imaging multiple labels and separating different spectral contributions as clusters, this approach is inherently limited in the number of labels that can be analyzed and displayed simultaneously. Prior works directly utilize phase and modulation for quantifying, categorizing, and representing features within Fluorescence Lifetime and Image Correlation Spectroscopy data. Our method differs from previous implementations, as it focuses instead on providing a quantitatively constructed, holistic pre-processing visualization of large hyperspectral data.

The solution we propose extracts from both the whole phasor and image to reconstruct a "one shot" view of the data and its intrinsic spectral information. Spectrally Encoded Enhanced Representations (SEER) is a dimensionality reduction-based approach, achieved by utilizing phasors, and automatically creating spectrally representative color maps. The results of SEER show an enhanced visualization of spectral properties, representing distinct fluorophores with distinguishable pseudo-colors and quantitatively highlighting differences between intrinsic signals during live-imaging. SEER has the potential of optimizing the experimental pipeline, from data collection during acquisition to data analysis, greatly improving image quality and data size.

Example 6. Spectrally Encoded Enhanced Representations (SEER)

The execution of SEER has a simple foundation. Each spectrum is assigned a pseudo-color, based on its real and imaginary Fourier components, by means of a reference color map.

This concept is illustrated in detail in FIG. 24 using an example of Zebrabow[34] embryo dataset, where cells within the sample express different ratios of cyan, yellow and red fluorescent proteins, resulting in a wide-ranging pallet of discrete spectral differences. The data is acquired as a hyperspectral volume (x, y, z, λ) (FIG. 24a), providing a spectrum for each voxel. The spectra obtained from multiple regions of interest are complex, showing both significant overlap and the expected difference in ratios (FIG. 24b). Discriminating the very similar spectra within the original acquisition space is challenging using standard multispectral dataset visualization approaches (FIG. 24c).

Figure 24C:
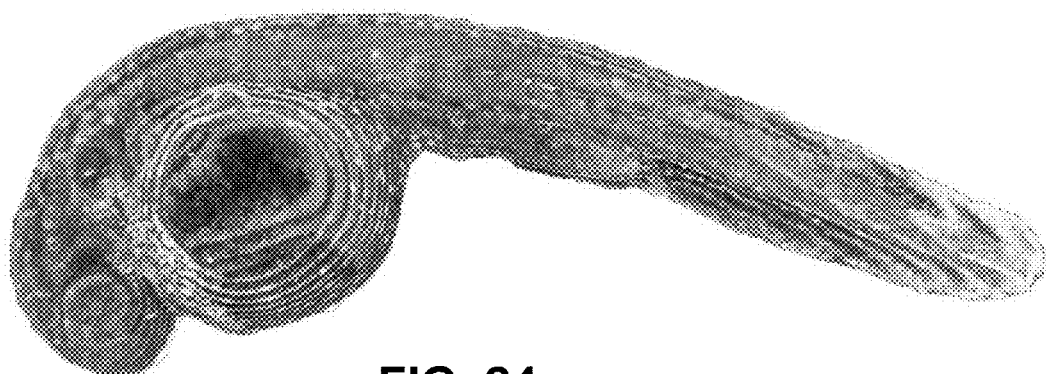
Figure 24D:
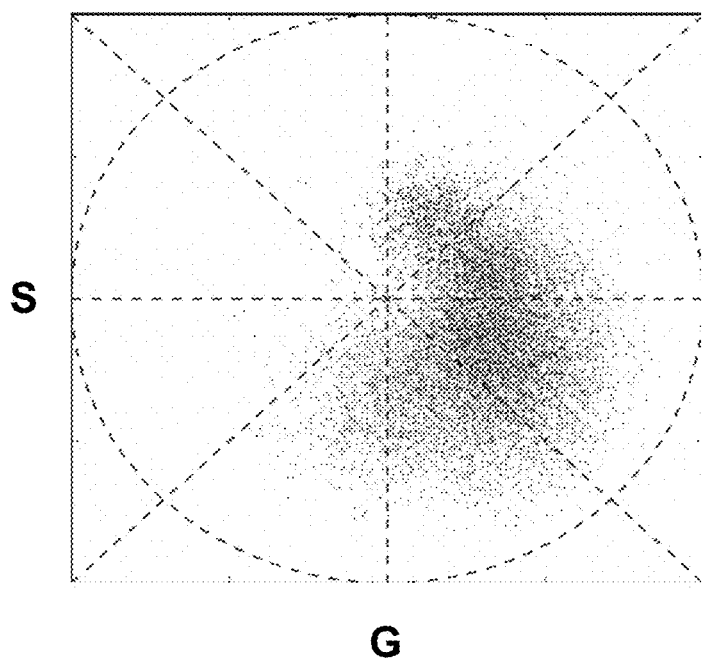

SEER was designed to create usable spectral contrast within the image by accomplishing five main steps. First, the Sine and Cosine Fourier transforms of the spectral dataset at one harmonic (usually 1st or 2nd owing to Riemann surfaces) provide the components for a 2D phasor plot (FIG. 24d). The phasor transformation compresses and normalizes the image information, reducing a multi-dimensional dataset into a 2D-histogram representation and normalizing it to the unit circle.

Second, the histogram representation of the phasor plot provides insight on the spectral population distribution and improvement of the signal through summation of spectra in the histogram bins. Pixels with very similar spectral features, for example expressing only a single fluorophore, will fall within the same bin in the phasor plot histogram. Because of the linear property of the phasor transform, if an image pixel contains a mixture of two fluorophores, its position on the phasor plot will lie proportionally along the line connecting the phasor coordinates of those two components. This step highlights importance of geometry and distribution of bins in the phasor representation.

Figure 24E:
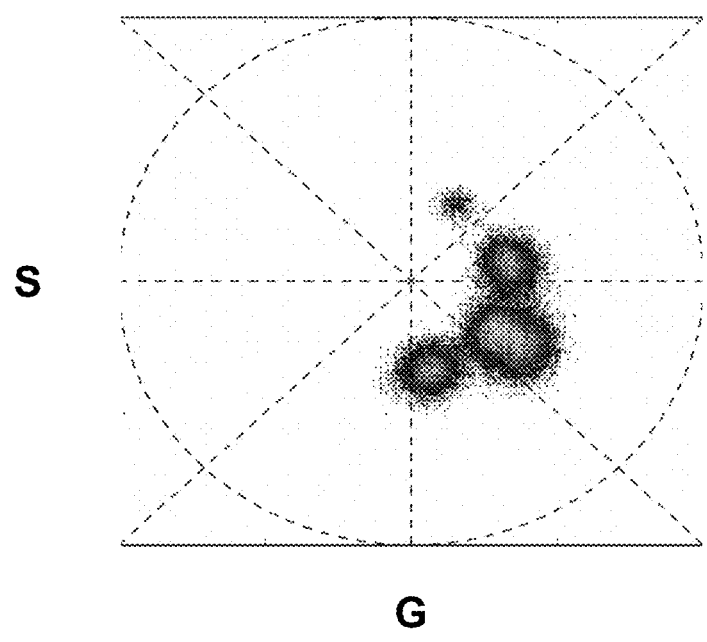

Third, spatially lossless spectral denoising is performed 1-2 times in phasor space to reduce spectral error. In short, median filters are applied on both the Sine and Cosine transformed images, reducing the spectral scatter error on the phasor plot, while maintaining the coordinates of the spectra in the original image (FIG. 24e). Filters affect only the phasor space, producing an improvement of the signal.

Figure 24F:
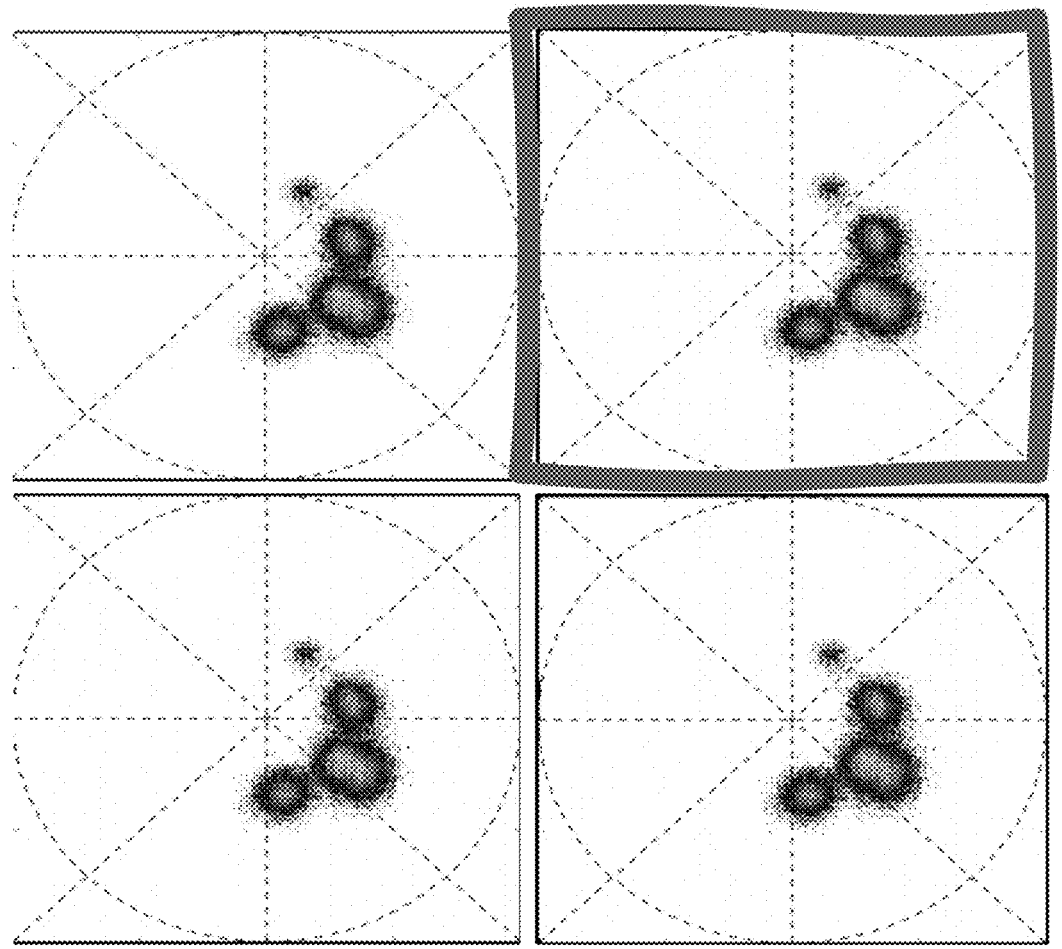
Figure 24G:
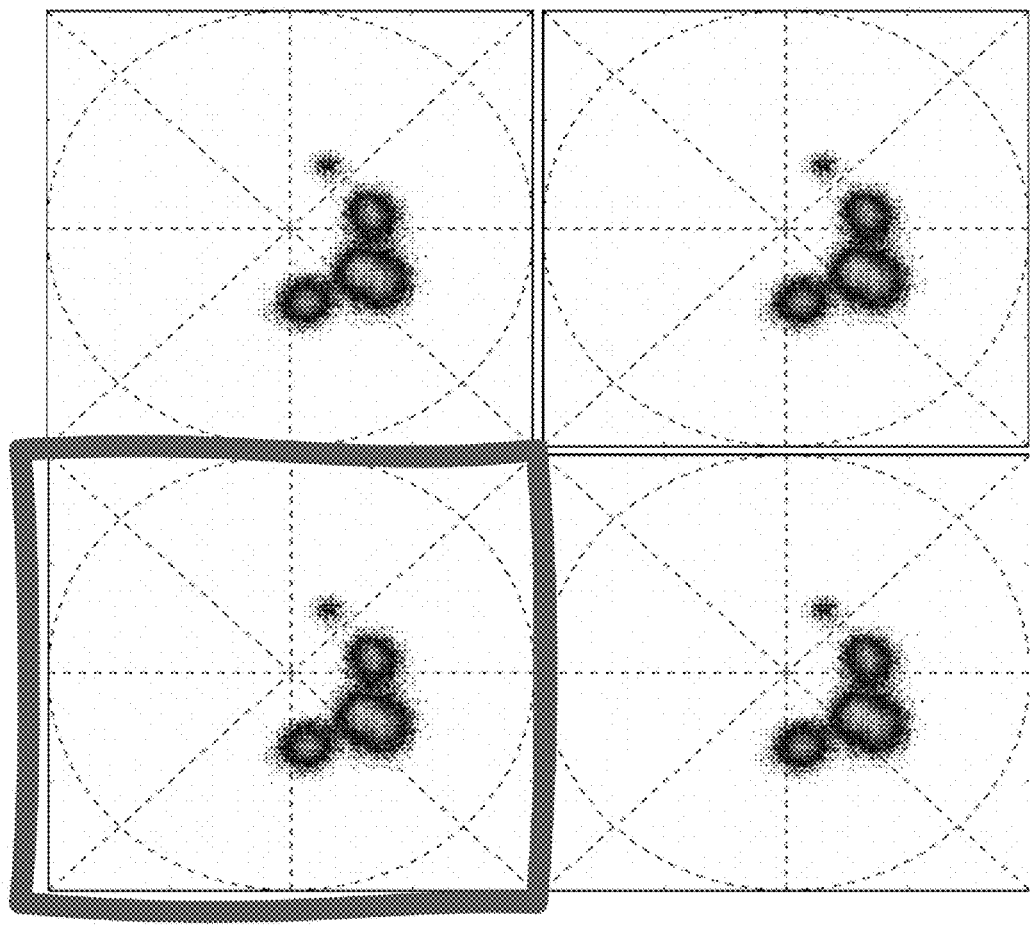

Fourth, we designed multiple SEER maps exploiting the geometry of phasors. For each bin, we assign RGB colors based on the phasor position in combination with a reference map (FIG. 24f). Subtle spectral variations can be further enhanced with multiple contrast modalities, focusing the map on the most frequent spectrum, the statistical center of mass of the distribution or scaling the colors to the extremes of the phasor distribution (FIG. 24g).

Figure 24H:
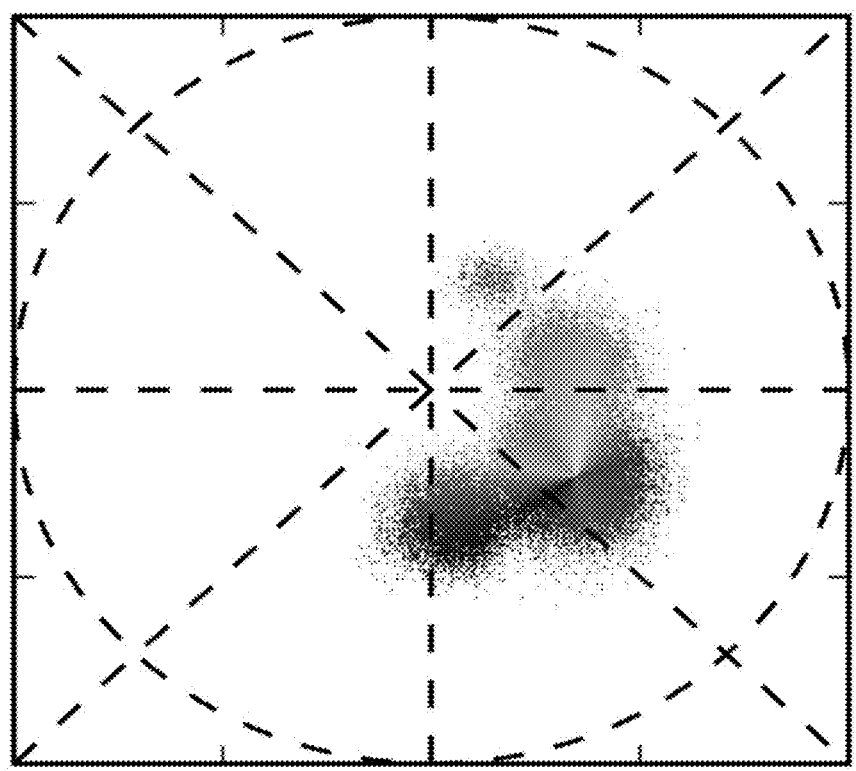
Figure 24I:
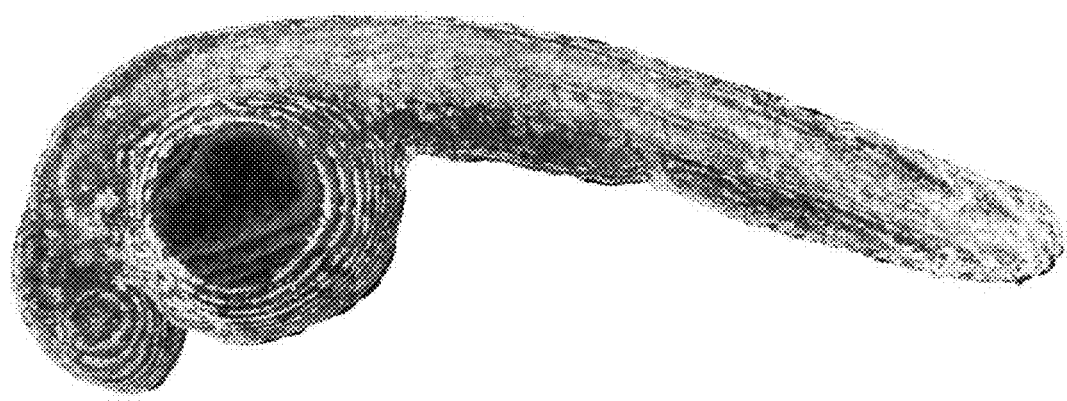

Finally, colors in the original dataset are remapped based on SEER results (FIG. 24h). This permits a dataset in which spectra are visually indistinguishable (FIG. 24a-c) to be rendered so that even these subtle spectral differences become readily discernible (FIG. 24i). SEER rapidly produces 3 channel color images (FIG. 31) that approximate the visualization resulting from a more complete spectral unmixing analysis (FIG. 32).

Example 7. Standard Reference Maps

Figure 25A:
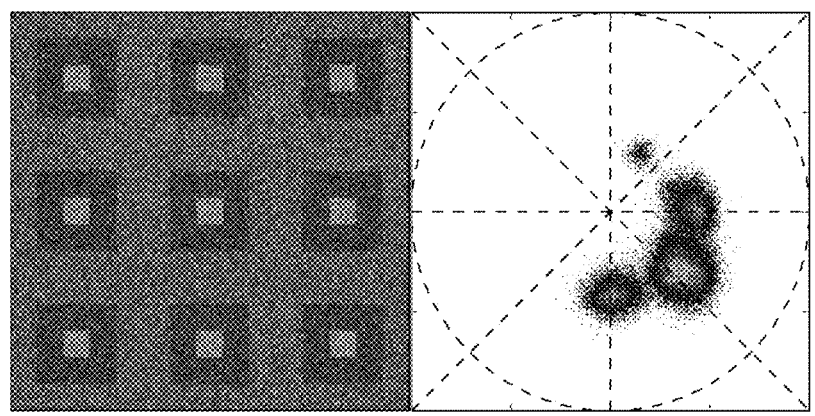
Figure 25B:
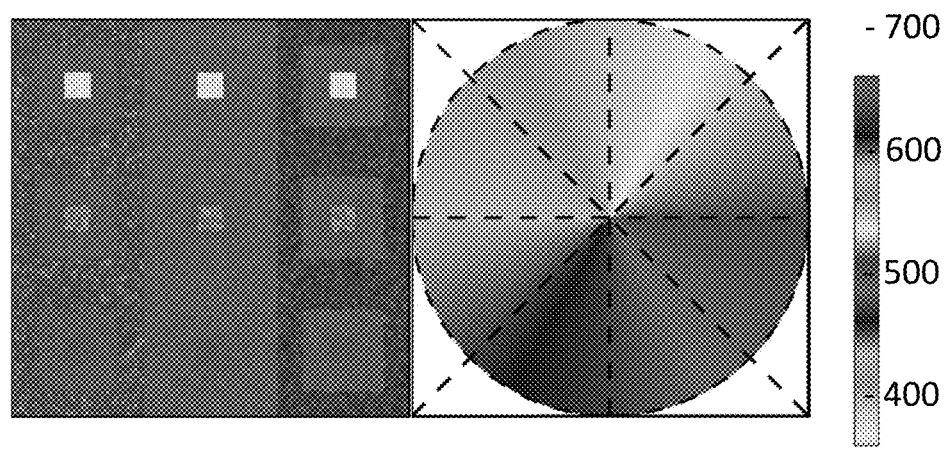
Figure 25C:
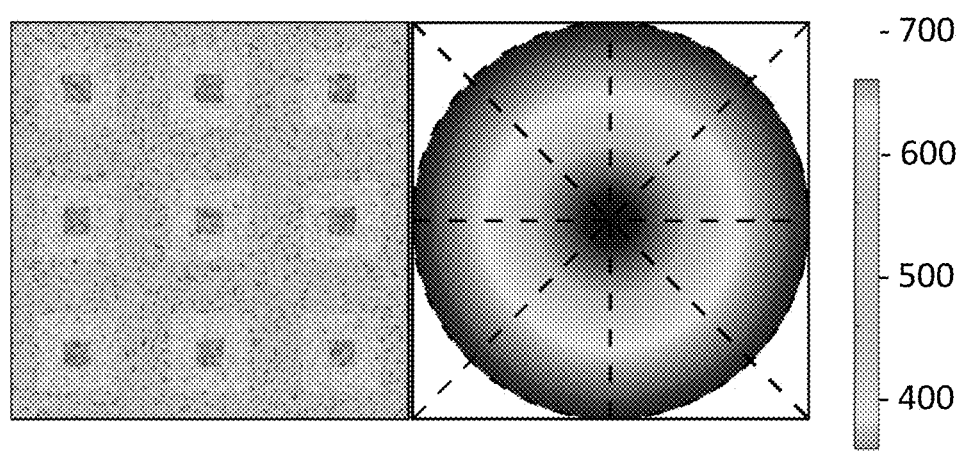
Figure 25D:
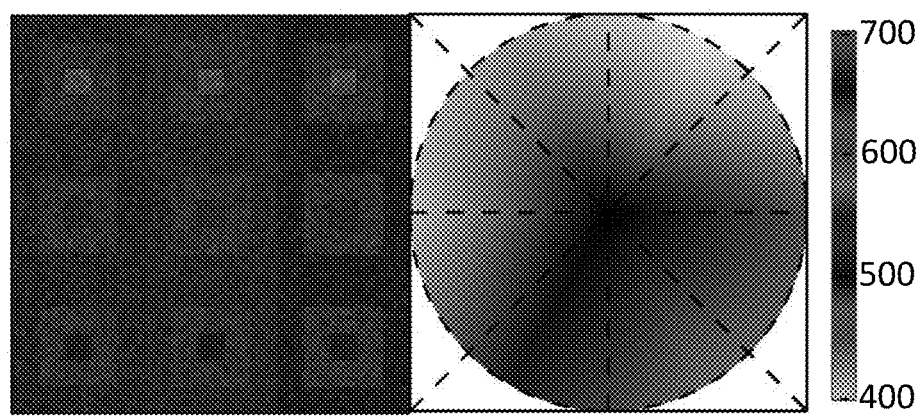
Figure 25E:
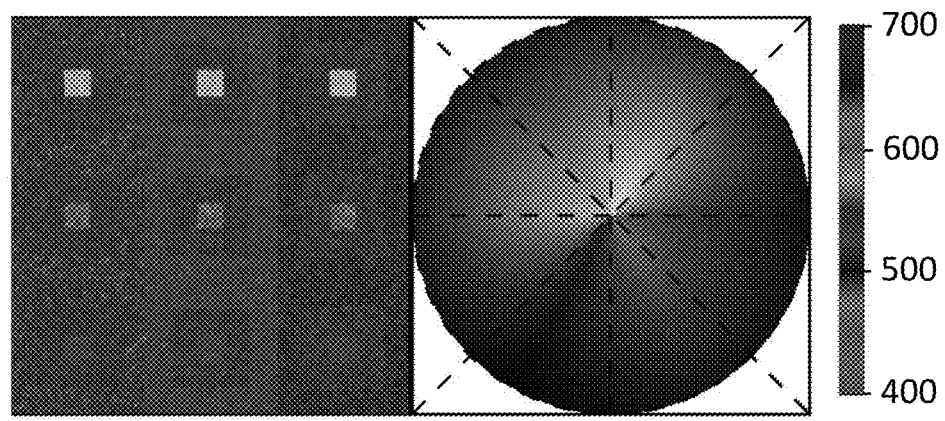

Biological samples can include a multitude of fluorescent spectral components, deriving from fluorescent labels as well as intrinsic signals, each with different characteristics and properties. Identifying and rendering these subtle spectral differences is the challenge. We found that no one rendering is sufficient for all cases, and thus created four specialized color map references to enhance color contrast in samples with different spectral characteristics. To simplify the testing of the color map references, we designed a Simulated Hyperspectral Test Chart (SHTC), in which defined areas contain the spectra we obtained from CFP, YFP, and RFP zebrafish embryos. Each section of the test chart offers different image contrast, obtained by shifting the CFP and RFP spectra maxima position with respect to the YFP spectrum (FIG. 33). We render the SHTC in grayscale image and with SEER for comparison (FIG. 25a). These representations can be rapidly shown separately to determine which has the highest information content.

A reference map is defined as an organization of the palette where each spectrum is associated with a color based on its phasor position. The color distribution in each of the reference maps is a function of the coordinates of the phasor plot. In the Angular map (FIG. 25b), hue is calculated as a function of angle, enhancing diversity in colors when spectra have different center wavelengths ("phases") on the phasor plot. For the Radial map (FIG. 25c), we assign colors with respect to different radii, highlighting spectral amplitude and magnitude. The radial position is, in general, related to the intensity integral of the spectrum, which in turn can depend on the shape of the spectrum, with the null-intensity localizing at the origin of the plot (FIG. 34). In our simulation (FIG. 25c), the colors obtained with this map mainly represent differences in shape, however in a scenario with large dynamic range of intensities, colors will mainly reflect changes in intensity, becoming affected, at low signal to noise, by the uncorrelated background (FIG. 35). In the Gradient Ascent and Descent models (FIG. 25d, e), the color groups differ according to angle as seen in the Angular map with an added variation of the color intensity strength in association with changes in the radius. Gradient maps enhance similar properties as the Angular map. However, the Gradient Ascent (FIG. 25d) map puts a greater focus on distinguishing the higher intensity spectra while de-emphasizing low intensity spectra; whereas, the Gradient Descent (FIG. 25e) map does the opposite, highlighting the spectral differences in signals with low intensity. The complementary attributes of these four maps permits renderings that distinguish a wide range of spectral properties in relation to the phasor positions. It is important to note that the idea of Angular and Radial maps have been previously utilized in a variety of applications and approaches and are usually introduced as "Phase" and "Modulation", respectively. Here, we have recreated and provided these maps for our hyperspectral fluorescence data as simpler alternatives to our more adaptable maps.

The Standard Reference Maps simplify comparisons between multiple fluorescently labeled specimens as the palette representation is unchanged across samples. These references are centered at the origin of the phasor plot, hence their color distributions remain constant, associating a predetermined color to each phasor coordinate. Fluorophores positions are constant on the phasor plot, unless their spectra are altered by experimental conditions. The ability of the Standard Reference Maps to capture either different ratios of labels or changes in a label, such as a calcium indicator, offers the dual advantage of providing a rapid, quantitative overview and simplifying the comparison between multiple samples.

Example 8. Tensor Map

Figure 25F:
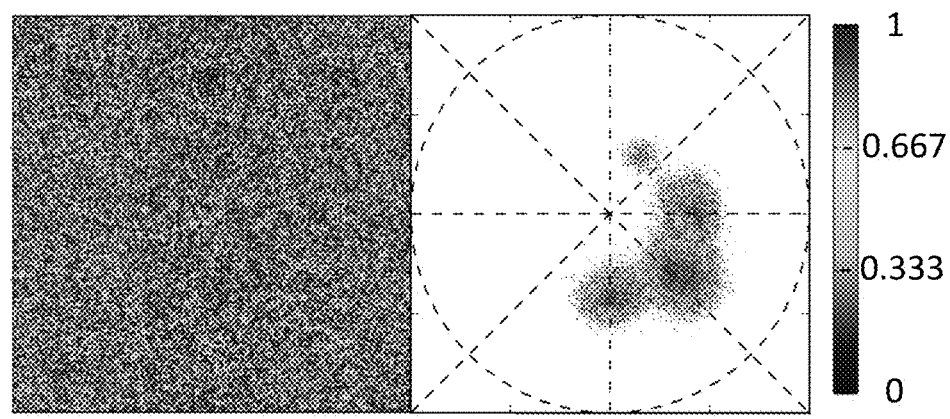

The SEER approach provides a straightforward means to assess statistical observations within spectral images. In addition to the four Standard Reference Maps, we designed a tensor map that recolors each image pixel based on the gradient of counts relative to its surrounding spectra (FIG. 25f). Considering that the phasor plot representation is a two-dimensional histogram of real and imaginary Fourier components, then the magnitude of each histogram bin is the number of occurrences of a particular spectrum. The tensor map is calculated as a gradient of counts between adjacent bins, and each resulting value is associated a color based on a color map (here we use a "jet" color map).

The image is recolored according to changes in spectral occurrences, enhancing the spectral statistical fluctuations for each phasor cluster. The change in frequency of appearance can provide insights in the dynamics of the population of spectra inside dataset. A visible result is a type of spectral edge detection that works in the wavelength dimension, facilitating detection of chromatic changes in the sample. Alternatively, tensor map can aid in identifying regions which contain less frequent spectral signatures relative to the rest of the sample. An example of such a case is shown in the upper left quadrant of the simulation (FIG. 25f) where the center part of each quadrant has different spectrum and appears with lower frequency compared to its surroundings.

Example 9. Modes (Scale and Morph)

We have implemented two different methods to improve our ability to enhance spectral properties: scaled mode and morphed mode.

Figure 26A:
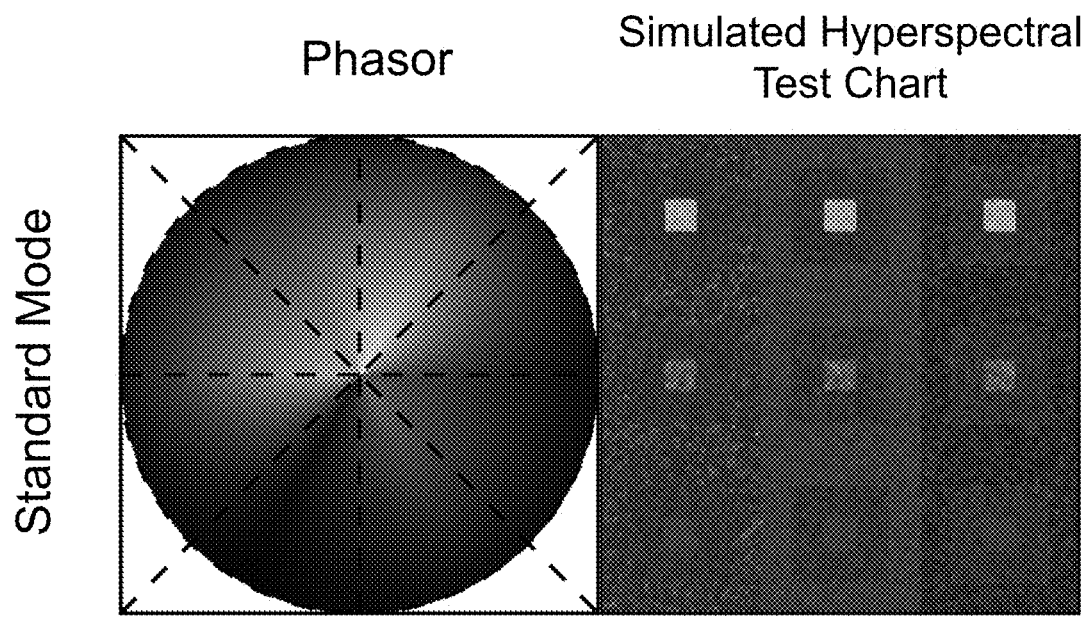
Figure 26B:
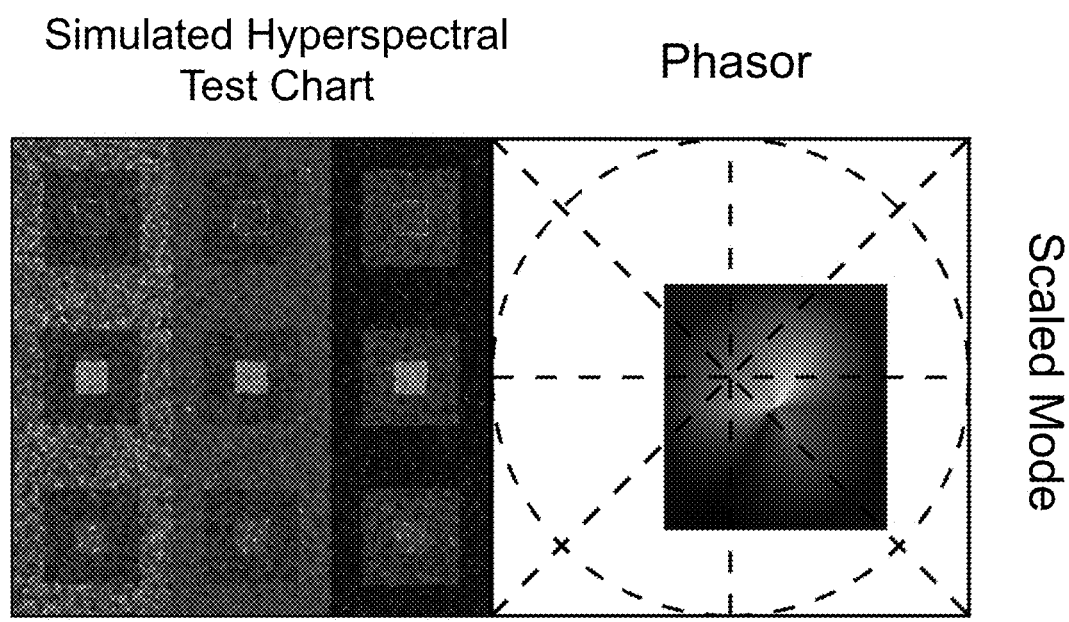

Scaled mode provides an adaptive map with increased color contrast by normalizing the Standard Reference map extreme values to the maximum and minimum phasor coordinates of the current dataset, effectively creating the smallest bounding unit circle that contains all phasor points (FIG. 26b). This approach maximizes the number of hues represented in the rendering by resizing the color map based on the spectral range within the image. Scaled mode increases the difference in hue and the contrast of the final false-color rendering. These characteristics set the scaled mode apart from the Standard Reference Maps (FIG. 26a), which constantly cover the full phasor plot area and eases comparisons between datasets. Scaled mode sacrifices this uniformity, but offers spectral contrast stretching that improves contrast depending on the values represented in individual image datasets. The boundaries of the Scaled mode can be set to a constant value across different samples to facilitate comparison.

Figure 26C:
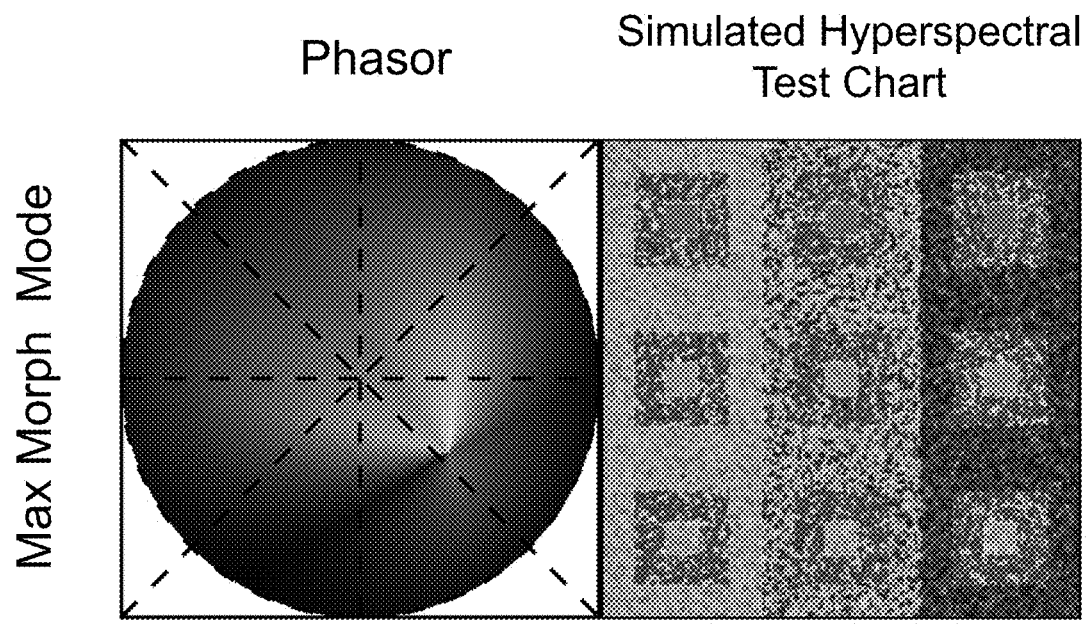
Figure 26D:
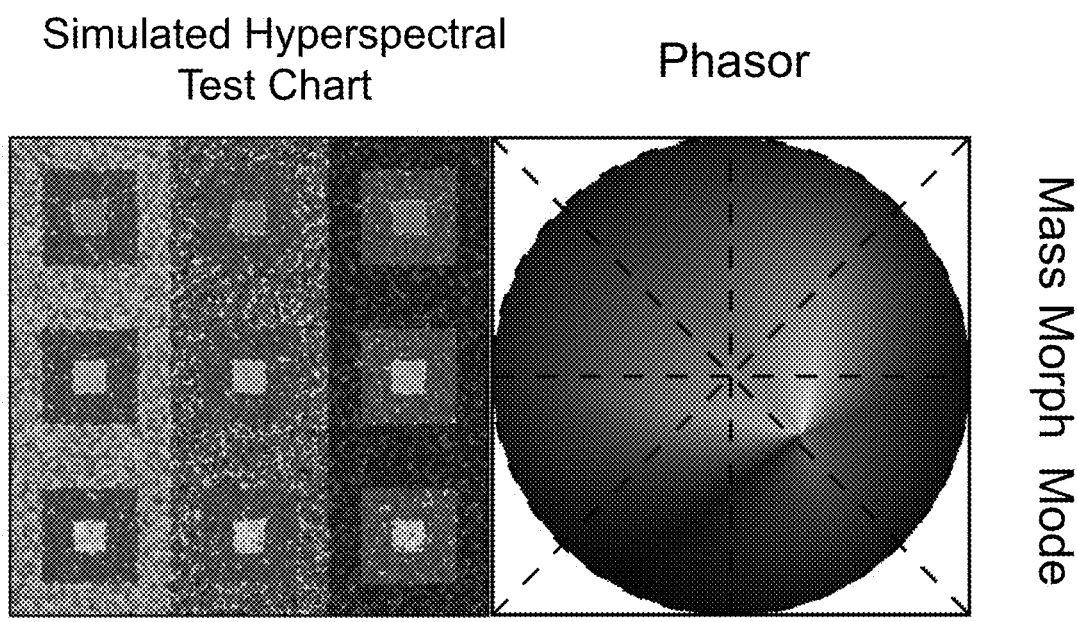

Morph mode exploits the dataset population properties captured in the image's phasor representation to enhance contrast. From the phasor histogram, either the most frequent spectral signature or the center of mass (in terms of histogram counts) are used as the new center reference point of the SEER maps. We call this new calculated center the apex of the SEER. The result is an adaptive palette that changes depending on the dataset. In this representation mode, the edges of the reference map are held anchored to the phasor plot circular boundary, while the center point is shifted, and the interior colors are linearly warped (FIG. 26c, d). By shifting the apex, contrast is enhanced for datasets with off-centered phasor clusters. A full list of the combination of Standard Reference Maps and modes is reported (FIGS. 36-37) for different levels of spectral overlap in the simulations and for different harmonics. The supplement presents results for SHTC with very similar spectra (FIG. 33), using second harmonic in the transform, and for an image with frequently encountered level of overlap (FIGS. 38-39) using first harmonic. In both scenarios, SEER improves visualization of multispectral datasets (FIGS. 36, 37, 39, 40) compared to standard approaches (FIGS. 33, 38). Implementation of 1× to 5× spectral denoising filters further enhances visualization (FIGS. 41, 42).

Example 10. Color Maps Enhance Different Spectral Gradients in Biological Samples To demonstrate the utility of SEER and its modes, we present four example visualizations of images taken from unlabeled mouse tissues and fluorescently tagged zebrafish.

In live samples, a number of intrinsic molecules are known to emit fluorescence, including: NADH, riboflavin, retinoids, folic acid. The contribution of these intrinsic signals to the overall fluorescence is generally called autofluorescence. Hyperspectral imaging and HySP can be employed to diminish the contribution of autofluorescence to the image. The improved sensitivity of the phasor, however, enables autofluorescence to become a signal of interest and allows for exploration of its multiple endogenous molecules contributions. SEER is applied here for visualizing multispectral autofluorescent data of an explant of freshly isolated trachea from a wildtype C57Bl mouse. The tracheal epithelium is characterized by a very low cellular turnover, and therefore the overall metabolic activity is attributable to the cellular function of the specific cell type. Club and ciliated cells are localized in the apical side of the epithelium and are the most metabolically active as they secrete cytokines and chemically and physically remove inhaled toxins and particles from the tracheal lumen. Contrarily, basal cells which represent the adult stem cells in the upper airways, are quiescent and metabolically inactive. Because of this dichotomy in activity, the tracheal epithelium at homeostasis constituted the ideal cellular system for testing SEER and validating with FLIM imaging. The slight bend on the trachea, caused by the cartilage rings, allowed us to visualize the mesenchymal collagen layer, the basal and apical epithelial cells and tracheal lumen in a single focal plane.

The explant was imaged with 2-photon laser scanning microscopy in multispectral mode. We compare the state of the art "true color" image (FIG. 27a), and SEER images (FIG. 27b-c). The Gradient Descent morphed map (FIG. 27b) enhances the visualization of metabolic activities within the tracheal specimen, showing different metabolic states when moving from the tracheal airway apical surface toward the more basal cells and the underlying collagen fibers (FIG. 27b). The visualization improvement is maintained against different implementations of RGB visualization (FIG. 43). The tensor map increases the contrast of cell boundaries (FIG. 27c). Changes in autofluorescence inside live samples are associated to variations in the ratio of NAD+/NADH, which in turn is related to the ratio of free to protein bound NADH. Despite very similar fluorescence emission spectra, these two forms of NADH are characterized by different decay times (0.4 ns free and 1.0-3.4 ns bound). FLIM provides a sensitive measurement for the redox states of NADH and glycolytic/oxidative phosphorylation. Metabolic imaging by FLIM is well established and has been applied for characterizing disease progression in multiple animal models, in single cells and in human as well as to distinguish stem cells differentiation and embryo development.

Here, the dashed squares highlight cells with distinct spectral representation through SEER, a difference which the FLIM image (FIG. 27d, FIG. 44) confirms.

The improvement of SEER in visualizing intrinsic signals is clear when compared to standard approaches.

Figure 28A:
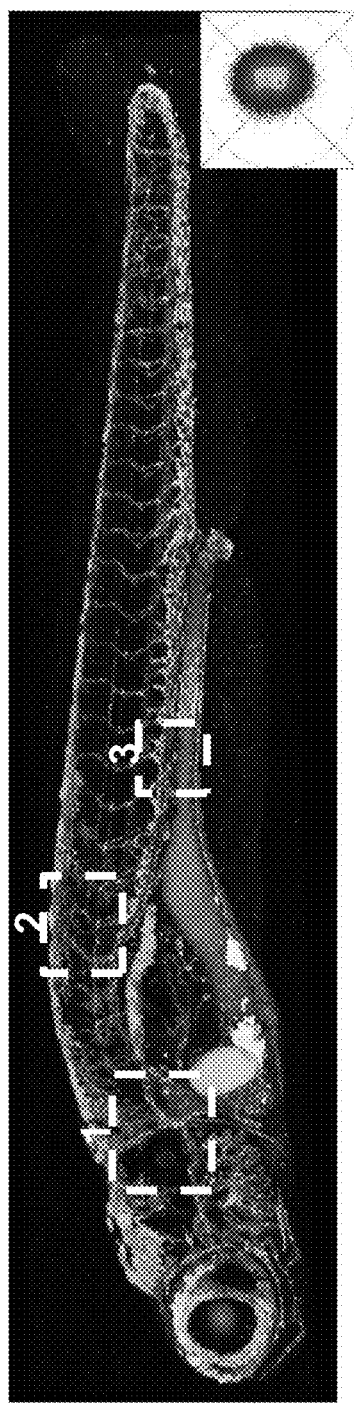
Figure 28B:
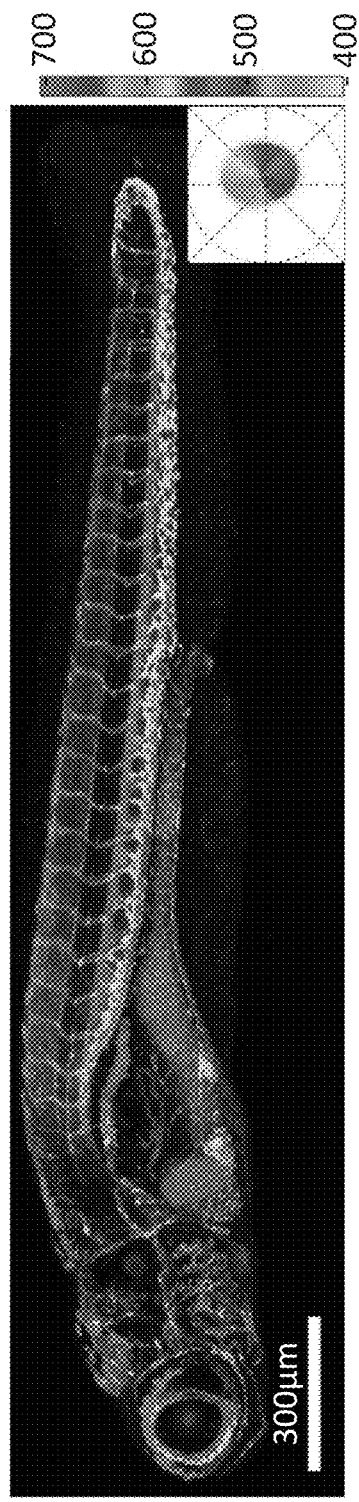
Figure 28G:
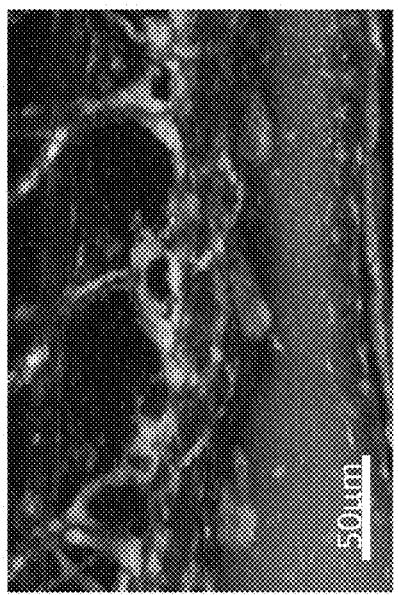
Figure 28H:
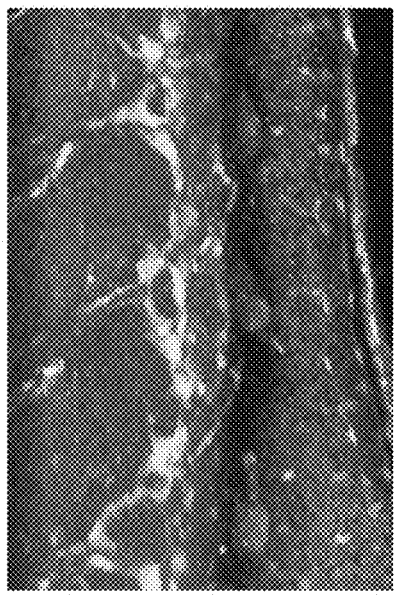
Figure 28E:
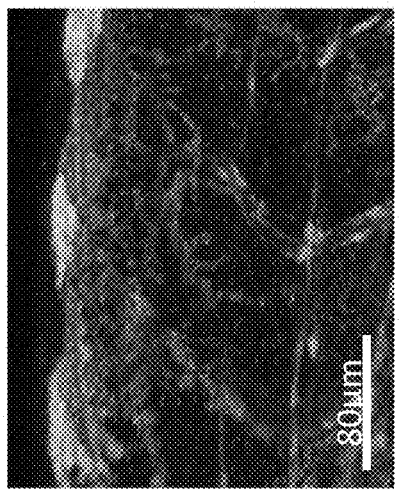
Figure 28F:
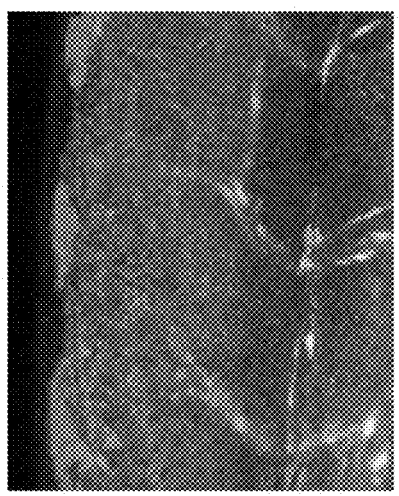
Figure 28C:
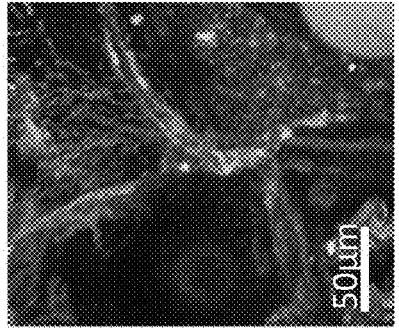
Figure 28D:
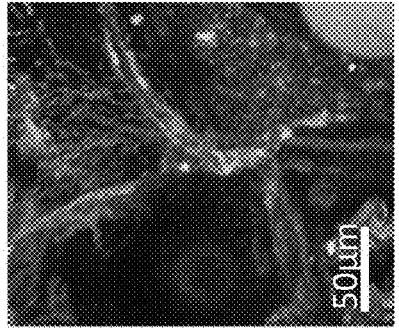

Microscopic imaging of fluorophores in the cyan to orange emission range in tissues is challenging due to intrinsic fluorescence. A common problem is bleed-through of autofluorescent signals into the emission wavelength of the label of interest. Bleed-through is the result of two fluorophores overlapping in emission and excitation profiles, so that photons from one fluorophore fall into the detection range of the other. While bleed-through artifacts can be partially reduced with a stringent choice of the emission filters, this requires narrow collection channels, which reject any ambiguous wavelength and greatly decreases collection efficiency. This strategy generally proves difficult when applied to broad-spectra autofluorescence. mKusabira-Orange 2 (mKO2) is a fluorescent protein whose emission spectrum significantly overlaps with autofluorescence in zebrafish. In a fli1:mKO2 zebrafish, where all of the vascular and endothelial cells are labelled, the fluorescent protein, mKO2, and autofluorescence signals due to pigments and yolk are difficult to distinguish (FIG. 28a, boxes). Grayscale renderings (FIG. 45) provide information on the relative intensity of the multiple fluorophores in the sample but are not sufficient for specifically detecting the spatial distribution of the mKO2 signal. True color representation (FIG. 28a, FIG. 46) is limited in visualizing these spectral differences. SEER's angular map (FIG. 28b) provides a striking contrast between the subtly different spectral components inside this 4D (x,y,z,λ) dataset. The angular reference map enhances changes in phase on the phasor plot which nicely discriminates shifts in the center wavelength of the spectra inside the sample). Autofluorescence from pigment cells is considerably different from the fli1:mKO2 fluorescence (FIG. 28c-h). For example, the dorsal area contains a combination of mKO2 and pigment cells (FIG. 28e-f) not clearly distinct in the standard approaches. The Angular map permits SEER to discriminate subtle spectral differences. Distinct colors represent the autofluorescence from yolk and from pigment cells (FIG. 28g-h), enriching the overall information provided by this single-fluorescently labeled specimen and enhancing the visualization of mKO2 fluorescently labeled pan-endothelial cells.

Imaging and visualization of biological samples with multiple fluorescent labels are hampered by the overlapping emission spectra of fluorophores and autofluorescent molecules in the sample, complicating the visualization of the sample. A triple labelled zebrafish embryo with Gt(desm-Citrine)$^{ct122a/+}$;Tg(kdrl:eGFP), H2B-Cerulean labelling respectively muscle, vasculature and nuclei, with contributions from pigments autofluorescence is rendered with standard approaches and SEER in 1 D and 3D (FIG. 29). TrueColor representation (FIG. 29a, FIG. 47) provides limited information on the inner details of the sample. Vasculature (eGFP) and nuclei (Cerulean) are highlighted with shades of cyan whereas autofluorescence and muscle (Citrine) are in shades of green (FIG. 29a) making both pairs difficult to distinguish. The intrinsic richness of colors in the sample is an ideal test for the gradient descent and radial maps.

The Angular map separates spectra based mainly on their central (peak) wavelength, which correspond to "phase" differences in the phasor plot. The gradient descent map separates spectra with a bias on subtle spectral differences closer to the center of the phasor plot. Here we applied the Mass Morph and Max Morph modes to further enhance the distinction of spectra (FIG. 29b-c). With the Mass Morph mode, the muscle outline and contrast of the nuclei are improved by increasing the spatial separation of the fluorophores and suppressing the presence of autofluorescence from skin pigment cells (FIG. 29e). With the Max Morph mode (FIG. 29c), pixels with spectra closer to skin autofluorescence are visibly separated from muscle, nuclei and vasculature.

The enhancements of SEER are also visible in volumetric visualizations. The Angular and Gradient maps are applied to the triple labelled 4D (x,y,z,λ) dataset and visualized as maximum intensity projections (FIG. 29d-f). The spatial localization of fluorophores is enhanced in the Mass Morphed Angular map, while the Max Morphed Gradient Descent map provides a better separation of the autofluorescence of skin pigment cells). These differences are also maintained in different visualization modalities (FIG. 48).

SEER helps to discern the difference between fluorophores even with multiple contributions from bleed though between labels and from autofluorescence. Particularly, morphed maps demonstrate a high sensitivity in the presence of subtle spectral differences. The triple-labeled example (FIG. 29) shows advantage of the morphed map, as it places the apex of the SEER map at the center of mass of the phasor histogram and compensates for the different excitation efficiencies of the fluorescent proteins at 458 nm.

Example 11. Quantitative Differences can be Visualized in Combinatorial Approaches Zebrabow is the result of a powerful genetic cell labeling technique based on stochastic and combinatorial expression of different relative amounts of a few genetically encoded, spectrally distinct fluorescent proteins. The Zebrabow (Brainbow) strategy combines the three primary colors red, green and blue, in different ratios, to obtain a large range of colors in the visual palette, similar to modern displays. Unique colors arise from the combination of different ratios of RFP, CFP and YFP, achieved by a stochastic Cre-mediated recombination.

This technique has been applied multiple applications, from axon and lineage tracing to cell tracking during development, in which a specific label can be used as a cellular identifier to track descendants of individual cells over time and space.

The challenge is acquiring and analyzing the subtle differences in hues among these hundreds of colors. Multispectral imaging provides the added dimension required for an improved acquisition; however, this modality is hampered by both instrumental limitations and spectral noise. Furthermore, current image analysis and visualization methods interpret the red, yellow and cyan fluorescence as an RGB additive combination and visualize it as a color picture, similar to the human eye perception of color. This approach is not well poised for distinguishing similar, yet spectrally unique, recombination ratios due to our difficulty in reliably identifying subtly different colors.

SEER overcomes this limitation by improving the analysis' sensitivity using our phasor-based interpretation of colors. Recombinations of labels belong to separate areas of the phasor plot, simplifying the distinction of subtle differences. The Standard Reference Maps and modes associate a color easily distinguishable by eye, enhancing the subtle spectral recombination. SEER simplifies the quantification of differences between cells for combinatorial strategies, opening a novel window of analysis for brainbow samples.

We imaged an Tg(ubi:Zebrabow) sample and visualized its multiple genetic recombinations using SEER. The results (FIG. 30, FIG. 49) highlight the difficulty of visualizing these datasets with standard approaches as well as how the compressive maps simplify the distinction of both spectrally close and more separated recombinations.

Example 12

Standard approaches for the visualization of hyperspectral datasets trade computational expense for improved visualization. In this work, we show that the phasor approach can define a new compromise between computational speed and rendering performance. The wavelength encoding can be achieved by proper conversion and representation by the spectral phasor plot of the Fourier transform real and imaginary components. The phasor representation offers effortless interpretation of spectral information. Originally developed for fluorescence lifetime analysis and subsequently brought to spectral applications, here the phasor approach has been applied to enhance the visualization of multi- and hyperspectral imaging. Because of the refined spectral discrimination achieved by these phasor-based tools, we call this approach Spectrally Enhanced Encoded Representations (SEER).

Spectrally Encoded Enhanced Representations (SEER) and robust method that converts spectral $(x,y,\lambda)$ information into a visual representation, enhancing the differences between labels. This approach makes more complete use of the spectral information. Prior analyses employed the principal components or specific spectral bands of the wavelength dimension. Similarly, previous phasor analyses interpreted the phasor using selected regions of interest. Our work explores the phasor plot as a whole and represents that complete information set as a color image, while maintaining efficiency and minimizing user interaction. The function can be achieved quickly and efficiently even with large data sizes, circumventing the typical computational expense of hyperspectral processing. Our tests show SEER can process a 3.7 GB dataset with 1.26.108 spectra in 6.6 seconds and a 43.88 GB dataset with 1.47-109 spectra in 87.3 seconds. Comparing with the python module, scikit-learn's implementation of fast Independent Component Analysis, SEER provides up to a 67 fold speed increase (FIG. 31) and lower virtual memory usage. The spectral maps presented here reduce the dimensionality of these large datasets and assign colors to a final image, providing an overview of the data prior to a full-scale analysis. Processing speed comparison between SEER and fastICA for the multispectral fluorescent data shown in FIGS. 27-30 is presented in Table 4. SEER's computation time ranged between 0.44 (for FIG. 27) and 6.27 seconds (FIG. 28) where the corresponding timing for fastICA was 3.45 and 256.86 seconds respectively, with a speed up in the range of 7.9 to 41 folds (FIG. 58), in accordance with the trend shown in FIG. 31.

TABLE 4

Processing time comparison SEER vs Independent Component Analysis (scikit-learn implementation) for FIGS. 27-30.

| | Processing Time | | |
| --- | --- | --- | --- |
| | SEER [sec] | ICA (3c) [sec] | Speed Up [folds] |
| FIG. 27 | 0.44 | 3.45 | 7.9 |
| FIG. 28 | 6.27 | 256.86 | 41.0 |

TABLE 4-continued

Processing time comparison SEER vs Independent Component Analysis (scikit-learn implementation) for FIGS. 27-30.

| | Processing Time | | |
| --- | --- | --- | --- |
| | SEER [sec] | ICA (3c) [sec] | Speed Up [folds] |
| FIG. 28 subset | 2.89 | 77.82 | 26.9 |
| FIG. 29 | 1.49 | 33.58 | 22.6 |
| FIG. 30 | 0.52 | 10.19 | 19.5 |

A simulation comparison with other common visualization approaches such as Gaussian kernel and peak wavelength selection (FIG. 50) shows an increased accuracy for SEER to associate distinct colors to closely overlapping spectra under different noise conditions (FIG. 51). The accuracy improvement was 1.4-2.6 fold for highly overlapping spectra, 0 nm-8.9 nm spectra maxima distance, and 1.5-2.3 fold for overlapping spectra with maxima separated by 17.8 nm-35.6 nm (FIGS. 52-53).

Quantification of RGB images by colorfulness, contrast and sharpness show that SEER generally performs better than standard visualization approaches (FIG. 58). SEER's average enhancement was 2%-19% for colorfulness, 11%-27% for sharpness and 2%-8% for contrast (Table 5) for the datasets of FIGS. 27-30. We then performed a measure of the Color Quality Enhancement (CQE), a metric of the human visual perception of color image quality, (Table 6). The CQE score of SEER was higher than the standard, with improvement of 11%-26% for FIG. 27, 7%-98% for FIG. 28, 14%-25% for FIGS. 29 and 12%-15% for FIG. 30 (see also FIG. 58).

TABLE 5

Average colorfulness, contrast and sharpness score across FIGS. 27-30 for different visualization methods

| | Average Score | | |
| --- | --- | --- | --- |
| | Colorfulness | Contrast | Sharpness |
| Gauss. Def. | 2.11 | 53.84 | 10.83 |
| Gauss r = .1 | 2.06 | 52.19 | 10.60 |
| Gauss r = .2 | 1.97 | 59.57 | 11.17 |
| Gauss r = .3 | 1.96 | 60.00 | 11.20 |
| Peak Wav. | 2.29 | 58.61 | 11.14 |
| SEER h = 1 | 2.34 | 66.32 | 11.40 |
| SEER h = 2 | 2.34 | 65.15 | 11.40 |

TABLE 6

Color Quality Enhancement score for datasets in FIGS. 27-30. Parameters calculations are reported in methods section.

| | Color Quality Enhancement | | | |
| --- | --- | --- | --- | --- |
| | FIG. 27 | FIG. 28 | FIG. 29 | FIG. 30 |
| Gauss. Def. | 39.47 | 22.72 | 58.37 | 46.64 |
| Gauss r = .1 | 38.26 | 16.39 | 61.29 | 46.34 |
| Gauss r = .2 | 43.55 | 30.11 | 62.53 | 46.71 |
| Gauss r = .3 | 43.07 | 30.26 | 63.89 | 46.89 |
| Peak Wav. | 43.15 | 29.09 | 61.70 | 47.27 |
| SEER h = 1 | 45.72 | 31.08 | 72.87 | 53.18 |
| SEER h = 2 | 48.38 | 32.37 | 69.33 | 49.58 |

Measuring Color Contrast in Fluorescent Images

There is an inherent difficulty in determining an objective method to measure the image quality of color images in relation to fluorescent images. The main challenge for fluorescent images is that for the majority of fluorescence microscopy experiments, a reference image does not exist because there is an inherent uncertainty related to the image acquisition. Therefore, any kind of color image quality assessment will need to be based solely on the distribution of colors within an image.

This type of assessment has its own further challenges. Although there have been a variety of quantitative methods formulated to determine the quality of intensity distributions in grayscale images, such methods for color images are still being debated and tested. This lack of suitable methods for color images mainly comes from the divide between the mathematical representation of the composition of different colors and human perception of those same colors. This divide occurs because human color perception varies widely and is nonlinear for different colors; whereas the quantitative representation of any color is usually a linear combination of base colors such as Red, Green, and Blue. This nonlinear human perception of color is closely related to the concept of hue. Loosely speaking, hue is the dominant wavelength that reflects the light. Hues perceived as blue tend to reflect light at the left end of the spectrum and red at the right end of the spectrum. Generally, each individual color has a unique holistic trait which is determined by its distinctive spectrum. Discretization of the spectrum into multiple components cannot fully describe the original richness in color.

The current methods for determining the quality of an RGB image usually adapt grayscale methods in two different ways. The first method involves either converting the three channel color image into a single channel grayscale image before measuring the quality. The second method measures the quality of each channel individually and then combines those measurements with different weights. However, both methods face limitations in providing a value of quality that correlates well with human perception. The first method loses information when converting the color image to grayscale. The second method tries to interpret the nonlinear human perception of the quality of a color image by separating it into three channels and measuring them individually. The inherent hue of a color, however, is more than the sum of the individual component colors, since each channel taken individually is not necessarily as colorful as the combined color.

A more complete color metric should take hue into account, such as by measuring the colorfulness loss between the original and processed images10. In conclusion, as a consequence of this limitation in measuring colorfulness for current methods, there is currently no established "true measure of contrast" within fluorescent color images.

Flexibility is a further advantage of our method. The users can apply several different Standard Reference Maps to determine which is more appropriate for their data and enhance the most important image features. The modes provide a supplementary enhancement by adapting the References to each dataset, in terms of size and distribution of spectra in the dataset. Scaling maximizes contrast by enclosing the phasor distribution, it maintains linearity of the color map. Max and Center of Mass modes shift the apex of the distribution to a new center, specifically the most frequent spectrum in the dataset or the weighted "color-frequency" Center of mass of the entire dataset. These modes adapt and improve the specific visualization properties for each map to the dataset currently being analyzed. As a result, each map offers increased sensitivity to specific properties of the data, amplifying, for example, minor spectral differences or focusing on major wavelength components. The adaptivity of the SEER modes can prove advantageous for visually correcting the effect of photobleaching in samples, by changing the apex of the map dynamically with the change of intensities (FIG. 54).

SEER can be applied to fluorescence, as performed here, or to standard reflectance hyper- and multi-spectral imaging. These phasor remapping tools can be used for applications in fluorescence lifetime or combined approaches of spectral and lifetime imaging. With multispectral fluorescence, this approach is promising for real-time imaging of multiple fluorophores, as it offers a tool for monitoring and segmenting fluorophores during acquisition. Live imaging visualization is another application for SEER. The Gradient Descent map, for example, in combination with denoising strategies can minimize photo-bleaching and -toxicity, by enabling the use of lower excitation power. SEER overcomes the challenges in visualization and analysis deriving from low signal-to-noise images, such as intrinsic signal autofluorescence imaging. Among other complications, such image data can result in a concentrated cluster proximal to the phasor center coordinates. The gradient descent map overcomes this limitation and provides bright and distinguishable colors that enhance subtle details within the dim image.

It is worth noticing that the method is generally indifferent to the dimension being compressed. While in this work we explore the wavelength dimension, SEER can be utilized, in principle, with any n-dimensional dataset where n is larger than two. For instance, it can be used to compress and compare the dimension of lifetime, space or time for multiple datasets. Some limitations that should be considered are that SEER pseudo-color representation sacrifices the "true color" of the image, creating inconsistencies with the human eyes' expectation of the original image and does not distinguish identical signals arising from different biophysical events.

New multi-dimensional, multi-modal instruments will more quickly generate much larger datasets. SEER offers the capability of processing this explosion of data, enabling the interest of the scientific community in multiplexed imaging.

Example 13. Simulated Hyperspectral Test Chart

To account for the Poisson noise and detector noise contributed by optical microscopy, we generated a simulated hyperspectral test chart starting from real imaging data with a size of x: 300 pixels, y: 300 pixels, and lambda: 32 channels. S1, S2 and S3 spectra were acquired respectively from zebrafish embryos labeled only with CFP, YFP, and RFP, where the spectrum in FIG. 24a is identical to the center cell of the test chart FIG. 24d. In each cell three spectra are represented after shifting the maxima by d1 or d2 nanometers with respect to S2. Each cell has its corresponding spectra of S1, S2, and S3 (FIG. 33).

Example 14. Standard RGB Visualizations

The TrueColor RGB image (FIGS. 33, 38, 50) is obtained through compression of the hyperspectral cube into the RGB 3 channels color space by generating a Gaussian radial basis function kernel K for each RGB channel. This kernel K acts as a similarity factor and is defined as:

$$K_i(x_i, x') = e^{\frac{-|x_i - x'|^2}{2\sigma^2}} \quad \text{(eq. 1)}$$

where x' is the center wavelength of R or B or G. For example, when x'=650 nm, the associated RGB color space is (R:1, G:0, B:0). Both x and K are defined as 32×1 vectors, representing, respectively, the 32-channel spectrum of one single pixel and the normalized weight of each R, G and B channel. i is the channel index of both vectors. $K_i$ represents how similar channel i is to each R/G/B channel, and $\sigma$ is the deviation parameter.

We compute RGB color space c by a dot product of the weight vector K and $\lambda$ at corresponding channel R/G/B:

$$c = \Sigma_{i=1}^{i=32} \lambda_i \times K_i \quad \text{(eq.2)}$$

where $\lambda$ is a vector of the wavelengths captured by the spectral detector in an LSM 780 inverted confocal microscope with lambda module (Zeiss, Jena, Germany) and $\lambda_i$ is the center wavelength of channel i. Gaussian kernel was set at 650 nm, 510 nm, 470 nm for RGB respectively as Default (FIG. 33s, FIG. 38, FIG. 43e, FIG. 46e, FIG. 47e, FIG. 49j).

The same Gaussian kernel was also changed adaptively to the dataset to provide a spectral contrast stretching on the visualization and focus the visualization on the most utilized channels. The average spectrum for the entire dataset is calculated and normalized. The intersect at 10% (FIG. 43f, 46f, 47f, 49f), 20% (FIG. 43g, 46g, 47g, 49g) and 30% (FIG. 43h, 46h, 47h, 49h). of the intensity is obtained and used as a center for the blue and red channels. The green channel is centered halfway between red and blue. Representations of these adaptations are reported in FIG. 50g,h,i.

The TrueColor 32 Channels image (FIG. 1c, FIG. 28a,c, e,g, FIG. 29a,d,e,f, FIG. 43c, 46c, 47c, 49c) was rendered as a 32 channels Maximum Intensity Projection using Bitplane Imaris (Oxford Instruments, Abingdon, UK). Each channel has a known wavelength center (32 bins, from 410.5 nm to 694.9 nm with 8.9 nm bandwidth). Each wavelength was associated with a color according to classical wavelength-to-RGB conversions[5] as reported in FIG. 50f. The intensity for all channels was contrast-adjusted (Imaris Display Adjustment Settings) based on the channel with the largest information. A meaningful range for rendering was identified as the top 90% in intensity of the normalized average spectrum for the dataset (FIG. 43b, 46j, 47j, 49b). Channels outside of this range were excluded for rendering. Furthermore, for 1 photon excitation, channels associated to wavelength lower than the laser excitation (for example channels 1 to 5 for laser 458 nm) were excluded from rendering.

Peak Wavelength representation (FIGS. 43d, 46d, 47d, 49d, 50 and 52) reconstructs an RGB image utilizing, for each pixel, the color associated to the wavelength at which maximum intensity is measured. Wavelength-to-RGB conversion was performed using a python function. A graphical representation is reported in FIG. 50f.

Example 15. Accuracy Calculation

We utilize the Simulated Hyperspectral Test Chart to produce a different levels of spectral overlap and signal to noise ratio (SNR). We utilize multiple RGB visualization approaches for producing compressed RGB images (FIG. 50, FIG. 51). Each panel of the simulation is constructed by three different spectra, organized as three concentric squares $Q_1$, $Q_2$, $Q_3$ (FIG. 33). Hence, the maximal contrast visualization is expected to have three well separated colors. For quantifying this difference, we consider each (R,G,B) vector, with colors normalized [0,1], in each pixel as a set of Euclidean coordinates (x,y,z) and for each pixel calculate the Euclidean distance:

$$l_{12} = \sqrt{\Sigma_{i=R}^{B}(p_{Q1}-p_{Q2})_i^2} \quad \text{(eq 3)}$$

where $l_{12}$ is the color distance between square $Q_1$ and $Q_2$, $p_{Q1}$ and $p_{Q2}$ are the (R,G,B) vectors in the pixels considered, i is the color coordinate R, G or B. The color distances $Q_1Q_3$, $l_{13}$, and $Q_2Q_3$ are calculated similarly. The accuracy (FIG. 52) is calculated as:

$$acc = \frac{(l_{12} + l_{13} + l_{23})}{3\sqrt{2}} \quad \text{(eq. 4)}$$

where the denominator is the largest color distance $l_{red-green} + l_{red-blue} + l_{green-blue}$.

Example 16. Compressive Spectral Algorithm and Map Reference Design

Phasor Calculations

For each pixel in an image, we acquire the sequence of intensities at different wavelengths $I(\lambda)$. Each spectrum $I(\lambda)$ is discrete Fourier transformed into a complex number $g_{x,y,z,t} + i\, s_{x,y,z,t}$. Here i is the imaginary unit, while (x,y,z,t) denotes the spatio-temporal coordinates of a pixel in a 5D dataset.

The transforms used for real and imaginary components are:

$$g_{x,y,z,t}(k)|_{k=2} = \frac{\sum_{\lambda_0}^{\lambda_N} I(\lambda) * \cos\left(\frac{2\pi k \lambda}{N}\right) * \Delta\lambda}{\sum_{\lambda_0}^{\lambda_N} I(\lambda) * \Delta\lambda} \quad \text{(eq. 5)}$$

$$s_{x,y,z,t}(k)|_{k=2} = \frac{\sum_{\lambda_0}^{\lambda_N} I(\lambda) * \sin\left(\frac{2\pi k \lambda}{N}\right) * \Delta\lambda}{\sum_{\lambda_0}^{\lambda_N} I(\lambda) * \Delta\lambda} \quad \text{(eq. 6)}$$

Where $\lambda_0$ and $\lambda_N$ are the initial and final wavelengths respectively, N is the number of spectral channels, $\Delta\lambda$ is the wavelength band width of a single channel. k is the harmonic. In this work, we utilized harmonic k=2.

Standard Map Reference

Association of a color to each phasor coordinate (g,s) is performed in two steps. First, the reference system is converted from Cartesian to polar coordinates (r,θ).

$$(r, \theta) = \left(\sqrt{g^2 + s^2}, \frac{s}{g}\right) \quad \text{(eq. 7)}$$

These polar coordinate values are then transformed to the Hue, Saturation, Value (HSV) color model utilizing specific settings for each map, as listed below. Finally, any color generated outside of the r=1 boundary is set to black.

Gradient Descent:
hue=θ
saturation=1
value=1−0.85*r

Gradient Ascent
hue=θ
saturation=1
value=r

Radius:

Each r value from 0 to 1 is associated to a level in the jet colormap from the matplotlib package Angle:

hue=$\theta$ saturation=1 value=1

Tensor Map

Visualization of statistics on the phasor plot is performed by means of the mathematical gradient. The gradient is obtained in a two-step process.

First, we compute the two-dimensional derivative of the phasor plot histogram counts by utilizing an approximation of the second order accurate central difference.

Each bin F(g,s) has a central difference:

$$\frac{\partial F}{\partial g}, \frac{\partial F}{\partial s},$$

with respect to the differences in g (horizontal) and s (vertical) directions with unitary spacing h. The approximation becomes $$\frac{\partial F}{\partial s} = \frac{F\left(s+\frac{1}{2}h, g\right) - F\left(s-\frac{1}{2}h, g\right)}{h} = \frac{\frac{F(s+h, g) + F(s, g)}{2} - \frac{F(s, g) + F(s-h, g)}{2}}{h} = \frac{F(s+h, g) - F(s-h, g)}{2h} \quad \text{(eq. 8)}$$

And similarly:

$$\frac{\partial F}{\partial g} = \frac{F(s, g+h) - F(s, g-h)}{2h} \quad \text{(eq. 9)}$$

Second, we calculate the square root of the sum of squared differences D(s,g) as:

$$D(g, s) = \sqrt{\left(\frac{\partial F}{\partial g}\right)^2 + \left(\frac{\partial F}{\partial s}\right)^2} \quad \text{(eq. 10)}$$

obtaining the magnitude of the derivative density counts. With this gradient histogram, we then connect the phasor coordinates with same D(s,g) gradients with one contour. All gradients are then normalized to (0,1). Finally, pixels in the hyperspectral image corresponding to the same contour in phasor space will be rendered the same color. In the reference map, red represents highly dense gradients, usually at the center of a phasor cluster. Blue, instead, represents the sparse gradient that appears at the edge circumference of the phasor distributions.

Scale Mode

In this mode, the original square Standard Reference Maps are transformed to a new boundary box adapted to each dataset's spectral distribution.

The process of transformation follows these steps. We first determine the boundary box (width $\omega$, height h) based on the cluster appearance on the phasor plot. We then determine the largest ellipsoid that fits in the boundary box. Finally, we warp the unit circle of the original map to the calculated ellipsoid.

Using polar coordinates, we represent each point P of the standard reference map with phasor coordinates $(g_i, s_i)$ as:

$$P(g_i, s_i) = P(r_i * \cos\theta_i, r_i * \sin\theta_i) \quad \text{(eq. 11)}$$

The ellipsoid has semi-major axes:

$$a = \frac{\omega}{2} \quad \text{(eq. 12)}$$

and semi-minor axes $$b = \frac{h}{2} \quad \text{(eq. 13)}$$

Therefore, the ellipse equation becomes:

$$\left(\frac{g_i}{\omega/2}\right)^2 + \left(\frac{s_t}{h/2}\right)^2 = \text{rad}^2 \quad \text{(eq. 14)}$$

Where rad is a ratio used to scale each radius $r_i$ in the reference map to a proportionally corresponding distance in the boundary box-adapted ellipse, which in polar coordinates becomes:

$$\text{rad}^2 = r_i^2 * \left(\left(\frac{\cos\theta_i}{\frac{\omega}{2}}\right)^2 + \left(\frac{\sin\theta_i}{\frac{h}{2}}\right)^2\right) \quad \text{(eq. 15)}$$

Each point $P(g_i, s_i)$ of the standard reference map is geometrically scaled to a new coordinate $(g_o, s_o)$ inside the ellipsoid using forward mapping, obtaining the equation:

$$(r_o, \theta_o) = \left(\sqrt{g_i^2 + s_i^2} / \text{rad}, \tan^{-1}\frac{g_i}{s_i}\right) \quad \text{(eq. 16)}$$

This transform is applied to all Standard Reference Maps to generate the respective scaled versions.

Morph Mode

We linearly morph each point $P(g_i, s_i)$ to a new point $P'(g_o, s_o)$ by utilizing a shifted-cone approach. Each standard map reference is first projected on to a 3D conical surface centered on the phasor plot origin and with unitary height (FIG. 55a-c). Each point P on the standard map is given a z value linearly, starting from the edge of the phasor universal circle. The original standard map (FIG. 55c) can, thus, be interpreted as a top view of a right cone with z=0 at the phasor unit circle and z=1 at the origin (FIG. 55a).

We then shift the apex A of the cone to the computed weighted average or maxima of the original 2d histogram, producing an oblique cone (FIG. 55b) centered in A'.

In this oblique cone, any horizontal cutting plane is always a circle with center O'. Its projection $O_\perp'$ is on the line joining the origin O and projection of the new center $A_\perp'$ (FIG. 55b-d). As a result, all of the points in each circle are shifted towards the new center $A_\perp'$ on the phasor plot. We first transform the coordinates $(g_i, s_i)$ of each point P to the morphed map coordinates $(s_o, g_o)$, and then obtain the corresponding $(r_o, \theta_o)$ necessary for calculating Hue, Saturation, and Value.

In particular, a cutting plane with center O' has a radius of r' (FIG. 55). This cross-section projects on a circle centered in $O_\perp'$ with the same radius. Using geometrical calculations, we obtain:

$$OO_\perp' = \alpha * OA_\perp', \quad \text{(eq. 17)}$$

where $\alpha$ is a scale parameter. By taking the approximation, $$\Delta O'OO_\perp' \sim \Delta A'OA_\perp', \quad \text{(eq. 18)}$$

we can obtain $$OO' = \alpha * OA'. \quad \text{(eq. 19)}$$

Furthermore, given a point N' on the circumference centered in O', eq.14 also implies that:

$$O'N' = (1-\alpha) * ON_\perp', \quad \text{(eq. 20)}$$

which is equivalent to $$r' = (1-\alpha) * R. \quad \text{(eq. 21)}$$

where R is the radius of the phasor plot unit circle.

With this approach, provided a new center $A_\perp'$ with a specific $\alpha$, we obtain a collection of scaled circles with centers on line $OA_\perp'$. In boundary cases, when $\alpha=0$, the scaled circle is the origin, while $\alpha=1$ is the unit circle. Given any cutting plane O', the radius of this cross section always satisfies this identity:

$$r'^2 = (g_i - \alpha * g_{A_\perp'})^2 + (s_i - \alpha * s_{A_\perp'})^2 = (1-\alpha)^2 \cdot R^2 \quad \text{(eq. 22)}$$

The coordinates of a point $P'(g_o, s_o)$ for a new morphed map centered in $A_\perp'$ are:

$$(g_o, s_o) = (g_i - \alpha * g_{A_\perp'}, s_i - \alpha * s_{A_\perp'}) \quad \text{(eq. 23)}$$

Finally, we compute $$(r_o, \theta_o) = \left( \sqrt{g_o^2 + s_o^2}, \tan^{-1} \frac{s_o}{g_o} \right) \quad \text{(eq. 24)}$$

and then assign colors based on the newly calculated Hue, Saturation, and Value to generate the morph mode references.

Color Image Quality Calculations

Colorfulness

Due to the inherent lack of "ground truth" in experimental fluorescence microscopy images, we utilized an established model for calculating the color quality of an image without a reference. The colorfulness is one of three parameters, together with sharpness and contrast, utilized by Panetta et al. to quantify the overall quality of a color image. Two opponent color spaces are defined as:

$$\alpha = R - G \quad \text{(eq. 25)}$$

$$\beta = 0.5(R+G) - B \quad \text{(eq. 26)}$$

Where R, G, B are the red, green and blue channels respectively, $\alpha$ and $\beta$ are red-green and yellow-blue spaces. The colorfulness utilized here is defined as:

$$\text{Colorfulness} = 0.02 \log\left( \frac{\sigma_\alpha^2}{|\mu_\alpha|^{0.2}} \right) \log\left( \frac{\sigma_\beta^2}{|\mu_\beta|^{0.2}} \right) \quad \text{(eq. 27)}$$

With $\sigma_\alpha^2$, $\sigma_\beta^2$, $\mu_\alpha$, $\mu_\beta$ respectively as the variances and mean values of the $\alpha$ and $\beta$ spaces.

Sharpness

We utilize EME, a Weber based measure of enhancement. EME is defined as follows:

$$EME_{sharp} = \frac{2}{k_1 k_2} \sum_{l=1}^{k_1} \sum_{l=1}^{k_2} \log\left( \frac{I_{max,k,l}}{I_{min,k,l}} \right) \quad \text{(eq. 28)}$$

Where $k_1$, $k_2$ are the blocks used to divide the image and $I_{max,k,l}$ and $I_{min,k,l}$ are the maximum and minimum intensities in the blocks. EME has been shown to correlate with a human observation of sharpness in color images when associated with a weight $\lambda_c$ for each color component.

$$\text{Sharpness} = \Sigma_{c=1}^{3} \lambda_c EME_{sharp} \quad \text{(eq. 29)}$$

Where the weights for different color components used in this article are $\lambda_R = 0.299$, $\lambda_G = 0.587$, $\lambda_B = 0.114$ in accordance with NTSC standard and values reported in literature[58].

Contrast

We utilize Michelson-Law measure of enhancement AME, an effective evaluation tool for contrast in grayscale images, designed to provide larger metric value for larger contrast images. AME is defined as:

$$AME_{contrast} = \frac{1}{k_1 k_2} \sum_{l=1}^{k_1} \left( \sum_{l=1}^{k_2} \log\left( \frac{I_{max,k,l} + I_{min,k,l}}{I_{max,k,l} - I_{min,k,l}} \right) \right)^{-0.5} \quad \text{(eq. 30)}$$

Where $k_1$, $k_2$ are the blocks used to divide the image and $I_{max,k,l}$ and $I_{min,k,l}$ are the maximum and minimum intensities in the blocks. The value of contrast for color images was then calculated as:

$$\text{Contrast} = \Sigma_{c=1}^{3} \lambda_c AME_{contrast} \quad \text{(eq. 31)}$$

With the same weights $\lambda_c$ utilized for sharpness.

Color Quality Enhancement

We utilize Color Quality Enhancement (CQE) a polling method to combine colorfulness, sharpness and contrast into a value that has both strong correlation and linear correspondence with human visual perception of quality in color images. CQE is calculated as:

$$CQE = c_1 \text{colorfulness} + c_2 \text{sharpness} + c_3 \text{contrast} \quad \text{(eq. 31)}$$

Where the linear combination coefficients for CQE measure were set to evaluate contrast change according to values reported in literature, $c_1 = 0.4358$, $c_2 = 0.1722$ and $c_3 = 0.3920$.

Example 17. Mouse Lines

Mice imaging was approved by the Institutional Animal Care and Use Committee (IACUC) of the Children's Hospital of Los Angeles (permit number: 38616) and of the University of Southern California (permit number: 20685). Experimental research on vertebrates complied with institutional, national and international ethical guidelines. Animals were kept on a 13:11 hours light:dark cycle. Animals were breathing double filtered air, temperature in the room was kept at 68-73 F, and cage bedding was changed weekly. All these factors contributed to minimize intra- and inter-experiment variability. Adult 8 weeks old C57Bl mice were euthanized with euthasol. Tracheas were quickly harvested from the mouse, washed in PBS, and cut longitudinally alongside the muscolaris mucosae in order to expose the lumen. A 3 mm×3 mm piece of the trachea was excised and arranged onto a microscope slide for imaging.

Example 18. Zebrafish Lines

Lines were raised and maintained following standard literature practice and in accordance with the *Guide for the Care and Use of Laboratory Animals* provided by the University of Southern California. Fish samples were part of a protocol approved by the IACUC (permit number: 12007 USC).

Transgenic FlipTrap Gt(desm-Citrine) ct122a/+ line is the result of previously reported screen, Tg(kdrl:eGFP)$^{s843}$ line was provided by the Stainier lab (Max Planck Institute for Heart and Lung Research). The Tg(ubi:Zebrabow) line was a kind gift from Alex Schier. Controllable recombination of fluorophores was obtained by crossing homozygous Tg(ubi:Zebrabow) adults with a Tg(hsp70I:Cerulean-P2A-CreER$^{T2}$) line. Embryos were raised in Egg Water (60 μg/ml of Instant Ocean and 75 μg/ml of CaSO4 in Milli-Q water) at 28.5° C. with addition of 0.003% (w/v) 1-phenyl-2-thiourea (PTU) around 18 hpf to reduce pigment formation.

Zebrafish samples with triple fluorescence were obtained by crossing Gt(desm-Citrine)ct122a/+ with Tg(kdrl:eGFP) fish followed by injection of 100 μg per embryo of mRNA encoding H2B-Cerulean at one cell stage as described in previous work[29]. Samples of Gt(desm-Citrine)ct122a/+;Tg(kdrl:eGFP); H2B-Cerulean were imaged with 458 nm laser to excite Cerulean, Citrine and eGFP and narrow 458-561 nm dichroic for separating excitation and fluorescence emission.

Example 19. Plasmid Constructions pDestTol2pA2-hsp70I:Cerulean-P2A-CreERT2 (for generating Tg(hsp70I:Cerulean-P2A-CreER$^{T2}$) line)

The coding sequences for Cerulean, CreERT2, and woodchuck hepatitis virus posttranscriptional regulatory element (WPRE) were amplified from the vector for Tg(bactin2:cerulean-cre), using primers #1 and #2 (complete list of primers is reported in Table 7), pCAG-ERT2CreERT2 (Addgene #13777) using primers #3 and #4, and the vector for Tg(PGK1:H2B-chFP) using primers #5 and #6, respectively. Then Cerulean and CreERT2 sequences were fused using a synthetic linker encoding P2A peptide. The resultant Cerulean-P2A-CreERT2 and WPRE sequences were cloned into pDONR221 and pDONR P2R-P3 (Thermo Fisher Scientific), respectively. Subsequent MultiSite Gateway reaction was performed using Tol2kit vectors according to developer's manuals[66]. p5E-hsp70I (Tol2kit #222), pDONR221-Cerulean-P2A-CreER, and pDONR P2R-P3-WPRE were assembled into pDestTol2pA2 (Tol2kit #394). pDestTol2pA2-fli1:mKO2 (for generating Tg(fli1:mKO2) line).

TABLE 7

Primer list for plasmid constructions

| # | Name | Sequence |
|---|------|----------|
| 1 | attB1-Cerulean-P2A1-F | ggggacaagtttgtacaaaaaagcaggctaccatggtgagcaagggcgaggagctg |
| 2 | attB1-Cerulean-P2A1-R | ggttctcctccacgtctccagcctgcttcagcaggctgaagttagtagctccgcttccttgtacagctcgtccatgccg |
| 3 | P2A1-CreERT2-attB2-F | caggctggagacgtggaggaaaccctggacctaatttactgaccgtacaccaaaatttg |
| 4 | P2A1-ERT2CreERT2-attB2-R | ggggaccactttgtacaagaaagctgggtaggagtgcggccgctatcaagc |
| 5 | attB2r-WPRE-attB3-F | ggggacagcttcttgtacaaagtggggtcaacctctggattacaaaatttgtg |
| 6 | attB2r-WPRE-attB3-R | ggggacaactttgtataataaagttggtgcggggaggcggcccaaagg |
| 7 | attB1-mKO2-F1 | ggggacaagtttgtacaaaaaagcaggcttcaccatggtgagtgtgattaaaccagag |
| 8 | mKO2-attB2-R1 | ggggaccactttgtacaagaaagctgggttttaatgagctactgcatcttctacctgc |

The coding sequence for mKO2 was amplified from mKO2-N1 (addgene #54625) using primers #7 and #8, and cloned into pDONR221. Then p5Efli1 ep (addgene #31160), pDONR221-mKO2, and pDONR P2R-P3-WPRE were assembled into pDestTol2pA2 as described above.

Example 20. Microinjection and Screening of Transgenic Zebrafish Lines 2.3 nL of a solution containing 20 μg/nL plasmid DNA and 20 μg/nL tol2 mRNA was injected into the one-cell stage embryo obtained through crossing AB with Casper zebrafish. The injected F0 embryos were raised and crossed to casper zebrafish for screening. The F1 embryos for prospective Tg(hsp70I:Cerulean-P2A-CreER$^{T2}$) line and Tg(fli1:mKO2) were screened for ubiquitous Cerulean expression after heat shock for 30 min at 37° C., and mKO2 expression restricted in vasculatures, respectively. Positive individual F1 adults were subsequently outcrossed to casper zebrafish, and their offspring with casper phenotype were then used for experiments when 50% transgene transmission was observed in the subsequent generation, indicating single transgene insertions.

Example 21. Sample Preparation and Multispectral Image Acquisition and Instrumentation Images were acquired on a Zeiss LSM780 inverted confocal microscope equipped with QUASAR detector (Carl Zeiss, Jena, Germany). A typical dataset included 32 spectral channels, covering the wavelengths from 410.5 nm to 694.9 nm with 8.9 nm bandwidth, generating an x,y,λ image cube. Detailed acquisition parameters are reported in Table 8.

UltraPure low-melting-point agarose (cat. 16520-050, Invitrogen) solution prepared in 30% Danieau (17.4 mM NaCl, 210 μM KCl, 120 μM MgSO47H2O, 180 μM Ca(NO3)2, 1.5 mM HEPES buffer in water, pH 7.6) with 0.003% PTU and 0.01% tricaine. This solution was subsequently added on top of the mounted embryos. Upon agarose solidification at room temperature (1-2 min), the imaging dish was topped with 30% Danieau solution and 0.01% tricaine at 28.5° C. Imaging on the inverted confocal microscope was performed by positioning the imaging dish on the microscope stage. For Tg(ubi:Zebrabow) samples, to initiate expression of Cre-ER[72], embryos were heat-shocked at 15 hours post fertilization at 370 in 50 ml falcon tubes within a water bath before being returned to a 28.60 incubator. To initiate recombination of the zebrabow transgene, 5 uM 4-OHT (Sigma; H7904) was added to culture media 24 hours post fertilization. Samples of Tg(ubi:Zebrabow) were imaged

TABLE 8

Parameters for in vivo imaging. All data points are 16 bit depth, acquired using LD C-Apochromat 40 x/11 W lens.

| | Scaling X-Y [μm] | Scaling Z [μm] | Imaged Volume (x, y, z, λ, t) [pixels] | Pixel Dwell [μs] | Gain [au] | Pinhole [μm] | Beam Splitters | Laser power [%] | Size [GB] |
|---|---|---|---|---|---|---|---|---|---|
| FIG. 24 | 1.661 | 15.837 | x: 2048, y: 768, z: 20, channels: 33 | 3.15 μs | 825 | 73 μm | 458 | 20% @ 458 nm | 1.93 |
| FIG. 27, FIGS. 43-44 | 0.208 | | x: 1024, y: 1024, channels: 33 | 12.6 μs | 820 | 601 μm | 690+ | 1.8% @ 740 nm | 0.06 |
| FIG. 28, FIGS. 45-46 | 0.923 | 6.000 | x: 3840, y: 768, z: 19, channels: 33 | 3.15 μs | 805 | 229 μm | 488 | 5.5% @ 488 nm | 3.44 |
| FIG. 29, FIGS. 32, 47, 48 | 0.415 | 5.000 | x: 2048, y: 512, z: 7, channels: 33 | 6.30 μs | 800 | 186 μm | 458 | 1.0% @ 458 nm | 0.45 |
| FIG. 30, FIG. 49 | 0.104 | | x: 2048, y: 1024, channels: 33 | 1.58 μs | 827 | 40 μm | 458 | 47.7% @ 458 nm | 0.13 |
| FIG. 54, | 0.069 | 0.069 | x: 1024, y: 1024, channels: 33, time: 100 | 1.59 μs | 800 | 70 μm | 488/561 | 1.2% @ 561 nm 6.5% @ 488 nm | 6.93 |
| FIG. 31 | 0.923 | 6 | x: 365, y: 196, z: 4, channels: 33 | 6.30 μs | 796 | 147 μm | 458 | 5.8% @ 458 nm | 0.02 |
| FIG. 31 | 0.052 | 1 | x: 451, y: 825, z: 6, channels: 33 | 6.30 μs | 827 | 40 μm | 458/690+ | 60% @ 458 nm | 0.14 |
| FIG. 31 | 0.052 | 1 | x: 1024, y: 1024, z: 6, channels: 33 | 6.30 μs | 827 | 40 μm | 458/690+ | 60% @ 458 nm | 0.39 |
| FIG. 31 | 0.865 | 2 | x: 512, y: 512, z: 70, channels: 32 | 1.58 μs | 827 | 601 μm | 690+ | 12% @ 900 nm | 1.10 |
| FIG. 31 | 0.346 | 2 | x: 1024, y: 1024, z: 60, channels: 32 | 1.58 μs | 727 | 75 μm | 405 | 0.3% @ 405 nm | 3.75 |
| FIG. 31 | 0.371 | 2 | x: 1024, y: 1024, z: 62, channels: 32 | 3.15 μs | 820 | 41 μm | 458/561 | 2% @ 561 nm | 3.88 |
| FIG. 31 | 0.865 | 2 | x: 512, y: 512, z: 70, channels: 32, time: 10 | 1.58 μs | 800 | 75 μm | 488/561 | 3% @ 561 nm 2.6% @ 488 nm | 10.97 |
| FIG. 31 | 0.865 | 2 | x: 512, y: 512, z: 70, channels: 32, time: 10 | 1.58 μs | 800 | 75 μm | 488/561 | 3% @ 561 nm 2.6% @ 488 nm | 21.94 |
| FIG. 31 | 0.865 | 2 | x: 512, y: 512, z: 70, channels: 32, time: 10 | 1.58 μs | 800 | 75 μm | 488/561 | 3% @ 561 nm 2.6% @ 488 nm | 43.88 |

Zebrafish samples for in vivo imaging were prepared by placing 5-6 embryos at 24 to 72 hpf into 1% agarose (cat. 16500-100, Invitrogen) molds created in an imaging dish with no. 1.5 coverglass bottom, (cat. D5040P, WillCo Wells) using a custom-designed negative plastic mold[45]. Stability of the embryos was ensured by adding ~2 ml of 1% using 458 nm laser to excite CFP, YFP and RFP in combination with a narrow 458 nm dichroic.

Mouse tracheal samples were collected from wild type C57Bl mice and mounted on a coverslip with sufficient Phosphate Buffered Saline to avoid dehydration of the sample. Imaging was performed in 2-photon mode exciting at 740 nm with a 690+nm dichroic.

Example 22. Non De-Scanned (NDD) Multiphoton Fluorescence Lifetime Imaging (FLIM) and Analysis Fluorescence Lifetime Imaging Microscopy (FLIM) data was acquired with a two-photon microscope (Zeiss LSM-780 inverted, Zeiss, Jena, Germany) equipped with a Ti:Sapphire laser system (Coherent Chameleon Ultra II, Coherent, Santa Clara, California) and an ISS A320 FastFLIM (ISS, Urbana-Champaign, Illinois). The objective used was a 2-p optimized 40×1.1 NA water immersion objective (Korr C-Apochromat, Zeiss, Jena, Germany). Images with size of 256×256 pixels were collected with pixel dwell time of 12.6 µs/pixel. A dichroic filter (690+nm) was used to separate the excitation light from fluorescence emission. Detection of fluorescence included a combination of a hybrid photomultiplier (R10467U-40, Hamamatsu, Hamamatsu City, Japan) and a 460/80 nm band-pass filter. Acquisition was performed using VistaVision software (ISS, Urbana-Champaign, Illinois). The excitation wavelength used was 740 nm with an average power of about 7 mW on the sample. Calibration of lifetimes for the frequency domain system was performed by measuring the known lifetime of the Coumarin 6 with a single exponential of 2.55 ns. FLIM data were collected until 100 counts in the brightest pixel of the image were acquired.

Data was processed using the SimFCS software developed at the Gratton Lab (Laboratory of Fluorescence Dynamics (LFD), University of California Irvine, www.lfd.uci.edu). FLIM analysis of intrinsic fluorophores was performed as previously described and reported in detail. Phasor coordinates (g,s) were obtained through Fourier transformations. Cluster identification was utilized to associate specific regions in the phasor to pixels in the FLIM dataset according to published protocols.

Example 23. Choice of Harmonic for Visualization

The distribution of spectral wavelengths on the phasor plot is highly dependent on the harmonic number used. Typically, the first and second harmonics are utilized for obtaining the hyperspectral phasor values due to visualization limitations imposed by branching within the Riemann surfaces in complex space.

The first harmonic results in a spectral distribution which approximately covers $3/2\pi$ radians for spectrum within the visible range (400 nm-700 nm), within the universal circle, along a counterclockwise path. As a result, spectra separated by any peak-to-peak distance will appear in different positions on the phasor plot. However, the first harmonic provides a less efficient use of the phasor space, leaving $1/2\pi$ radians non utilized and leading to a lower dynamic range of separation as can be seen in FIGS. 39 and 40.

Similarly, the second harmonic approximately spans over $(3/2+2)\pi$ radians on the phasor for spectrum within the visible range (400 nm-700 nm), distributing spectra in a more expansive fashion within the universal circle, simplifying the distinction of spectra which may be closely overlapping and providing a higher dynamic range of separation as demonstrated in FIGS. 36 and 37. The downside of this harmonic is the presence of an overlap region from orange to deep red fluorescence. Within this region, spectra separated by 140 nm (in our system with 32 bands, 410.5 nm to 694.9 nm with 8.9 nm bandwidth), may end up overlapping within the phasor plot. In this scenario, it would not be possible to differentiate those well-separated spectra using the second harmonic, requiring the use of the first. Thanks to SEER, the choice of which harmonic to use for visualization can be quickly verified and changed within the HySP software.

In the common scenario of imaging with a single laser line, the range of the majority of the signal emitted from multiple common fluorophores is likely to be much smaller than 150 nm due to the Stokes' shift usually in the 20-25 nm range. Excitation spectra of fluorescent proteins separated by 140 nm is generally not well overlapping, requiring utilization of a second excitation wavelength to obtain the signal.

The SEER method presented here has utilized the second harmonic in order to maximize the dynamic range of the phasor space and separate closely overlapping spectra. However, SEER can work with the first harmonic seamlessly, maintaining swift visualization of multiple fluorophores that may be far in peak spectral wavelength.

Example 24. Color Visualization Limitations for SEER

The SEER maps are built based on the frequency domain values generated by applying the phasor method to hyperspectral and multispectral fluorescent data. RGB colors are used to directly represent these values. As such, the quality of color separation has a maximum resolution limited by the spectral separation provided by the phasor method itself. Therefore, as long as the phasor method can differentiate between spectra which have a higher amount of fluorescent signal vs noise (high signal to noise) and spectra with a higher combination of the noise versus the signal (low signal to noise), the SEER maps will assign different colors to these spectra. In the scenario where spectra derived from two different effects are exactly the same, for example, a case where low protein expression is on an outer layer and a high level expression is attenuated at a deeper level, the phasor method and the SEER maps, in their current implementation, will not be able to differentiate between the two effects. The separation of these two effects is a different and complex problem which depends on the optical microscopy components, the sample, the labels, the multispectral imaging approach and more factors in the experimental design, and we believe this separation falls outside of the scope of this paper and constitutes a project on its own.

Any combination of above features/configurations is within the scope of this disclosure.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

We claim:

1. A hyperspectral imaging system for generating an unmixed color image of a target, comprising:
   an optics system; and
   an image forming system;
   wherein:
      the optics system comprises at least one optical component;
      the at least one optical component comprises at least one optical detector;
      the at least one optical detector has a configuration that:
         detects a target radiation, which is absorbed, transmitted, refracted, reflected, and/or emitted by at least one physical point on the target, wherein the target radiation comprises at least two target waves, each wave having an intensity and a different wavelength;
         detects the intensity and the wavelength of each target wave; and
         transmits the detected target radiation, and each target wave's detected intensity and wavelength to the image forming system;
      the image forming system comprises a control system, a hardware processor, a memory, and a display; and
      the image forming system has a configuration that:
         forms a target image of the target using the detected target radiation, wherein the target image comprises at least two pixels, and wherein each pixel corresponds to one physical point on the target;
         forms at least one intensity spectrum for each pixel using the detected intensity and wavelength of each target wave;
         transforms the formed intensity spectrum of each pixel by using a Fourier transform into a complex-valued function based on the intensity spectrum of each pixel, wherein each complex-valued function has at least one real component and at least one imaginary component;
         forms one phasor point on a phasor plane for each pixel by plotting the real value against the imaginary value of each pixel;
         maps back the phasor point to a corresponding target image pixel on the target image based on the phasor point's geometric position on the phasor plane;
         generates or uses a reference color map;
         assigns a color for each phasor point on the phasor plane by using the reference color map;
         transfers the assigned color to the corresponding target image pixel;
         generates a color image of the target based on the assigned color; and
         displays the color image of the target on the image forming system's display.

2. The hyperspectral imaging system of claim 1, wherein the image forming system has a configuration that generates the reference color map by using phase modulation and/or phase amplitude of the phasor points.

3. The hyperspectral imaging system of claim 1, wherein the reference color map has a uniform color along at least one of its coordinate axes.

4. The hyperspectral imaging system of claim 1, wherein:
   the reference color map has a circular shape, which forms a circular reference color map;
   the circular reference color map has an origin, and a radial direction, and an angular direction with respect to the origin of the circular reference color map; and
   wherein the image forming system has a configuration that:
      varies color in the radial direction and keeps color uniform in the angular direction to form a radial reference color map;
      varies color in the angular direction and keeps color uniform in the radial direction to form an angular color reference map; and/or
      varies brightness in the radial direction and/or angular direction; and
      forms the reference color map.

5. The hyperspectral imaging system of claim 1, wherein:
   the reference circle map has a circular shape, which forms a circular reference color map;
   the circular reference color map has an origin; and a radial direction and an angular direction, with respect to the origin of the circular reference color map; and wherein the image forming system has a configuration that:
varies color in the radial direction and keeps color uniform in the angular direction to form a radial reference color map; and/or varies color in the angular direction and keeps color uniform in the radial direction to form an angular reference color map;
decreases brightness in the radial direction to form a gradient descent color map; and/or
increases brightness in the radial direction to form a gradient ascent reference color map; and
forms the reference color map.

6. The hyperspectral imaging system of claim 1, wherein:
the reference color map has a circular shape, which forms a circular reference color map;
the circular reference color map has an origin; and a radial direction and an angular direction with respect to the origin of the circular reference color map;
the image forming system has a configuration that:
determines a maximum value of a phasor histogram to form a maximum phasor value;
assigns a center to a circle that corresponds to coordinates of the maximum phasor value to form the circular reference color map's maximum center;
varies color in the radial direction and keeps color uniform in the angular direction, with respect to the circular reference color map's maximum center, to form a morph maximum value mode; and/or
varies color in the angular direction and keeps color uniform in the radial direction, with respect to the circular reference color map's maximum center, to form a morph center-of-mass value mode; and
forms the reference color map.

7. The hyperspectral imaging system of claim 1, wherein the image forming system has a configuration that:
applies a denoising filter on both the real component and the imaginary component of each complex-valued function at least once so as to produce a denoised real value and a denoised imaginary value for each pixel;
wherein the denoising filter is applied:
after the hyperspectral imaging system transforms the formed intensity spectrum of each pixel using the Fourier transform into the complex-valued function; and
before the hyperspectral imaging system forms one point on the phasor plane for each pixel; and
uses the denoised real value and the denoised imaginary value for each pixel as the real value and the imaginary value for each pixel to form one point on the phasor plane for each pixel.

8. The hyperspectral imaging system of claim 7, wherein the image forming system has a further configuration that estimates error after it applies the denoising filter.

9. The hyperspectral imaging system of claim 7, wherein the image forming system uses a first harmonic and/or a second harmonic of the Fourier transform to generate the unmixed color image of the target.

10. The hyperspectral imaging system of claim 1, wherein:
each phasor point has a real value and an imaginary value;
the image forming system has a configuration that:
forms a phasor plane by using a coordinate axis for the imaginary value and a coordinate axis for the real value;
forms a phasor bin, wherein the phasor bin comprises phasor points and has a specified area on the phasor plane, and wherein a number of the phasor points that belong to the same phasor bin forms a magnitude of the phasor bin; and
forms a phasor histogram by plotting the phasor bin magnitudes.

11. The hyperspectral imaging system of claim 10, wherein the hyperspectral imaging system has a configuration that forms a tensor map by calculating a gradient of the phasor bin magnitude between adjacent phasor bins; and assigning a color to each pixel based on the reference color map.

12. The hyperspectral imaging system of claim 10, wherein the hyperspectral imaging system is a system for real-time intrinsic signal image processing, a system for separation of 1 to 3 extrinsic labels from multiple intrinsic labels, a system for separation of 1 to 7 extrinsic labels from multiple intrinsic labels, and/or a system for combinatorial label visualization.

13. The hyperspectral imaging system of claim 10, wherein the image forming system uses at least a first harmonic and/or a second harmonic of the Fourier transform to generate the unmixed color image of the target.

14. The hyperspectral imaging system of claim 10, wherein the image forming system uses a first harmonic and/or a second harmonic of the Fourier transform to generate the unmixed color image of the target.

15. The hyperspectral imaging system of claim 10, wherein the target radiation comprises at least four wavelengths.

16. The hyperspectral imaging system of claim 10, wherein the target radiation has four wavelengths or eight wavelengths.

17. The hyperspectral imaging system of claim 10, wherein the hyperspectral imaging system forms the unmixed color image of the target at a signal-to-noise ratio of the at least one intensity spectrum in a range of 1.2 to 50.

18. The hyperspectral imaging system of claim 10, wherein the hyperspectral imaging system forms the unmixed color image of the target at a signal-to-noise ratio of the at least one intensity spectrum in the range of 1.2 to less than 3.

19. The hyperspectral imaging system of claim 10, wherein the image forming system has a further configuration that performs multispectral volumetric time-lapses with reduced photo-damage after it forms the at least one intensity spectrum for each pixel.

20. The hyperspectral imaging system of claim 10, wherein the image forming system has a further configuration that identifies autofluorescence as a spectral fingerprint and removes the autofluorescence.

* * * * *

UNITED STATES PATENT AND TRADEMARK OFFICE
CERTIFICATE OF CORRECTION

PATENT NO. : 11,869,176 B2
APPLICATION NO. : 17/427890
DATED : January 9, 2024
INVENTOR(S) : Wen Shi et al.

It is certified that error appears in the above-identified patent and that said Letters Patent is hereby corrected as shown below:

In the Specification

Column 1, Line 18:
Please delete "This invention was made with government support from Department of Defense under Grant No. PR150666. The government has certain rights in the invention." and insert --The invention was made with government support under W81XWH-16-1-0253 awarded by the Medical Research and Development Command. The government has certain rights in the invention.--

Signed and Sealed this
Twelfth Day of March, 2024

Katherine Kelly Vidal
*Director of the United States Patent and Trademark Office*